US008153776B2

(12) United States Patent
Hannon et al.

(10) Patent No.: US 8,153,776 B2
(45) Date of Patent: *Apr. 10, 2012

(54) METHODS AND COMPOSITIONS FOR RNA INTERFERENCE

(75) Inventors: Gregory J. Hannon, Huntington, NY (US); Patrick Paddison, Seattle, WA (US); Emily Bernstein, New York, NY (US); Amy Caudy, Lawrenceville, NJ (US); Douglas Conklin, Cold Spring Harbor, NY (US); Scott Hammond, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/894,676

(22) Filed: Aug. 20, 2007

(65) Prior Publication Data

US 2008/0213861 A1     Sep. 4, 2008

Related U.S. Application Data

(63) Continuation of application No. 10/997,086, filed on Nov. 23, 2004, and a continuation-in-part of application No. 10/055,797, filed on Jan. 22, 2002.

(51) Int. Cl.
    *C07H 21/04*     (2006.01)
(52) U.S. Cl. .................. 536/24.5; 536/24.31; 536/24.1; 435/6; 435/325; 435/375; 514/44
(58) Field of Classification Search .................. None
    See application file for complete search history.

(56) References Cited

U.S. PATENT DOCUMENTS

| 5,246,921 | A | | 9/1993 | Reddy et al. |
|---|---|---|---|---|
| 5,624,803 | A | * | 4/1997 | Noonberg et al. ............... 435/6 |
| 5,814,500 | A | | 9/1998 | Dietz |
| 5,998,148 | A | | 12/1999 | Bennett et al. |
| 6,107,027 | A | | 8/2000 | Kay et al. |
| 6,130,092 | A | | 10/2000 | Lieber et al. |
| 6,326,193 | B1 | | 12/2001 | Liu et al. |
| 6,506,559 | B1 | | 1/2003 | Fire et al. |
| 6,541,248 | B1 | | 4/2003 | Kingsman et al. |
| 6,573,099 | B2 | | 6/2003 | Graham et al. |
| 6,605,429 | B1 | | 8/2003 | Barber et al. |
| 7,691,995 | B2 | | 4/2010 | Zamore et al. |
| 2002/0086356 | A1 | | 7/2002 | Tuschl et al. |
| 2002/0114784 | A1 | | 8/2002 | Li et al. |
| 2002/0160393 | A1 | * | 10/2002 | Symonds et al. ............... 435/6 |
| 2003/0051263 | A1 | | 3/2003 | Fire et al. |
| 2003/0055020 | A1 | | 3/2003 | Fire et al. |
| 2003/0056235 | A1 | | 3/2003 | Fire et al. |
| 2003/0084471 | A1 | | 5/2003 | Beach et al. |
| 2004/0001811 | A1 | | 1/2004 | Kreutzer et al. |
| 2004/0018999 | A1 | | 1/2004 | Beach et al. |
| 2004/0086884 | A1 | | 5/2004 | Beach et al. |
| 2004/0102408 | A1 | * | 5/2004 | Kreutzer et al. ............... 514/44 |
| 2004/0229266 | A1 | | 11/2004 | Tuschl et al. |
| 2005/0164210 | A1 | | 7/2005 | Mittal et al. |
| 2005/0197315 | A1 | | 9/2005 | Taira et al. |

FOREIGN PATENT DOCUMENTS

| CA | 2470903 | 7/2003 |
|---|---|---|
| EP | 1462525 | 9/2004 |
| WO | WO-94/01550 | 1/1994 |
| WO | 99/32619 | 7/1999 |
| WO | WO-99/32619 | 7/1999 |
| WO | WO-99/49029 | 9/1999 |
| WO | WO-00/01846 | 1/2000 |
| WO | WO-00/44895 | 8/2000 |
| WO | WO-00/44914 | 8/2000 |
| WO | WO-00/63364 | 10/2000 |
| WO | WO-01/29058 | 4/2001 |
| WO | WO-01/36646 | 5/2001 |
| WO | WO-01/48183 | 7/2001 |
| WO | WO-01/49844 | 7/2001 |
| WO | WO-01/68836 | 9/2001 |
| WO | WO-01/75164 | 10/2001 |
| WO | WO-02/44321 | 6/2002 |
| WO | WO-02/059300 | 8/2002 |
| WO | WO-02/068635 | 9/2002 |
| WO | WO-03/020931 | 3/2003 |
| WO | WO-2004/029219 | 4/2004 |

OTHER PUBLICATIONS

Caplen et al. Specific inhibition of gene expression by small double-stranded RNAs in invertebrate and vertebrate systems. PNAS 2001, vol. 98, No. 17: 9742-9747.*
Agrawal, et al., "Antisense therapeutics: is it as simple as complementary base recognition?," Molecular Medicine Today, 61:72-81 (2000).
Ambros, "Dicing Up RNAs," Science 293: 811-813 (2001).
Bass, "Double-Stranded RNA as a Template for Gene Silencing," Cell, 101:235-238 (2000).
Baulcombe, "Gene silencing: RNA makes RNA makes no protein," Curr. Biol., 9:R599-R601 (1999).
Baulcombe, "RNA as a target and an initiator of post-transcriptional gene silencing in transgenic plants," Plant Mol. Biol., 32:79-88 (1996).
Bernstein, et al., "Dicer is essential for mouse development," Nat Genet., 35(3):215-7 (2003).
Bernstein, et al., "Role for a bidentate ribonuclease in the initiation step of RNA interference," Nature 409(6818):363-6 (2001).
Bernstein, et al., "The rest is silence," RNA 7(11):1509-21 (2001).
Bohmert, et al., "AGO1 defines a novel locus of *Arabidopsis* controlling leaf development," EMBO J., 17:170-180 (1998).

(Continued)

*Primary Examiner* — Kimberly Chong
(74) *Attorney, Agent, or Firm* — Wilmer Cutler Pickering Hale and Dorr LLP

(57) ABSTRACT

The present invention provides methods for attenuating gene expression in a cell, especially in a mammalian cell, using gene-targeted double stranded RNA (dsRNA), such as a hairpin RNA. The dsRNA contains a nucleotide sequence that hybridizes under physiologic conditions of the cell to the nucleotide sequence of at least a portion of the gene to be inhibited (the "target" gene).

10 Claims, 68 Drawing Sheets

OTHER PUBLICATIONS

Bosher, et al., "RNA Interference Can Target Pre-mRNA: Consequences for Gene Expression in a *Caenorhabditis elegans* Operon," Genetics, 153:1245-1256 (1999).

Bosher, et al., "RNA interference: genetic wand and genetic watchdog," Nat. Cell Biol., 2:E31-36 (2000).

Caplen, N.J., et al., "dsRNA-mediated gene silencing in cultured *Drosophila* cells: a tissue culture model for the analysis of RNA interference," Gene, 252:95-105 (2000).

Caplen, N.J., et al., "RNAi as a gene therapy approach," Expert Opin. Biol. Ther., 3(4):575-586 (2003).

Carmell et al., "The Argonaute family: tentacles that reach into RNAi, developmental control, stem cell maintenance, and tumorigenesis," Genes Dev., 16(21):2733-42 (2002).

Carmell MA, et al., "RNase III enzymes and the initiation of gene silencing," Nat Struct Mol Biol., 11(3):214-8 (2004).

Carmell, et al., "Germline transmission of RNAi in mice," Nat Struct Biol., 10(2):91-2 (2003).

Catalanotto, et al. "Gene silencing in worms and fungi," Nature 404:245 (2000).

Caudy, et al., "A micrococcal nuclease homologue in RNAi effector complexes," Nature 425(6956):411-4 (2003).

Caudy, et al., "Fragile X-related protein and VIG associate with the RNA interference machinery," Genes Dev., 16(19):2491-6 (2002).

Caudy, et al., "Induction and biochemical purification of RNA-induced silencing complex from *Drosophila* S2 cells," Methods Mol. Biol., 265:59-72 (2004).

Check, E., "RNA to the rescue? Disease therapies based on a technique for gene silencing called RNA interference are racing towards the clinic. Erika Check investigates molecular medicine's next big thing," Nature, 425:10-12 (2003).

Cleary, et al., "Production of complex nucleic acid libraries using highly parallel in situ oligonucleotide synthesis," Nat Methods, 1(3):241-8 (2004).

Cogoni, et al., "Gene silencing in *Neurospora crassa* requires a protein homologous to RNA-dependent RNA polymerase," Nature 399:166-169 (1999).

Cogoni, et al., "Posttranscriptional Gene Silencing in *Neurospora* by a RecQ DNA Helicase," Science, 286:2342-2344 (1999).

Connelly, et al., "The sbcC and sbcD genes of *Escherichia coli* encode a nuclease involved in palindrome inviability and genetic recombination," Genes Cell 1:285-291 (1996).

Crooke, "Basic Principles of Antisense Therapeutics," Antisense Research and Application, Chapter 1, Springer-Verlag, New York (1998).

Dalmay, et al., "An RNA-Dependent RNA Polymerase Gene in *Arabidopsis* is Required for Posttranscriptional Gene Silencing Mediated by a Transgene but Not by a Virus," Cell, 101:543-553 (2000).

Denli, et al., "Processing of primary microRNAs by the Microprocessor complex," Nature, 432(7014):231-5 (2004).

Denli, et al., "RNAi: an ever-growing puzzle," Trends Biochem. Sci., 28(4):196-201 (2003).

Di Nocera, et al., "Transient expression of genes introduced into cultured cells of *Drosophila*," PNAS, 80:7095-7098 (1983).

Eck, et al., "Gene-based therapy, Goodman & Gilman's," The Pharmacological Basis of Therapeutics, 9th Edition, 5:77-101 (1996).

Elbashir, et al., "Functional anatomy of siRNAs for mediating efficient RNAi in *Drosophila melanogaster* embryo lysate," The EMBO Journal, 20(23):6877-6888 (2001).

Fagard, et al., "AG01, QDE-2, and RDE-1 are related proteins required for post-transcriptional gene silencing in plants, quelling in fungi, and RNA interference in animals," PNAS 97:11650-11654 (2000).

Fire, "RNA-triggered gene silencing," Trends Genet., 15:358-363 (1999).

Fire, et al. "Potent and specific genetic interference by double-stranded RNA in *Caenorhabditis elegans*," Nature, 391:806-811 (1998).

Fortier, "Temperature-Dependent Gene Silencing by an Expressed Inverted Repeat in *Drosophila*," Genesis 26:240-244 (2000).

Fraser, "Human Genes Hit the Big Screen," Nature, 428:375-378 (2004).

Gillespie, et al., "Homeless is required for RNA localization in *Drosophila* oogenesis and encodes a new member of the DE-H family of RNA-dependent ATPases," Genes Dev. 9:2495-2508 (1995).

Good et al., "Expression of small, therapeutic RNAs in human cell nuclie," Gene Therapy 4:45- 54 (1997).

Guo, "par-1, a Gene Required for Establishing Polarity in *C. elegans* Embryos, Encodes a Putative Ser/Thr Kinase that is Asymmetrically Distributed," Cell 81:611-620 (1995).

Gupta, et al., "Inducible, reversible, and stable RNA interference in mammalian cells," Proc Natl Acad Sci USA 101(7):1927-32 (2004).

Hamilton, et al., "A Species of Small Antisense RNA in Post-transcriptional Gene Silencing in Plants," Science 286:950-952 (1999).

Hammond, et al., "An RNA-directed nuclease mediates post-transcriptional gene silencing in *Drosophila* cells," Nature 404:293-296 (2000).

Hammond, SM, et al., "Post-transcriptional gene silencing by double-stranded RNA," Nat Rev Genet. 2(2):110-9 (2001).

Hammond, S., et al., "Argonaute2, a Link Between Genetic and Biochemical Analyses RNAi," Science, 293:1146-1150 (2001).

Hannon, "RNA interference," Nature 418(6894):244-51 (2002).

Hannon, et al., "RNA interference by short hairpin RNAs expressed in vertebrate cells," Methods Mol Biol., 257:255-66 (2004).

Hannon, et al., "Unlocking the potential of the human genome with RNA interference," Nature, 431(7006):371-8 (2004).

Hasuwa, H., et al., "Small interfering RNA and gene silencing in transgenic mice and rats," FEBS Letters, 532:227-230 (2002).

He, et al., "A microRNA polycistron as a potential human oncogene," Nature, 435(7043):828-33 (2005).

He, et al., "MicroRNAs: small RNAs with a big role in gene regulation," Nat Rev Genet., 5(7):522-31 (2004).

Hemann, et al., "An epi-allelic series of p53 hypomorphs created by stable RNAi produces distinct tumor phenotypes in vivo," Nat Genet. 33(3):396-400 (2003).

Hunter, "Genetics: A touch of elegance with RNAi," Curr. Biol., 9:R440-R442 (1999).

Jackson, et al., "Expression profiling reveals off-target gene regulation by RNAi", Nature Biotechnology 21(6), 635-638 (2003).

Jacobsen, et al., "Disruption of an RNA helicase/RNAse III gene in *Arabidopsis* causes unregulated cell division in floral meristems," Development 126:5231-5243 (1999).

Jen, K.Y., et al., "Suppression of Gene Expression by Targeted Disruption of Messenger RNA: Available Options and Current Strategies," Stem Cells, 18:307-319 (2000).

Jones, et al., "De novo methylation and co-suppression induced by a cytoplamically replicating plant RNA virus," EMBO J. 17:6385-6393 (1998).

Jones, et al., "RNA-DNA Interactions and DNA Methylation in Post-Transcriptional Gene Silencing," Plant Cell, 11:2291-2301 (1999).

Jorgensen, et al., "An RNA-Based Information Superhighway in Plants," Science, 279:1486-1487 (1998).

Kalejta, et al., "An Integral Membrane Green Fluorescent Protein Marker, Us9-GFP, is Quantitatively Retained in Cells during Propidium Iodide-Based Cell Cycle Analysis by Flow Cytometry," Exp. Cell. Res. 248:322-328 (1999).

Kennerdell, et al., "Heritable gene silencing in *Drosophila* using double-stranded RNA," Nat. Biotechnol., 17:896-898 (2000).

Kennerdell, et al., "Use of dsRNA-Mediated Genetic Interference to Demonstrate that frizzled and frizzled 2 Act in the Wingless Pathway," Cell 95:1017-1026 (1998).

Ketting, et al., "mut-7 of *C. elegans*, Required for Transposon Silencing and RNA Interference, Is a Homolog of Werner Syndrome Helicase and RNaseD," Cell 99:133-141 (1999).

Ketting, R. F. et al., "Dicer functions in RNA interference and in synthesis of small RNA involved in developmental timing in *C. elegans*", Genes Dev 15:2654-2659 (2001).

Kramer, et al., "Activation of the human anaphase-promoting complex by proteins of the CDC20/Fizzy family," Curr. Biol. 8:1207-1210 (1998).

Lam, et al., "Inducible expression of double-stranded RNA directs specific genetic interference in *Drosophila*," Curr. Biol., 10:957-963 (2000).

Lee, et al., "Distinct Roles for *Drosophila* Dicer-1 and Dicer-2 in the siRNA/miRNA Silencing Pathways", Cell 117:69-81 (2004).
Lingel, et al., "Nucleic acid 3'-end recognition by the Argonaute2 PAZ domain," Nature Structural & Molecular Biology, 11(6):576-577 (2004).
Lipardi, et al., "RNAi as Raondon Degradative PCR: siRNA Primers Convert mRNA into dsRNAs that are Degraded to Generate New siRNAs," Cell, 107:297-307 (2001).
Liu J, et al., MicroRNA-dependent localization of targeted mRNAs to mammalian P-bodies, Nat Cell Biol. 7(7):719-23 (2005); Epub Jun. 5, 2005.
Liu, et al., "Argonaute2 is the catalytic engine of mammalian RNAi," Science, 305(5689):1437- 41 (2004).
Lohmann, et al., "Silencing of Developmental Genes in Hydra," Dev. Biol., 214: 211-214 (1999).
Lund, et al., "Nuclear Export of MicroRNA Precursors," Science 303:95-98 (2004).
Manche, et al., "Interactions between Double-Stranded RNA Regulators and the Protein Kinase DAI," Molecular and Cellular Biology, 12(11):5238-5248 (1992).
Marshall, "Gene therapy's growing pains," Science, 269:1050-1055 (1995).
Matsuda, et al., "Molecular cloning and characterization of a novel human gene (HERNA) which encodes a putative RNA-helicase," Biochim. Biophys., Acta 1490:163-169 (2000).
McCaffrey, et al., "RNA interference in adult mice," Nature 418(6893):38-9 (2002).
Mette, et al., "Transcriptional silencing and promoter methylation triggered by double stranded RNA," The EMBO Journal, 19(19):5194-5201 (2000).
Misquitta, et al., "Targeted disruption of gene function in *Drosophila* by RNA interference (RNA-i): A role for nautilus in embryonic somatic muscle formation," PNAS 96:1451-1456 (1999).
Montgomery, et al., "Double-stranded RNA as a mediator in sequence-specific genetic silencing and co-suppression," Trends Genet., 14:255-258 (1998).
Montgomery, M.K. et al., "RNA as a target of double-stranded RNA-mediated genetic interference in *Caenorhabditis elegans*," PNAS 95:15502-15507 (1998).
Moss, Eric G., "RNA interference: It's a small RNA world," Current Biology, 11(19):R772-R775 (2001).
Mourrain, et al., "*Arabidopsis* SGS2 and SGS3 Genes are Required for Posttranscriptional Gene Silencing and Natural Virus Resistance," Cell 101:533-542 (2000).
Murchison, et al., "miRNAs on the move: miRNA biogenesis and the RNAi machinery," Curr Opin Cell Biol. 16(3):223-9 (2004).
Ngo, et al., "Double-stranded RNA induces mRNA degradation in*Trypanosoma brucei*," PNAS 95:14687-14692 (1998).
Novina, et al., "The RNAi Revolution," Nature 430:161-164 (2004).
Opalinska, et al., "Nucleic acid based therapeutics: basic principals and recent applications," Nature Reviews: Drug Discovery, 1:503-514 (2002).
Paddison, et al., "A resource for large-scale RNA-interference-based screens in mammals," Nature, 428(6981):427-31 (2004).
Paddison, et al., "Cloning of short hairpin RNAs for gene knockdown in mammalian cells," Nature Meth., 1(2):163-167 (2004).
Paddison, et al., "RNA interference: the new somatic cell genetics?" Cancer Cell, 2(1):17-23 (2002).
Paddison, et al., "Short hairpin activated gene silencing in mammalian cells," Methods Mol Biol., 265:85-100 (2004).
Paddison, et al., "Short hairpin RNAs (shRNAs) induce sequence-specific silencing in mammalian cells," Genes & Development, 16:948-958 (2002).
Paddison, et al., "siRNAs and shRNAs: skeleton keys to the human genome," Curr Opin Mol Ther., 5(3):217-24 (2003).
Paddison, et al., "Stable suppression of gene expression by RNAi in mammalian cells," 99(3):1443-1448 (2002).
Paroo, et al., "Challenges for RNAi in vivo," TRENDS in Biotechnology 22:390-394 (2004).
Pham, et al., "A Dicer-2-Dependent 80S Complex Cleaves Targeted mRNAs during RNAi in *Drosophila*," Cell 117:83-94 (2004).
Piccin, et al., "Efficient and heritable functional knock-out of an adult phenotype in *Drosophilia* using a GAL4-driven hairpin RNA incorporating a heterologous spacer," Nucleic Acids Research, 29(12)e55:1-5 (2001).
Qi, et al., "Biochemical Specialization within *Arabidopsis* RNA Silencing Pathways," Mol Cell. 19(3):421-8 (2005).
Ratcliff, et al., "A Similarity Between Viral Defense and Gene Silencing in Plants," Science 276:1558-1560 (1997).
Rivas, et al., "Purified Argonaute2 and an siRNA form recombinant human RISC," Nat Struct Mol Biol., 12(4):340-9 (2005).
Sanchez, "Double-stranded RNA specifically disrupts gene expression during planarian regeneration," PNAS 96:5049-5054 (1999).
Schneider, "Cell lines derived from late embryonic stages of *Drosophila melanogaster*," J. Embryol. Exp. Morpho., 27:353-365 (1972).
Schramke, et al., "RNA-interference-directed chromatin modification coupled to RNA polymerase II transcription," Nature, 435(7046):1275-9 (2005).
Sharp, "RNAi and double-strand RNA," Genes Dev., 13:139-141 (1999).
Shi, et al. "Genetic interference in *Typanosoma brucei* by heritable and inducible double-stranded RNA," RNA, 6:1069-1076 (2000).
Shuttleworth, et al., "Antisense oligonucleotide-directed cleavage of mRNA in Xenopus oocytes and eggs," EMBO J., 7:427-434 (1988).
Sijen, "Post-transcriptional gene-silencing: RNAs on the attack or on the defense?" Bioessays, 22:520-531 (2000).
Silva, et al., "Free energy lights the path toward more effective RNAi," Nat Genet. 35(4):303-5 (2003).
Silva, et al., "RNA interference microarrays: High-throughput loss-of-function genetics in mammalian cells," Proceedings of the National Academy of Sciences of USA, 101(17):6548-6552 (2004).
Silva, et al., "RNA interference: a promising approach to antiviral therapy?" Trends Mol Med. 8(11):505-8 (2002).
Silva, et al., "RNA-interference-based functional genomics in mammalian cells: reverse genetics coming of age," Oncogene, 23(51):8401-9 (2004).
Silva, et al., "Second-generation shRNA libraries covering the mouse and human genomes," Nature Genetics, 37(11):1281-1288 (2005).
Singh, et al., "Inverted-repeat DNA: a new gene-silencing tool for seed lipid modification," Biochemical Society, 28(6):925-927 (2000).
Siolas, et al., "Synthetic shRNAs as potent RNAi triggers," Nature Biotechnology, 23(2):227-231 (2005).
Smardon, et al., "EGO-1 is related to RNA-directed RNA polymerase and functions in germ-line development and RNA interference in *C. elegans*," Curr. Biol. 10:169-178 (2000).
Smith, et al., "Total silencing by intron-spliced hairpin RNAs," Nature, 407:319-320 (2000).
Song, et al., "Crystal structure of Argonaute and its implications for RISC slicer activity," Science, 305(5689):1434-7 (2004).
Song, et al., "The crystal structure of the Argonaute2 PAZ domain reveals an RNA binding motif in RNAi effector complexes," Nat. Struct. Biol. 10(12):1026-32 (2003).
Svoboda, et al., "RNAi and expression of retrotransposons MuERV-L and IAP in preimplantation mouse embryos," Dev. Biol., 269(1):276-85 (2004).
Tabara, et al., "RNAi in *C. elegans*: Soaking in the Genome Sequence," Science, 282:430-432 (1998).
Tabara, et al., "The dsRNA Binding Protein RDE-4 Interacts with RDE-1, DCR-1, and a DExH-Box Helicase to Direct RNAi in *C. elegans*," Cell, 109:861-871. (2002).
Tabara, et al., "The rde-1 Gene, RNA Interference, and Transposon Silencing in *C. elegans*," Cell, 99:123-132 (1999).
Tavernarakis, et al., "Heritable and inducible genetic interference by double-stranded RNA encoded by transgenes," Nat. Genet., 24:180-183 (2000).
Timmons, et al., "Specific interference by ingested dsRNA," Nature, 395:854 (1998).
Tomari, et al., "RISC Assembly Defects in the *Drosophila* RNAi Mutant armitage", Cell 116:831-841 (2004).
Tuschl, et al. "Targeted mRNA degradation by double-stranded RNA in vitro," Genes Dev., 13:3191-3197 (1999).

Ui-Tei, et al., "Sensitive Assay of RNA Interference in *Drosophila* and Chinese Hamster Cultured Cells Using Firefly Luciferase Gene as Target," FEBS Letters, 479:79-82 (2000).

Vaucheret, et al., "Transgene-induced gene silencing in plants," Plant J. 16:651-659 (1998).

Wadhwa, et al., "Know-how of RNA interference and its applications in research and therapy," Mutation Research, 567:71-84 (2004).

Wassenegger, "A model for RNA-mediated gene silencing in higher plants," Plant Mol. Biol. 37:349-362 (1998).

Waterhouse, et al., "Virus resistance and gene silencing in plants can be induced by simultaneous expression of sense and antisense RNA," PNAS 95:13959-13964 (1998).

Wianny, "Specific interference with gene function by double-stranded RNA in early mouse development," Nature Cell Biol., 2:70-75 (2000).

Wolf, et al., "Cell cycle: Oiling the gears of anaphase," Curr. Biol. 8:R636-R639 (1998).

Zamore, et al., "RNAi: Double-Stranded RNA Directs the ATP-Dependent Cleavage of mRNA at 21 to 23 Nucleotide Intervals." Cell 101:25-33 (2000).

Zhang, et al., "Human Dicer preferentially cleaves dsRNAs at their termini without a requirement for ATP," The Embo Journal, 21:5875-5885. (2002).

Zhang, et al., "Single Processing Center Models for Human Dicer and Bacterial RNase III," Cell, 118:57-68 (2004).

Zhang, et al., "Targeted gene silencing by small interfering RNA based knock down technology," Curr. Pharma. Biotech., 5:1-7 (2004).

European Search Report for European PAtent Application No. 05857008.6, mailed May 8, 2008.

Bosher et al., "RNA interference can target pre-mRNA: consequences for gene expression in a *Caenorhabditis elegans* operon," Genetics, vol. 153, No. 3, p. 1245-1256 (Nov. 1999).

European Search report for European Patent application No. 03732052.0, mailed May 23, 2008.

Hasuwa et al., "Small interfering RNA and gene silencing in transgenic mice and rats," FEBS Letters, Elsevier, Amsterdam, NL, vol. 532, pp. 227-230 (Dec. 2002).

Manche et al., "Interactions between double-stranded RNA regulators and the proteinkinase Dai," Molecular and cellular Biology, Amercian Society for Microbiology, Washington, US, vol. 12, pp. 5238-5248 (Nov. 1992).

Marked-up U.S. Appl. No. 09/866,557, filed May 24, 2001.

Marked-up U.S. Appl. No. 60/243,097, filed Oct. 24, 2000.

Declaration of Dr. Vladimir Drozdoff (executed Aug. 5, 2008).

Declaration of Mr. John Maroney (executed Aug. 5, 2008).

Declaration of Professor Gregory Hannon (executed Aug. 5, 2008).

Letter of Apr. 22, 2008 from Douglass N. Ellis, Jr. of Ropes & Gray LLP to John Maroney, Esq. of Cold Spring Harbor Laboratory.

Letter of Apr. 28, 2008 from John Maroney of Cold Spring Harbor Laboratory to Douglass N. Ellis, Jr. of Robes & Gray LLP.

Letter of Apr. 29, 2008 from Douglass N. Ellis, Jr. from Robes & Gray LLP to John Maroney, Esq. of Cold Spring Harbor Laboratory.

Letter of May 9, 2008 to Eric R. Hubbard, Esq. of Robes & Gray LLP from John Maroney, Esq. of Cold Spring Harbor Laboratory.

Letter of Jun. 4, 2008 from Eric R. Hubbard of Robes & Gray LLP to John Maroney, Esq. of Cold Spring Harbor Laboratory.

Letter of Jun. 13, 2008 from John Maroney, Esq. of Cold Spring Harbor Laboratory to James Haley, Esq. of Robes & Gray LLP.

Buchholz et al., "Enzymatically prepared RNAi libraries," Nature Methods, vol. 3, No. 9, pp. 696-700 (Sep. 2006).

Caplen et al., "Rescue of polyglutamine-mediated cytotoxicity by double-stranded RNA-mediated RNA interference," Human Molecular Genetics, vol. 11, pp. 175-184 (2002).

Chang et al., "Lessons from Nature: microRNA-based ShRNA libraries," Nature Methods, vol. 3, No. 9, pp. 707-714 (Sep. 2006).

Cullen, "Enhancing and confirming the specificity of RNAi experiments," Nature Methods, vol. 3, pp. 677-681 (Sep. 2006).

Elbashir et al., "Duplexes of 21-nucleotide RNA's mediate RNA interference in cultured mammalian cells," Nature, vol. 411, pp. 494-498 (May 2001).

Elbashir et al., "RNA interference is mediated by 21- and 22-nucleotide RNA,s," Gene and Development, vol. 15, pp. 188-200 (2001).

Gil et al., "Induction of apoptosis by the DsRNA-dependent protein Kinase (PKR): mechanism of Action," Apoptosis, vol. 5, pp. 107-114 (2000).

Hutvagner et al., 'A Cellular Function for the RNA-Interference Enzyme Dicer i the maturation of the let-7 Small Temporal RNA, Science, vol. 293, pp. 834-838 (Aug. 2001).

McManus et al., "Gene Silencing in mammals by small interfering RNA's," Nature Reviews, vol. 3, pp. 737-747 (Oct. 2002).

Pei et al., "On the art of identifying effective and specific siRNAs," Nature Methods, vol. 3, No. 9, pp. 670-676 (Sep. 2006).

Sen et al., "A brief history of RNAi: the silence of the genes," FASEB J., vol. 20, pp. 1293-1299 (2006).

Snove Jr et al., "Expressing short Hairpin RNAs in vivo," Nature Methods, vol. 3 No. 9, pp. 689-695 (Sep. 2006).

Svoboda et al., "RNAI in mouse Oocytes and Preimplantation Embryos: effectiveness of Hairpin dsRNA," Biochem. Biophys. Res. Commum. vol. 287, pp. 1099-1104 (2001).

Vermeulen et al., "the contributions of DsRNA structure to Dicer specificity and efficiency," RNA, vol. 11, pp. 674-682 (2005).

Brummelkamp et al., "A system for stable expression of short interfering RNAs in mammalian cells," Science, vol. 296, pp. 550-553 (Apr. 2002).

European Search Result mailed on Feb. 17, 2010, for European Application No. EP 03732052 filed Jan. 22, 2003.

European Search Result mailed on Sep. 22, 2009 for European Application No. EP 03732052 filed Jan. 22, 2003.

Miller et al., "Improved retroviral vectors for gene transfer and expression," Biotechniques, vol. 7(9), pp. 980-990 (1989).

Non final office action mailed on Feb. 9, 2005 for U.S. Appl. No. 10/055,797, filed Jan. 22, 2002.

Non final office action mailed on Nov. 8, 2005 for U.S. Appl. No. 10/055,797, filed Jan. 22, 2002.

Non final office action mailed on Jun. 23, 2010, for U.S. Appl. No. 12/152,837, filed Jan. 22, 2002.

Final office action mailed on Apr. 17, 2007, for U.S. Appl. No. 10/055,797, filed Jan. 22, 2002.

Non final office action mailed on Jul. 26, 2006, for U.S. Appl. No. 10/055,797, filed Jan. 22, 2002.

Final Office Action mailed on May 12, 2009, for U.S. Appl. No. 10/997,086, filed Nov. 23, 2004.

Final Office Action mailed on Jul. 2, 2010, for U.S. Appl. No. 10/997,086, filed Nov. 23, 2004.

Non Final Office Action mailed on Aug. 26, 2009, for U.S. Appl. No. 10/997,086, filed Nov. 23, 2004.

Non Final Office Action mailed on Feb. 12, 2007, for U.S. Appl. No. 10/997,086, filed Nov. 23, 2004.

Brummelkamp et al., "Stable suppression of tumorigenicity by virus-mediated RNA interference," Cancer cell, vol. 2, pp. 243-247 (2002).

Final Office Action mailed on Mar. 18, 2011 for U.S. Appl. No. 12/152,837, filed May 16, 2008.

McManus et al., "Gene silencing using micro-RNA designed hairpins," RNA, vol. 8, pp. 842-850 (2002).

Sorensen et al., "Gene Silencing by systemic delivery of Synthetic siRNAs in adult Mice," J. Mol. Biol., vol. 327, pp. 761-766 (2003).

U.S. Appl. No. 60/305,185 filed Jul. 12, 2001.

* cited by examiner

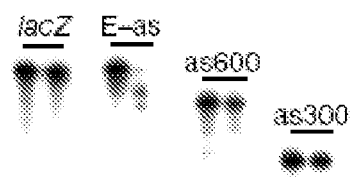
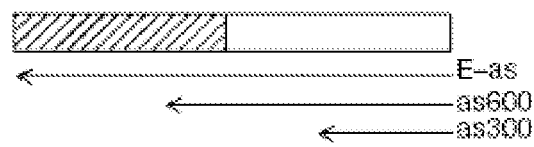
Fig. 2C

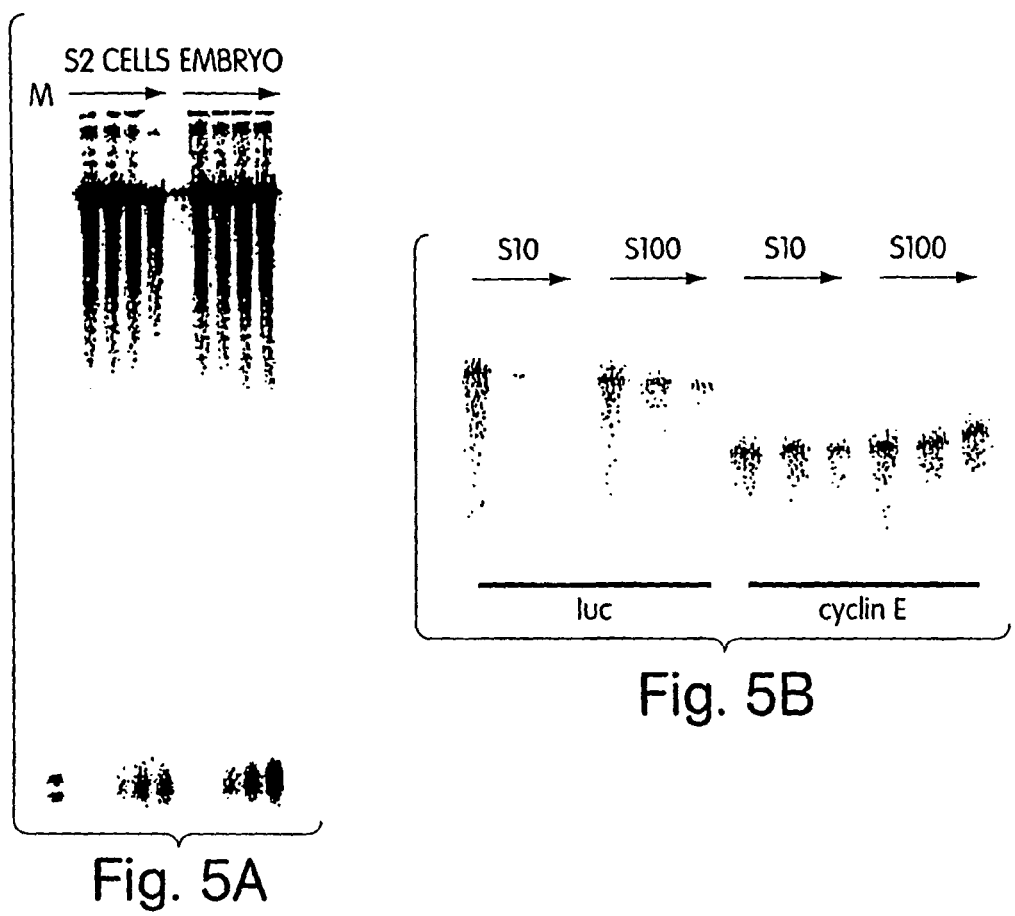
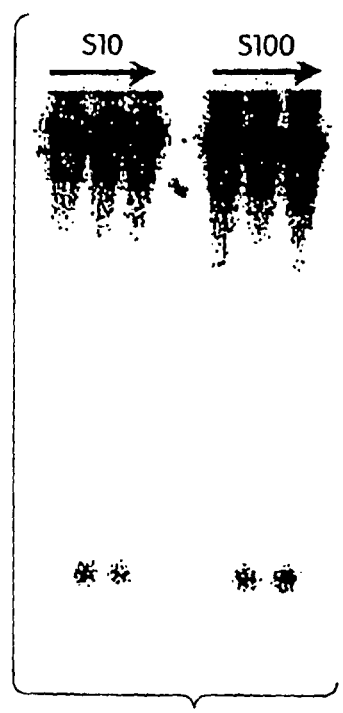
Fig. 5A
Fig. 5B
Fig. 5C

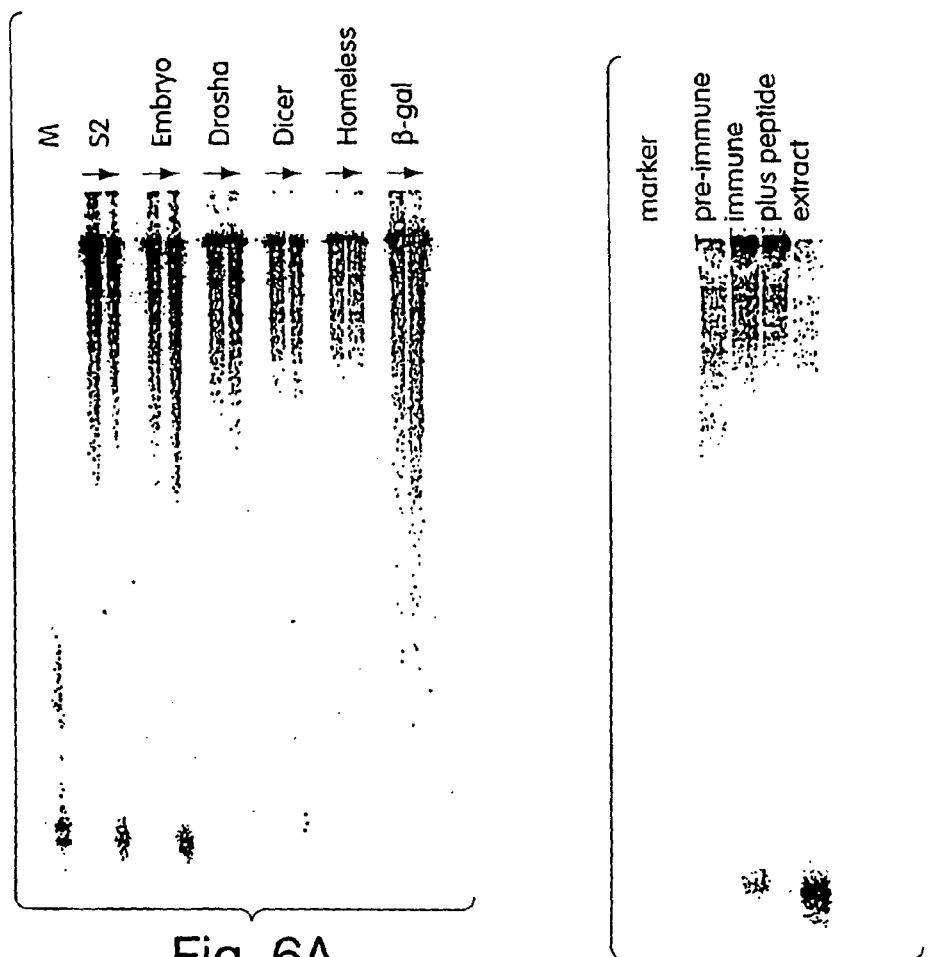
Fig. 6A
Fig. 6C
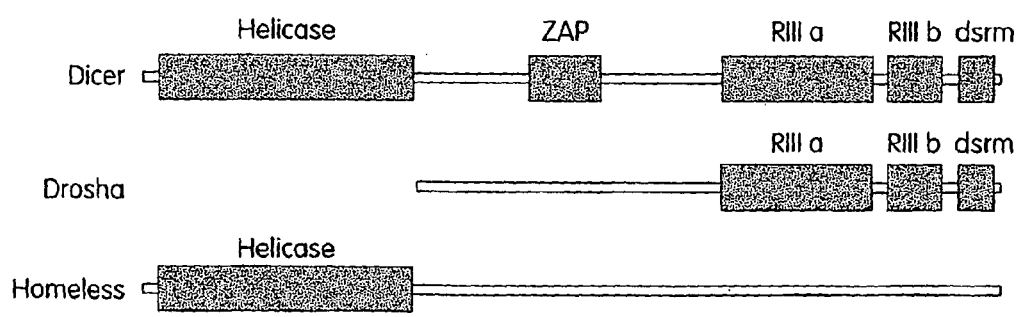
Fig. 6B

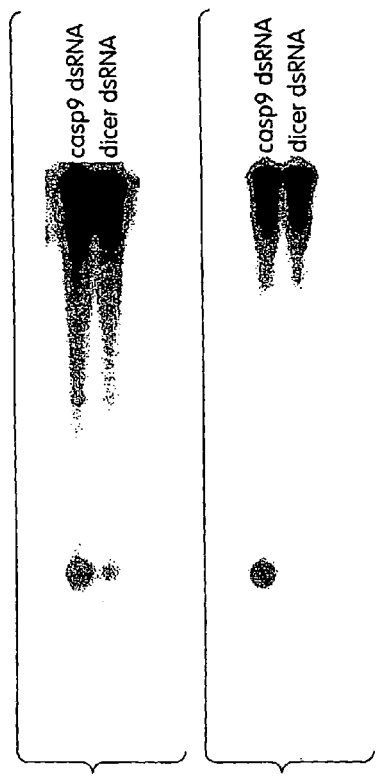
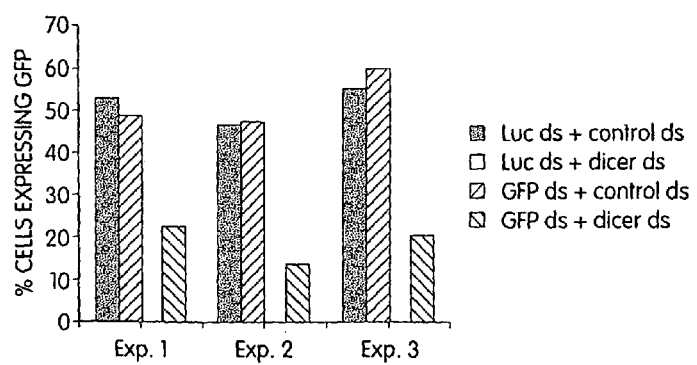
Fig. 7A  Fig. 7B
Fig. 7C

Purification of the 22-mer generating enzyme

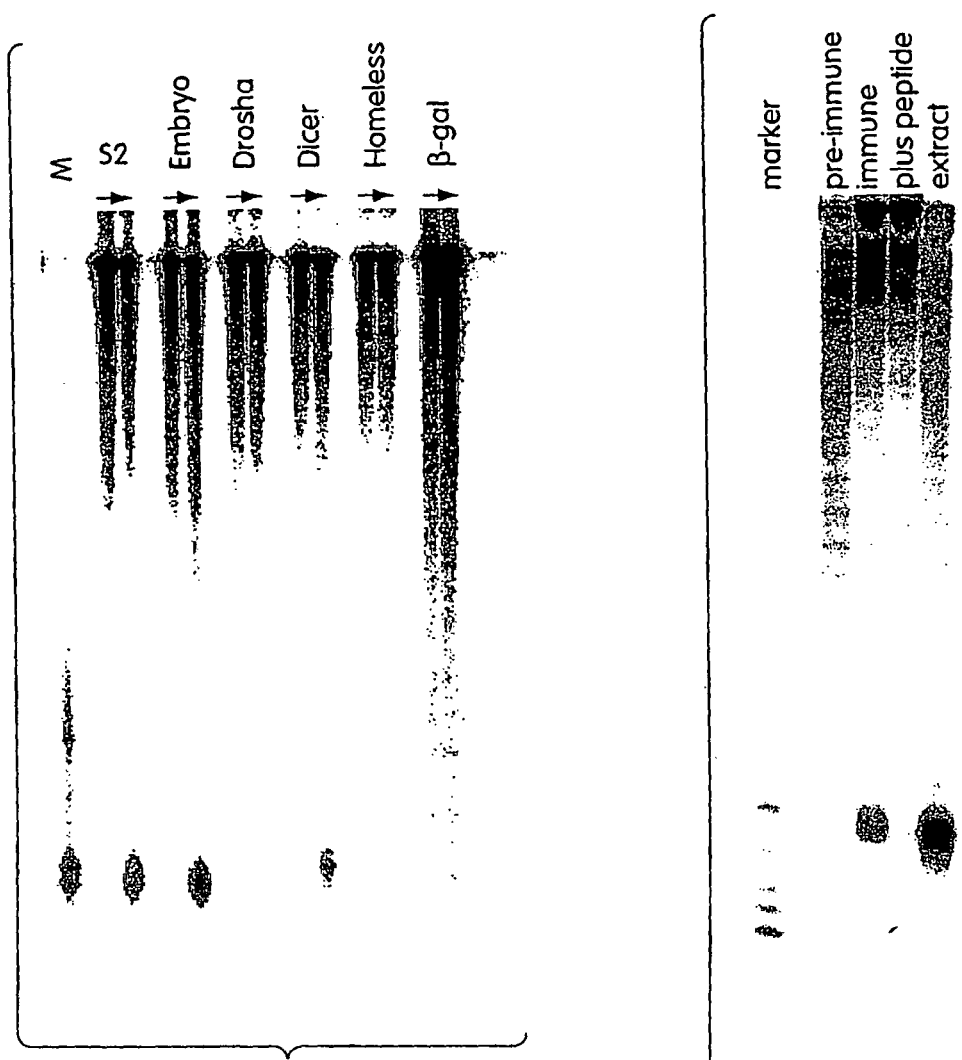
Fig. 20A
Fig. 20C
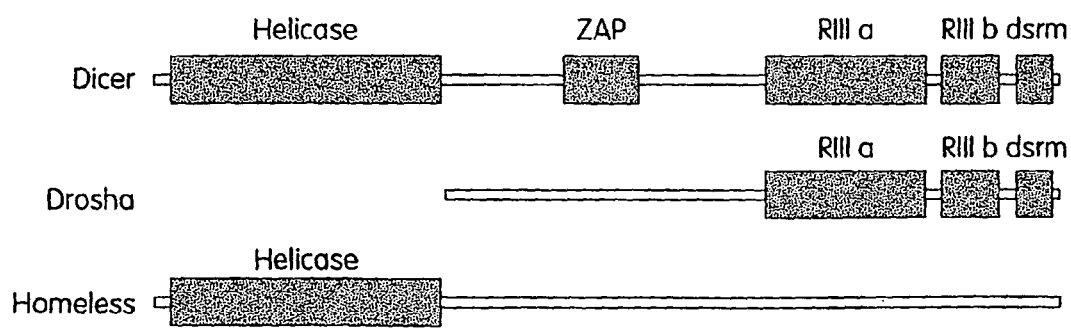
Fig. 20B

MGKKDKNKKGGQDSAAAPQPQQQQKQQQQRQQQPQQLQQPQQLQQPQQLQQPQQQQQ
QPHQQQQQSSRQQPSTSSGGSRASGFQQGGQQQKSQDAEGWTAQKKQGKQQVQGWTKQ
GQQGGHQQGRQGQDGGYQQRPPGQQQGGHQQGRQGQEGGYQQRPPGQQQGGHQQGRQG
QEGGYQQRPSGQQQGGHQQGRQGQEGGYQQRPPGQQQGGHQQGRQGQEGGYQQRPSGQ
QQGGHQQGRQGQEGGYQQRPSGQQQGGHQQGRQGQEGGYQQRPSGQQQGGHQQGRQGQ
EGGYQQRPPGQQPNQTQSQGQYQSRGPPQQQQAAPLPLPPQPAGSIKRGTIGKPGQVG
INYLDLDLSKMPSVAYHYDVKIMPERPKKFYRQAFEQFRVDQLGGAVLAYDGKASCYS
VDKLPLNSQNPEVTVTDRNGRTLRYTIEIK<u>ETGDSTIDLKS</u>LTTYMNDRI<u>FDKPMRAM</u>
QCVEVVLASPCHNKAIRVGR<u>SFFKM</u>SDPNNRHELDDGYEALVGLYQAFMLGDRPFLNV
DISHKSFPISMPMIEYLERFSLKAK<u>INNTTNLDY</u>SRRFLEPFLRGINVVYTPPQSFQS
APRVYRVNGLSR<u>APASSETFEH</u>DGKKVTIASYFHSRNYPLKFPQLHCLNVGSSIKSIL
LPIELCSIEEGQALNRKDGATQVANMIKYAATSTNVRKRKIMNLLQYFQHNLDPTISR
FGIRIANDFIVVSTRVLSPPQVEYHSKRFTMVKNGSWRMDGMK<u>FLEPKPK</u>AHKCAVLY
CDPRSGRKMNYTQLNDFGNLIISQGKAVNISLDSDVTYRPFTDDERSLDTIFADLKRS
QHDLAIVIIPQFRISYDTIKQKAELQHGILTQCIKQFTVERKCNNQTIGNILLKINSK
LNGINHKIKDDPRLPMMKNTMYIGADVTHPSPDQREIPSVVGVAASHDPYGASYNMQY
RLQRGALEEIEDMFSITLEHLRVYKEYRNAYPDHIIYYRDGVSDGQFPKIKNEELRCI
KQACDKVGCKPKICCVIVVKRHHTRFFPSGDVTTSNKFNNVDPGTVVDRTIVHPNEMQ
FFMVSHQAIQGTAKPTRYNVIENTGNLDIDLLQQLTYNLCHMFPRCNRSVSYPAPAYL
AHLVAARGR<u>VYLTGTNR</u>FLDLKKEYAKRTIVPEFMKKNPMYFV

Fig. 24

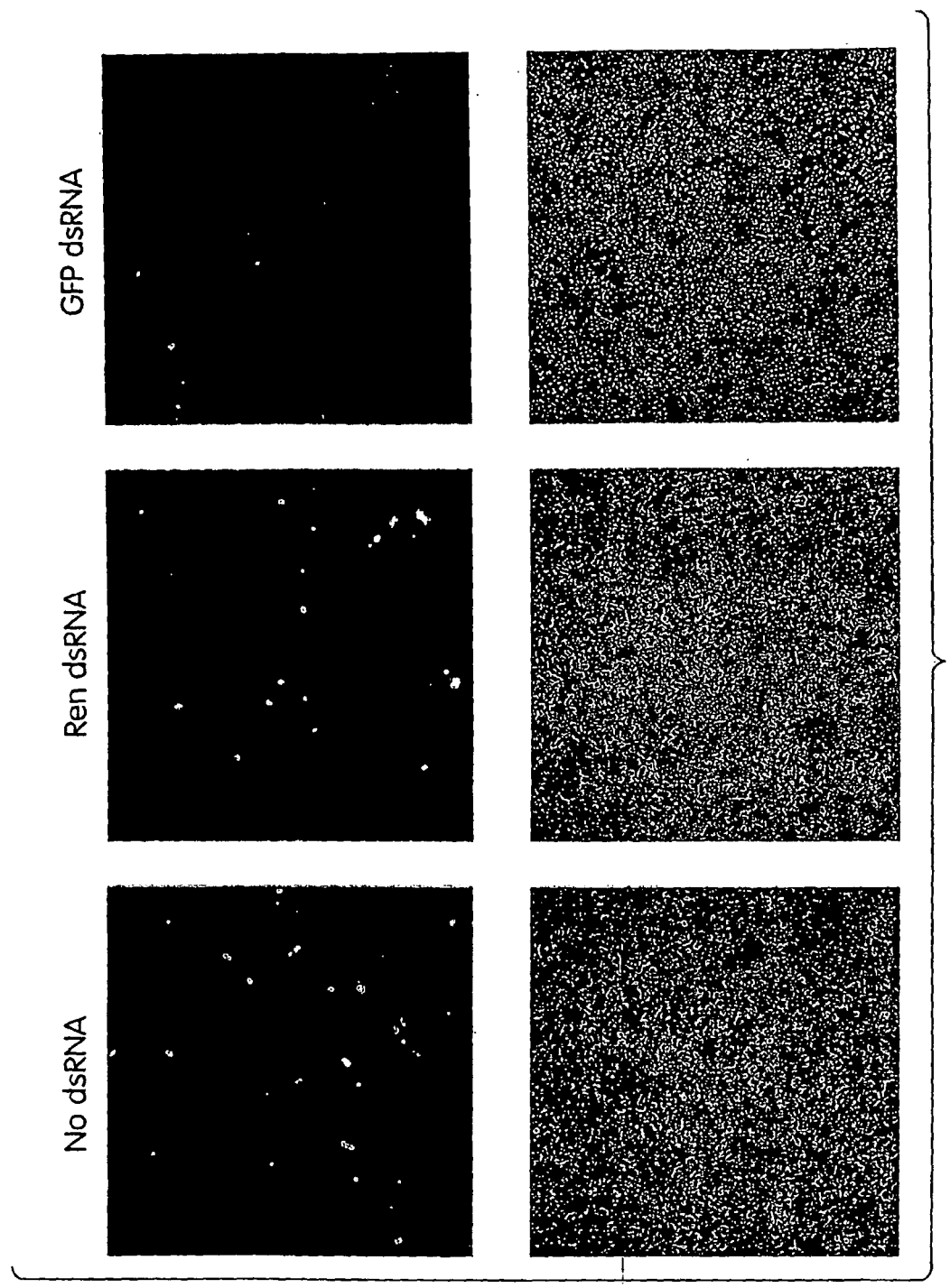

P19 GFP HAIRPIN CLONE NUMBER #10
48 HRS POST-TRANSFECTION
FLUORESCENT MICROSCOPY SUPERIMPOSED WITH BRIGHT FIELD siRNA
    UCGAAGUACUCAGCGUAAGUG
AAAGCUUCAUGAGUCGCAUUC
cshFf
                                    U
CAUCGACUGAAAUCCCUGGUAAUCCGUUG U
GUAGCUGACUUUAGGGACCAUUAGGCAAC A
                                    A
cshFf-L7
                                    ---------- U
CAUCGACUGAAAUCCCUGGUAAUCCGUUU        GGGGC \
GUAGCUGAUUUUAGGGACUAUUAGGUAAA        UCCCG C
                        UAGGGUAUCG        U
cshFf-L7m
            GCC                     ---------- U
CAUCGACUGAAAUCCC    GUAAUCCGUUU        GGGGC \
GUAGCUGAUUUUAGGG    UAUUAGGUAAA        UCCCG C
            AC-           UAGGGUAUCG        U
Fig. 39A
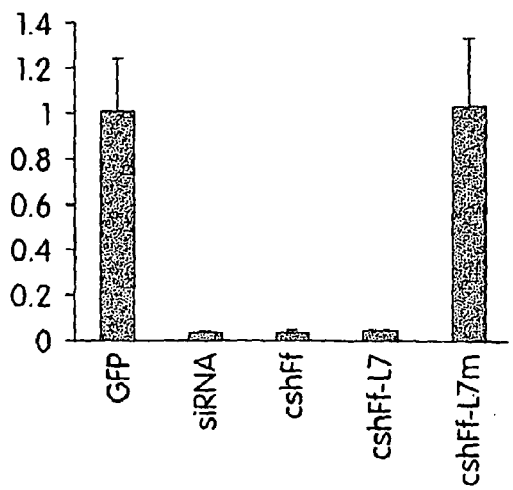
Fig. 39B
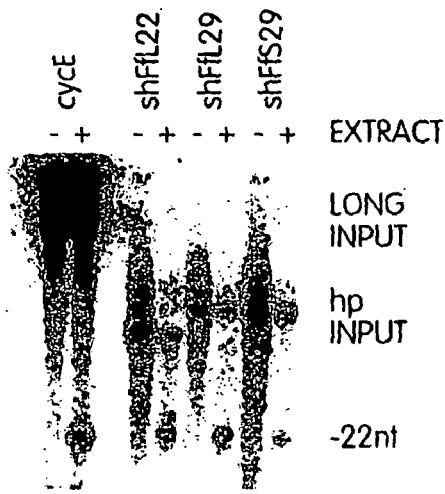
Fig. 39C siRNA
```
  UCGAAGUACUCAGCGUAAGUG
AAAGCUUCAUGAGUCGCAUUC
```
T7siRNA
```
GGUCGAAGUACUCAGCGUAAGAA
AAAGCUUCATGAGUCGCAUUCGG
```
T7siFf-2
```
  GGUUGUGGAUCUGGAUACCGG
UUCCAACACCUAGACCUAUGG
```
T7siFf-3
```
  GGUGCCAACCCUAUUCUCCUU
GACCACGGUUGGGAUAAGAGG
```
T7siFf-8
```
  GGCUAUGAAGAGAGUACGCCCU
UUCCGAUACUUCUCUCAUGCGG
```

Fig. 41A

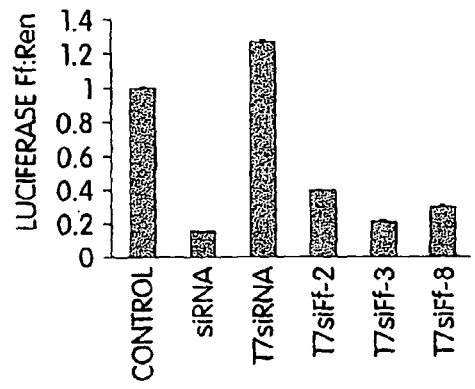

Fig. 41B

T7shFf29
```
GGU|                              U
   CGAAGUACUCAGCGUAAGUGAUGUCCAC U
   GUUUUGUGGGUUGUGUUUGUUGUGGGUG A
  G^                              A
```
T7shFf27
```
GGU|                            U
   CGAAGUACUCAGCGUAAGUGAUGUCC U
   GUUUUGUGGGUUGUGUUUGUUGUGGG A
  G^                            A
```
T7shFf25
```
GGU|                          U
   CGAAGUACUCAGCGUAAGUGAUGU U
   GUUUUGUGGGUUGUGUUUGUUGUG A
  G^                          A
```
T7shFf22
```
GGU|                       U
   CGAAGUACUCAGCGUAAGUGA U
   GUUUUGUGGGUUGUGUUUGUU A
  G^                       A
```
T7shFf29-5'T
```
GGCUCGAGU|                              U
         CGAAGUACUCAGCGUAAGUGAUGUCCAC U
         GUUUUGUGGGUUGUGUUUGUUGUGGGUG A
 G--------^                              A
```
T7shFf29-3'T
```
-----G|                                U
      GUCGAAGUACUCAGCGUAAGUGAUGUCCAC U
      CGGUUUUGUGGGUUGUGUUUGUUGUGGGUG A
  GAGCU^                                A
```

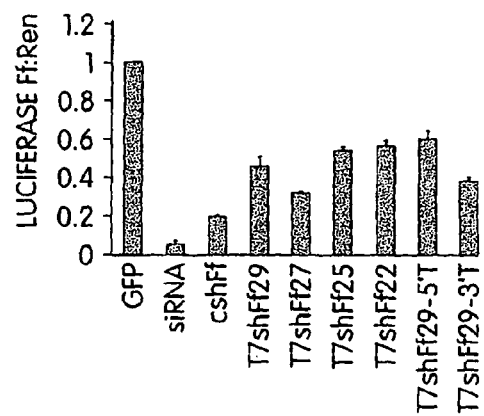

"SENSE" STRAND
```
                                    GAA
GGUCUAAGUGGAGCCCUUCGAGUGUUA    G
CCGGGUUCACUUCGGGAGGCUCACAGU    C
UU                                  GUU
```
"ANTI-SENSE" STRAND
Fig. 44A
RasV12 MEF
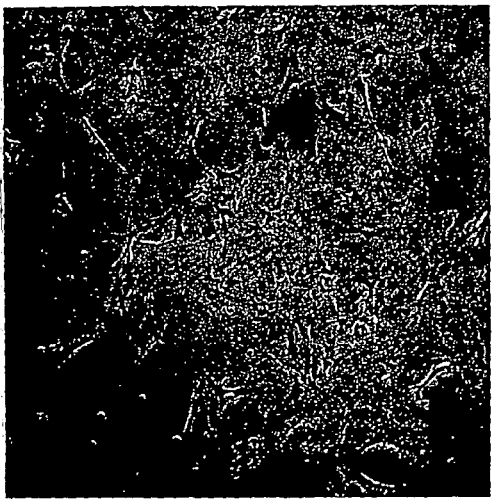
pShh      pShh-p53
Fig. 44B

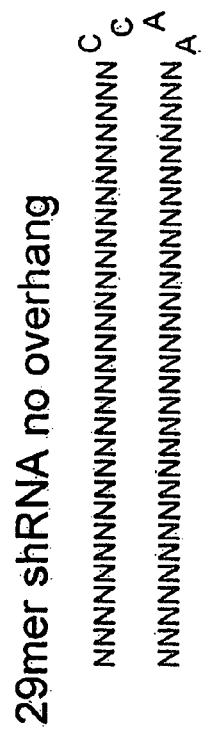
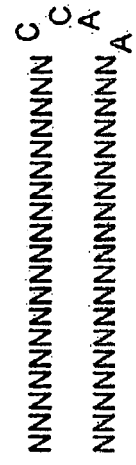
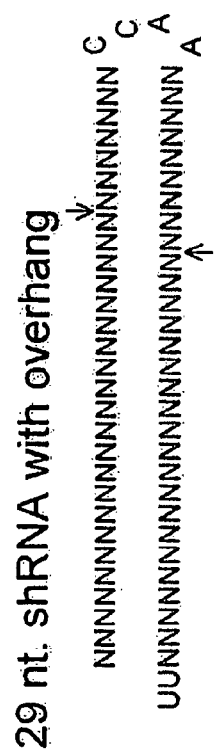
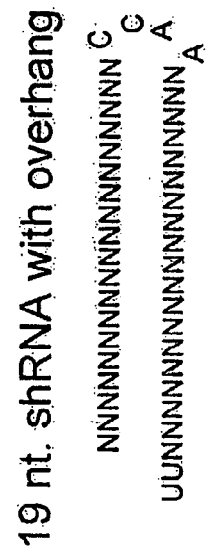
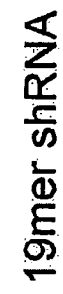
Fig. 57 A

Fig. 59 A siRNAs

```
         19mer
   ┌──────────────┐
   NNNNNNNNNNNNNNNNNNNdTdT
dTdTNNNNNNNNNNNNNNNNNNN
```

Synthetic 19mer shRNAs

```
      19mer of siRNA
   ┌──────────────┐          U  U
   NNNNNNNNNNNNNNNNNNN
   UUNNNNNNNNNNNNNNNNNNN  G
                              G
```

Synthetic 29mer shRNAs

```
        19mer of siRNA
    ┌──────────────┐                U  U
   XNNNNNNNNNNNNNNNNNNNXXXXXXXXXX
   UUXNNNNNNNNNNNNNNNNNNNXXXXXXXXXX  G
                                       G
```

Fig. 59 B
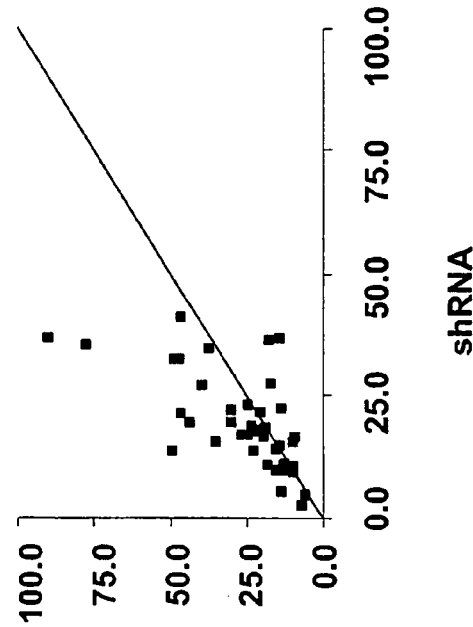
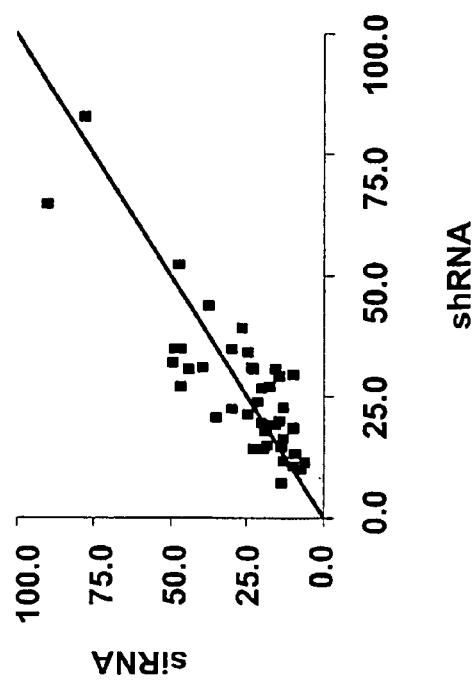

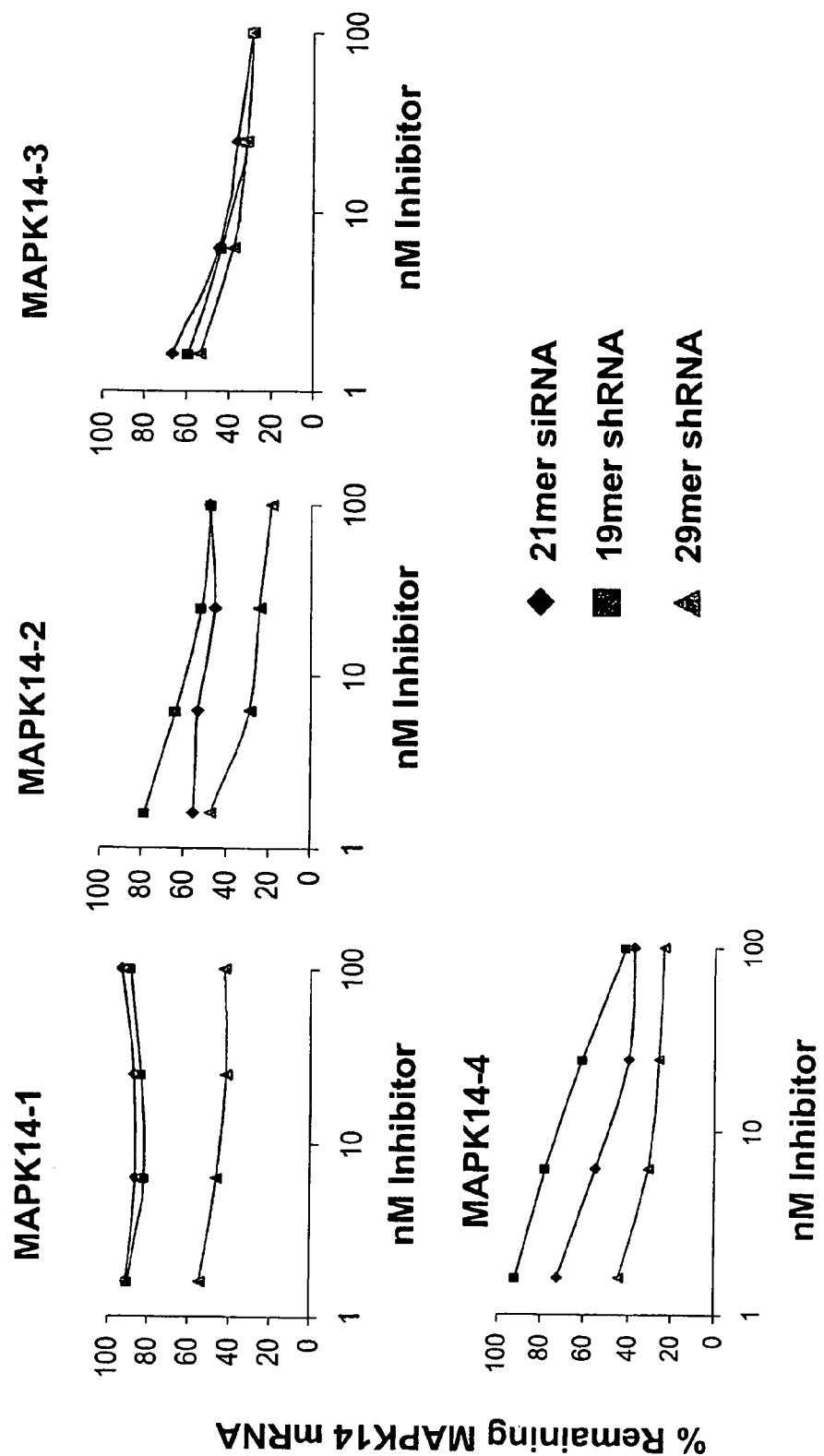

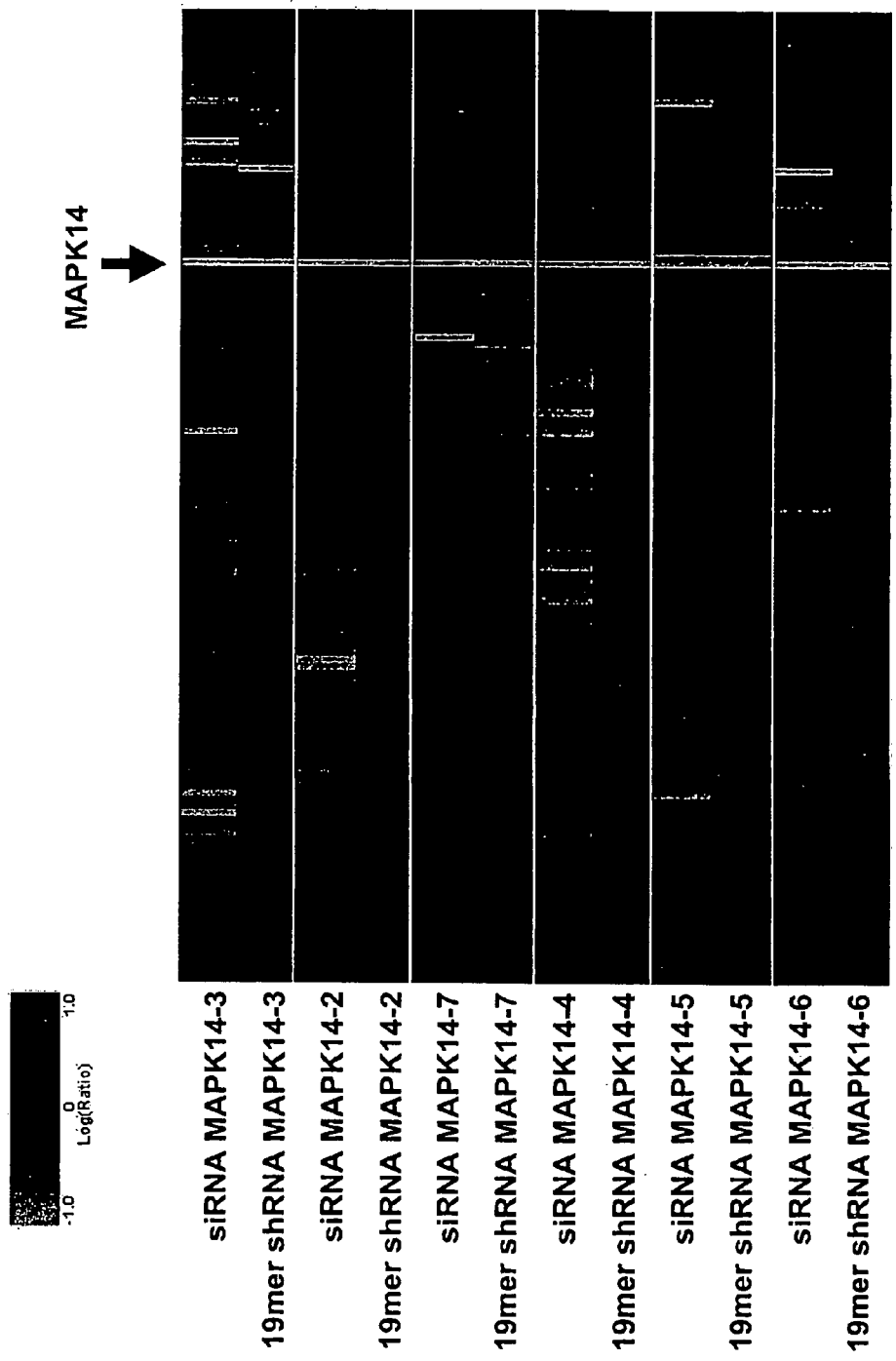

METHODS AND COMPOSITIONS FOR RNA INTERFERENCE

RELATED APPLICATIONS:

This application is a continuation application of U.S. Ser. No. 10/997,086, filed on Nov. 23, 2004, which is a continuation-in-part of U.S. Ser. No. 10/055,797, filed on Jan. 22, 2002, which is incorporated by reference herein.

GOVERNMENT SUPPORT

Work described herein was supported by National Institutes of Health Grant R01-GM62534. The United States Government may have certain rights in the invention.

BACKGROUND OF THE INVENTION

"RNA interference", "post-transcriptional gene silencing", "quelling"—these different names describe similar effects that result from the overexpression or misexpression of transgenes, or from the deliberate introduction of double-stranded RNA into cells (reviewed in Fire, *Trends Genet.* 15: 358-363, 1999; Sharp, *Genes Dev* 13: 139-141, 1999; Hunter, *Curr Biol* 9: R440-R442, 1999; Baulcombe, *Curr Biol* 9: R599-R601, 1999; Vaucheret et al., *Plant J* 16: 651-659, 1998). The injection of double-stranded RNA into the nematode *Caenorhabditis elegans*, for example, acts systemically to cause the post-transcriptional depletion of the homologous endogenous RNA (Fire et al., *Nature* 391: 806-811, 1998; and Montgomery et al., *PNAS* 95: 15502-15507, 1998). RNA interference, commonly referred to as RNAi, offers a way of specifically and potently inactivating a cloned gene, and is proving a powerful tool for investigating gene function. Although the phenomenon is interesting in its own right; the mechanism has been rather mysterious, but recent research—for example that recently reported by Smardon et al., *Curr Biol* 10: 169-178, 2000—is beginning to shed light on the nature and evolution of the biological processes that underlie RNAi.

RNAi was discovered when researchers attempting to use the antisense RNA approach to inactivate a *C. elegans* gene found that injection of sense-strand RNA was actually as effective as the antisense RNA at inhibiting gene function (Guo et al., *Cell* 81: 611-620, 1995). Further investigation revealed that the active agent was modest amounts of double-stranded RNA that contaminate in vitro RNA preparations. Researchers quickly determined the 'rules' and effects of RNAi which have become the paradigm for thinking about the mechanism which mediates this affect. Exon sequences are required, whereas introns and promoter sequences, while ineffective, do not appear to compromise RNAi (though there may be gene-specific exceptions to this rule). RNAi acts systemically—injection into one tissue inhibits gene function in cells throughout the animal. The results of a variety of experiments, in *C. elegans* and other organisms, indicate that RNAi acts to destabilize cellular RNA after RNA processing.

The potency of RNAi inspired Timmons and Fire (*Nature* 395: 854, 1998) to do a simple experiment that produced an astonishing result. They fed to nematodes bacteria that had been engineered to express double-stranded RNA corresponding to the *C. elegans* unc-22 gene. Amazingly, these nematodes developed a phenotype similar to that of unc-22 mutants that was dependent on their food source. The ability to conditionally expose large numbers of nematodes to gene-specific double-stranded RNA formed the basis for a very powerful screen to select for RNAi-defective *C. elegans* mutants and then to identify the corresponding genes.

Double-stranded RNAs (dsRNAs) can provoke gene silencing in numerous in vitro contexts including *Drosophila, Caenorhabditis elegans*, planaria, hydra, trypanosomes, fungi and plants. However, the ability to recapitulate this phenomenon in higher eukaryotes, particularly mammalian cells, has not been accomplished in the art. Nor has the prior art demonstrated that this phenomena can be observed in cultured eukaryotic cells. Additionally, the 'rules' established by the prior art have taught that RNAi requires exon sequences, and thus constructs consisting of intronic or promoter sequences were not believed to be effective reagents in mediating RNAi. The present invention aims to address each of these deficiencies in the prior art and provides evidence both that RNAi can be observed in cultured eukaryotic cells and that RNAi constructs consisting of non-exon sequences can effectively repress gene expression.

SUMMARY OF THE INVENTION

One aspect of the present invention provides a method for attenuating expression of a target gene in cultured cells, comprising introducing double stranded RNA (dsRNA) into the cells in an amount sufficient to attenuate expression of the target gene, wherein the dsRNA comprises a nucleotide sequence that hybridizes under stringent conditions to a nucleotide sequence of the target gene.

Another aspect of the present invention provides a method for attenuating expression of a target gene in a mammalian cell, comprising: (i) activating one or both of a Dicer activity or an Argonaut activity in the cell, and (ii) introducing into the cell a double stranded RNA (dsRNA) in an amount sufficient to attenuate expression of the target gene, wherein the dsRNA comprises a nucleotide sequence that hybridizes under stringent conditions to a nucleotide sequence of the target gene.

In certain embodiments, the cell is suspended in culture; while in other embodiments the cell is in a whole animal, such as a non-human mammal.

In certain preferred embodiments, the cell is engineered with (i) a recombinant gene encoding a Dicer activity, (ii) a recombinant gene encoding an Argonaut activity, or (iii) both. For instance, the recombinant gene may encode, for a example, a protein which includes an amino acid sequence at least 50 percent identical to SEQ ID NO: 2 or 4; or be defined by a coding sequence which hybridizes under wash conditions of 2×SSC at 22° C. to SEQ ID NO: 1 or 3. In certain embodiments, the recombinant gene may encode, for a example, a protein which includes an amino acid sequence at least 50 percent identical to the Argonaut sequence shown in FIG. 24. In certain embodiments, the recombinant gene may encode a protein which includes an amino acid sequence at least 60%, 70%, 80%, 85%, 90%, or 95% identical to SEQ ID NO: 2 or 4. In certain embodiments, the recombinant gene may be defined by a coding sequence which hybridizes under stringent conditions, including a wash step selected from 0.2-2.0×SSC at from 50° C.-65° C., to SEQ ID NO: 1 or 3.

In certain embodiments, rather than use a heterologous expression construct(s), an endogenous Dicer gene or Argonaut gene can be activated, e.g. by gene activation technology, expression of activated transcription factors or other signal transduction protein(s), which induces expression of the gene, or by treatment with an endogenous factor which upregulates the level of expression of the protein or inhibits the degradation of the protein.

In certain preferred embodiments, the target gene is an endogenous gene of the cell. In other embodiments, the target gene is a heterologous gene relative to the genome of the cell, such as a pathogen gene, e.g., a viral gene.

In certain embodiments, the cell is treated with an agent that inhibits protein kinase RNA-activated (PKR) apoptosis, such as by treatment with agents which inhibit expression of PKR, cause its destruction, and/or inhibit the kinase activity of PKR.

In certain preferred embodiments, the cell is a primate cell, such as a human cell.

In certain preferred embodiments, the length of the dsRNA is at least 20, 21 or 22 nucleotides in length, e.g., corresponding in size to RNA products produced by Dicer-dependent cleavage. In certain embodiments, the dsRNA construct is at least 25, 50, 100, 200, 300 or 400 bases. In certain embodiments, the dsRNA construct is 400-800 bases in length.

In certain preferred embodiments, expression of the target gene is attenuated by at least 5 fold, and more preferably at least 10, 20 or even 50 fold, e.g., relative to the untreated cell or a cell treated with a dsRNA construct which does not correspond to the target gene.

Yet another aspect of the present invention provides a method for attenuating expression of a target gene in cultured cells, comprising introducing an expression vector having a "coding sequence" which, when transcribed, produces double stranded RNA (dsRNA) in the cell in an amount sufficient to attenuate expression of the target gene, wherein the dsRNA comprises a nucleotide sequence that hybridizes under stringent conditions to a nucleotide sequence of the target gene. In certain embodiments, the vector includes a single coding sequence for the dsRNA which is operably linked to (two) transcriptional regulatory sequences which cause transcription in both directions to form complementary transcripts of the coding sequence. In other embodiments, the vector includes two coding sequences which, respectively, give rise to the two complementary sequences which form the dsRNA when annealed. In still other embodiments, the vector includes a coding sequence which forms a hairpin. In certain embodiments, the vectors are episomal, e.g., and transfection is transient. In other embodiments, the vectors are chromosomally integrated, e.g., to produce a stably transfected cell line. Preferred vectors for forming such stable cell lines are described in U.S. Pat. No. 6,025,192 and PCT publication WO 98/12339, which are incorporated by reference herein.

Another aspect of the present invention provides a method for attenuating expression of a target gene in cultured cells, comprising introducing an expression vector having a "non-coding sequence" which, when transcribed, produces double stranded RNA (dsRNA) in the cell in an amount sufficient to attenuate expression of the target gene. The non-coding sequence may include intronic or promoter sequence of the target gene of interest, and the dsRNA comprises a nucleotide sequence that hybridizes under stringent conditions to a nucleotide sequence of the promoter or intron of the target gene. In certain embodiments, the vector includes a single sequence for the dsRNA which is operably linked to (two) transcriptional regulatory sequences which cause transcription in both directions to form complementary transcripts of the sequence. In other embodiments, the vector includes two sequences which, respectively, give rise to the two complementary sequences which form the dsRNA when annealed. In still other embodiments, the vector includes a coding sequence which forms a hairpin. In certain embodiments, the vectors are episomal, e.g., and transfection is transient. In other embodiments, the vectors are chromosomally integrated, e.g., to produce a stably transfected cell line. Preferred vectors for forming such stable cell lines are described in U.S. Pat. No. 6,025,192 and PCT publication WO 98/12339, which are incorporated by reference herein.

Another aspect the present invention provides a double stranded (ds) RNA for inhibiting expression of a mammalian gene. The dsRNA comprises a first nucleotide sequence that hybridizes under stringent conditions, including a wash step of 0.2×SSC at 65° C., to a nucleotide sequence of at least one mammalian gene and a second nucleotide sequence which is complementary to the first nucleotide sequence.

In one embodiment, the first nucleotide sequence of said double-stranded RNA is at least 20, 21, 22, 25, 50, 100, 200, 300, 400, 500, 800 nucleotides in length.

In another embodiment, the first nucleotide sequence of said double-stranded RNA is identical to at least one mammalian gene. In another embodiment, the first nucleotide sequence of said double-stranded RNA is identical to one mammalian gene. In yet another embodiment, the first nucleotide sequence of said double-stranded RNA hybridizes under stringent conditions to at least one human gene. In still another embodiment, the first nucleotide sequence of said double-stranded RNA is identical to at least one human gene. In still another embodiment, the first nucleotide sequence of said double-stranded RNA is identical to one human gene.

The double-stranded RNA may be an siRNA or a hairpin, and may be expressed transiently or stably. In one embodiment, the double-stranded RNA is a hairpin comprising a first nucleotide sequence that hybridizes under stringent conditions to a nucleotide sequence of at least one mammalian gene, and a second nucleotide sequence which is a complementary inverted repeat of said first nucleotide sequence and hybridizes to said first nucleotide sequence to form a hairpin structure.

The first nucleotide sequence of said double-stranded RNA can hybridize to either coding or non-coding sequence of at least one mammalian gene. In one embodiment, the first nucleotide sequence of said double-stranded RNA hybridizes to a coding sequence of at least one mammalian gene. In another embodiment, the first nucleotide sequence of said double-stranded RNA hybridizes to a coding sequence of at least one human gene. In another embodiment, the first nucleotide sequence of said double-stranded RNA is identical to a coding sequence of at least one mammalian gene. In still another embodiment, the first nucleotide sequence of said double-stranded RNA is identical to a coding sequence of at least one human gene.

In another embodiment, the first nucleotide sequence of said double-stranded RNA is hybridizes to a non-coding sequence of at least one mammalian gene. In another embodiment, the first nucleotide sequence of said double-stranded RNA hybridizes to a non-coding sequence of at least one human gene. In another embodiment, the first nucleotide sequence of said double-stranded RNA is identical to a non-coding sequence of at least one mammalian gene. In still another embodiment, the first nucleotide sequence of said double-stranded RNA is identical to a non-coding sequence of at least one human gene. In any of the foregoing embodiments, the non-coding sequence may be a non-transcribed sequence.

Still another aspect of the present invention provides an assay for identifying nucleic acid sequences, either coding or non-coding sequences, responsible for conferring a particular phenotype in a cell, comprising: (i) constructing a variegated library of nucleic acid sequences from a cell in an orientation relative to a promoter to produce double stranded DNA; (ii) introducing the variegated dsRNA library into a culture of target cells; (iii) identifying members of the library which confer a particular phenotype on the cell, and identifying the sequence from a cell which correspond, such as being identical or homologous, to the library member.

Yet another aspect of the present invention provides a method of conducting a drug discovery business comprising: (i) identifying, by the subject assay, a target gene which provides a phenotypically desirable response when inhibited by RNAi; (ii) identifying agents by their ability to inhibit expression of the target gene or the activity of an expression product of the target gene; (iii) conducting therapeutic profiling of agents identified in step (b), or further analogs thereof, for efficacy and toxicity in animals; and (iv) formulating a pharmaceutical preparation including one or more agents identified in step (iii) as having an acceptable therapeutic profile.

The method may include an additional step of establishing a distribution system for distributing the pharmaceutical preparation for sale, and may optionally include establishing a sales group for marketing the pharmaceutical preparation.

Another aspect of the present invention provides a method of conducting a target discovery business comprising: (i) identifying, by the subject assay, a target gene which provides a phenotypically desirable response when inhibited by RNAi; (ii) (optionally) conducting therapeutic profiling of the target gene for efficacy and toxicity in animals; and (iii) licensing, to a third party, the rights for further drug development of inhibitors of the target gene.

Another aspect of the invention provides a method for inhibiting RNAi by inhibiting the expression or activity of an RNAi enzyme. Thus, the subject method may include inhibiting the activity of Dicer and/or the 22-mer RNA.

Still another aspect relates to a method for altering the specificity of an RNAi by modifying the sequence of the RNA component of the RNAi enzyme.

In another aspect, gene expression in an undifferentiated stem cell, or the differentiated progeny thereof, is altered by introducing dsRNA of the present invention. In one embodiment, the stem cells are embryonic stem cells. Preferably, the embryonic stem cells are derived from mammals, more preferably from non-human primates, and most preferably from humans.

The embryonic stem cells may be isolated by methods known to one of skill in the art from the inner cell mass (ICM) of blastocyst stage embryos. In one embodiment the embryonic stem cells are obtained from previously established cell lines. In a second embodiment, the embryonic stem cells are derived de novo by standard methods.

In another aspect, the embryonic stem cells are the result of nuclear transfer. The donor nuclei are obtained from any adult, fetal, or embryonic tissue by methods well known in the art. In one embodiment, the donor nuclei is transferred to a recipient oocyte which had previously been modified. In one embodiment, the oocyte is modified using one or more dsRNAs. Exemplary modifications of the recipient oocyte include any changes in gene or protein expression that prevent an embryo derived from said modified oocyte from successfully implanting in the uterine wall. Since implantation in the uterine wall is essential for fertilized mammalian embryos to progress from beyond the blastocyst stage, embryos made from such modified oocytes could not give rise to viable organisms. Non-limiting examples of such modifications include those that decrease or eliminate expression of cell surface receptors (i.e., integrins) required for the recognition between the blastocyst and the uterine wall, modifications that decrease or eliminate expression of proteases (i.e., collagenase, stromelysin, and plasminogen activator) required to digest matrix in the uterine lining and thus allow proper implantation, and modifications that decrease or eliminate expression of proteases (i.e., trypsin) necessary for the blastocyst to hatch from the zona pellucida. Such hatching is required for implantation.

In another embodiment, embryonic stem cells, embryonic stem cells obtained from fertilization of modified oocytes, or the differentiated progeny thereof, can be modified or further modified with one or more dsRNAs. In a preferred embodiment, the modification decreases or eliminates MHC expression. Cells modified in this way will be tolerated by the recipient, thus avoiding complications arising from graft rejection. Such modified cells are suitable for transplantation into a related or unrelated patient to treat a condition characterized by cell damage or cell loss.

In another aspect of the invention, the undifferentiated stem cell is an adult stem cell. Exemplary adult stem cells include, but are not limited to, hematopoietic stem cells, mesenchymal stem cells, cardiac stem cells, pancreatic stem cells, and neural stem cells. Exemplary adult stem cells include any stem cell capable of forming differentiated ectodermal, mesodermal, or endodermal derivatives. Non-limiting examples of differentiated cell types which arise from adult stem cells include: blood, skeletal muscle, myocardium, endocardium, pericardium, bone, cartilage, tendon, ligament, connective tissue, adipose tissue, liver, pancreas, skin, neural tissue, lung, small intestine, large intestine, gall bladder, rectum, anus, bladder, female or male reproductive tract, genitals, and the linings of the body cavity.

In one embodiment, an undifferentiated adult stem cell, or the differentiated progeny thereof, is altered with one or more dsRNAs to decrease or eliminate MHC expression. Cells modified in this way will be tolerated by the recipient, thus avoiding complications arising from graft rejection. Such modified cells are suitable for transplantation into a related or unrelated patient to treat a condition characterized by cell damage or cell loss.

In another aspect of the invention, an embryonic stem cell, an undifferentiated adult stem cell, or the differentiated progeny of either an embryonic or adult stem cell is altered with one or more dsRNA to decrease or eliminate expression of genes required for HIV infection. In a preferred embodiment, the stem cell is one capable of giving rise to hematopoietic cells. Modified cells with hematopoietic potential can be transplanted into a patient as a preventative therapy or treatment for HIV or AIDS.

Another aspect of the invention relates to purified or semi-purified preparations of the RNAi enzyme or components thereof. In certain embodiments, the preparations are used for identifying compounds, especially small organic molecules, which inhibit or potentiate the RNAi activity. Small molecule inhibitors, for example, can be used to inhibit dsRNA responses in cells which are purposefully being transfected with a virus which produces double stranded RNA.

The dsRNA construct may comprise one or more strands of polymerized ribonucleotide. It may include modifications to either the phosphate-sugar backbone or the nucleoside. The double-stranded structure may be formed by a single self-complementary RNA strand or two complementary RNA strands. RNA duplex formation may be initiated either inside or outside the cell. The dsRNA construct may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. In certain embodiments, dsRNA constructs containing a nucleotide sequences identical to a portion of the target gene are preferred for inhibition. RNA sequences with insertions, deletions, and single point mutations relative to the target sequence (i.e., RNA sequences similar to the target sequence) have also been found to be effective for inhibition. Thus, sequence identity may be optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript. In another embodiment, dsRNA constructs containing nucleotide sequences identical to a non-coding portion of the target gene are preferred for inhibition. Exemplary non-coding regions include introns and the promoter region. Sequences with insertions, deletions, and single point mutations relative to the target non-coding sequence may also be used.

Yet another aspect of the invention pertains to transgenic non-human mammals which include a transgene encoding a dsRNA construct, wherein the dsRNA is identical or similar to either the coding or non-coding sequence of the target gene, preferably which is stably integrated into the genome of cells in which it occurs. The animals can be derived by oocyte microinjection, for example, in which case all of the nucleated cells of the animal will include the transgene, or can be derived using embryonic stem (ES) cells which have been transfected with the transgene, in which case the animal is a chimera and only a portion of its nucleated cells will include the transgene. In certain instances, the sequence-independent dsRNA response, e.g., the PKR response, is also inhibited in those cells including the transgene.

In still other embodiments, dsRNA itself can be introduced into an ES cell in order to effect gene silencing, and that phenotype will be carried for at least several rounds of division, e.g., into the progeny of that cell.

Another aspect of the invention provides a method for attenuating expression of a target gene in mammalian cells, comprising introducing into the mammalian cells a single-stranded hairpin ribonucleic acid (shRNA) comprising self complementary sequences of 19 to 100 nucleotides that form a duplex region, which self complementary sequences hybridize under intracellular conditions to a target gene, wherein said hairpin RNA: (i) is a substrate for cleavage by a RNaseIII enzyme to produce a double-stranded RNA product, (ii) does not produce a general sequence-independent killing of the mammalian cells, and (iii) reduces expression of said target gene in a manner dependent on the sequence of said complementary regions. Preferably, the shRNA comprises a 3' overhang of about 14 nucleotides.

A related aspect of the invention provides a method for attenuating expression of a target gene in mammalian cells, comprising introducing into the mammalian cells a single-stranded hairpin ribonucleic acid (shRNA) comprising self complementary sequences of 19 to 100 nucleotides that form a duplex region, which self complementary sequences hybridize under intracellular conditions to a target gene, wherein said hairpin RNA: (i) is cleaved in the mammalian cells to produce an RNA guide sequence that enters an Argonaut-containing complex, (ii) does not produce a general sequence-independent killing of the mammalian cells, and (iii) reduces expression of said target gene in a manner dependent on the sequence of said complementary regions. Preferably, the shRNA comprises a 3' overhang of about 1-4 nucleotides.

Yet another related aspect of the invention provides a method for attenuating expression of one or more target genes in mammalian cells, comprising introducing into the mammalian cells a variegated library of single-stranded hairpin ribonucleic acid (shRNA) species, each shRNA species comprising self complementary sequences of 19 to 100 nucleotides that form duplex regions and which hybridize under intracellular conditions to a target gene, wherein each of said hairpin RNA species: (i) is a substrate for cleavage by a RNaseIII enzyme to produce a double-stranded RNA product, (ii) does not produce a general sequence-independent killing of the mammalian cells, and (iii) if complementary to a target sequence, reduces expression of said target gene in a manner dependent on the sequence of said complementary regions. Preferably, the shRNA comprises a 3' overhang of about 1-4 nucleotides.

In one embodiment, the shRNA comprises a 3' overhang of 2 nucleotides.

In one embodiment, the shRNA comprises self-complementary sequences of 25 to 29 nucleotides that form duplex regions.

In one embodiment, the self-complementary sequences are 29 nucleotides in length.

In one embodiment, the shRNA is transfected or microinjected into said mammalian cells.

In one embodiment, the shRNA is a transcriptional product that is transcribed from an expression construct introduced into said mammalian cells, which expression construct comprises a coding sequence for transcribing said shRNA, operably linked to one or more transcriptional regulatory sequences. The transcriptional regulatory sequences may include a promoter for an RNA polymerase, such as a cellular RNA polymerase.

In one embodiment, the promoter is a U6 promoter, a T7 promoter, a T3 promoter, or an SP6 promoter.

In one embodiment, the transcriptional regulatory sequences includes an inducible promoter.

In one embodiment, the mammalian cells are stably transfected with said expression construct.

In one embodiment, the mammalian cells are primate cells, such as human cells.

In one embodiment, the shRNA is introduced into the mammalian cells in cell culture or in an animal.

In one embodiment, the expression of the target is attenuated by at least 33 percent relative expression in cells not treated said hairpin RNA.

In one embodiment, the target gene is an endogenous gene or a heterologous gene relative to the genome of the mammalian cell.

In one embodiment, the self complementary sequences hybridize under intracellular conditions to a non-coding sequence of the target gene selected from a promoter sequence, an enhancer sequence, or an intronic sequence.

In one embodiment, the shRNA includes one or more modifications to phosphate-sugar backbone or nucleosides residues.

In one embodiment, the variegated library of shRNA species are arrayed a solid substrate.

In one embodiment, the method includes the further step of identifying shRNA species of said variegated library which produce a detected phenotype in said mammalian cells.

In one embodiment, the shRNA is a chemically synthesized product or an in vitro transcription product.

Another aspect of the invention provides a method of enhancing the potency/activity of an RNAi therapeutic for a mammalian patient, said RNAi therapeutic comprising an siRNA of 19-22 paired polynucleotides, the method comprising replacing said siRNA with a single-stranded hairpin RNA (shRNA) of claim 1 or 2, wherein said duplex region comprises the same 19-22 paired polynucleotides of said siRNA.

In one embodiment, the shRNA comprises a 3' overhang of 2 nucleotides.

In one embodiment, the half-maximum inhibition by said RNAi therapeutic is achieved by a concentration of said shRNA at least about 20% lower than that of said siRNA.

In one embodiment, the half-maximum inhibition by said RNAi therapeutic is achieved by a concentration of said shRNA at least about 100% lower than that of said siRNA.

In one embodiment, the end-point inhibition by said shRNA is at least about 40% higher than that of said siRNA.

In one embodiment, the end-point inhibition by said shRNA is at least about 2-6 fold higher than that of said siRNA.

Another aspect of the invention provides a method of designing a short hairpin RNA (shRNA) construct for RNAi, said shRNA comprising a 3' overhang of about 14 nucleotides, the method comprising selecting the nucleotide about 21 bases 5' to the most 3'-end nucleotide as the first paired nucleotide in a cognate doubled-stranded siRNA with the same 3' overhang.

In one embodiment, the shRNA comprises 25-29 paired polynucleotides.

In one embodiment, the shRNA, when cut by a Dicer enzyme, produces a product siRNA that is either identical to, or differ by a single basepair immediately 5' to the 3' overhang from, said cognate siRNA.

In one embodiment, the Dicer enzyme is a human Dicer.

In one embodiment, the 3' overhang has 2 nucleotides.

In one embodiment, the shRNA is for RNAi in mammalian cells.

All embodiments described above can be freely combined with one or more other embodiments whenever appropriate. Such combination also includes embodiments described under different aspects of the invention.

BRIEF DESCRIPTION OF THE DRAWINGS

FIG. 5: Generation of 22mers and degradation of mRNA are carried out by distinct enzymatic complexes. (a) Extracts prepared either from 0-12 hour *Drosophila* embryos or *Drosophila* S2 cells (see Methods) were incubated for 0, 15, 30, or 60 minutes (left to right) with a uniformly-labeled double-stranded RNA corresponding to the first 500 nucleotides of the *Drosophila cyclin* E coding region. M indicates a marker prepared by in vitro transcription of a synthetic template. The template was designed to yield a 22 nucleotide transcript. The doublet most probably results from improper initiation at the +1 position. (b) Whole-cell extracts were prepared from S2 cells that had been transfected with a dsRNA corresponding to the first 500 nt. of the luciferase coding region. S10 extracts were spun at 30,000×g for 20 minutes which represents our standard RISC extract. S100 extracts were prepared by further centrifugation of S10 extracts for 60 minutes at 100,000×g. Assays for mRNA degradation were carried out as described previously for 0, 30 or 60 minutes (left to right in each set) with either a single-stranded luciferase mRNA or a single-stranded cyclin E mRNA, as indicated. (c) S10 or S100 extracts were incubated with cyclin E dsRNAs for 0, 60 or 120 minutes (L to R).

FIG. 7: Dicer participates in RNAi. (a) *Drosophila* S2 cells were transfected with dsRNAs corresponding to the two *Drosophila* Dicers (CG4792 and CG6493) or with a control dsRNA corresponding to murine caspase 9. Cytoplasmic extracts of these cells were tested for Dicer activity. Transfection with Dicer dsRNA reduced activity in lysates by 7.4-fold. (b) The Dicer-1 antiserum (CG4792) was used to prepare immunoprecipitates from S2 cells that had been treated as described above. Dicer dsRNA reduced the activity of Dicer-1 in this assay by 6.2-fold. (c) Cells that had been transfected two days previously with either mouse caspase 9 dsRNA or with Dicer dsRNA were cotransfected with a GFP expression plasmid and either control, luciferase dsRNA or GFP dsRNA. Three independent experiments were quantified by FACS. A comparison of the relative percentage of GFP-positive cells is shown for control (GFP plasmid plus luciferase dsRNA) or silenced (GFP plasmid plus GFP dsRNA) populations in cells that had previously been transfected with either control (caspase 9) or Dicer dsRNAs.

FIG. 20: Identification of dicer as enzyme which can process dsRNA into 22mers. Various RNaseIII family members were expressed with n terminal tags, immunoprecipitated, and assayed for 22-mer generating activity (left panel). In right panel, antibodies to dicer could also precipitate 22-mer generating activity.

FIG. 24: Sequence of *Drosophila* argonaute 2 (SEQ ID NO: 5). Peptides identified by microsequencing are shown in underline.

FIG. 28: RNAi in P19 embryonal carcinoma cells. Ten-centimeter plates of P19 cells were transfected by using 5 µg of GFP plasmid and 40 µg of the indicated dsRNA (or no RNA). Cells were photographed by fluorescent (tope panel)

and phase-contrast microscopy (bottom panel) at 72 h after transfection; silencing was also clearly evident at 48 h post-transfection.

FIG. 29: RNAi of firefly and *Renilla* luciferase in P19 cells. (A and B) P19 cells were transfected with plasmids that direct the expression of firefly and *Renilla* luciferase and dsRNA 500mers (25 or 250 ng, as indicated in A and B, respectively), that were either homologous to the firefly luciferase mRNA (dsFF) or nonhomologous (dsGFP). Luciferase activities were assayed at various times after transfection, as indicated. Ratios of firefly to *Renilla* activity are normalized to dsGFP controls. (C and D) P19 cells in 12-well culture dishes (2 ml of media) were transfected with 0.25 μg of a 9:1 mix of pGL3-Control and pRL-SV40 as well as 2 μg of the indicated RNA. Extracts were prepared 9 h after transfection. (C) Ratio of firefly to *Renilla* luciferase is shown. (D) Ratio of *Renilla* to firefly luciferase is shown. Values are normalized to dsGFP. The average of three independent experiments is shown; error bars indicate standard deviation.

Figure 30:
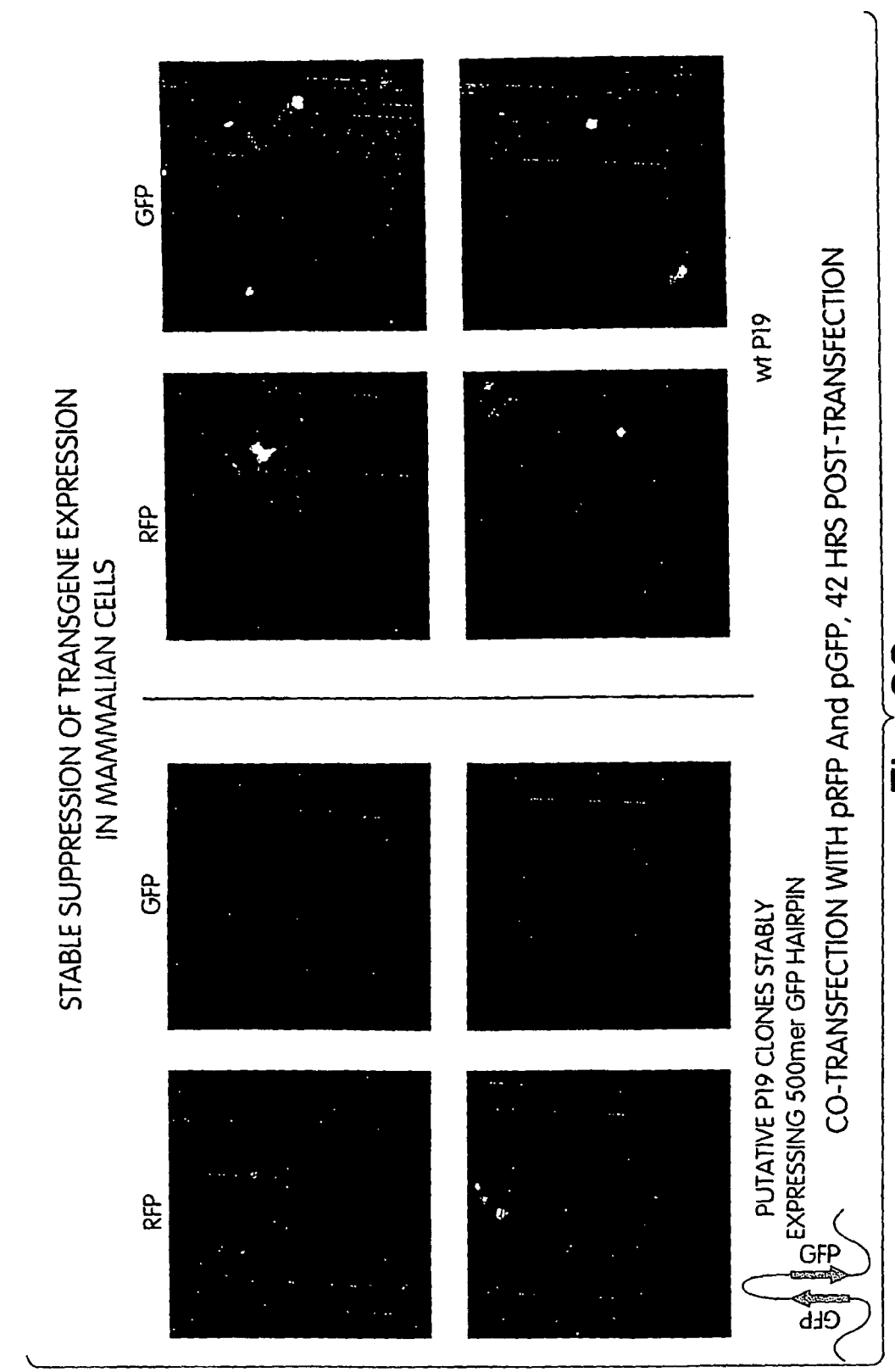

FIG. 30: The panels at the right show expression of either RFP or GFP following transient transfection into wild type P19 cells. The panels at the left demonstrate the specific suppression of GFP expression in P19 clones which stably express a 500 nt double stranded GFP hairpin. P19 clones which stably express the double stranded GFP hairpin were transiently transfected with RFP or GFP, and expression of RFP or GFP was assessed by visual inspection.

Figure 31:
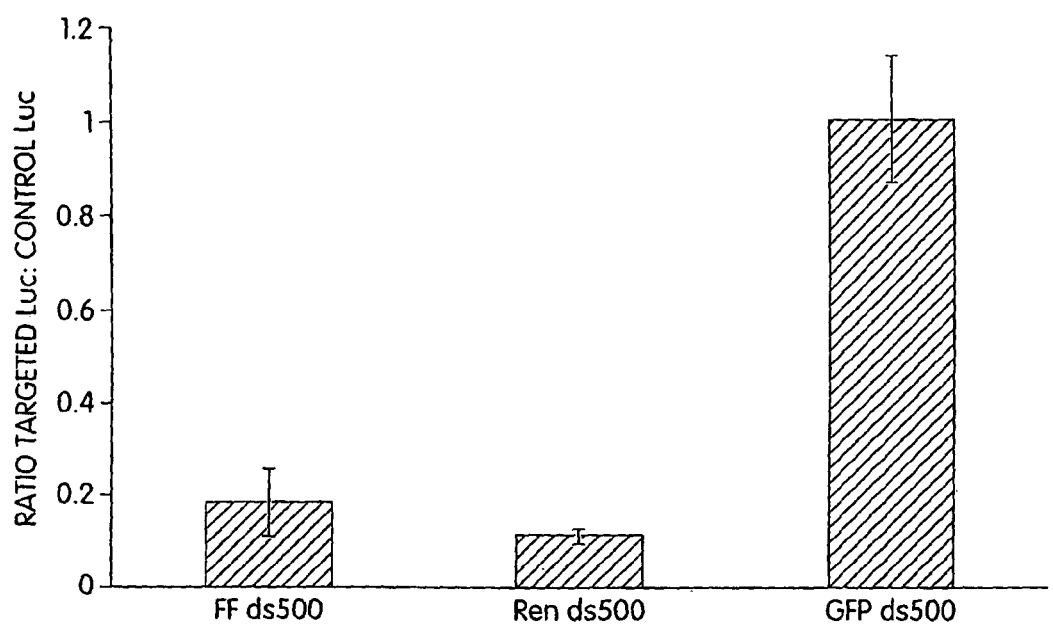

FIG. 31: Specific silencing of luciferase expression by dsRNA in murine embryonic stem cells. Mouse embryonic stem cells in 12-well culture dishes (1 ml of media) were transfected with 1.5 μg of dsRNA along with 0.25 μg of a 10:1 mixture of the reporter plasmids pGL3-Control and pRL-SV40. Extracts were prepared and assayed 20 h after transfection. The ratio of firefly to *Renilla* luciferase expression is shown for FF ds500; the ratio of *Renilla* to firefly is shown for Ren ds500. Both are normalized to ratios from the dsGFP transfection. The average of three independent experiments is shown; error bars indicate standard deviation.

Figure 32A:
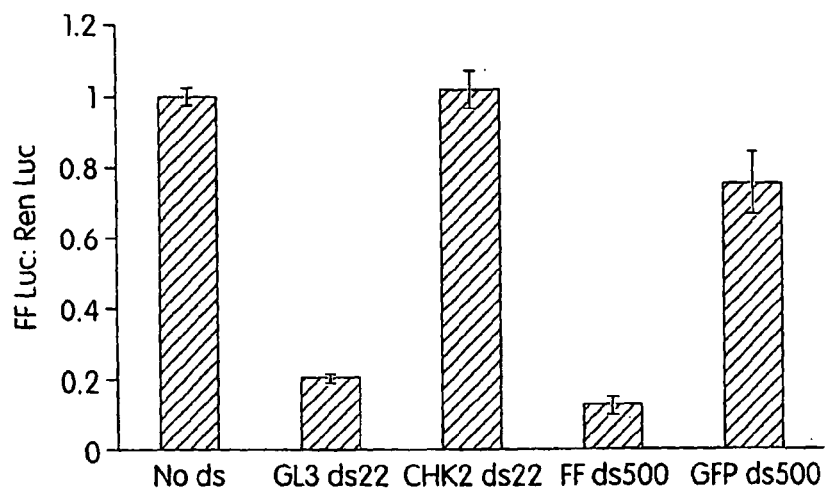

FIG. 32: RNAi in C2C12 murine myoblast cells. (A) Mouse C2C12 cells in 12-well culture dishes (1 ml of media) were transfected with 1 μg of the indicated dsRNA along with 0.250 μg of the reporter plasmids pGL3-Control and pRL-SV40. Extracts were prepared and assayed 24 h after transfection. The ratio of firefly to *Renilla* luciferase expression is shown; values are normalized to ratios from the no dsRNA control. The average of three independent experiments is shown; error bars indicate standard deviation. (B) C2C12 cells cotransfected with 1 μg of either plasmid alone or a plasmid containing a hyperactive mutant of vaccinia virus K3L (Kawagishi-Kobayashi et al. 2000, Virology 276: 424-434). The absolute counts of *Renilla* and firefly luciferase activity are shown. (C) The ratios of firefly/*Renilla* activity from B, normalized to no dsRNA controls.

Figure 33:
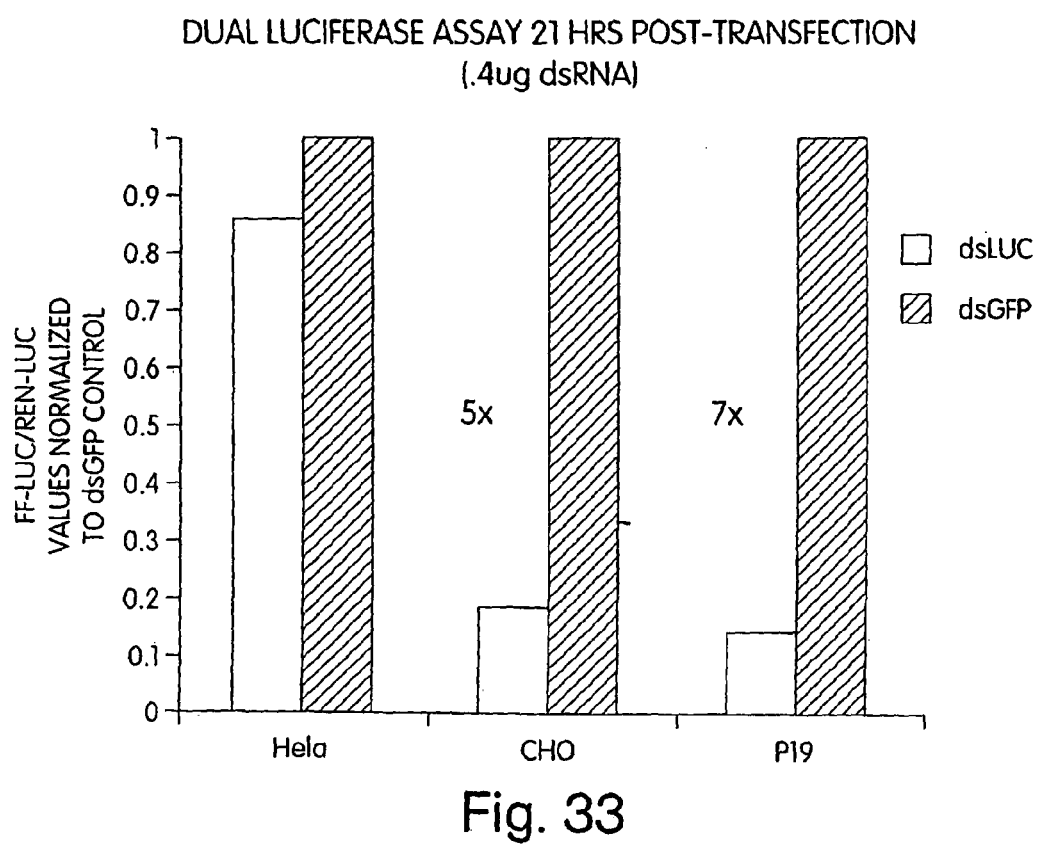

FIG. 33: Hela, Chinese hamster ovary, and P19 (pluripotent, mouse embryonic carcinoma) cell lines transfected with plasmids expressing *Photinus* pyralis (firefly) and *Renilla* reniformis (sea pansy) luciferases and with dsRNA 500mers (400 ng), homologous to either firefly luciferase mRNA (dsLUC) or non-homologous (dsGFP). Dual luciferase assays were carried out using an Analytical Scientific Instruments model 3010 Luminometer. In this assay *Renilla* luciferase serves as an internal control for dsRNA-specific suppression of firefly luciferase activity. These data demonstrate that 500-mer dsRNA can specifically suppress cognate gene expression in vitro.

FIG. 34: Expression of a hairpin RNA produces P19 EC cell lines that stably silence GFP. (A) A cartoon of the FLIP cassette used to construct the GFP hairpin. GFP represents the first 500 coding base pairs of EGFP. Zeo, zeocin resistance gene; L, Lox; P, the cytomegalovirus promoter in the expression plasmid pcDNA3. Homologous GFP fragments are first cloned as direct repeats into the FLIP cassette. To create inverted repeats for hairpin production, the second repeat is flipped by using Cre recombinase. When transcribed, the inverted repeat forms a GFP dsRNA with a hairpin loop. (B) P19 cell lines stably expressing the GFP hairpin plasmid, GFPhp.1 (clone 10) and GFPhp.2 (clone 12), along with wt P19 were transfected with 0.25 μg each of GFP and RFP reporter genes. Fluorescence micrographs were taken by using filters appropriate for GFP and RFP. Magnification is 200×. (C) P19 GFPhp.1 cells were transfected with pEGFP and 0, 0.5, or 1 μg of Dicer or firefly dsRNA. Fluorescence micrographs were taken at 48 h post-transfection and are superimposed with bright field images to reveal non-GFP expressing cells. Magnification is 100×. (D) In vitro and in vitro processing of dsRNA in P19 cells. In vitro Dicer assays were performed on S2 cells and three independently prepared P19 extracts by using $^{32}$P-labeled dsRNA (30° C. for 30 min). A Northern blot of RNA extracted from control and GFPhp.1 P19-cells shows the production of ≈22-mer RNA species in hairpin-expressing cells but not in control cells. Blots were probed with a $^{32}$P-labeled "sense" GFP transcript.

Figure 35:
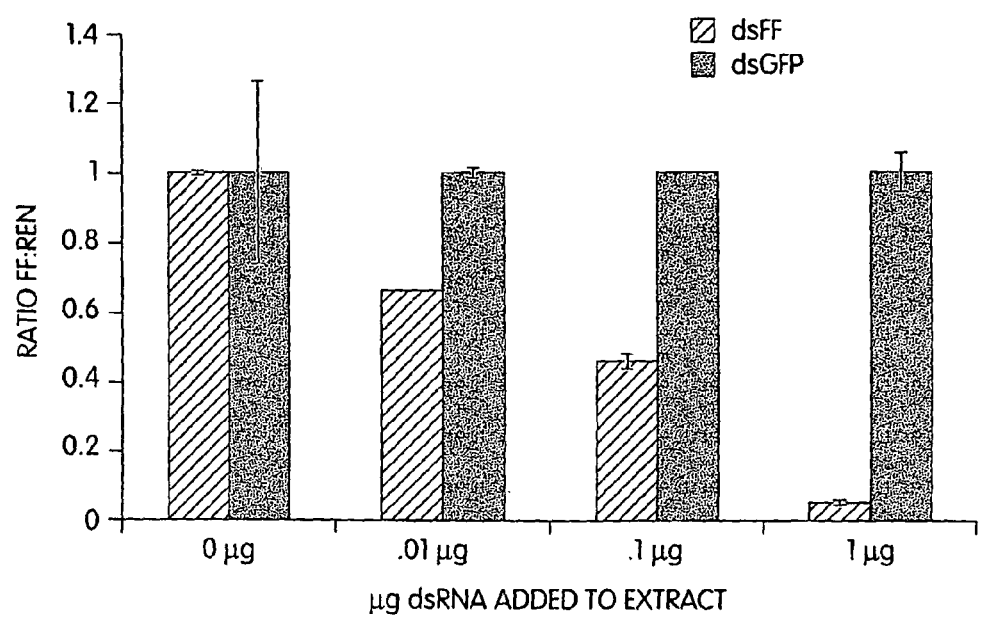

FIG. 35: dsRNA induces silencing at the posttranscriptional level. P19 cell extracts were used for in vitro translation of firefly and *Renilla* luciferase mRNA (100 ng each). Translation reactions were programmed with various amounts of dsRNA 500mers, either homologous to firefly luciferase mRNA (dsLUC) or nonhomologous (dsGFP). Luciferase assays were carried out after a 1 h incubation at 30° C. Ratios of firefly to *Renilla* activity are normalized to no dsRNA controls. Standard deviations from the mean are shown.

Figure 36:
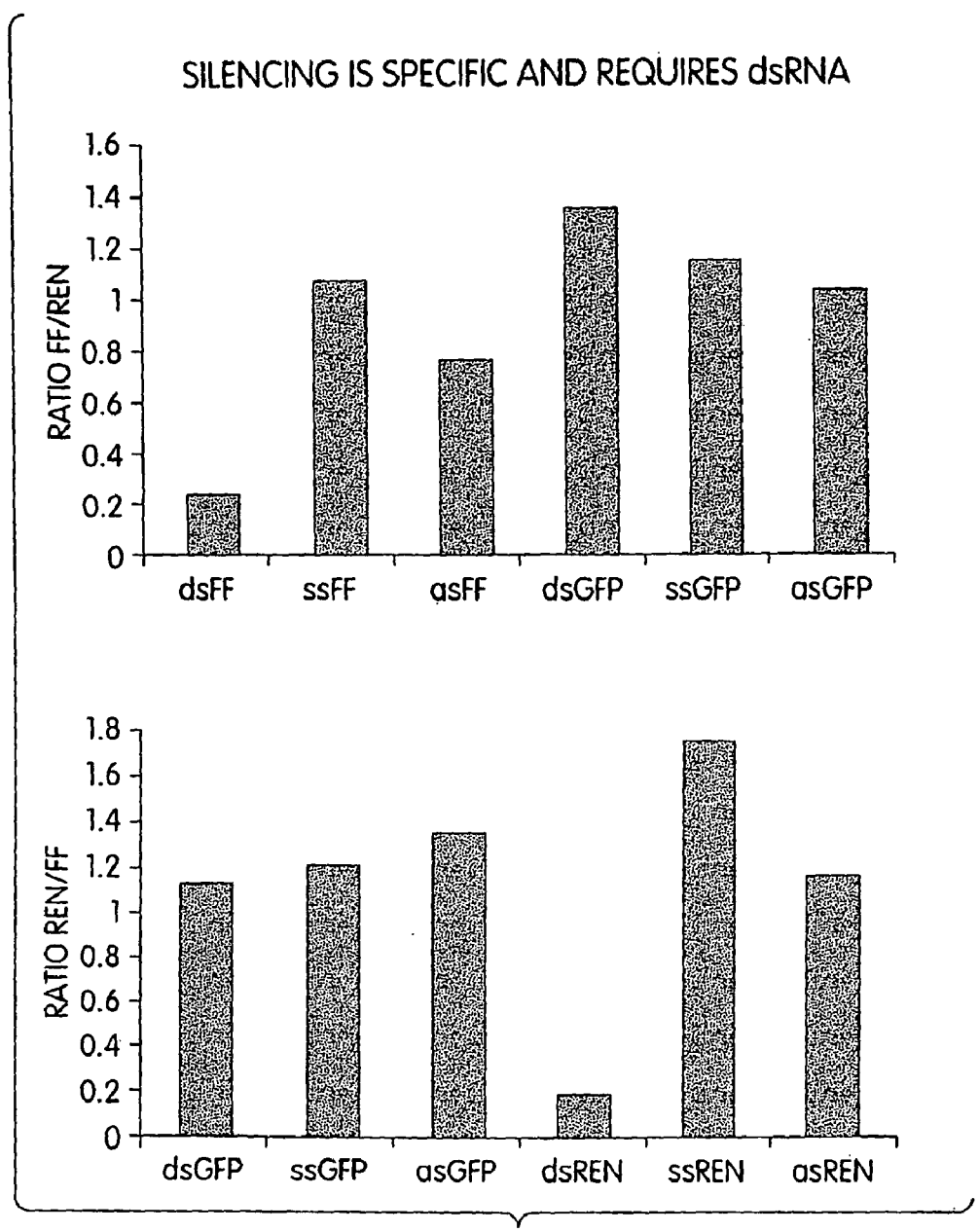

FIG. 36: S10 fractions from P19 cell lysates were used for in vitro translations of mRNA coding for *Photinus pyralis* (firefly) and *Renilla reniformis* (sea pansy) luciferases. Translation reactions were programmed with dsRNA, ssRNA, or asRNA 500mers, either complementary to firefly luciferase mRNA (dsFF, ssFF, or asFF), complementary to *Renilla* luciferase (dsREN, ssREN, or asREN) or non-complementary (dsGFP). Reactions were carried out at 30° C. for 1 hour, after a 30 min preincubation with dsRNA, ssRNA, or asRNA. Dual luciferase assays were carried out using an Analytical Scientific Instruments model 3010 Luminometer. On the left, *Renilla* luciferase serves as an internal control for dsRNA-specific suppression of firefly luciferase activity. On the right, firefly luciferase serves as an internal control for dsRNA-specific suppression of *Renilla* luciferase activity. These data demonstrate that 500-mer double-stranded RNA (dsRNA) but not single-stranded (ssRNA) or anti-sense RNA (asRNA) suppresses cognate gene expression in vitro in a manner consistent with post-transcriptional gene silencing.

Figure 37:
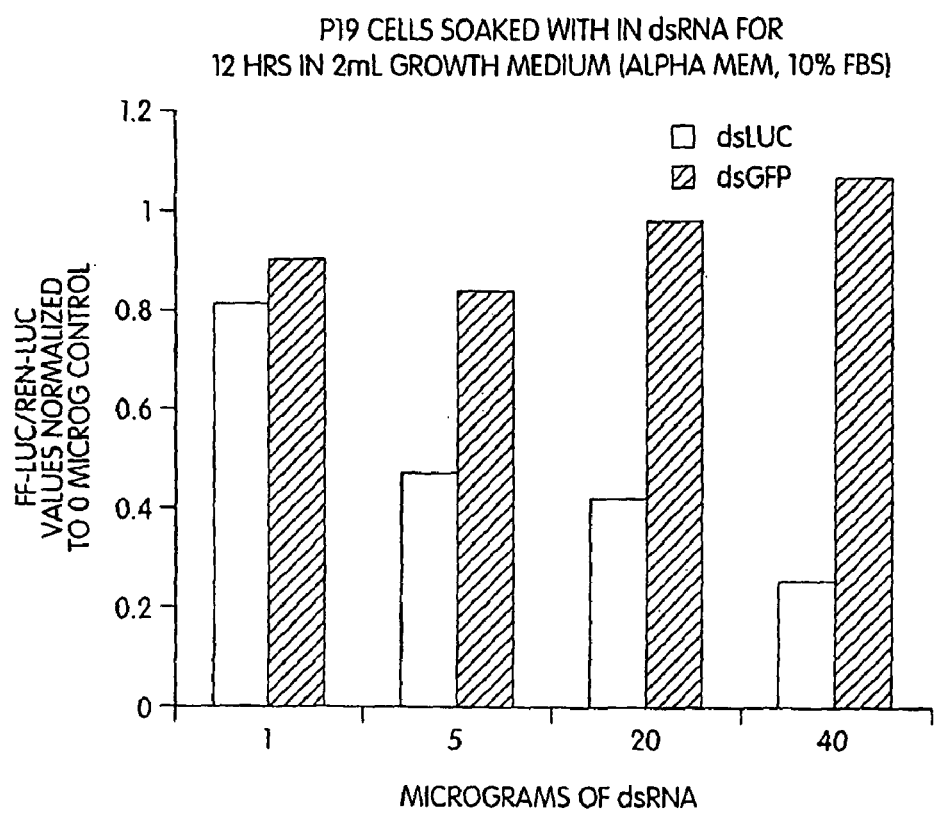

FIG. 37: P19 cells were grown in 6-well tissue culture plates to approximately 60% confluence. Various amounts of dsRNA, either homologous to firefly luciferase mRNA (dsLUC) or non-homologous (dsGFP), were added to each well and incubated for 12 hrs under normal tissue culture conditions. Cells were then transfected with plasmids expressing *Photinus pyralis* (firefly) and *Renilla reniformis* (sea pansy) luciferases and with dsRNA 500mers (500 ng). Dual luciferase assays were carried out 12 hrs post-transfection using an Analytical Scientific Instruments model 3010 Luminometer. In this assay *Renilla* luciferase serves as an internal control for dsRNA-specific suppression of firefly luciferase activity. These data show that 500-mer dsRNA can specifically suppress cognate gene expression in vitro without transfection under normal tissue culture conditions.

Figure 38:
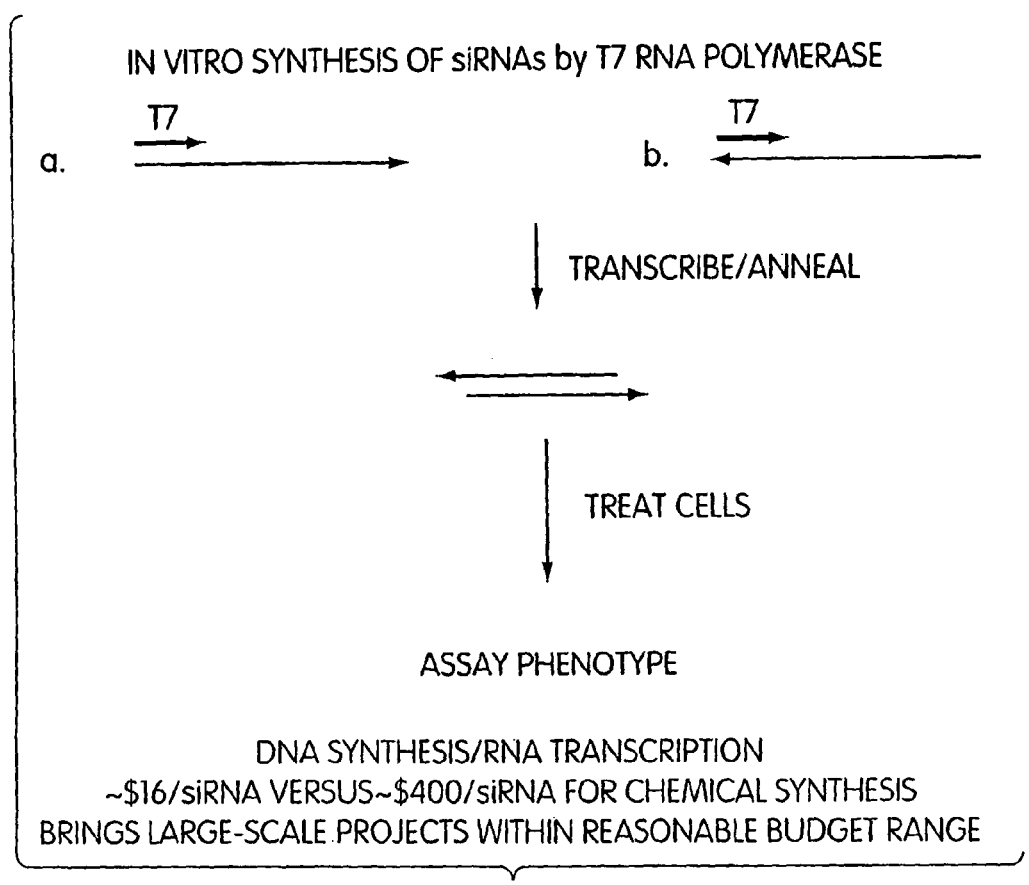

FIG. 38: Previous methods for generating siRNAs required costly chemical synthesis. The invention provides an in vitro method for synthesizing siRNAs using standard RNA transcription reactions.

FIG. 39: Short hairpins suppress gene expression in *Drosophila* S2 cells. (A) Sequences and predicted secondary structure of representative chemically synthesized RNAs. Sequences correspond to positions 112-134 (siRNA) and 463-491 (shRNAs) of Firefly luciferase carried on pGL3-Control. An siRNA targeted to position 463-485 of the luciferase sequence was virtually identical to the 112-134 siRNA in suppressing expression, but is not shown. These sequences are represented by SEQ ID NOs: 6-10. (B) Exogenously supplied short hairpins suppress expression of the targeted Firefly luciferase gene in vitro. Six-well plates of S2 cells were transfected with 250 ng/well of plasmids that direct the expression of firefly and *Renilla* luciferase and 500 ng/well of the indicated RNA. Luciferase activities were assayed 48 h after transfection. Ratios of firefly to *Renilla* luciferase activity were normalized to a control transfected with an siRNA directed at the green fluorescent protein (GFP). The average of three independent experiments is shown; error bars indicate standard deviation. (C) Short hairpins are processed by the *Drosophila* Dicer enzyme. T7 transcribed hairpins shFfL22, shFfL29, and shFfS29 were incubated with (+) and without (−) 0-2-h *Drosophila* embryo extracts. Those incubated with extract produced ~22-nt siRNAs, consistent with the ability of these hairpins to induce RNA interference. A long dsRNA input (cyclin E 500-mer) was used as a control. Cleavage reactions were performed as described in Bernstein et al., 2001, Nature, 409:363-366.

Figure 40:
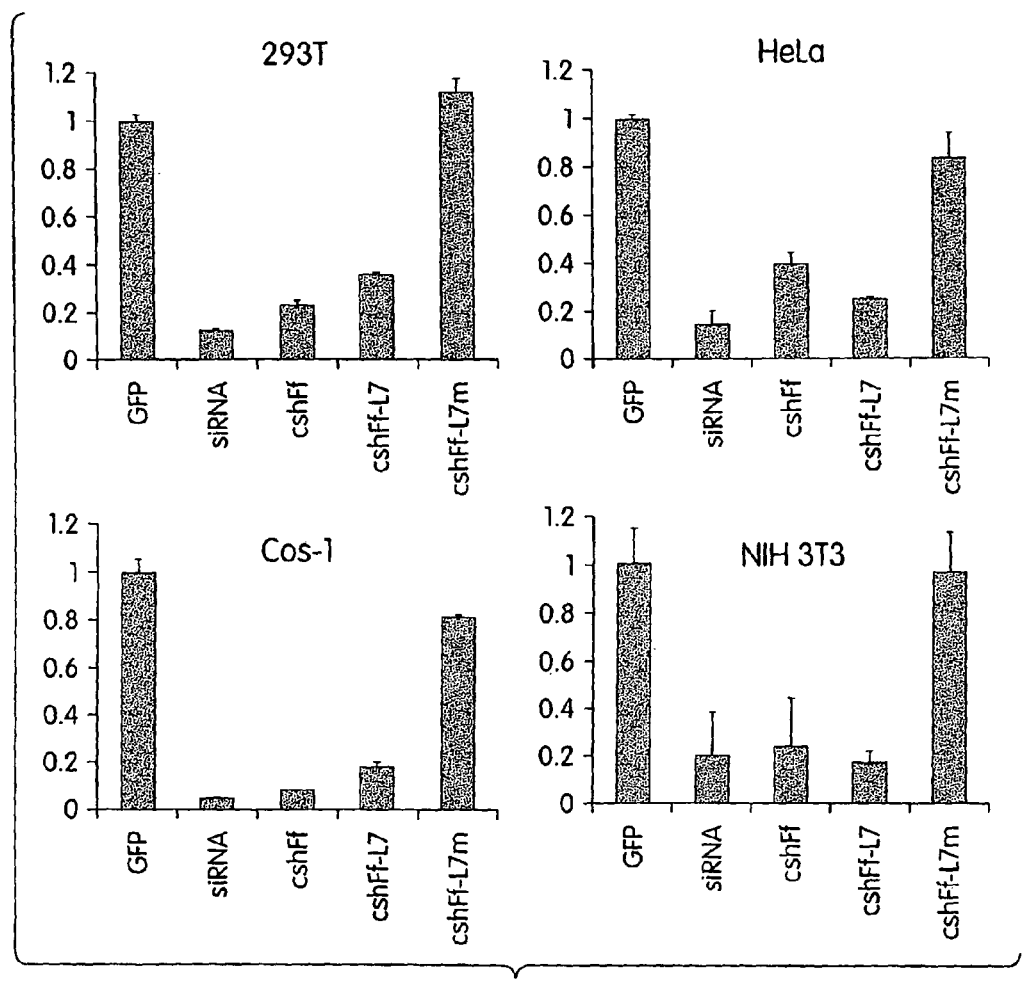

FIG. 40: Short hairpins function in mammalian cells. HEK 293T, HeLa, COS-1, and NIH 3T3 cells were transfected with plasmids and RNAs as in FIG. 1 and subjected to dual luciferase assays 48 h post-transfection. The ratios of firefly to *Renilla* luciferase activity are normalized to a control transfected with an siRNA directed at the green fluorescent protein (GFP). The average of three independent experiments is shown; error bars indicate standard deviation.

FIG. 41: siRNAs and short hairpins transcribed in vitro suppress gene expression in mammalian cells. (A) Sequences and predicted secondary structure of representative in vitro transcribed siRNAs. Sequences correspond to positions 112-134 (siRNA) and 463-491 (shRNAs) of firefly luciferase carried on pGL3-Control. These sequences are represented by SEQ ID NOs: 11-20. (B) In vitro transcribed siRNAs suppress expression of the targeted firefly luciferase gene in vitro. HEK 293T cells were transfected with plasmids as in FIG. 2. The presence of non-base-paired guanosine residues at the 5' end of siRNAs significantly alters the predicted end structure and abolishes siRNA activity. (C) Sequences and predicted secondary structure of representative in vitro transcribed shRNAs. Sequences correspond to positions 112-141 of firefly luciferase carried on pGL3-Control. These sequences are represented by SEQ ID NOs: 21-26. (D) Short hairpins transcribed in vitro suppress expression of the targeted firefly luciferase gene in vitro. HEK 293T cells were transfected with plasmids as in FIG. 2.

Figure 42A:
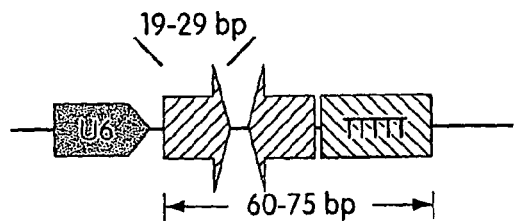
Figure 42B:
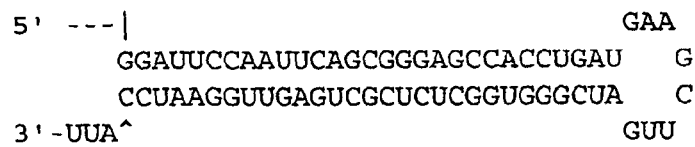

FIG. 42: Transcription of functional shRNAs in vitro. (A) Schematic of the pShh1 vector. Sequences encoding shRNAs with between 19 and 29 bases of homology to the targeted gene are synthesized as 60-75-bp double-stranded DNA oligonucleotides and ligated into an EcoRV site immediately downstream of the U6 promoter. This sequence is represented by SEQ ID NO: 27. (B) Sequence and predicted secondary structure of the Ff1 hairpin. (C) An shRNA expressed from the pShh1 vector suppresses luciferase expression in mammalian cells. HEK 293T, HeLa, COS-1, and NIH 3T3 cells were transfected with reporter plasmids as in FIG. 1, and pShh1 vector, firefly siRNA, or pShh1 firefly shRNA constructs as indicated. The ratios of firefly to *Renilla* luciferase activity were determined 48 h after transfection and represent the average of three independent experiments; error bars indicate standard deviation.

Figure 43:
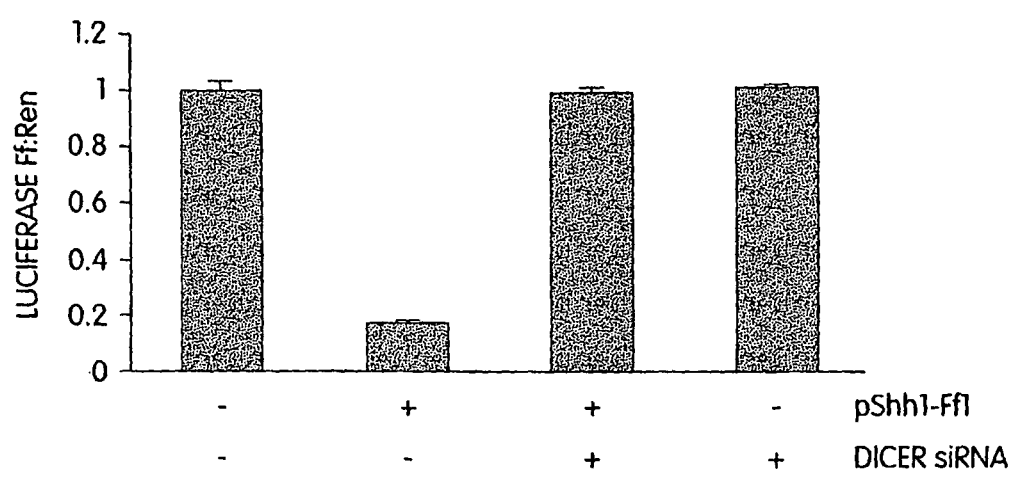

FIG. 43: Dicer is required for shRNA-mediated gene silencing. HEK 293T cells were transfected with luciferase reporter plasmids as well as pShh1-Ff1 and an siRNA targeting human Dicer either alone or in combination, as indicated. The Dicer siRNA sequence (TCAACCAGCCACTGCTGGA, SEQ ID NO: 37) corresponds to coordinates 3137-3155 of the human Dicer sequence. The ratios of firefly to *Renilla* luciferase activity were determined 26 h after transfection and represent the average of three independent experiments; error bars indicate standard deviation.

FIG. 44: Stable shRNA-mediated gene silencing of an endogenous gene. (A) Sequence and predicted secondary structure of the p53 hairpin. The 5' shRNA stem contains a 27-nt sequence derived from mouse p53 (nucleotides 166-192), whereas the 3' stem harbors the complimentary antisense sequence. This sequence is represented by SEQ ID NO: 28. (B) Senescence bypass in primary mouse embryo fibroblasts (MEFs) expressing an shRNA targeted at p53. Wild-type MEFs, passage 5, were transfected with pBabe-RasV12 with control plasmid or with p53hp (5 µg each with FuGENE; Roche). Two days after transfection, cells were trypsinized, counted, and plated at a density of $1 \times 10^5$/10-cm plate in media containing 2.0 µg/mL of puromycin. Control cells cease proliferation and show a senescent morphology (left panel). Cells expressing the p53 hairpin continue to grow (right panel). Photos were taken 14 d post-transfection.

Figure 45:
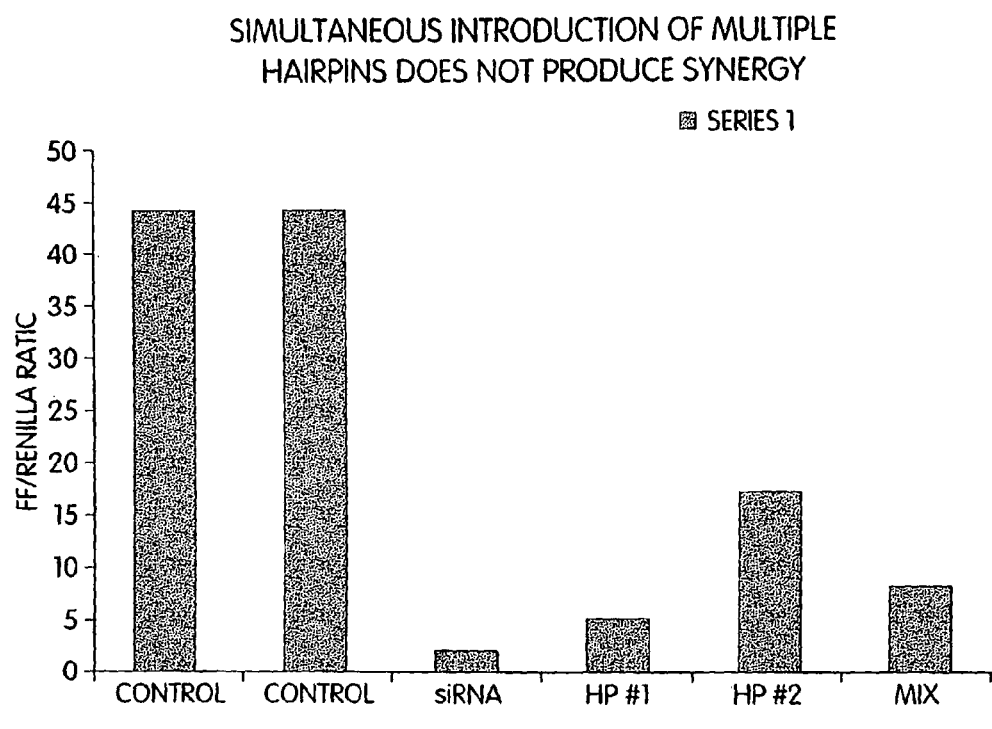

FIG. 45: A mixture of two short hairpins, both corresponding to firefly luciferase, does not result in a synergistic suppression of gene expression. Suppression of firefly luciferase gene expression resulting from transfection of a mixture of two different short hairpins (HP #1 and HP #2) was examined. The mixture of HP #1 and HP #2 did not have a more robust effect on the suppression of firefly luciferase gene expression than expression of HP#1 alone.

Figure 46:
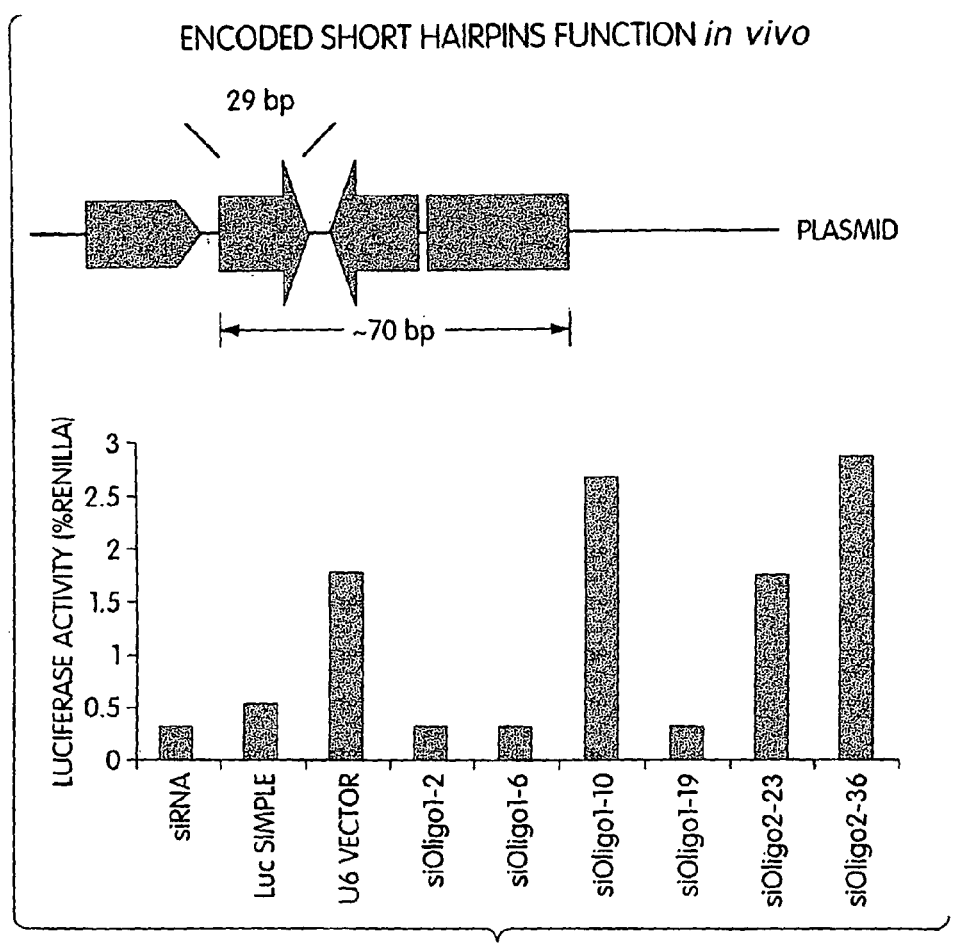

FIG. 46: Encoded short hairpins specifically suppress gene expression in vitro. DNA oligonucleotides encoding 29 nucleotide hairpins corresponding to firefly luciferase were inserted into a vector containing the U6 promoter. Three independent constructs were examined for their ability to specifically suppress firefly luciferase gene expression in 293T cells. siOligo1-2, siOligo1-6, and siOligo1-19 (construct in the correct orientation) each suppressed gene expression as effectively as siRNA. In contrast, siOligo1-10 (construct in the incorrect orientation) did not suppress gene expression. An independent construct targeted to a different portion of the firefly luciferase gene did not effectively suppress gene expression in either orientation (SiOligo2-23, SiOligo2-36).

Figure 47:
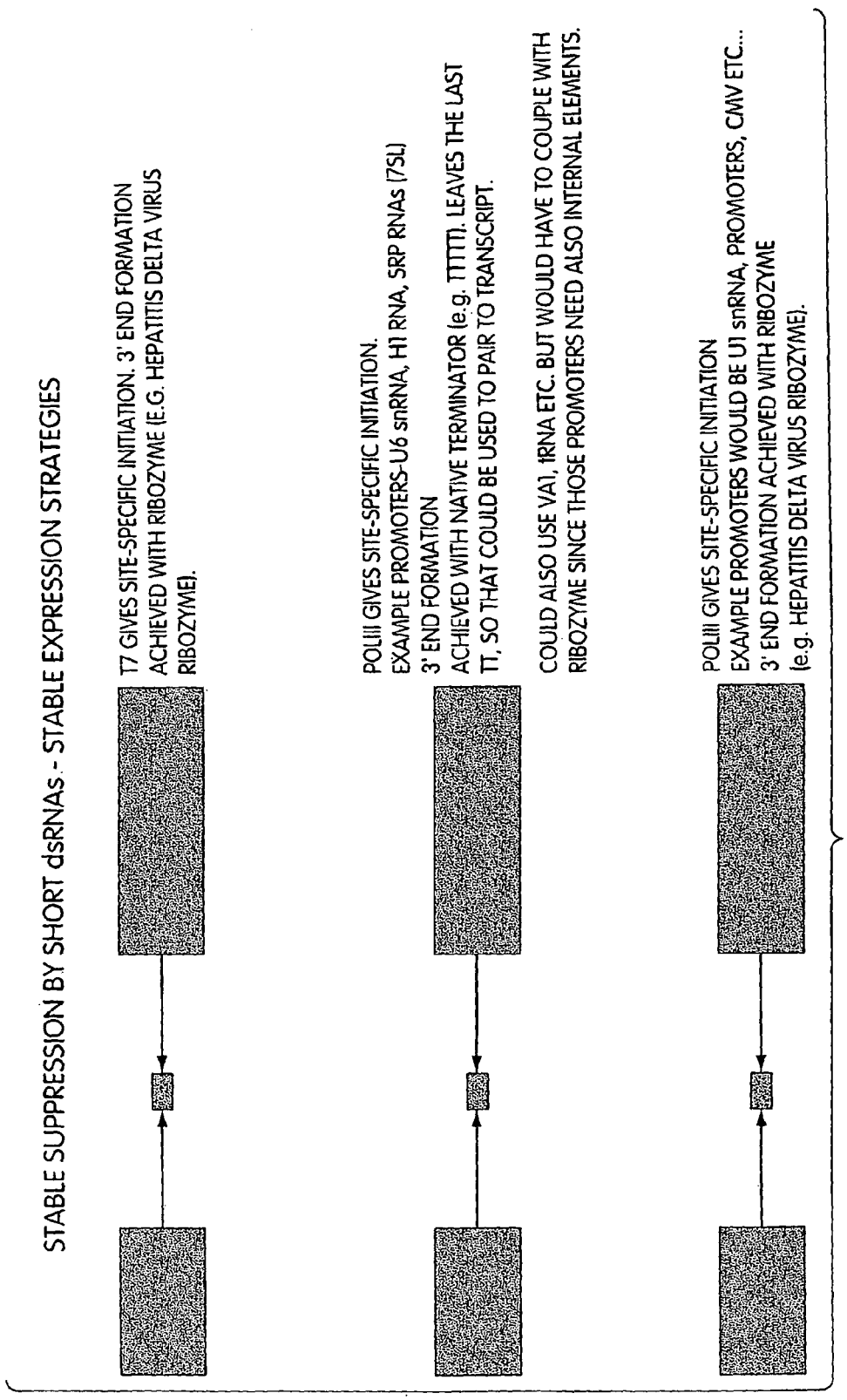
Figure 48:
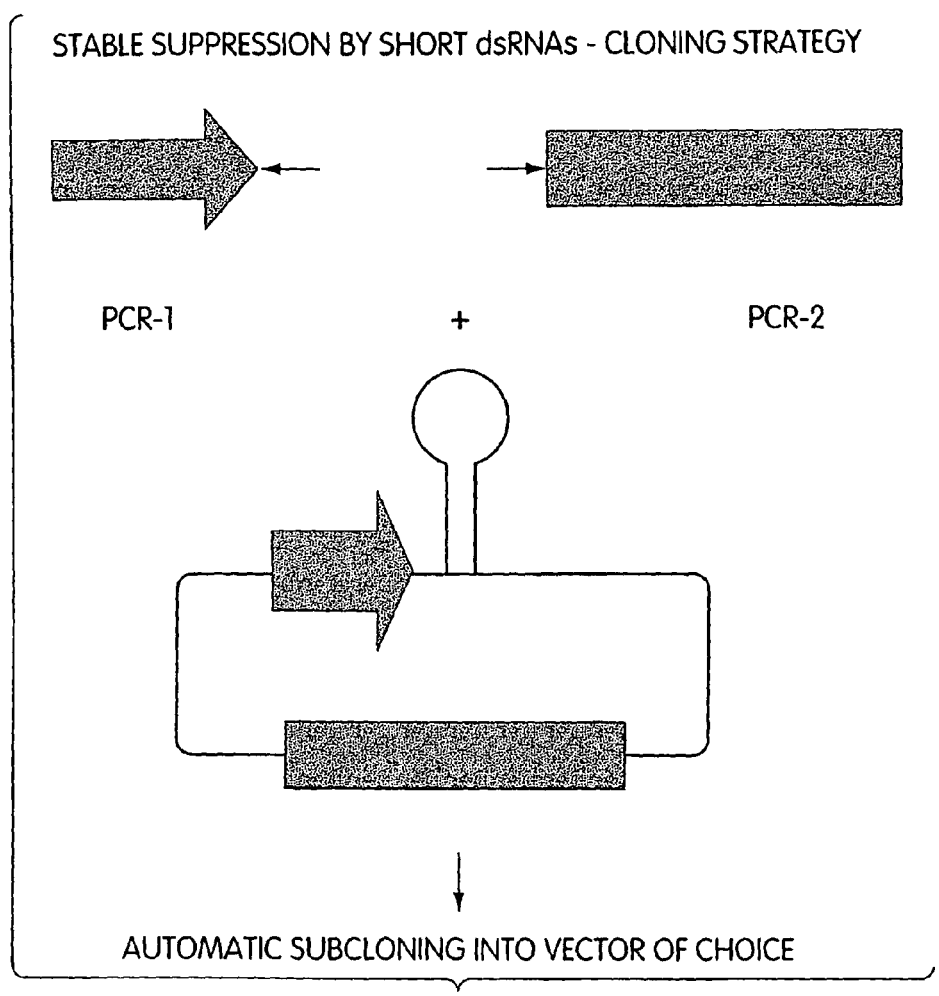
Figure 49:
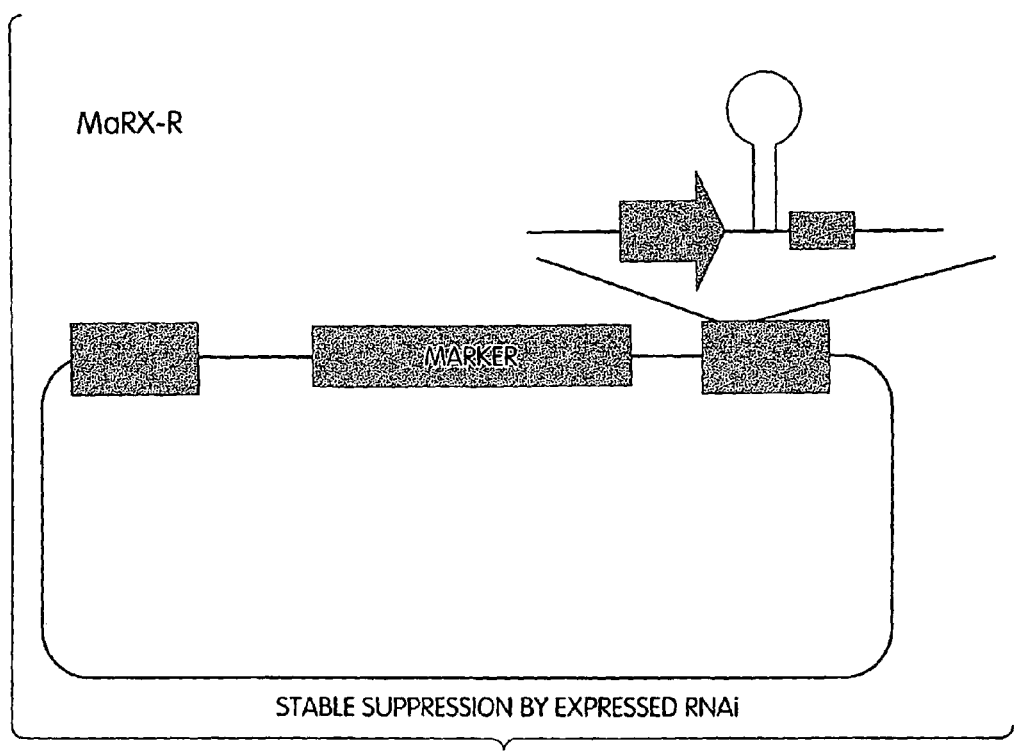

FIGS. 47-49: Strategies for stable expression of short dsRNAs.

Figure 50:
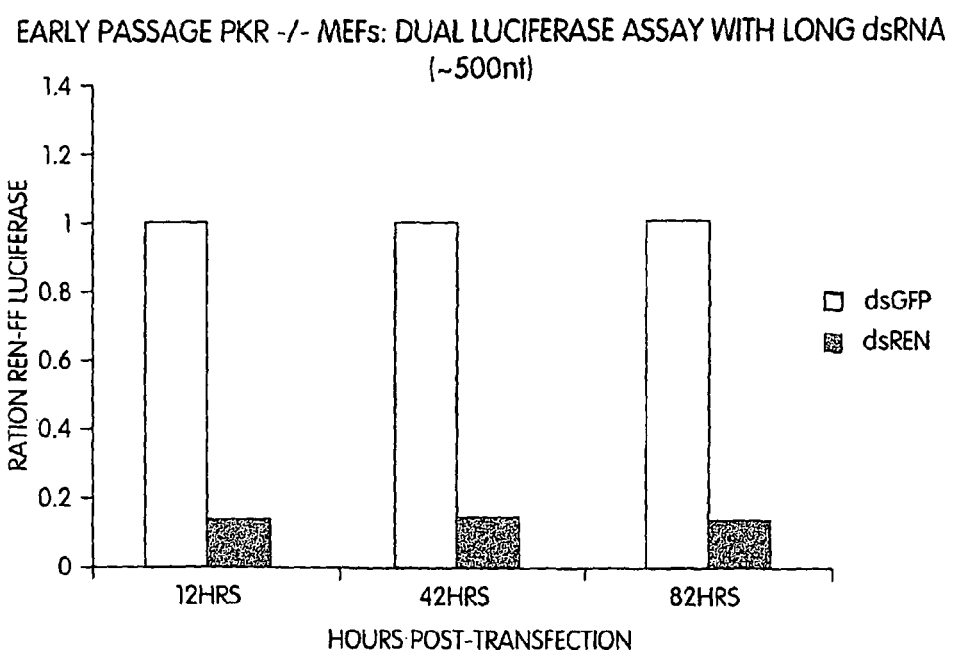

FIG. 50: Dual luciferase assays were performed as described in detail in FIGS. 28-35, however the cells used in these experiments were $PKR^{-/-}$ murine embryonic fibroblasts (MEFs). Briefly, RNAi using long dsRNAs typically envokes a non-specific response in MEFs (due to PKR activity). To evaluate the effect of long dsRNA constructs to specifically inhibit gene expression in MEFs, RNAi was examined in $PKR^{-/-}$ MEFs. Such cells do not respond to dsRNA with a non-specific response. The data summarized in this figure demonstrates that in the absence of the non-specific PKR response, long dsRNA constructs specifically suppress gene expression in MEFs.

Figure 51:
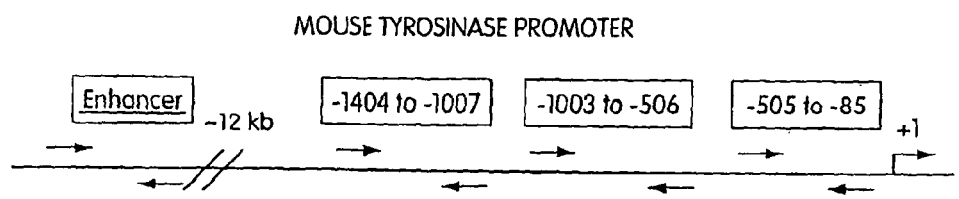

FIG. 51: Is a schematic representation of the mouse tyrosinase promoter. Primers were used to amplify three separate regions in the proximal promoter, or to amplify sequence corresponding to an enhancer located approximately 12 kb upstream.

Figure 52:
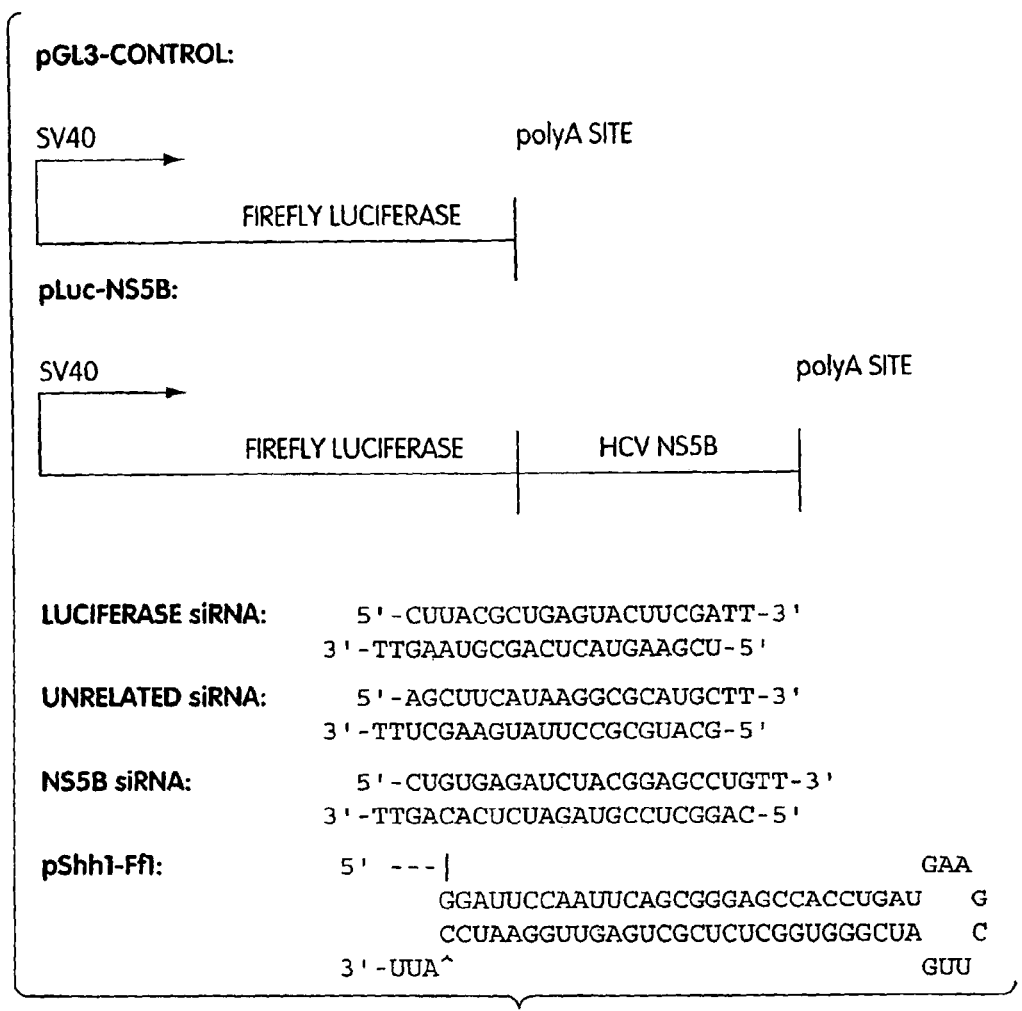

FIG. 52: Reporter expression plasmids and siRNA sequences used in Figures X and Y. PGL-3-Control and Pluc-NS5B are the expression plasmids used for transfection into mouse liver. The nucleotide sequences of the siRNAs used in the study are shown underneath. These sequences are represented by SEQ ID NOs: 29-35.

FIG. 53: RNA interference in adult mice using siRNAs. (a) Representative images of light emitted from mice co-transfected with the luciferase plasmid pGL3-control and either no siRNA, luciferase siRNA or unrelated siRNA. A pseudocolour image representing intensity of emitted light (red, most intense; blue, least intense) superimposed on a greyscale reference image (for orientation) shows that RNAi functions in adult mice. Annealed 21-nucleotide siRNAs (40 µg; Dharmacon) were co-injected into the livers of mice with 2 µg pGL3-control DNA (Promega) and 800 units of RNasin (Promega) in 1.8 ml PBS buffer in 5-7 s. After 72 h, mice were anaesthetized and given 3 mg luciferin intraperitoneally 15 min before imaging. (b) siRNA results (six mice per group) from a representative experiment. Mice receiving luciferase siRNA emitted significantly less light than reporter-alone controls (one-way ANOVA with post hoc Fisher's test). Results for reporter alone and unrelated siRNA were statistically similar. Animals were treated according to the US National Institutes of Health's guidelines for animal care and the guidelines of Stanford University.

Figure 54A:
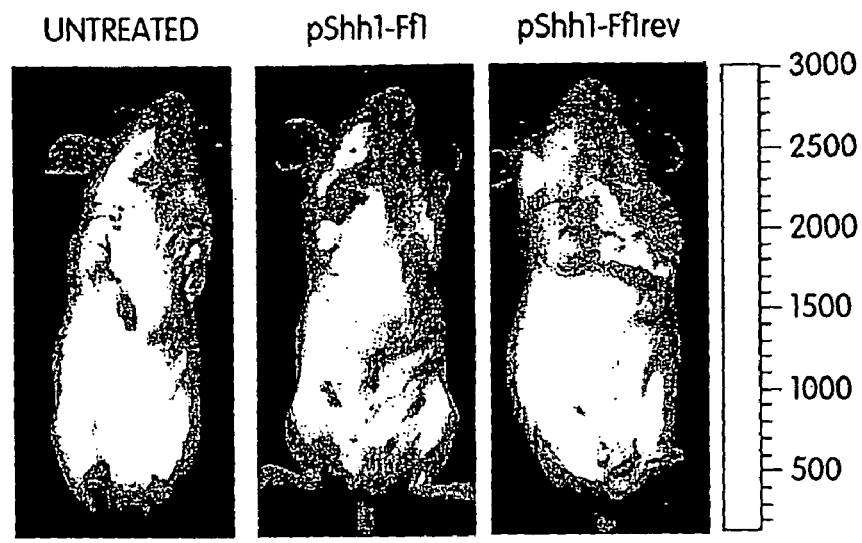
Figure 54B:
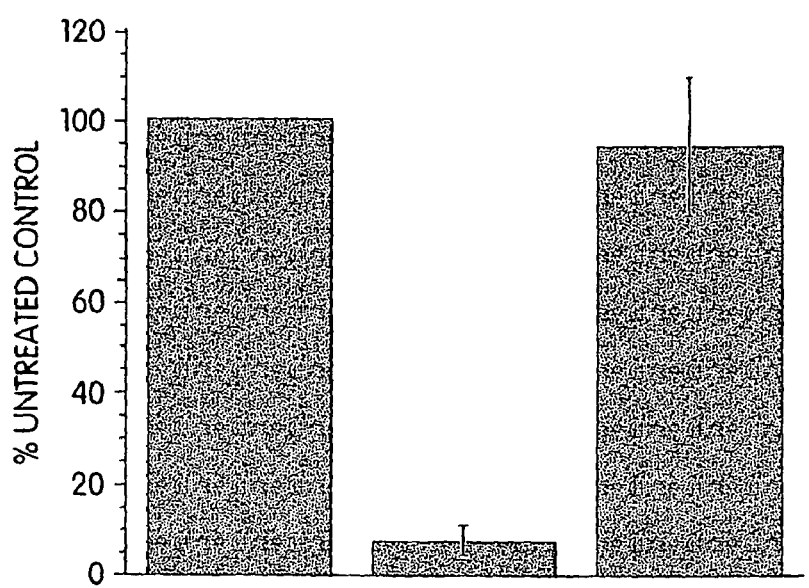

FIG. 54: RNA interference in adult mice using shRNAs. (a) Representative images of light emitted from mice co-transfected with the luciferase plasmid control, pShh1-Ff1, and pShh1-Ff1rev. pShh1-Ff1, but not pShh1-Ff1rev, reduced luciferase expression in mice relative to the reporter-alone control. pShh1-Ff1 or pShh1-rev (10 µg) were co-injected with 2 µg pGL3-control in 1.8 ml PBS buffer. (b) Average of three independent shRNA experiments (n=5). Average values for the reporter-alone group are designated as 100% in each of the three experiments. Animals were treated according to the US National Institutes of Health's guidelines for animal care and the guidelines of Stanford University.

Figure 55A:
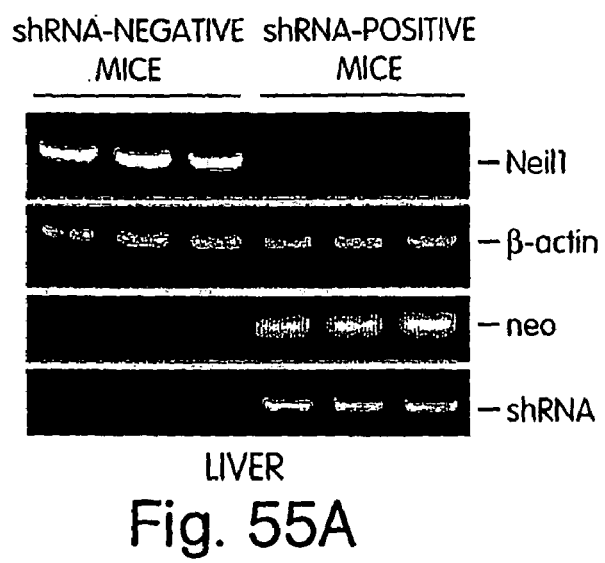
Figure 55B:
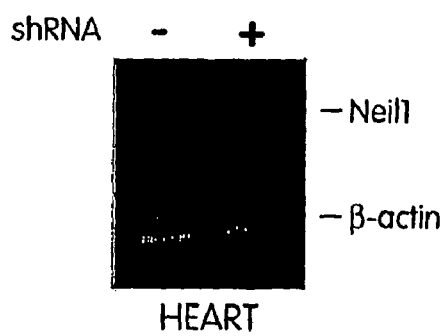
Figure 55C:
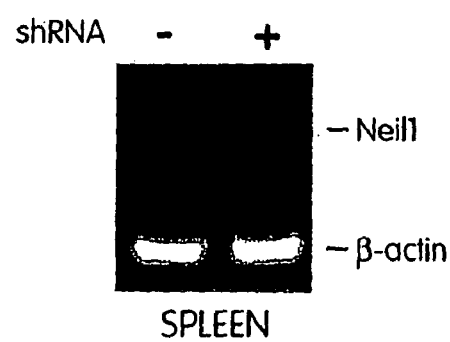

FIG. 55: Heritable repression of Neil1 expression by RNAi in several tissues. (a) Expression of Neil1 mRNA in the livers of three mice containing the Neil1 shRNA transgene (shRNA-positive) or three siblings lacking the transgene (shRNA-negative) was assayed by RT-PCR (top row is Neil1). An RT-PCR of β-actin was done to ensure that equal quantities of mRNAs were tested for each mouse (second row). Expression of the neomycin resistance gene (neo), carried on the shRNA vector, was tested similarly (third row). Finally, the mice were genotyped using genomic DNA that was PCR-amplified with vector-specific primers (bottom row). (b) Similar studies were performed in the heart. (c) Similar studies were performed in the spleen. Animal procedures have been approved by the SUNY, Stony Brook Institutional Animal Care and Use Committee (IACUC).

Figure 56A:
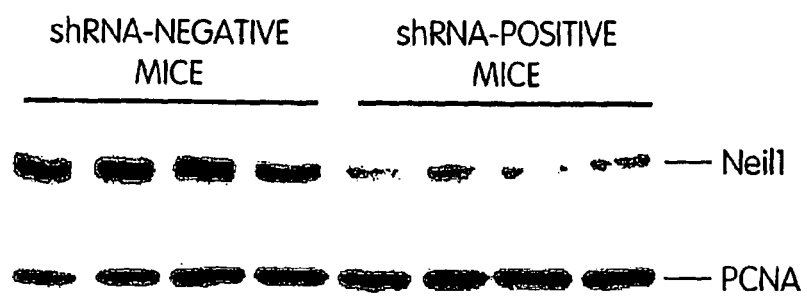

FIG. 56: Reduction in Neil1 protein correlates with the presence of siRNAs. (a) Expression of Neil1 protein was examined in protein extracts from the livers of mice carrying the shRNA transgene (shRNA-positive) or siblings lacking the transgene (shRNA-negative) by western blotting with Neil1-specific antiserum. A western blot for PCNA was used to standardize loading. (b) The presence of siRNAs in RNA derived from the livers of transgenic mice as assayed by northern blotting using a 300 nt probe, part of which was complementary to the shRNA sequence. We note siRNAs only in mice transgenic for the shRNA expression cassette.

Figure 57:
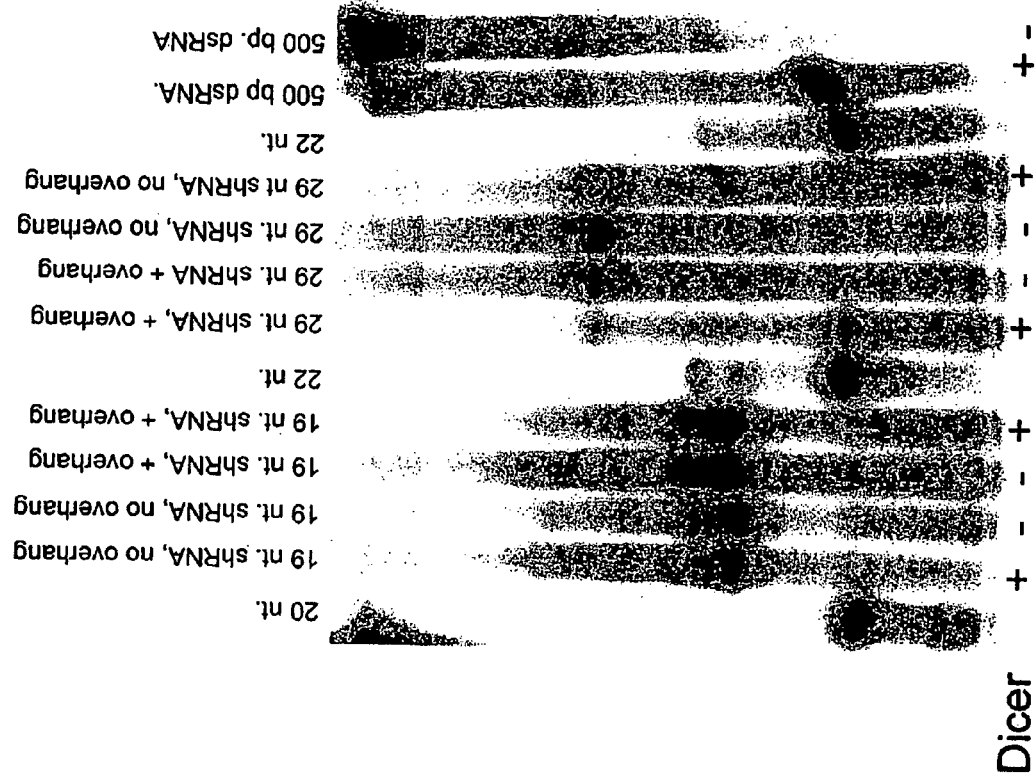
Figure 57:
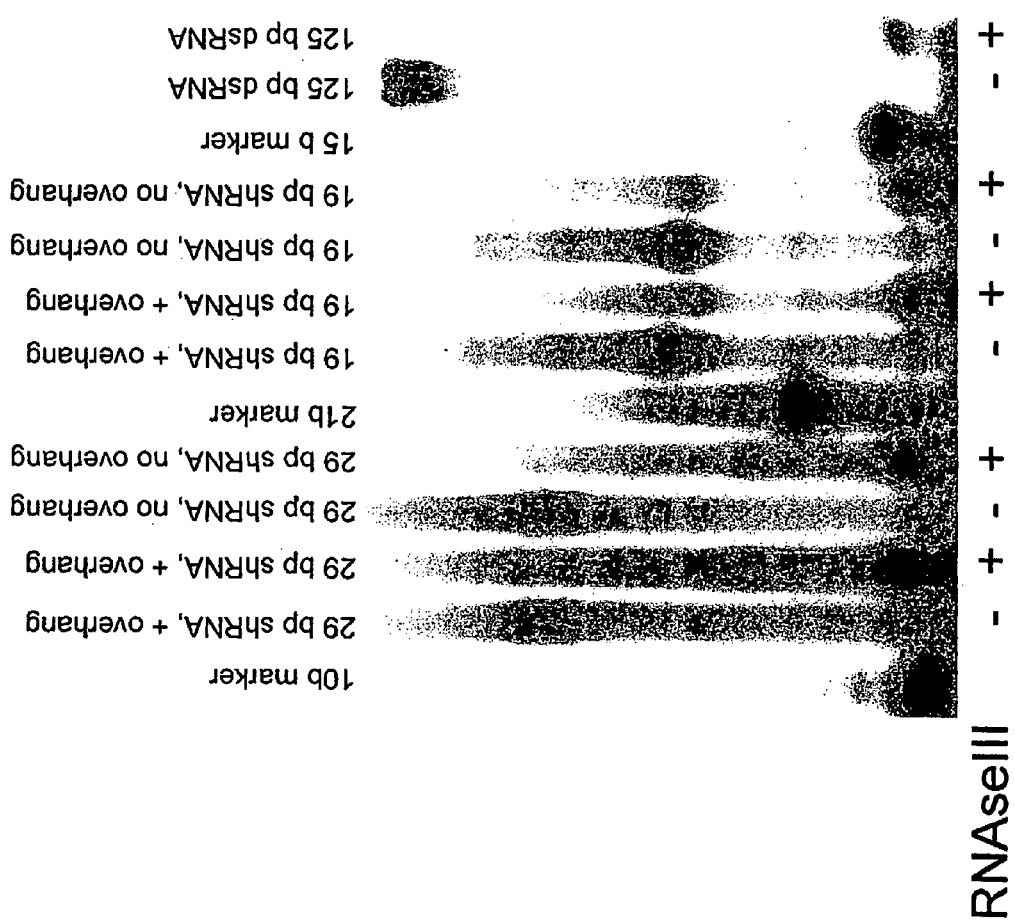

FIG. 57: In vitro processing of 29 nt. shRNAs by Dicer generates a single siRNA from the end of each short hairpin. a) The set of shRNAs containing 19 or 29 nt stems and either bearing or lacking a 2 nucleotide 3'overhang is depicted schematically. For reference the 29 nt sequence from luciferase (top, blue) strand is given. The presumed cleavage sites are indicated in green and by the arrows. b) In vitro Dicer processing of shRNAs. Substrates as depicted in a) were incubated either in the presence or absence of recombinant human Dicer (as indicated). Processing of a 500 bp. blunt-ended dsRNA is shown for comparison. Markers are end-labeled, single-stranded, synthetic RNA oligonucleotides. c) All shRNA substrates were incubated with bacterial RNase III to verify their double-stranded nature. This sequence is represented by SEQ ID NO: 36.

Figure 58:
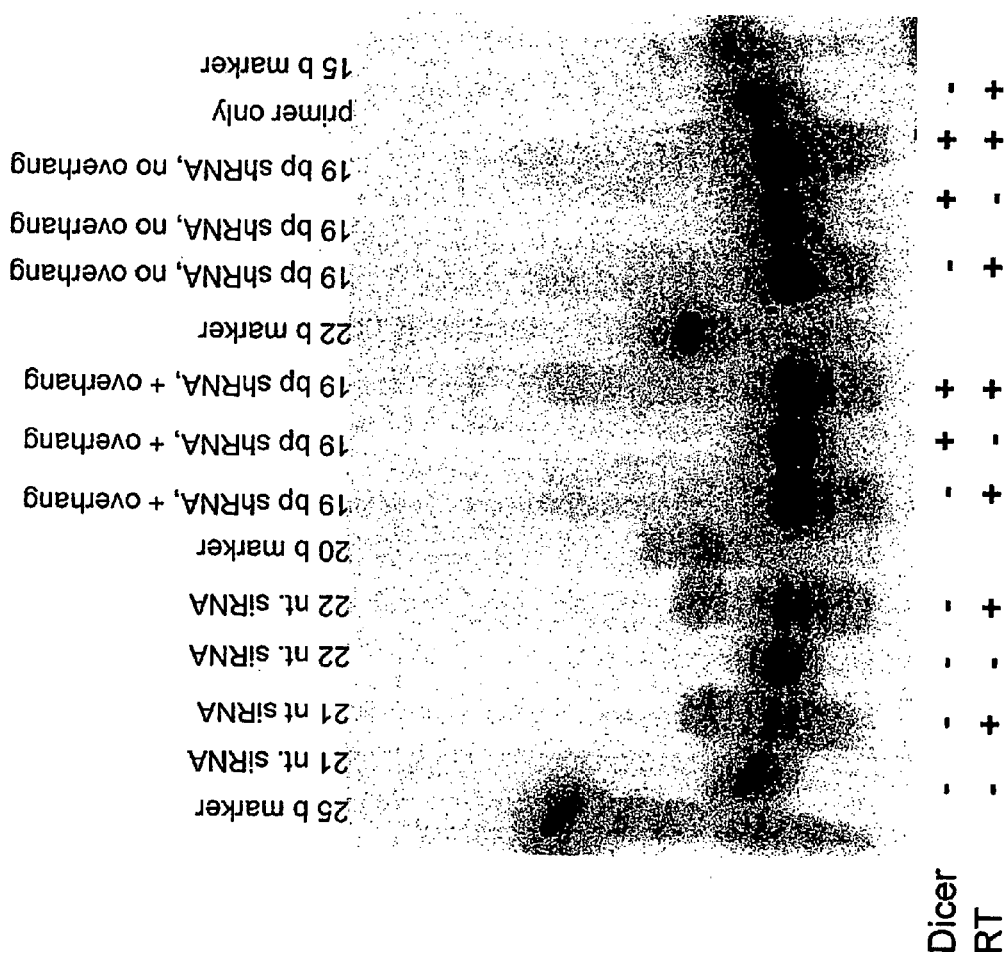
Figure 58:
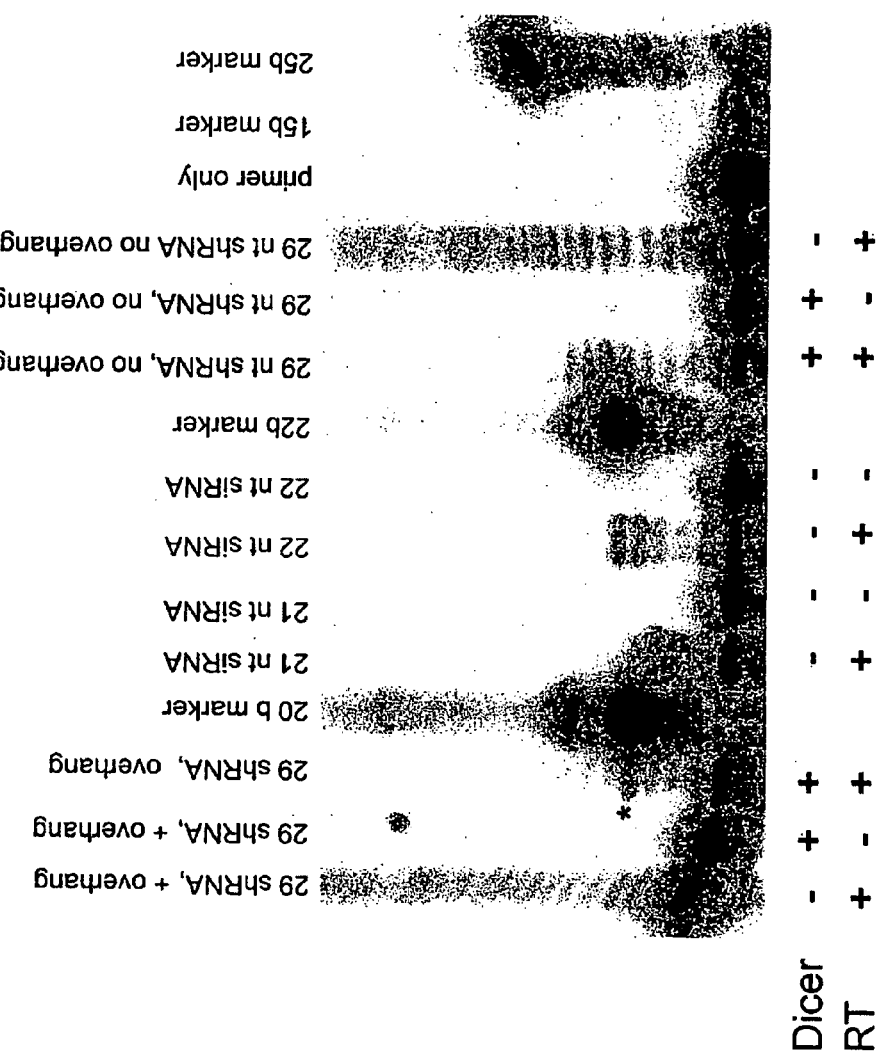
Figure 58:
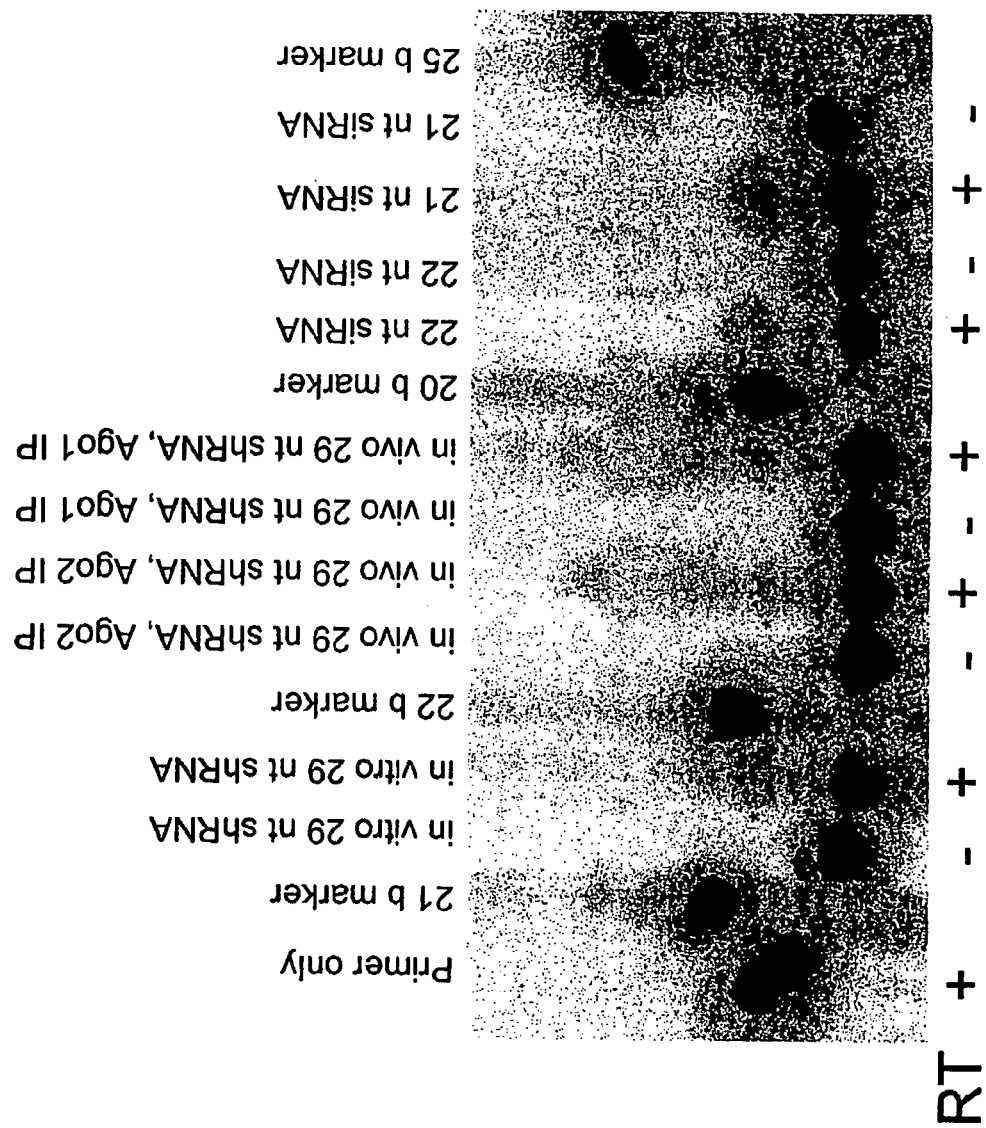

FIG. 58: Primer extension analysis reveal a single siRNA generated from Dicer processing of shRNA both in vitro and in vivo. a) 19 nt. shRNAs, as indicated (see FIG. 57a), were processed by Dicer in vitro. Reacted RNAs were extended with a specific primer that yields a 20 base product if cleavage occurs 22 bases from the 3' end of the overhung RNA (see FIG. 57a). Lanes labeled siRNA are extensions of synthetic RNAs corresponding to predicted siRNAs that would be released by cleavage 21 or 22 nucleotides from the 3' end of the overhung precursor. Observation of extension products dependents entirely on the inclusion of RT (indicated). Markers are phosphorylated, synthetic DNA oligonucleotides. b) Analysis as described in a) for 29 nt. shRNAs. The * indicates the specific extension product from the overhung shRNA species. c) Primer extension were used to analyze products from processing of overhung 29 nt. shRNAs in vivo. For comparison, extensions of in vitro processed material are also shown. Again, the * indicates the specific extension product.

FIG. 59: Gene suppression by shRNAs is comparable to or more effective than that achieved by siRNAs targeting the same sequences. a) Structures of synthetic RNAs used for these studies. b) mRNA suppression levels achieved by 43 siRNAs targeting 6 different genes compared with levels achieved by 19-mer (left) or 29-mer (right) shRNAs derived from the same target sequences. All RNAs were transfected at a final concentration of 100 nM. Values indicated on the X and Y axes reflect the percentage of mRNA remaining in HeLa cells 24 hours after RNA transfection compared with cells treated with transfection reagent alone. c) Titration analysis comparing efficacies of four siRNA/shRNA sets targeting MAPK14. Curves are graphed from data derived from transfections at 1.56, 6.25, 25, and 100 nM final concentrations of RNA. (diamonds: 21-mer siRNAs; squares: 19-mer shRNAs; triangles: 29-mer shRNAs).

Figure 60:
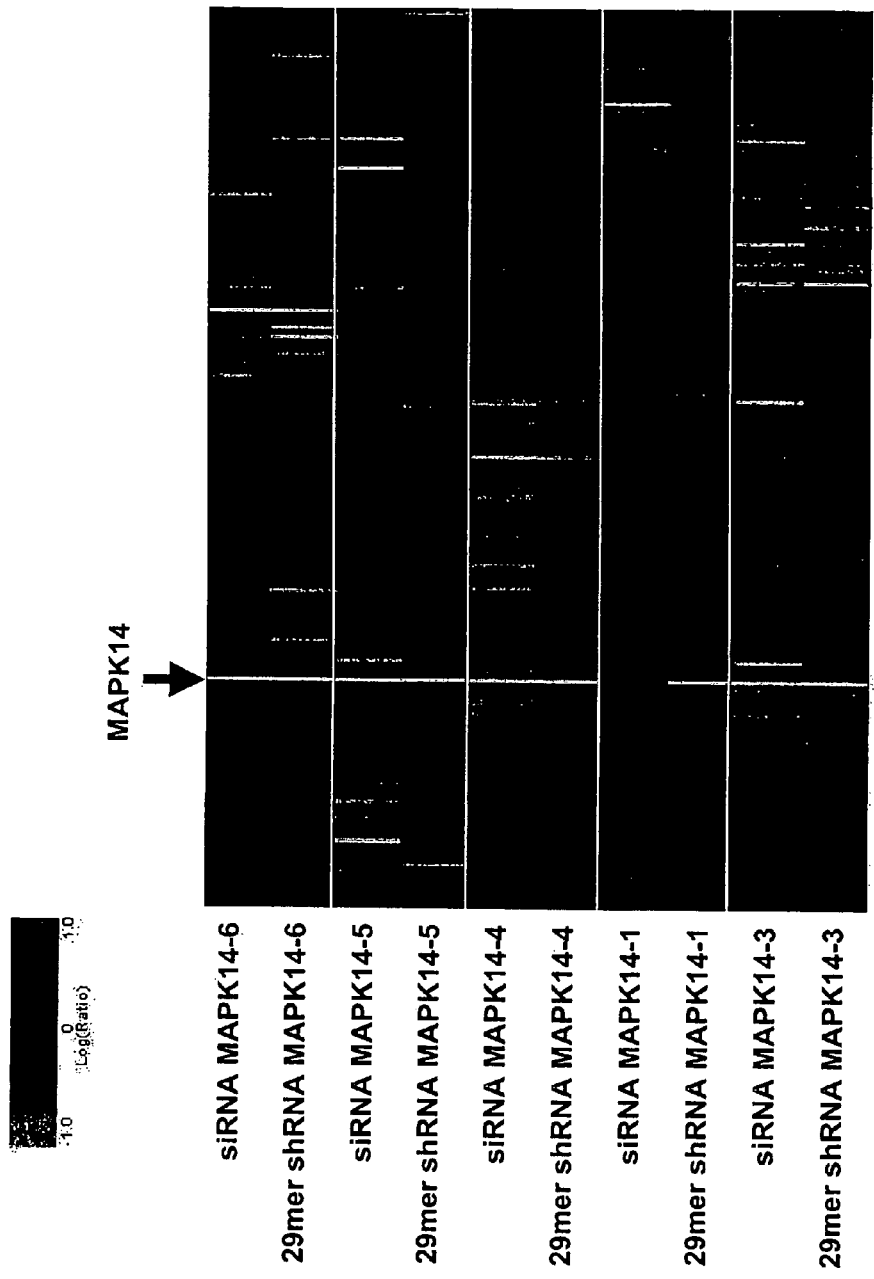

FIG. 60: Microarray profiling reveals sequence-specific gene expression profiles and more similarity between 29-mer shRNAs and cognate siRNAs than observed for 19-mer shRNAs. Each row of the heat maps reports the gene expression signature resulting from transfection of an individual RNA. Data shown represent genes that display at least a 2-fold change in expression level (P value <0.01 and log 10 intensity >1) relative to mock-transfected cells. Green indicates decreased expression relative to mock transfection whereas red indicates elevated expression. a) 19-mer shRNAs and siRNAs designed for six different target sequences within the coding region of the MAPK14 gene were tested for gene silencing after 24 hours in HeLa cells. b) A similar experiment to that described in a) but carried out with five 29-mer shRNAs targeting MAPK14.

DETAILED DESCRIPTION OF CERTAIN PREFERRED EMBODIMENTS

I. Overview

The present invention provides methods for attenuating gene expression in a cell using gene-targeted double stranded RNA (dsRNA). The dsRNA contains a nucleotide sequence that hybridizes under physiologic conditions of the cell to the nucleotide sequence of at least a portion of the gene to be inhibited (the "target" gene). The nucleotide sequence can hybridize to either coding or non-coding sequence of the target gene.

A significant aspect to certain embodiments of the present invention relates to the demonstration in the present application that RNAi can in fact be accomplished both in cultured mammalian cells and in whole organisms. This had not been previously described in the art.

Another salient feature of the present invention concerns the ability to carry out RNAi in higher eukaryotes, particularly in non-oocytic cells of mammals, e.g., cells from adult mammals as an example.

Furthermore, in contrast to the teachings of the prior art, we demonstrate that RNAi in mammalian systems can be mediated with dsRNA identical or similar to non-coding sequence of a target gene. It was previously believed that although dsRNA identical or similar to non-coding sequences (i.e., promoter, enhancer, or intronic sequences) did not inhibit RNAi, such dsRNAs were not thought to mediate RNAi.

In addition, the instant invention also demonstrates that short hairpin RNA (shRNA) may effectively be used in the subject RNAi methods. In certain embodiments, shRNAs specifically designed as Dicer substrates can be used as more potent inducers of RNAi than siRNAs. Not only is maximal inhibition achieved at much lower levels of transfected RNA, but also endpoint inhibition is often greater. In certain other embodiments, mimicking natural pre-miRNAs by inclusion of a 1-5 nucleotide(s), especially a 2 nucleotide 3' overhang, enhances the efficiency of Dicer cleavage and directs cleavage to a specific position in the precursor. The presence of this specific processing site further permits the application of rules for siRNA design to shRNAs, both for chemical synthesis and vector-based delivery of such shRNA constructs. These teachings provide improved methods for evoking RNAi in mammalian cells, and thus improved ability to produce highly potent silencing triggers in therapeutic application of RNAi.

As described in further detail below, the present invention(s) are based on the discovery that the RNAi phenomenon is mediated by a set of enzyme activities, including an essential RNA component, that are evolutionarily conserved in eukaryotes ranging from plants to mammals.

One enzyme contains an essential RNA component. After partial purification, a multi-component nuclease (herein "RISC nuclease") co-fractionates with a discrete, 22-nucleotide RNA species which may confer specificity to the nuclease through homology to the substrate mRNAs. The short RNA molecules are generated by a processing reaction from the longer input dsRNA. Without wishing to be bound by any particular theory, these 22-mer guide RNAs may serve as guide sequences that instruct the RISC nuclease to destroy specific mRNAs corresponding to the dsRNA sequences.

As illustrated, double stranded forms of the 22-mer guide RNA can be sufficient in length to induce sequence-dependent dsRNA inhibition of gene expression. In the illustrated example, dsRNA constructs are administered to cells having a recombinant luciferase reporter gene. In the control cell, e.g., no exogenously added RNA, the level of expression of the luciferase reporter is normalized to be the value of "1". As illustrated, both long (500-mer) and short (22-mer) dsRNA constructs complementary to the luciferase gene could inhibit expression of that gene product relative to the control cell. On the other hand, similarly sized dsRNA complementary to the coding sequence for another protein, green fluorescence protein (GFP), did not significantly effect the expression of luciferase—indicating that the inhibitory phenomena was in each case sequence-dependent. Likewise, single stranded 22-mers of luciferase did not inhibit expression of that gene—indicating that the inhibitory phenomena is double stranded-dependent.

The appended examples also identify an enzyme, Dicer, that can produce the putative guide RNAs. Dicer is a member of the RNAse III family of nucleases that specifically cleave dsRNA and is evolutionarily conserved in worms, flies, plants, fungi and, as described herein, mammals. The enzyme has a distinctive structure which includes a helicase domain and dual RNAse III motifs. Dicer also contains a region of homology to the RDE1/QDE2/ARGONAUTE family, which have been genetically linked to RNAi in lower eukaryotes. Indeed, activation of, or overexpression of Dicer may be sufficient in many cases to permit RNA interference in otherwise non-receptive cells, such as cultured eukaryotic cells, or mammalian (non-oocytic) cells in culture or in whole organisms.

In certain embodiments, the cells can be treated with an agent(s) that inhibits the general double-stranded RNA response(s) by the host cells, such as may give rise to sequence-independent apoptosis. For instance, the cells can be treated with agents that inhibit the dsRNA-dependent protein kinase known as PKR (protein kinase RNA-activated). Double stranded RNAs in mammalian cells typically activate protein kinase PKR and lead to apoptosis. The mechanism of action of PKR includes phosphorylation and inactivation of eIF2α (Fire, Trends Genet. 15: 358, 1999). It has also been reported that induction of NF-κB by PKR is involved in apoptosis commitment and this process is mediated through activation of the IKK complex. This sequence-independent response may reflect a form of primitive immune response, since the presence of dsRNA is a common feature of many viral lifecycles.

As described herein, Applicants have demonstrated that the PKR response can be overcome in favor of the sequence-specific RNAi response. However, in certain instances, it may be desirable to treat the cells with agents which inhibit expression of PKR, cause its destruction, and/or inhibit the kinase activity of PKR, and such methods are specifically contemplated for use in the present invention. Likewise, overexpression of agents which ectopically activate eIF2α can be used. Other agents which can be used to suppress the PKR response include inhibitors of IKK phosphorylation of IκCB, inhibitors of IκB ubiquitination, inhibitors of IκB degradation, inhibitors of NF-κB nuclear translocation, and inhibitors of NF-κB interaction with κB response elements.

Other inhibitors of sequence-independent dsRNA response in cells include the gene product of the vaccinia virus E3L. The E3L gene product contains two distinct domains. A conserved carboxy-terminal domain has been shown to bind double-stranded RNA (dsRNA) and inhibit the antiviral dsRNA response by cells. Expression of at least that portion of the E3L gene in the host cell, or the use of polypeptide or peptidomimetics thereof, can be used to suppress the general dsRNA response. Caspase inhibitors sensitize cells to killing by double-stranded RNA. Accordingly, ectopic expression or activation of caspases in the host cell can be used to suppress the general dsRNA response.

In other embodiments, the subject method is carried out in cells which have little or no general response to double stranded RNA, e.g., have no PKR-dependent dsRNA response, at least under the culture conditions. As illustrated in FIGS. 28-32, CHO and P19 cells can be used without having to inhibit PKR or other general dsRNA responses.

Also as described in further detail below, the present invention(s) are partially based on the discovery that short hairpin RNA specifically designed as Dicer substrates are more potent inducers of RNAi than siRNAs. In certain embodiments, shRNA constructs with 1-5, preferably two 3' overhang nucleotides are substrates particularly well-adapted for Dicer-mediated cleavage, and are more potent inhibitors of target genes then their siRNA counterparts with identical complementary sequences. Such shRNA can be formed either in vitro or in vivo by, for example, sequence-specific pairing after chemical synthesis, or transcription from a promoter operatively-linked to a DNA encoding such hairpin structure.

Thus, the present invention provides a process and compositions for inhibiting expression of a target gene in a cell, especially a mammalian cell. In certain embodiments, the process comprises introduction of RNA (the "dsRNA construct") with partial or fully double-stranded character into the cell or into the extracellular environment. Inhibition is specific in that a nucleotide sequence from a portion of the target gene is chosen to produce the dsRNA construct. The dsRNA may be identical or similar to coding or non-coding sequence of the target gene. In preferred embodiments, the method utilizes a cell in which Dicer and/or Argonaute activities are recombinantly expressed or otherwise ectopically activated. This process can be (1) effective in attenuating gene expression, (2) specific to the targeted gene, and (3) general in allowing inhibition of many different types of target gene.

II. Definitions

For convenience, certain terms employed in the specification, examples, and appended claims are collected here.

As used herein, the term "vector" refers to a nucleic acid molecule capable of transporting another nucleic acid to which it has been linked. One type of vector is a genomic integrated vector, or "integrated vector", which can become integrated into the chromosomal DNA of the host cell. Another type of vector is an episomal vector, i.e., a nucleic acid capable of extra-chromosomal replication. Vectors capable of directing the expression of genes to which they are operatively linked are referred to herein as "expression vectors". In the present specification, "plasmid" and "vector" are used interchangeably unless otherwise clear from the context.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides.

As used herein, the term "gene" or "recombinant gene" refers to a nucleic acid comprising an open reading frame encoding a polypeptide of the present invention, including both exon and (optionally) intron sequences. The nucleic acid may also optionally include non-coding sequences such as promoter or enhancer sequences. A "recombinant gene" refers to nucleic acid encoding such regulatory polypeptides, that may optionally include intron sequences that are derived from chromosomal DNA. The term "intron" refers to a DNA sequence present in a given gene that is not translated into protein and is generally found between exons.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

Likewise, "encodes", unless evident from its context, will be meant to include DNA sequences that encode a polypeptide, as the term is typically used, as well as DNA sequences that are transcribed into inhibitory antisense molecules.

The term "loss-of-function", as it refers to genes inhibited by the subject RNAi method, refers to a diminishment in the level of expression of a gene(s) in the presence of one or more dsRNA construct(s) when compared to the level in the absence of such dsRNA construct(s).

The term "expression" with respect to a gene sequence refers to transcription of the is gene and, as appropriate, translation of the resulting mRNA transcript to a protein. Thus, as will be clear from the context, expression of, a protein coding sequence results from transcription and translation of the coding sequence.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "cultured cells" refers to cells suspended in culture, e.g., dispersed in culture or in the form tissue. It does not, however, include oocytes or whole embryos (including blastocysts and the like) which may be provided in culture. In certain embodiments, the cultured cells are adults cells, e.g., non-embryonic.

By "recombinant virus" is meant a virus that has been genetically altered, e.g., by the addition or insertion of a heterologous nucleic acid construct into the particle.

As used herein, the terms "transduction" and "transfection" are art recognized and mean the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a dsRNA construct.

"Transient transfection" refers to cases where exogenous DNA does not integrate into the genome of a transfected cell, e.g., where episomal DNA is transcribed into mRNA and translated into protein.

A cell has been "stably transfected" with a nucleic acid construct when the nucleic acid construct is capable of being inherited by daughter cells.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences can be directly or indirectly regulated by the target receptor protein. Exemplary transcriptional control sequences are promoter sequences. A reporter gene is meant to include a promoter-reporter gene construct that is heterologously expressed in a cell.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

As used herein, "proliferating" and "proliferation" refer to cells undergoing mitosis.

As used herein, "immortalized cells" refers to cells that have been altered via chemical, genetic, and/or recombinant means such that the cells have the ability to grow through an indefinite number of divisions in culture.

The "growth state" of a cell refers to the rate of proliferation of the cell and the state of differentiation of the cell.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes.

The term "histocompatibility" refers to the similarity of tissue between different individuals. The level of histocompatibility describes how well matched the patient and donor are. The major histocompatibility determinants are the human leukocyte antigens (HLA). HLA typing is performed between the potential marrow donor and the potential transplant recipient to determine how close a HLA match the two are. The closer the match the less the donated marrow and the patient's body will react against each other.

The term "human leukocyte antigens" or "HLA", refers to proteins (antigens) found on the surface of white blood cells and other tissues that are used to match donor and patient. For instances, a patient and potential donor may have their white blood cells tested for such HLA antigens as, HLA-A, B and DR. Each individual has two sets of these antigens, one set inherited from each parent. For this reason, it is much more likely for a brother or sister to match the patient than an unrelated individual, and much more likely for persons of the same racial and ethnic backgrounds to match each other.

III. Exemplary Embodiments of Isolation Method

One aspect of the invention provides a method for potentiating RNAi by induction or ectopic activation of an RNAi enzyme in a cell (in vitro or in vitro) or cell-free mixtures. In preferred embodiments, the RNAi activity is activated or added to a mammalian cell, e.g., a human cell, which cell may be provided in vitro or as part of a whole organism. In other embodiments, the subject method is carried out using eukaryotic cells generally (except for oocytes) in culture. For instance, the Dicer enzyme may be activated by virtue of being recombinantly expressed or it may be activated by use of an agent which (i) induces expression of the endogenous gene, (ii) stabilizes the protein from degradation, and/or (iii) allosterically modifies the enzyme to increase its activity (by altering its $k_{cat}$, $K_m$ or both).

A. Dicer and Argonaut Activities

In certain embodiments, at least one of the activated RNAi enzymes is Dicer, or a homolog thereof. In certain preferred embodiments, the present method provides for ectopic activation of Dicer. As used herein, the term "Dicer" refers to a protein which (a) mediates an RNAi response and (b) has an amino acid sequence at least 50 percent identical, and more preferably at least 75, 85, 90 or 95 percent identical to SEQ ID NO: 2 or 4, and/or which can be encoded by a nucleic acid which hybridizes under wash conditions of 2×SSC at 22° C., and more preferably 0.2×SSC at 65° C., to a nucleotide represented by SEQ ID NO: 1 or 3. Accordingly, the method may comprise introducing a dsRNA construct into a cell in which Dicer has been recombinantly expressed or otherwise ectopically activated.

In certain embodiment, at least one of the activated RNAi enzymes is Argonaut, or a homolog thereof. In certain preferred embodiments, the present method provides for ectopic activation of Argonaut. As used herein, the term "Argonaut" refers to a protein which (a) mediates an RNAi response and (b) has an amino acid sequence at least 50 percent identical, and more preferably at least 75, 85, 90 or 95 percent identical to the amino acid sequence shown in FIG. 24. Accordingly, the method may comprise introducing a dsRNA construct into a cell in which Argonaut has been recombinantly expressed or otherwise ectopically activated.

This invention also provides expression vectors containing a nucleic acid encoding a Dicer or Argonaut polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject is Dicer or Argonaut proteins. Accordingly, the term transcriptional regulatory sequence includes promoters, enhancers and other expression control elements. Such regulatory sequences are described in Goeddel, *Gene Expression Technology*: Methods in Enzymology 185, Academic Press, San Diego, Calif., 1990. For instance, any of a wide variety of expression control sequences, sequences that control the expression of a DNA sequence when operatively linked to it, may be used in these vectors to express DNA sequences encoding Dicer or Argonaut polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Moreover, the vector's copy number, the ability to control that copy number and the expression of any other proteins encoded by the vector, such as antibiotic markers, should also be considered.

The recombinant Dicer or Argonaut genes can be produced by ligating a nucleic acid encoding a Dicer or Argonaut polypeptide into a vector suitable for expression in either prokaryotic cells, eukaryotic cells, or both. Expression vectors for production of recombinant forms of the subject Dicer or Argonaut polypeptides include plasmids and other vectors. For instance, suitable vectors for the expression of a Dicer or Argonaut polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as Ampicillin can be used. In an illustrative embodiment, a Dicer or Argonaut polypeptide is produced recombinantly utilizing an expression vector generated by sub-cloning the coding sequence of a Dicer or Argonaut gene.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In yet another embodiment, the subject invention provides a "gene activation" construct which, by homologous recombination with a genomic DNA, alters the transcriptional regulatory sequences of an endogenous Dicer or Argonaut gene. For instance, the gene activation construct can replace the endogenous promoter of a Dicer or Argonaut gene with a heterologous promoter, e.g., one which causes constitutive expression of the Dicer or Argonaut gene or which causes inducible expression of the gene under conditions different from the normal expression pattern of Dicer or Argonaut. A variety of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous Dicer or Argonaut gene (exon sequence, intron sequence, promoter sequences, etc.) which direct recombination and (2) heterologous transcriptional regulatory sequence(s) which is to be operably linked to the coding sequence for the genomic Dicer or Argonaut gene upon recombination of the gene activation construct. For use in generating cultures of Dicer or Argonaut producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native Dicer or Argonaut gene. Such insertion occurs by homologous recombination, i.e., recombination regions of the activation construct that are homologous to the endogenous Dicer or Argonaut gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety of elements, including: promoters (such as constitutive or inducible promoters), enhancers, negative regulatory elements, locus control regions, transcription factor binding sites, or combinations thereof.

Promoters/enhancers which may be used to control the expression of the targeted gene in vitro include, but are not limited to, the cytomegalovirus (CMV) promoter/enhancer (Karasuyama et al., *J. Exp. Med.* 169: 13, 1989), the human β-actin promoter (Gunning et al., PNAS 84: 48314835, 1987), the glucocorticoid-inducible promoter present in the mouse mammary tumor virus long terminal repeat (MMTV LTR) (Klessig et al., *Mol. Cell. Biol.* 4: 1354-1362, 1984), the long terminal repeat sequences of Moloney murine leukemia virus (MuLV LTR) (Weiss et al. (1985) *RNA Tumor Viruses*, Cold Spring Harbor Laboratory, Cold Spring Harbor, N.Y.), the SV40 early or late region promoter (Bemoist et al., *Nature* 290: 304-310, 1981; Templeton et al., *Mol. Cell. Biol.* 4: 817, 1984; and Sprague et al., *J. Virol.* 45: 773, 1983), the promoter contained in the 3' long terminal repeat of Rous sarcoma virus (RSV) (Yamamoto et al., *Cell* 22: 787-797, 1980), the herpes simplex virus (HSV) thymidine kinase promoter/enhancer (Wagner et al., *PNAS* 82: 3567-71, 1981), and the herpes simplex virus LAT promoter (Wolfe et al., *Nature Genetics* 1: 379-384, 1992).

In still other embodiments, the replacement region merely deletes a negative transcriptional control element of the native gene, e.g., to activate expression, or ablates a positive control element, e.g., to inhibit expression of the targeted gene.

B. Cell/Organism

The cell with the target gene may be derived from or contained in any organism (e.g., plant, animal, protozoan, virus, bacterium, or fungus). The dsRNA construct may be synthesized either in vitro or in vitro. Endogenous RNA polymerase of the cell may mediate transcription in vitro, or cloned RNA polymerase can be used for transcription in vitro or in vitro. For generating double stranded transcripts from a transgene in vitro, a regulatory region may be used to transcribe the RNA strand (or strands). Furthermore, dsRNA can be generated by transcribing an RNA strand which forms a hairpin, thus producing a dsRNA.

Genetic manipulation becomes possible in organisms that are not classical genetic models. Breeding and screening programs may be accelerated by the ability to rapidly assay the consequences of a specific, targeted gene disruption. Gene disruptions may be used to discover the function of the target gene, to produce disease models in which the target gene are involved in causing or preventing a pathological condition, and to produce organisms with improved economic properties.

The cell with the target gene may be derived from or contained in any organism. The organism may be a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies.

Plants include *arabidopsis*; field crops (e.g., alfalfa, barley, bean, corn, cotton, flax, pea, rape, rice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, blackberry, blueberry, cacao, cherry, coconut, cranberry, date, faJoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber).

Examples of vertebrate animals include fish, mammal, cattle, goat, pig, sheep, rodent, hamster, mouse, rat, primate, and human.

Invertebrate animals include nematodes, other worms, *Drosophila*, and other insects. Representative generae of nematodes include those that infect animals (e.g., *Ancylostoma, Ascaridia, Ascaris, Bunostomum, Caenorhabditis, Capillaria, Chabertia, Cooperia, Dictyocaulus, Haemonchus, Heterakis, Nematodirus, Oesophagostomum, Ostertagia, Oxyuris, Parascaris, Strongylus, Toxascaris, Trichuris, Trichostrongylus, Tflichonema, Toxocara, Uncinaria*) and those that infect plants (e.g., *Bursaphalenchus, Criconeriella, Diiylenchus, Ditylenchus, Globodera, Helicotylenchus, Heterodera, Longidorus, Melodoigyne, Nacobbus, Paratylenchus, Pratylenchus, Radopholus, Rotelynchus, Tylenchus,* and *Xiphinerna*). Representative orders of insects include *Coleoptera, Diptera, Lepidoptera,* and *Homoptera*.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

C. Targeted Genes

The target gene may be a gene derived from the cell, an endogenous gene, a transgene, or a gene of a pathogen which is present in the cell after infection thereof. Depending on the particular target gene and the dose of double stranded RNA material delivered, the procedure may provide partial or complete loss of function for the target gene. Lower doses of injected material and longer times after administration of dsRNA may result in inhibition in a smaller fraction of cells. Quantitation of gene expression in a cell may show similar amounts of inhibition at the level of accumulation of target mRNA or translation of target protein.

"Inhibition of gene expression" refers to the absence (or observable decrease) in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxy acid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of dsRNA may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

As disclosed herein, the present invention is not limited to any type of target gene or nucleotide sequence. But the following classes of possible target genes are listed for illustrative purposes: developmental genes (e.g., adhesion molecules, cyclin kinase inhibitors, Writ family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA 1, BRCA2, MADH4, MCC, NF 1, NF2, RB 1, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

D. dsRNA constructs

The dsRNA construct may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. The dsRNA construct may be produced enzymatically or by partial/total organic synthesis, any modified ribonucleotide can be introduced by in vitro enzymatic or organic synthesis.

The dsRNA construct may be directly introduced into the cell (i.e., intracellularly); or introduced extracellularly into a cavity, interstitial space, into the circulation of an organism, introduced orally, or may be introduced by bathing an organism in a solution containing RNA. Methods for oral introduction include direct mixing of RNA with food of the organism, as well as engineered approaches in which a species that is used as food is engineered to express an RNA, then fed to the organism to be affected. Physical methods of introducing nucleic acids include injection of an RNA solution directly into the cell or extracellular injection into the organism.

The double-stranded structure may be formed by a single self-complementary RNA strand (such as in the form of shRNA) or two complementary RNA strands (such as in the form of siRNA). RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition.

dsRNA constructs containing a nucleotide sequences identical to a portion, of either coding or non-coding sequence, of the target gene are preferred for inhibition. RNA sequences with insertions, deletions, and single point mutations relative to the target sequence (ds RNA similar to the target gene) have also been found to be effective for inhibition. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). In certain preferred embodiments, the length of the dsRNA is at least 20, 21 or 22 nucleotides in length, e.g., corresponding in size to RNA products produced by Dicer-dependent cleavage. In certain embodiments, the dsRNA construct is at least 25, 50, 100, 200, 300 or 400 bases. In certain embodiments, the dsRNA construct is 400-800 bases in length.

In one embodiment, the dsRNA is a single-stranded hairpin ribonucleic acid (shRNA) comprising self complementary sequences of 19 to 100 nucleotides that form a duplex region, which self complementary sequences hybridize under intracellular conditions to a target gene, wherein said hairpin RNA: (i) is a substrate for cleavage by a RNaseIII enzyme to produce a double-stranded RNA product, (ii) does not produce a general sequence-independent killing of the mammalian cells, and (iii) reduces expression of said target gene in a manner dependent on the sequence of said complementary regions. In a preferred embodiment, the shRNA comprises a 3' overhang of about 14 nucleotides.

In a related embodiment, he dsRNA is a single-stranded hairpin ribonucleic acid (shRNA) comprising self complementary sequences of 19 to 100 nucleotides that form a duplex region, which self complementary sequences hybridize under intracellular conditions to a target gene, wherein said hairpin RNA: (i) is cleaved in the mammalian cells to produce an RNA guide sequence that enters an Argonaut-containing complex, (ii) does not produce a general sequence-independent killing of the mammalian cells, and (iii) reduces expression of said target gene in a manner dependent on the sequence of said complementary regions. In a preferred embodiment, the shRNA comprises a 3' overhang of about 1-4 nucleotides.

The size of the duplex region of the subject shRNA may be longer (e.g., anywhere between 19 to about 1000 nucleotides, or 19-about 500 nt, or 19-about 250 nt, etc.), but in many applications, about 29 nucleotides is sufficient. In certain embodiments, the duplex region is any where between about 25-29 nt. In other embodiments, the duplex region is any where between about 19-25 nt.

The size of the 3' overhang may be 1-5 nucleotides, preferably 2-4 nucleotides. In one embodiment, the 3' overhang is 2 nucleotides. The specific sequences of the 3' overhang nucleotides are less important. In one embodiment, the overhang nucleotides can be any nucleotides, including "non-standard" or modified nucleotides. In other embodiments, the overhang sequences are mostly pyrimidines, such as U, C, or T. In one embodiment, the 2-nucleotide overhang is UU.

In certain embodiments, the 5' of the shRNA may have 1-5 nt overhang that does not pair with the 3' overhang.

The size of the "loop" between the paired duplex region may vary, but preferably contains at least about 3-8 nucleotides, such as 4 nucleotides.

100% sequence identity between the RNA and the target gene is not required to practice the present invention. Thus the invention has the advantage of being able to tolerate sequence variations that might be expected due to genetic mutation, strain polymorphism, or evolutionary divergence.

The dsRNA construct may be synthesized either in vitro or in vitro. Endogenous RNA polymerase of the cell may mediate transcription in vitro, or cloned RNA polymerase can be used for transcription in vitro or in vitro. For transcription from a transgene in vitro or an expression construct, a regulatory region (e.g., promoter, enhancer, silencer, splice donor and acceptor, polyadenylation) may be used to transcribe the dsRNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. The dsRNA construct may be chemically or enzymatically synthesized by manual or automated reactions. The dsRNA construct may be synthesized by a cellular RNA polymerase or a bacteriophage RNA polymerase (e.g., T3, T7, SP6). The use and production of an expression construct are known in the art (see also WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography or a combination thereof. Alternatively, the dsRNA construct may be used with no or a minimum of purification to avoid losses due to sample processing. The dsRNA construct may be dried for storage or dissolved in an aqueous solution. The solution may contain buffers or salts to promote annealing, and/or stabilization of the duplex strands.

Physical methods of introducing nucleic acids include injection of a solution containing the dsRNA construct, bombardment by particles covered by the dsRNA construct, soaking the cell or organism in a solution of the RNA, microinjected into the target (e.g., mammalian target) cells, or electroporation of cell membranes in the presence of the dsRNA construct. A viral construct packaged into a viral particle would accomplish both efficient introduction of an expression construct into the cell and transcription of dsRNA construct encoded by the expression construct. In one embodiment, the shRNA is a transcriptional product that is transcribed from an expression construct introduced into the target (e.g., mammalian target) cells, which expression construct comprises a coding sequence for transcribing said shRNA, operably linked to one or more transcriptional regulatory sequences. Such transcriptional regulatory sequences may include a promoter for an RNA polymerase, such as a cellular RNA polymerase. Exemplary but not limiting promoters include: a U6 promoter, a T7 promoter, a T3 promoter, or an SP6 promoter. In certain embodiments, the transcriptional regulatory sequences includes an inducible promoter.

The dsRNA constructs may be integrated into the host genome, such that the target cells are stably transfected with the dsRNA expression constructs. The constructs may be suitable for stable integration into either cells in culture or in an animal. For example, the constructs may be integrated into embryonic cells, such as a mouse ES cell, to generate a transgenic animal. The constructs may also be integrated into adult somatic cells, either primary cell or established cell line.

In certain embodiments, the expression of a target gene (either endogenous or heterologous gene) is attenuated by at least about 33%, or about 50%, about 60%, 70%, 80%, 90%, 95%, or 99% or more, relative to expression in cells not treated with the dsRNA (e.g., shRNA).

The shRNA may be chemically synthesized, or in vitro transcripted, and may further include one or more modifications to phosphate-sugar backbone or nucleosides residues.

Other methods known in the art for introducing nucleic acids to cells may be used, such as lipid-mediated carrier transport, chemical mediated transport, such as calcium phosphate, and the like. Thus the dsRNA construct may be introduced along with components that perform one or more of the following activities: enhance RNA uptake by the cell, promote annealing of the duplex strands, stabilize the annealed strands, or other-wise increase inhibition of the target gene.

E. Illustrative Uses

One utility of the present invention is as a method of identifying gene function in an organism, especially higher eukaryotes, comprising the use of double-stranded RNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceuticals, understanding normal and pathological events associated with development, determining signaling pathways responsible for postnatal development/aging, and the like. The increasing speed of acquiring nucleotide sequence information from genomic and expressed gene sources, including total sequences for mammalian genomes, can be coupled with the invention to determine gene function in a cell or in a whole organism. The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which the dsRNA construct can be introduced into an intact cell/organism containing the target gene allows the present invention to be used in high throughput screening (HTS). For example, duplex RNA can be produced by an amplification reaction using primers flanking the inserts of any gene library derived from the target cell or organism. Inserts may be derived from genomic DNA or mRNA (e.g., cDNA and cRNA). Individual clones from the library can be replicated and then isolated in separate reactions, but preferably the library is maintained in individual reaction vessels (e.g., a 96 well microtiter plate) to minimize the number of steps required to practice the invention and to allow automation of the process.

In an exemplary embodiment, the subject invention provides an arrayed library of RNAi constructs. The array may be in the form of solutions, such as multi-well plates, or may be "printed" on solid substrates upon which cells can be grown. To illustrate, solutions containing duplex RNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity.

In one embodiment, the subject method uses an arrayed library of RNAi constructs to screen for combinations of RNAi that are lethal to host cells. Synthetic lethality is a bedrock principle of experimental genetics. A synthetic lethality describes the properties of two mutations which, individually, are tolerated by the organism but which, in combination, are lethal. The subject arrays can be used to identify loss-of-function mutations that are lethal in combination with alterations in other genes, such as activated oncogenes or loss-of-function mutations to tumor suppressors. To achieve this, one can create "phenotype arrays" using cultured cells. Expression of each of a set of genes, such as the host cell's genome, can be individually systematically disrupted using RNA interference. Combination with alterations in oncogene and tumor suppressor pathways can be used to identify synthetic lethal interactions that may identify novel therapeutic targets.

In certain embodiments, the RNAi constructs can be fed directly to, or injected into, the cell/organism containing the target gene. Alternatively, the duplex RNA can be produced by in vitro or in vitro transcription from an expression construct used to produce the library. The construct can be replicated as individual clones of the library and transcribed to produce the RNA; each clone can then be fed to, injected into, or delivered by another method known in the art to, the cell/organism containing the target gene. The function of the target gene can be assayed from the effects it has on the cell/organism when gene activity is inhibited. This screening could be amenable to small subjects that can be processed in large number, for example, tissue culture cells derived from mammals, especially primates, and most preferably humans.

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be amplified to produce an RNA, the duplex RNA can be introduced to the organism or cell, and whether an alteration in the characteristic is correlated with inhibition can be determined. Of course, there may be trivial explanations for negative results with this type of assay, for example: inhibition of the target gene causes lethality, inhibition of the target gene may not result in any observable alteration, the fragment contains nucleotide sequences that are not capable of inhibiting the target gene, or the target gene's activity is redundant.

The present invention may be useful in allowing the inhibition of essential genes. Such genes may be required for cell or organism viability at only particular stages of development or only in specific cellular compartments or tissues. The functional equivalent of conditional mutations may be produced by inhibiting activity of the target gene when or where it is not required for viability. The invention allows addition of RNA at specific times of development and locations in the organism without introducing permanent mutations into the target genome.

The present invention may be useful in allowing the inhibition of genes that have been difficult to inhibit using other methods due to gene redundancy. Since the present methods may be used to deliver more than one dsRNA to a cell or organism, dsRNA identical or similar to more than one gene, wherein the genes have a redundant function during normal development, may be delivered.

If alternative splicing produced a family of transcripts that were distinguished by usage of characteristic exons, the present invention can target inhibition through the appropriate exons to specifically inhibit or to distinguish among the functions of family members. For example, a protein factor that contained an alternatively spliced transmembrane domain may be expressed in both membrane bound and secreted forms. Instead of isolating a nonsense mutation that terminates translation before the transmembrane domain, the functional consequences of having only secreted hormone can be determined according to the invention by targeting the exon containing the transmembrane domain and thereby inhibiting expression of membrane-bound hormone. That is, the subject method can be used for selected ablation of splicing variants.

The present invention may be used alone or as a component of a kit having at least one of the reagents necessary to carry out the in vitro or in vitro introduction of RNA to test samples or subjects. Preferred components are the dsRNA and a vehicle that promotes introduction of the dsRNA. Such a kit may also include instructions to allow a user of the kit to practice the invention.

Alternatively, an organism may be engineered to produce dsRNA which produces commercially or medically beneficial results, for example, resistance to a pathogen or its pathogenic effects, improved growth, or novel developmental patterns.

Another aspect of the invention provides a method for attenuating expression of a target gene in mammalian cells, comprising introducing into the mammalian cells a single-stranded hairpin ribonucleic acid (shRNA) comprising self complementary sequences of 19 to 100 nucleotides that form a duplex region, which self complementary sequences hybridize under intracellular conditions to a target gene, wherein said hairpin RNA: (i) is a substrate for cleavage by a RNaseIII enzyme to produce a double-stranded RNA product, (ii) does not produce a general sequence-independent killing of the mammalian cells, and (iii) reduces expression of said target gene in a manner dependent on the sequence of said complementary regions. In a preferred embodiment, the shRNA comprises a 3' overhang of about 14 nucleotides.

In a related aspect, the invention provides a method for attenuating expression of a target gene in mammalian cells, comprising introducing into the mammalian cells a single-stranded hairpin ribonucleic acid (shRNA) comprising self complementary sequences of 19 to 100 nucleotides that form a duplex region, which self complementary sequences hybridize under intracellular conditions to a target gene, wherein said hairpin RNA: (i) is cleaved in the mammalian cells to produce an RNA guide sequence that enters an Argonaut-containing complex, (ii) does not produce a general sequence-independent killing of the mammalian cells, and (iii) reduces expression of said target gene in a manner dependent on the sequence of said complementary regions. In a preferred embodiment, the shRNA comprises a 3' overhang of about 14 nucleotides.

In yet another embodiment, the invention provides a method for attenuating expression of one or more target genes in mammalian cells, comprising introducing into the mammalian cells a variegated library of single-stranded hairpin ribonucleic acid (shRNA) species, each shRNA species comprising self complementary sequences of 19 to 100 nucleotides that form duplex regions and which hybridize under intracellular conditions to a target gene, wherein each of said hairpin RNA species: (i) is a substrate for cleavage by a RNaseIII enzyme to produce a double-stranded RNA product, (ii) does not produce a general sequence-independent killing of the mammalian cells, and (iii) if complementary to a target sequence, reduces expression of said target gene in a manner dependent on the sequence of said complementary regions. In a preferred embodiment, the shRNA comprises a 3' overhang of about 1-4 nucleotides.

In certain embodiments, the variegated library of shRNA species are arrayed a solid substrate.

In another embodiment, the method includes the further step of identifying shRNA species of said variegated library which produce a detected phenotype in the mammalian cells.

Yet another aspect of the invention provide a method of enhancing the potency/activity of an RNAi therapeutic for a mammalian patient, the RNAi therapeutic comprising an siRNA of 19-22 paired polynucleotides, the method comprising replacing the siRNA with a single-stranded hairpin RNA (shRNA) of the subject invention, wherein said duplex region comprises the same 19-22 paired polynucleotides of the siRNA. This aspect of the invention is partly based on the surprising discovery that shRNA constructs designed as Dicer substrates perform at least as well as, and in most cases much better/potent than the corresponding siRNA form of dsRNA (e.g., with the same eventual target guide sequence of about 22 nucleotides).

In certain embodiments, the half-maximum inhibition by the RNAi therapeutic is achieved by a concentration of the shRNA at least about 20%, or about 30%, 40%, 50%, 60%, 70%, 80%, 90% lower than that of the corresponding siRNA.

In another embodiment, the end-point inhibition by the shRNA is at least about 40%, or about 50%, 75%, 100%, 2-fold, 3-fold, 4-fold, 5-fold, 6-fold, or 10-fold higher than that of the siRNA.

Another aspect of the invention provides a method of designing a short hairpin RNA (shRNA) construct for RNAi, the shRNA comprising a 3' overhang of about 14 nucleotides, the method comprising selecting the nucleotide about 21 bases 5' to the most 3'-end nucleotide as the first paired nucleotide in a cognate doubled-stranded siRNA with the same 3' overhang. Such shRNA can be used, for example, for RNAi in mammalian cells.

In one embodiment, the shRNA comprises about 15-45, preferably about 25-29 paired polynucleotides.

In one embodiment, the 3' overhang has 2 nucleotides.

In one embodiment, the shRNA, when cut by a Dicer enzyme (e.g., a human Dicer enzyme), produces a product siRNA that is either identical to, or differ by a single basepair immediately 5' to the 3' overhang from the cognate siRNA.

In one embodiment, the shRNA construct has substantially the same profiles of off-target gene inhibition effects as compared to the cognate siRNA construct with substantially identical target sequences.

IV. Exemplification

The invention, now being generally described, will be more readily understood by reference to the following examples, which are included merely for purposes of illustration of certain aspects and embodiments of the present invention and are not intended to limit the invention.

EXAMPLE 1

An RNA-Directed Nuclease Mediates RNAi Gene Silencing

In a diverse group of organisms that includes *Caenorhabditis elegans, Drosophila*, planaria, hydra, trypanosomes, fungi and plants, the introduction of double-stranded RNAs inhibits gene expression in a sequence-specific manner (Sharp, *Genes and Development* 13: 139-141, 1999; Sanchez-Alvarado and Newmark, *PNAS* 96: 5049-5054, 1999; Lohman et al., *Developmental Biology* 214: 211-214, 1999; Cogoni and Macino, *Nature* 399: 166-169, 1999; Waterhouse et al., *PNAS* 95: 13959-13964, 1998; Montgomery and Fire, *Trends Genet.* 14: 225-228, 1998; Ngo et al., *PNAS* 95: 14687-14692, 1998). These responses, called RNA interference or post-transcriptional gene silencing, may provide anti-viral defense, modulate transposition or regulate gene expression (Sharp, *Genes and Development* 13: 139-141, 1999; Montgomery and Fire, *Trends Genet.* 14: 225-228, 1998; Tabara et al., *Cell* 99: 123-132, 1999; Ketting et al., *Cell* 99: 133-141, 1999; Ratcliff et al., *Science* 276: 1558-1560, 1997). We have taken a biochemical approach towards elucidating the mechanisms underlying this genetic phenomenon. Here we show that 'loss-of-function' phenotypes can be created in cultured *Drosophila* cells by transfection with specific double-stranded RNAs. This coincides with a marked reduction in the level of cognate cellular messenger RNAs. Extracts of transfected cells contain a nuclease activity that specifically degrades exogenous transcripts homologous to transfected double-stranded RNA. This enzyme contains an essential RNA component. After partial purification, the sequence-specific nuclease co-fractionates with a discrete, ~25-nucleotide RNA species which may confer specificity to the enzyme through homology to the substrate mRNAs.

Although double-stranded RNAs (dsRNAs) can provoke gene silencing in numerous biological contexts including *Drosophila* (Kennerdell et al., *Cell* 95: 1017-1026, 1998; Misquitta and Paterson, *PNAS* 96: 1451-1456, 1999), the mechanisms underlying this phenomenon have remained mostly unknown. We therefore wanted to establish a biochemically tractable model in which such mechanisms could be investigated.

Figure 1A:
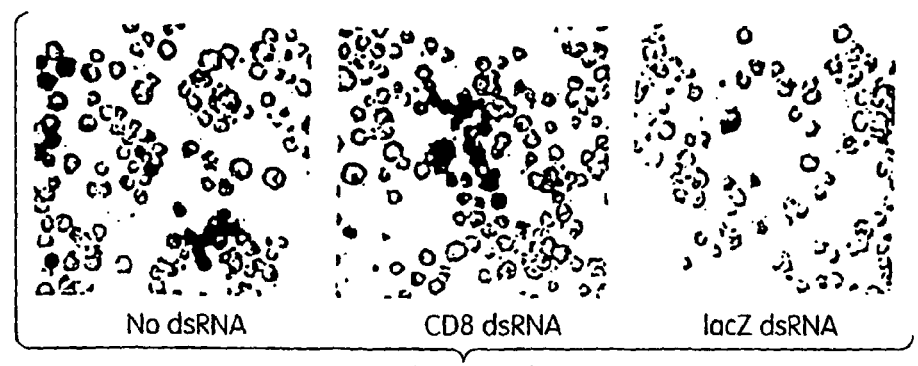
FIG. 1: RNAi in S2 cells. (a) *Drosophila* S2 cells were transfected with a plasmid that directs lacZ expression from the copia promoter in combination with dsRNAs corresponding to either human CD8 or lacZ, or with no dsRNA, as indicated. (b) S2 cells were co-transfected with a plasmid that directs expression of a GFP-US9 fusion protein and dsRNAs of either lacZ or cyclin E, as indicated. Upper panels show FACS profiles of the bulk population. Lower panels show FACS profiles from GFP-positive cells. (c) Total RNA was extracted from cells transfected with lacZ, cyclin E, fizzy or cyclin A dsRNAs, as indicated. Northern blots were hybridized with sequences not present in the transfected dsRNAs.

Transient transfection of cultured, *Drosophila* S2 cells with a lacZ expression vector resulted in β-galactosidase activity that was easily detectable by an in situ assay (FIG. 1a). This activity was greatly reduced by co-transfection with a dsRNA corresponding to the first 300 nucleotides of the lacZ sequence, whereas co-transfection with a control dsRNA (CD8) (FIG. 1a) or with single-stranded RNAs of either sense or antisense orientation (data not shown) had little or no effect. This indicated that dsRNAs could interfere, in a sequence-specific fashion, with gene expression in cultured cells.

To determine whether RNA interference (RNAi) could be used to target endogenous genes, we transfected S2 cells with a dsRNA corresponding to the first 540 nucleotides of *Drosophila cyclin* E, a gene that is essential for progression into S phase of the cell cycle.

Figure 1B:
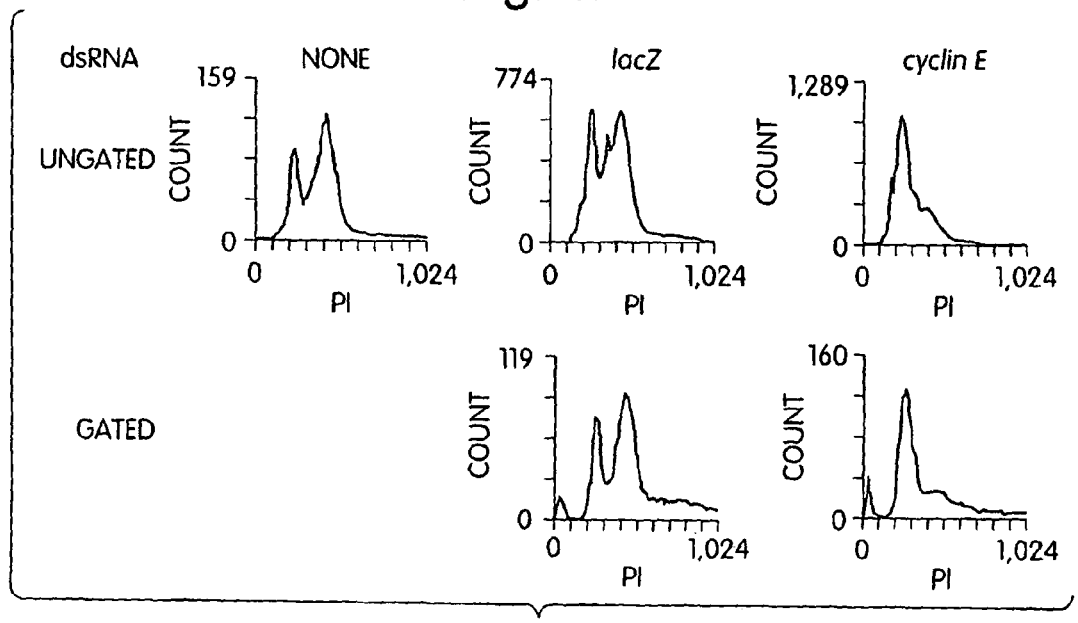

During log-phase growth, untreated S2 cells reside primarily in G2/M (FIG. 1b). Transfection with lacZ dsRNA had no effect on cell-cycle distribution, but transfection with the cyclin E dsRNA caused a G1-phase cell-cycle arrest (FIG. 1b). The ability of cyclin E dsRNA to provoke this response was length-dependent. Double-stranded RNAs of 540 and 400 nucleotides were quite effective, whereas dsRNAs of 200 and 300 nucleotides were less potent. Double-stranded cyclin E RNAs of 50 or 100 nucleotides were inert in our assay, and transfection with a single-stranded, antisense cyclin E RNA had virtually no effect.

Figure 1C:
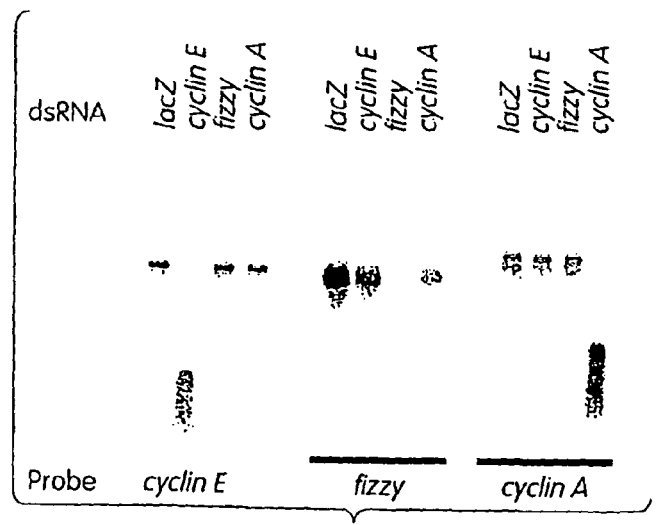

One hallmark of RNAi is a reduction in the level of mRNAs that are homologous to the dsRNA. Cells transfected with the cyclin E dsRNA (bulk population) showed diminished endogenous cyclin E mRNA as compared with control cells (FIG. 1c). Similarly, transfection of cells with dsRNAs homologous to fizzy, a component of the anaphase-promoting complex (APC) or cyclin A, a cyclin that acts in S, G2 and M, also caused reduction of their cognate mRNAs (FIG. 1c). The modest reduction in fizzy mRNA levels in cells transfected with cyclin A dsRNA probably resulted from arrest at a point in the division cycle at which fizzy transcription is low (Wolf and Jackson, *Current Biology* 8: R637-R639, 1998; Kramer et al., *Current Biology* 8: 1207-1210, 1998). These results indicate that RNAi may be a generally applicable method for probing gene function in cultured *Drosophila* cells.

The decrease in mRNA levels observed upon transfection of specific dsRNAs into *Drosophila* cells could be explained by effects at transcriptional or post-transcriptional levels. Data from other systems have indicated that some elements of the dsRNA response may affect mRNA directly (reviewed in Sharp, *Genes and Development* 13: 139-141, 1999; Montgomery and Fire, *Trends Genet.* 14: 225-228, 1998). We therefore sought to develop a cell-free assay that reflected, at least in part, RNAi.

Figure 2A:
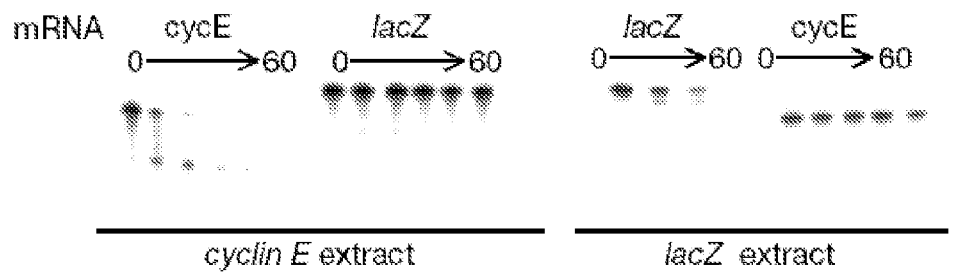
FIG. 2: RNAi in vitro. (a) Transcripts corresponding to either the first 600 nucleotides of *Drosophila cyclin* E (E600) or the first 800 nucleotides of lacZ (Z800) were incubated in lysates derived from cells that had been transfected with either lacZ or cyclin E (cycE) dsRNAs, as indicated. Time points were 0, 10, 20, 30, 40 and 60 min for cyclin E and 0, 10, 20, 30 and 60 min for lacZ. (b) Transcripts were incubated in an extract of S2 cells that had been transfected with cyclin E dsRNA (cross-hatched box, below). Transcripts corresponded to the first 800 nucleotides of lacZ or the first 600, 300, 220 or 100 nucleotides of cyclin E, as indicated. Eout is a transcript derived from the portion of the cyclin E cDNA not contained within the transfected dsRNA. E-ds is identical to the dsRNA that had been transfected into S2 cells. Time points were 0 and 30 min. (c) Synthetic transcripts complementary to the complete cyclin E cDNA (Eas) or the final 600 nucleotides (Eas600) or 300 nucleotides (Eas300) were incubated in extract for 0 or 30 min.

S2 cells were transfected with dsRNAs corresponding to either cyclin E or lacZ. Cellular extracts were incubated with synthetic mRNAs of lacZ or cyclin E. Extracts prepared from cells transfected with the 540-nucleotide cyclin E dsRNA efficiently degraded the cyclin E transcript; however, the lacZ transcript was stable in these lysates (FIG. 2a). Conversely, lysates from cells transfected with the lacZ dsRNA degraded the lacZ transcript but left the cyclin E mRNA intact. These results indicate that RNAi ablates target mRNAs through the generation of a sequence-specific nuclease activity. We have termed this enzyme RISC (RNA-induced silencing complex). Although we occasionally observed possible intermediates in the degradation process (see FIG. 2), the absence of stable cleavage end-products indicates an exonuclease (perhaps coupled to an endonuclease). However, it is possible that the RNAi nuclease makes an initial endonucleolytic cut and that non-specific exonucleases in the extract complete the degradation process (Shuttleworth and Colman, *EMBO J.* 7: 427-434, 1988). In addition, our ability to create an extract that targets lacZ in vitro indicates that the presence of an endogenous gene is not required for the RNAi response.

Figure 2B:
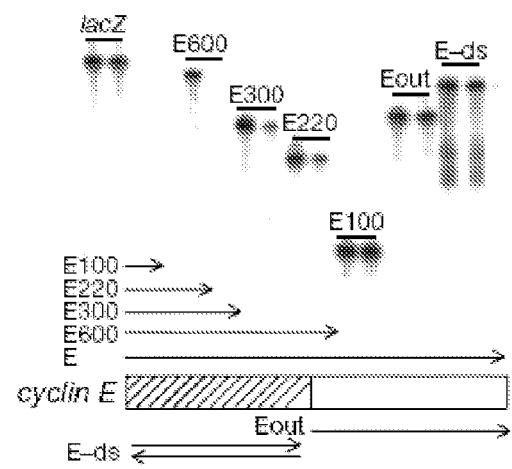

To examine the substrate requirements for the dsRNA-induced, sequence-specific nuclease activity, we incubated a variety of cyclin-E-derived transcripts with an extract derived from cells that had been transfected with the 540-nucleotide cyclin E dsRNA (FIGS. 2b, c). Just as a length requirement was observed for the transfected dsRNA, the RNAi nuclease activity showed a dependence on the size of the RNA substrate. Both a 600-nucleotide transcript that extends slightly beyond the targeted region (FIG. 2b) and an ~1-kilobase (kb) transcript that contains the entire coding sequence (data not shown) were completely destroyed by the extract. Surprisingly, shorter substrates were not degraded as efficiently. Reduced activity was observed against either a 300- or a 220-nucleotide transcript, and a 100-nucleotide transcript was resistant to nuclease in our assay. This was not due solely to position effects because ~100-nucleotide transcripts derived from other portions of the transfected dsRNA behaved similarly (data not shown). As expected, the nuclease activity (or activities) present in the extract could also recognize the antisense strand of the cyclin E mRNA. Again, substrates that contained a substantial portion of the targeted region were degraded efficiently whereas those that contained a shorter stretch of homologous sequence (~130 nucleotides) were recognized inefficiently (FIG. 2c, as600). For both the sense and antisense strands, transcripts that had no homology with the transfected dsRNA (FIG. 2b, Eout; FIG. 2c, as300) were not degraded. Although we cannot exclude the possibility that nuclease specificity could have migrated beyond the targeted region, the resistance of transcripts that do not contain homology to the dsRNA is consistent with data from *C. elegans*. Double-stranded RNAs homologous to an upstream cistron have little or no effect on a linked downstream cistron, despite the fact that unprocessed, polycistronic mRNAs can be readily detected (Tabara et al., *Science* 282: 430-432, 1998; Bosher et al., *Genetics* 153: 1245-1256, 1999). Furthermore, the nuclease was inactive against a dsRNA identical to that used to provoke the RNAi response in vitro (FIG. 2b). In the in vitro system, neither a 5' cap nor a poly(A) tail was required, as such transcripts were degraded as efficiently as uncapped and non-polyadenylated RNAs.

Figure 3:
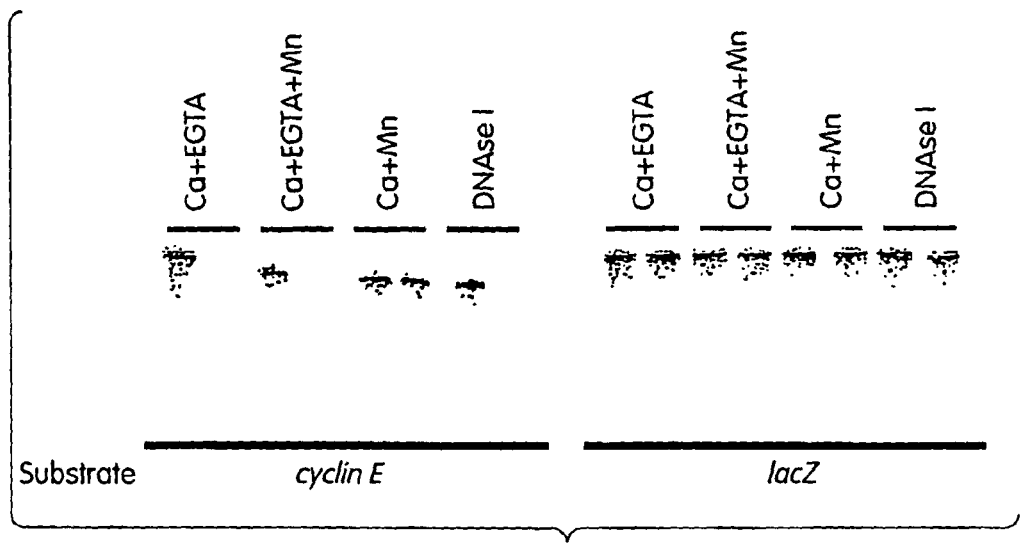
FIG. 3: Substrate requirements of the RISC. Extracts were prepared from cells transfected with cyclin E dsRNA. Aliquots were incubated for 30 min at 30° C. before the addition of either the cyclin E (E600) or lacZ (Z800) substrate. Individual 20 μl aliquots, as indicated, were pre-incubated with 1 mM $CaCl_2$ and 5 mM EGTA, 1 mM $CaCl_2$, 5 mM EGTA and 60 U of micrococcal nuclease, 1 mM $CaCl_2$ and 60 U of micrococcal nuclease or 10 U of DNase I (Promega) and 5 mM EGTA. After the 30 min pre-incubation, EGTA was added to those samples that lacked it. Yeast tRNA (1 μg) was added to all samples. Time points were at 0 and 30 min.

Gene silencing provoked by dsRNA is sequence specific. A plausible mechanism for determining specificity would be incorporation of nucleic-acid guide sequences into the complexes that accomplish silencing (Hamilton and Baulcombe, *Science* 286: 950-952, 1999). In accord with this idea, pretreatment of extracts with a $Ca^{2+}$-dependent nuclease (micrococcal nuclease) abolished the ability of these extracts to degrade cognate mRNAs (FIG. 3). Activity could not be rescued by addition of non-specific RNAs such as yeast transfer RNA. Although micrococcal nuclease can degrade both DNA and RNA, treatment of the extract with DNAse I had no effect (FIG. 3). Sequence-specific nuclease activity, however, did require protein (data not shown). Together, our results support the possibility that the RNAi nuclease is a ribonucleoprotein, requiring both RNA and protein components. Biochemical fractionation (see below) is consistent with these components being associated in extract rather than being assembled on the target mRNA after its addition.

Figures 4A, 4B:
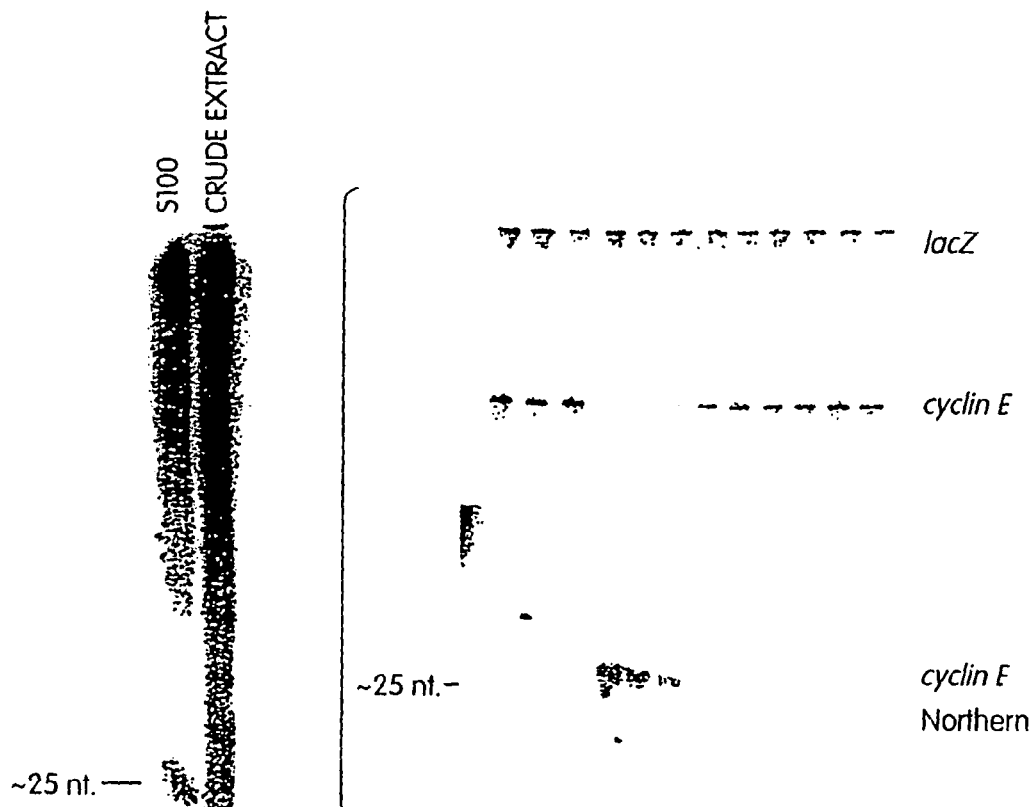
FIG. 4: The RISC contains a potential guide RNA. (a) Northern blots of RNA from either a crude lysate or the S100 fraction (containing the soluble nuclease activity, see Methods) were hybridized to a riboprobe derived from the sense strand of the cyclin E mRNA. (b) Soluble cyclin-E-specific nuclease activity was fractionated as described in Methods. Fractions from the anion-exchange resin were incubated with the lacZ, control substrate (upper panel) or the cyclin E substrate (centre panel). Lower panel, RNA from each fraction was analysed by northern blotting with a uniformly labeled transcript derived from sense strand of the cyclin E cDNA. DNA oligonucleotides were used as size markers.

In plants, the phenomenon of co-suppression has been associated with the existence of small (~25-nucleotide) RNAs that correspond to the gene that is being silenced (Hamilton and Baulcombe, *Science* 286: 950-952, 1999). To address the possibility that a similar RNA might exist in *Drosophila* and guide the sequence-specific nuclease in the choice of substrate, we partially purified our activity through several fractionation steps. Crude extracts contained both sequence-specific nuclease activity and abundant, heterogeneous RNAs homologous to the transfected dsRNA (FIGS. 2 and 4a). The RNAi nuclease fractionated with ribosomes in a high-speed centrifugation step. Activity could be extracted by treatment with high salt, and ribosomes could be removed by an additional centrifugation step. Chromatography of soluble nuclease over an anion-exchange column resulted in a discrete peak of activity (FIG. 4b, cyclin E). This retained specificity as it was inactive against a heterologous mRNA (FIG. 4b, lacZ). Active fractions also contained an RNA species of 25 nucleotides that is homologous to the cyclin E target (FIG. 4b, northern). The band observed on northern blots may represent a family of discrete RNAs because it could be detected with probes specific for both the sense and antisense cyclin E sequences and with probes derived from distinct segments of the dsRNA (data not shown). At present, we cannot determine whether the 25-nucleotide RNA is present in the nuclease complex in a double-stranded or single-stranded form.

RNA interference allows an adaptive defense against both exogenous and endogenous dsRNAs, providing something akin to a dsRNA immune response. Our data, and that of others (Hamilton and Baulcombe, *Science* 286: 950-952, 1999), is consistent with a model in which dsRNAs present in a cell are converted, either through processing or replication, into small specificity determinants of discrete size in a manner analogous to antigen processing. Our results suggest that the post-transcriptional component of dsRNA-dependent gene silencing is accomplished by a sequence-specific nuclease that incorporates these small RNAs as guides that target specific messages based upon sequence recognition. The identical size of putative specificity determinants in plants (Hamilton and Baulcombe, supra) and animals predicts a conservation of both the mechanisms and the components of dsRNA-induced, post-transcriptional gene silencing in diverse organisms. In plants, dsRNAs provoke not only post-transcriptional gene silencing but also chromatin remodeling and transcriptional repression (Jones et al., *EMBO J.* 17: 6385-6393, 1998; Jones et al., *Plant Cell* 11: 2291-2301, 1999). It is now critical to determine whether conservation of gene-silencing mechanisms also exists at the transcriptional level and whether chromatin remodeling can be directed in a sequence-specific fashion by these same dsRNA-derived guide sequences.

Methods:

Cell culture and RNA methods S2 cells (Schneider, *J Embryol Exp Morpho* 27: 353-365, 1972) were cultured at 27° C. in 90% Schneider's insect media (Sigma), 10% heat inactivated fetal bovine serum (FBS). Cells were transfected with dsRNA and plasmid DNA by calcium phosphate coprecipitation (DiNocera and Dawid, PNAS 80: 7095-7098, 1983). Identical results were observed when cells were transfected using lipid reagents (for example, Superfect, Qiagen). For FACS analysis, cells were additionally transfected with a vector that directs expression of a green fluorescent protein (GFP)-US9 fusion protein (Kalejta et al., *Exp Cell Res.* 248: 322-328, 1999). These cells were fixed in 90% ice-cold ethanol and stained with propidium iodide at 25 µg/ml. FACS was performed on an Elite flow cytometer (Coulter). For northern blotting, equal loading was ensured by over-probing blots with a control complementary DNA (RP49). For the production of dsRNA, transcription templates were generated by polymerase chain reaction such that they contained T7 promoter sequences on each end of the template. RNA was prepared using the RiboMax kit (Promega). Confirmation that RNAs were double stranded came from their complete sensitivity to RNAse III. Target mRNA transcripts were synthesized using the Riboprobe kit (Promega) and were gel purified before use.

Extract preparation Log-phase S2 cells were plated on 15-cm tissue culture dishes and transfected with 30 µg dsRNA and 30 µg carrier plasmid DNA. Seventy-two hours after transfection, cells were harvested in PBS containing 5 mM EGTA, washed twice in PBS and once in hypotonic buffer (10 mM HEPES pH 7.3, 6 mM α-mercaptoethanol). Cells were suspended in 0.7 packed-cell volumes of hypotonic buffer containing Complete protease inhibitors (Boehringer) and 0.5 units/ml of RNasin (Promega). Cells were disrupted in a dounce homogenizer with a type B pestle, and lysates were centrifuged at 30,000 g for 20 min. Supernatants were used in an in vitro assay containing 20 mM HEPES pH 7.3, 110 mM KOAc, 1 mM Mg(OAc)$_2$, 3 mM EGTA, 2 mM CaCl$_2$, 1 mM DTT. Typically, 5 µl extract was used in a 10 µl assay that contained also 10,000 c.p.m. synthetic mRNA substrate.

Extract fractionation Extracts were centrifuged at 200,000 g for 3 h and the resulting pellet (containing ribosomes) was extracted in hypotonic buffer containing also 1 mM MgCl$_2$ and 300 mM KOAc. The extracted material was spun at 100,000 g for 1 h and the resulting supernatant was fractionated on Source 15% column (Pharmacia) using a KCl gradient in buffer A (20 mM HEPES pH 7.0, 1 mM dithiothreitol, 1 mM MgCl$_2$). Fractions were assayed for nuclease activity as described above. For northern blotting, fractions were proteinase K/SDS treated, phenol extracted, and resolved on 15% acrylamide 8M urea gels. RNA was electroblotted onto Hybond N+ and probed with strand-specific riboprobes derived from cyclin E mRNA. Hybridization was carried out in 500 mM NaPO$_4$ pH 7.0, 15% formamide, 7% SDS, 1% BSA. Blots were washed in 1xSSC at 37-45° C.

EXAMPLE 2

Role for a Bidentate Ribonuclease in the Initiation Step of RNA Interference

Genetic approaches in worms, fungi and plants have identified a group of proteins that are essential for double-stranded RNA-induced gene silencing. Among these are ARGONAUTE family members (e.g. RDE1, QDE2) (Tabara et al., *Cell* 99: 123-132, 1999; Catalanotto et al., *Nature* 404: 245, 2000; Fagard et al., *PNAS* 97: 11650-11654, 2000), recQ-family helicases (MUT-7, QDE3) (Ketting et al., *Cell* 99: 133-141, 1999; Cogoni and Macino, *Science* 286: 2342-2344, 1999), and RNA-dependent RNA polymerases (e.g., EGO-1, QDE1, SGS2/SDE1) (Cogoni and Macino, *Nature* 399: 166-169, 1999; Smardon et al., *Current Biology* 10: 169-178, 2000; Mourrain et al., *Cell* 101: 533-542, 2000; Dalmay et al., *Cell* 101: 543-553, 2000). While potential roles have been proposed, none of these genes has been assigned a definitive function in the silencing process. Biochemical studies have suggested that PTGS is accomplished by a multicomponent nuclease that targets mRNAs for degradation (Hammond et al., *Nature* 404: 293-296, 2000; Zamore et al., *Cell* 101: 25-33, 2000; Tuschl et al., *Genes and Development* 13: 3191-3197, 1999). We have shown that the specificity of this complex may derive from the incorporation of a small guide sequence that is homologous to the mRNA substrate (Hammond et al., *Nature* 404: 293-296, 2000). Originally identified in plants that were actively silencing transgenes (Hamilton and Baulcombe, *Science* 286: 950-952, 1999), these ~22 nt. RNAs have been produced during RNAi in vitro using an extract prepared from *Drosophila* embryos (Zamore et al., *Cell* 101: 25-33, 2000). Putative guide RNAs can also be produced in extracts from *Drosophila* S2 cells (FIG. 5a). With the goal of understanding the mechanism of post-transcriptional gene silencing, we have undertaken both biochemical fractionation and candidate gene approaches to identify the enzymes that execute each step of RNAi.

Our previous studies resulted in the partial purification of a nuclease, RISC, that is an effector of RNA interference. See Example 1. This enzyme was isolated from *Drosophila* S2 cells in which RNAi had been initiated in vitro by transfection with dsRNA. We first sought to determine whether the RISC enzyme and the enzyme that initiates RNAi via processing of dsRNA into 22mers are distinct activities. RISC activity could be largely cleared from extracts by high-speed centrifugation (100,000xg for 60 min.) while the activity that produces 22mers remained in the supernatant (FIGS. 5b,c). This simple fractionation indicated that RISC and the 22mer-generating activity are separable and thus distinct enzymes. However, it seems likely that they might interact at some point during the silencing process.

RNAse III family members are among the few nucleases that show specificity for double-stranded RNA (Nicholson, *FEMS Microbiol Rev* 23: 371-390, 1999). Analysis of the *Drosophila* and *C. elegans* genomes reveals several types of RNAse III enzymes. First is the canonical RNAse III which contains a single RNAse III signature motif and a double-stranded RNA binding domain (dsRBD; e.g. RNC_CAEEL). Second is a class represented by Drosha (Filippov et al., *Gene* 245: 213-221, 2000), a *Drosophila* enzyme that contains two RNAse III motifs and a dsRBD (CeDrosha in *C. elegans*). A third class contains two RNAse III signatures and an amino terminal helicase domain (e.g. *Drosophila* CG4792, CG6493, *C. elegans* K12H4.8), and these had previously been proposed by Bass as candidate RNAi nucleases (Bass, Cell 101: 235-238, 2000). Representatives of all three classes were tested for the ability to produce discrete, ~22 nt. RNAs from dsRNA substrates.

Partial digestion of a 500 nt. cyclin E dsRNA with purified, bacterial RNAse III produced a smear of products while nearly complete digestion produced a heterogeneous group of ~11-17 nucleotide RNAs (not shown). In order to test the dual-RNAse III enzymes, we prepared T7 epitope-tagged versions of Drosha and CG4792. These were expressed in transfected S2 cells and isolated by immunoprecipitation using antibody-agarose conjugates. Treatment of the dsRNA with the CG4792 immunoprecipitate yielded ~22 nt. fragments similar to those produced in either S2 or embryo extracts (FIG. 6a). Neither activity in extract nor activity in immunoprecipitates depended on the sequence of the RNA substrate since dsRNAs derived from several genes were processed equivalently (see Supplement 1). Negative results were obtained with Drosha and with immunoprecipitates of a DExH box helicase (Homeless (Gillespie et al., *Genes and Development* 9: 2495-2508, 1995); see FIGS. 6a,b). Western blotting confirmed that each of the tagged proteins was expressed and immunoprecipitated similarly (see Supplement 2). Thus, we conclude that CG4792 may carry out the initiation step of RNA interference by producing ~22 nt. guide sequences from dsRNAs. Because of its ability to digest dsRNA into uniformly sized, small RNAs, we have named this enzyme Dicer (Dcr). Dicer mRNA is expressed in embryos, in S2 cells, and in adult flies, consistent with the presence of functional RNAi machinery in all of these contexts (see Supplement 3).

Figure 6D:
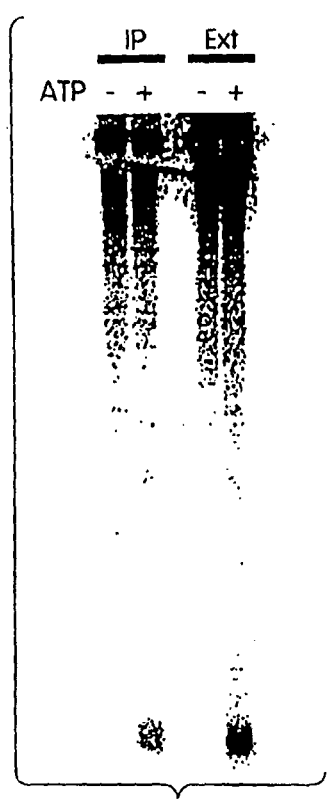
FIG. 6: Production of 22mers by recombinant CG4792/Dicer. (a) *Drosophila* S2 cells were transfected with plasmids that direct the expression of T7-epitope tagged versions of Drosha, CG4792/Dicer-1 and Homeless. Tagged proteins were purified from cell lysates by immunoprecipitation and were incubated with cyclin E dsRNA. For comparison, reactions were also performed in *Drosophila* embryo and S2 cell extracts. As a negative control, immunoprecipitates were prepared from cells transfected with a β-galactosidase expression vector. Pairs of lanes show reactions performed for 0 or 60 minutes. The synthetic marker (M) is as described in the legend to FIG. 1. (b) Diagrammatic representations of the domain structures of CG4792/Dicer-1, Drosha and Homeless are shown. (c) Immunoprecipitates were prepared from detergent lysates of S2 cells using an antiserum raised against the C-terminal 8 amino acids of *Drosophila* Dicer-1 (CG4792). As controls, similar preparations were made with a pre-immune serum and with an immune serum that had been pre-incubated with an excess of antigenic peptide. Cleavage reactions in which each of these precipitates was incubated with an ~500 nt. fragment of *Drosophila cyclin* E are shown. For comparison, an incubation of the substrate in *Drosophila* embryo extract was electrophoresed in parallel. (d) Dicer immunoprecipitates were incubated with dsRNA substrates in the presence or absence of ATP. For comparison, the same substrate was incubated with S2 extracts that either contained added ATP or that were depleted of ATP using glucose and hexokinase (see methods). (e) *Drosophila* S2 cells were transfected with uniformly, $^{32}$P-labelled dsRNA corresponding to the first 500 nt. of GFP. RISC complex was affinity purified using a histidine-tagged version of *Drosophila* Ago-2, a recently identified component of the RISC complex (Hammond et al., in prep). RISC was isolated either under conditions in which it remains ribosome associated (ls, low salt) or under conditions that extract it from the ribosome in a soluble form (hs, high salt). For comparison, the spectrum of labeled RNAs in the total lysate is shown. (f) Guide RNAs produced by incubation of dsRNA with a Dicer immunoprecipitate are compared to guide RNAs present in an affinity-purified RISC complex. These precisely co-migrate on a gel that has single-nucleotide resolution. The lane labeled control is an affinity selection for RISC from a cell that had been transfected with labeled dsRNA but not with the epitope-tagged *Drosophila* Ago-2.
Figure 6E:
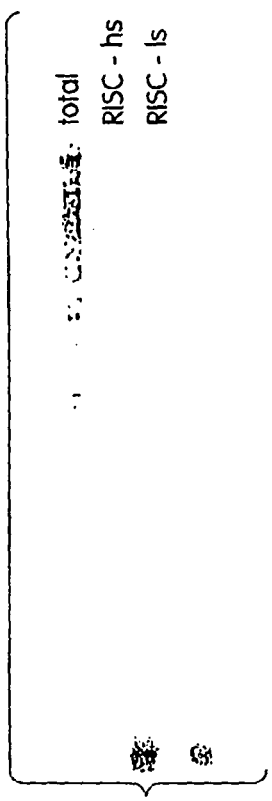
Figure 6F:
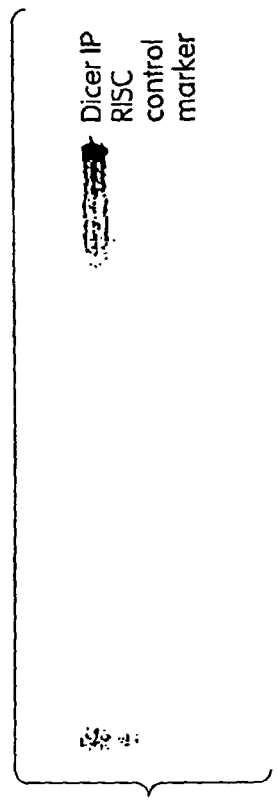

The possibility that Dicer might be the nuclease responsible for the production of guide RNAs from dsRNAs prompted us to raise an antiserum directed against the carboxy-terminus of the Dicer protein (Dicer-1, CG4792). This antiserum could immunoprecipitate a nuclease activity from either *Drosophila* embryo extracts or from S2 cell lysates that produced ~22 nt. RNAs from dsRNA substrates (FIG. 6C). The putative guide RNAs that are produced by the Dicer-1 enzyme precisely co-migrate with 22mers that are produced in extract and with 22mers that are associated with the RISC enzyme (FIG. 6 D,F). It had previously been shown that the enzyme that produced guide RNAs in *Drosophila* embryo extracts was ATP-dependent (Zamore et al., *Cell* 101: 25-33, 2000). Depletion of this cofactor resulted in an ~6-fold lower rate of dsRNA cleavage and in the production of RNAs with a slightly lower mobility. Of interest was the fact that both Dicer-1 immunoprecipitates and extracts from S2 cells require ATP for the production of ~22mers (FIG. 6D). We do not observe the accumulation of lower mobility products in these cases, although we do routinely observe these in ATP-depleted embryo extracts. The requirement of this nuclease for ATP is a quite unusual property. We hypothesize that this requirement could indicate that the enzyme may act processively on the dsRNA, with the helicase domain harnessing the energy of ATP hydrolysis both for unwinding guide RNAs and for translocation along the substrate.

Efficient induction of RNA interference in *C. elegans* and in *Drosophila* has several requirements. For example, the initiating RNA must be double-stranded, and it must be several hundred nucleotides in length. To determine whether these requirements are dictated by Dicer, we characterized the ability of extracts and of immunoprecipitated enzyme to digest various RNA substrates. Dicer was inactive against single stranded RNAs regardless of length (see Supplement 4). The enzyme could digest both 200 and 500 nucleotide dsRNAs but was significantly less active with shorter substrates (see Supplement 4). Double-stranded RNAs as short as 35 nucleotides could be cut by the enzyme, albeit very inefficiently (data not shown). In contrast, *E. coli* RNAse III could digest to completion dsRNAs of 35 or 22 nucleotides (not shown). This suggests that the substrate preferences of the Dicer enzyme may contribute to but not wholly determine the size dependence of RNAi.

To determine whether the Dicer enzyme indeed played a role in RNAi in vitro, we sought to deplete Dicer activity from S2 cells and test the effect on dsRNA-induced gene silencing. Transfection of S2 cells with a mixture of dsRNAs homologous to the two *Drosophila* Dicer genes (CG4792 and CG6493) resulted in an ~6-7 fold reduction of Dicer activity either in whole cell lysates or in Dicer-1 immunoprecipitates (FIG. 7A,B). Transfection with a control dsRNA (murine caspase 9) had no effect. Qualitatively similar results were seen if Dicer was examined by Northern blotting (not shown). Depletion of Dicer in this manner substantially compromised the ability of cells to silence subsequently an exogenous, GFP transgene by RNAi (FIG. 7C). These results indicate that Dicer is involved in RNAi in vitro. The lack of complete inhibition of silencing could result from an incomplete suppression of Dicer (which is itself required for RNAi) or could indicate that in vitro, guide RNAs can be produced by more than one mechanism (e.g. through the action of RNA-dependent RNA polymerases).

Our results indicate that the process of RNA interference can be divided into at least two distinct steps. According to this model, initiation of PTGS would occur upon processing of a double-stranded RNA by Dicer into ~22 nucleotide guide sequences, although we cannot formally exclude the possibility that another, Dicer-associated nuclease may participate in this process. These guide RNAs would be incorporated into a distinct nuclease complex (RISC) that targets single-stranded mRNAs for degradation. An implication of this model is that guide sequences are themselves derived directly from the dsRNA that triggers the response. In accord with this model, we have demonstrated that $^{32}$P-labeled, exogenous dsRNAs that have been introduced into S2 cells by transfection are incorporated into the RISC enzyme as 22 mers (FIG. 7E). However, we cannot exclude the possibility that RNA-dependent RNA polymerases might amplify 22mers once they have been generated or provide an alternative method for producing guide RNAs.

Figure 8A:
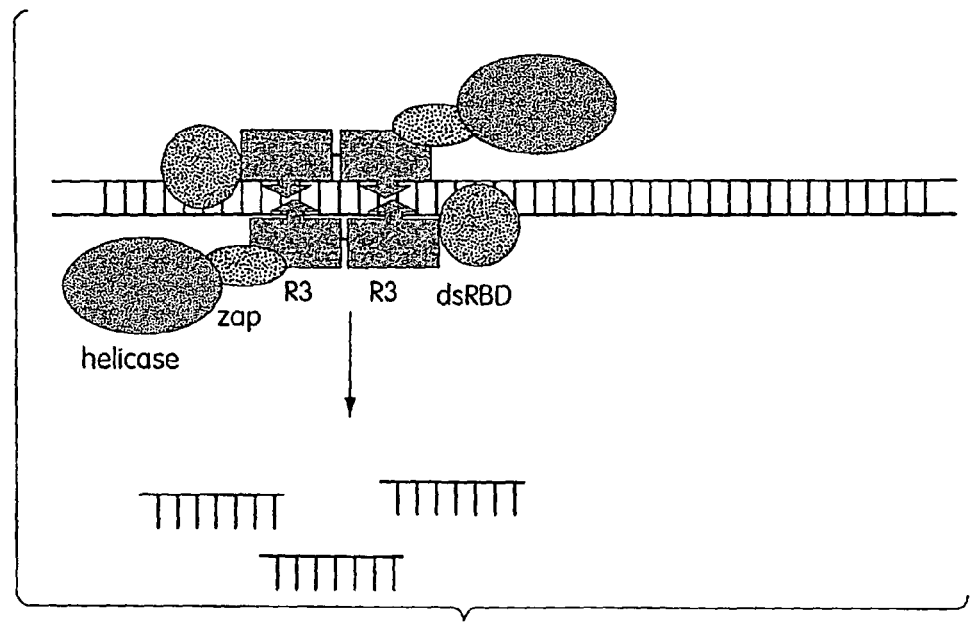
FIG. 8: Dicer is an evolutionarily conserved ribonuclease. (a) A model for production of 22mers by Dicer. Based upon the proposed mechanism of action of Ribonuclease III, we propose that Dicer acts on its substrate as a dimer. The positioning of the two ribonuclease domains (RIIIa and RIIIb) within the enzyme would thus determine the size of the cleavage product. An equally plausible alternative model could be derived in which the RIIIa and RIIIb domains of each Dicer enzyme would cleave in concert at a single position. In this model, the size of the cleavage product would be determined by interaction between two neighboring Dicer enzymes. (b) Comparison of the domain structures of potential Dicer homologs in various organisms (Drosophila—CG4792, CG6493, C. elegans-K12H4.8, Arabidopsis—CARPEL FACTORY, T25K16.4, AC012328_1, human Helicase-MOI and S. pombe—YC9A_SCHPO). The ZAP domains were identified both by analysis of individual sequences with Pfam and by Psi-blast searches. The ZAP domain in the putative *S. pombe* Dicer is not detected by PFAM but is identified by Psi-Blast and is thus shown in a different color. For comparison, a domain structure of the RDE1/QDE2/ARGONAUTE family is shown. It should be noted that the ZAP domains are more similar within each of the Dicer and ARGONAUTE families than they are between the two groups. (c) An alignment of the ZAP domains in selected Dicer and Argonaute family members is shown. The alignment was produced using ClustalW.

The structure of the Dicer enzyme provokes speculation on the mechanism by which the enzyme might produce discretely sized fragments irrespective of the sequence of the dsRNA (see Supplement 1, FIG. 8a). It has been established that bacterial RNAse III acts on its substrate as a dimer (Nicholson, *FEMS Microbiol Rev* 23: 371-390, 1999; Robertson et al., *J Biol Chem* 243: 82-91, 1968; Dunn, *J Biol Chem* 251: 3807-3814, 1976). Similarly, a dimer of Dicer enzymes may be required for cleavage of dsRNAs into ~22 nt. pieces. According to one model, the cleavage interval would be determined by the physical arrangement of the two RNAse III domains within Dicer enzyme (FIG. 8a). A plausible alternative model would dictate that cleavage was directed at a single position by the two RIII domains in a single Dicer protein. The 22 nucleotide interval could be dictated by interaction of neighboring Dicer enzymes or by translocation along the mRNA substrate. The presence of an integral helicase domain suggests that the products of Dicer cleavage might be single-stranded 22 mers that are incorporated into the RISC enzyme as such.

Figure 8B:
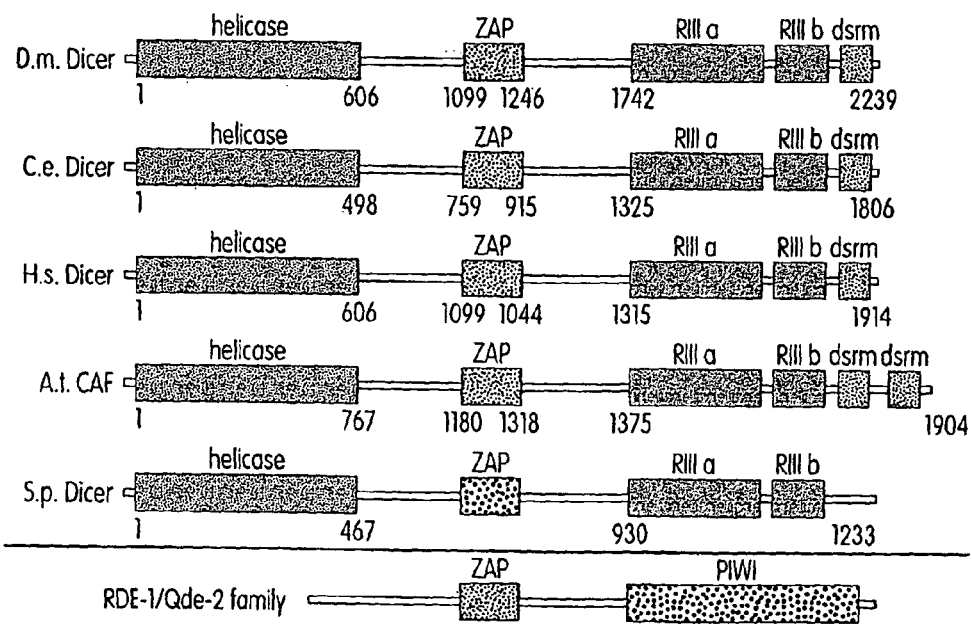
Figure 9:
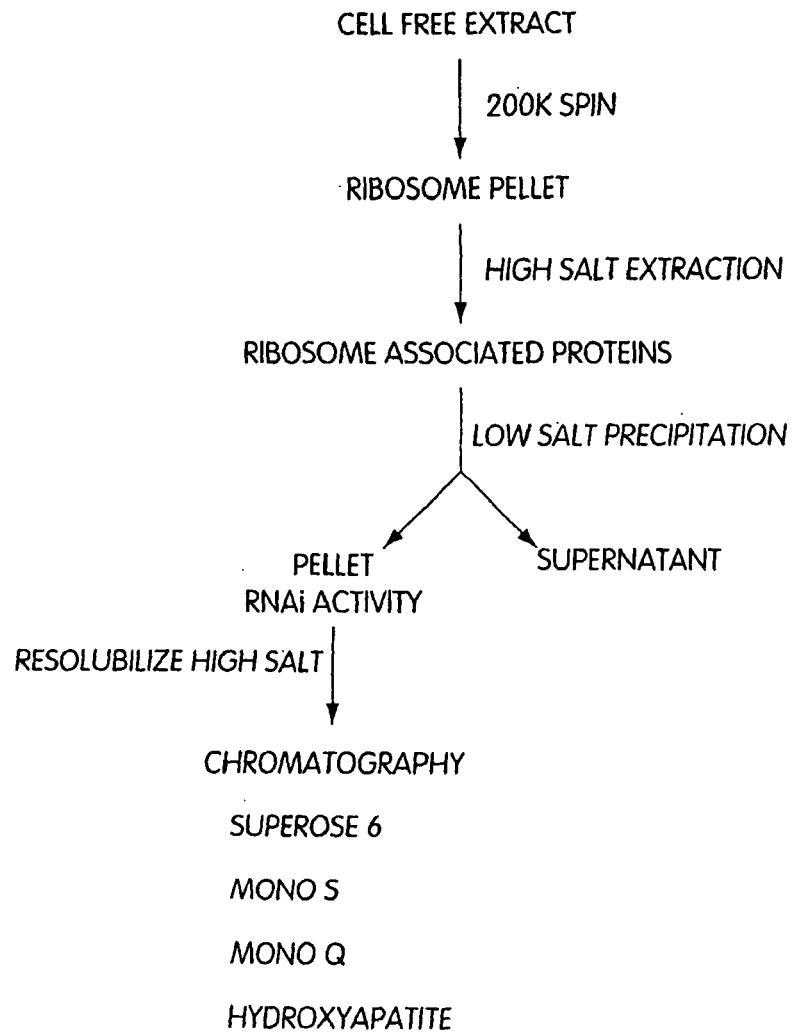
FIG. 9: Purification strategy for RISC. (second step in RNAi model).
Figure 10:
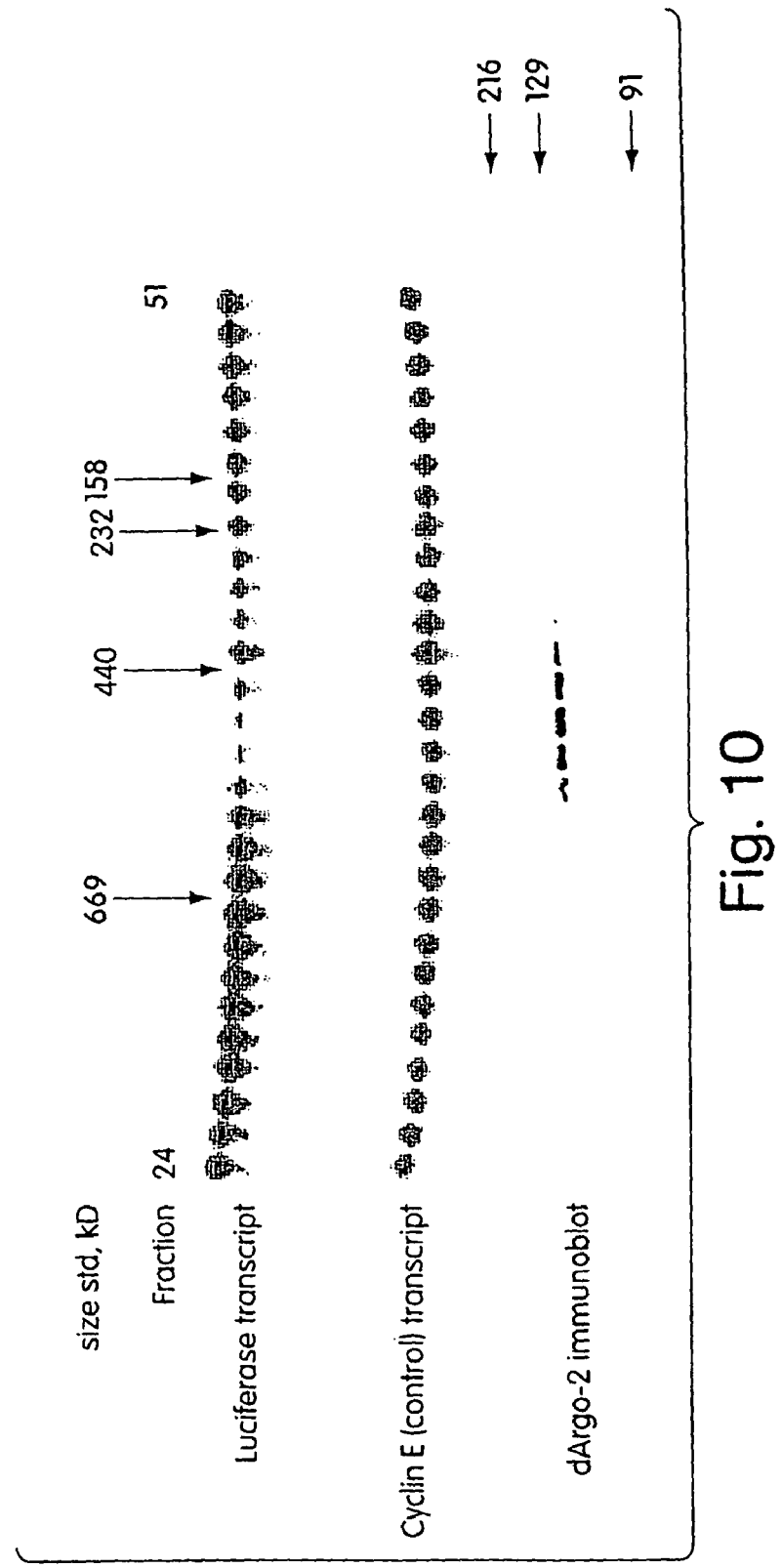
FIG. 10: Fractionation of RISC activity over sizing column. Activity fractionates as 500 KDa complex. Also, antibody to *Drosophila* argonaute 2 cofractionates with activity.
Figure 11:
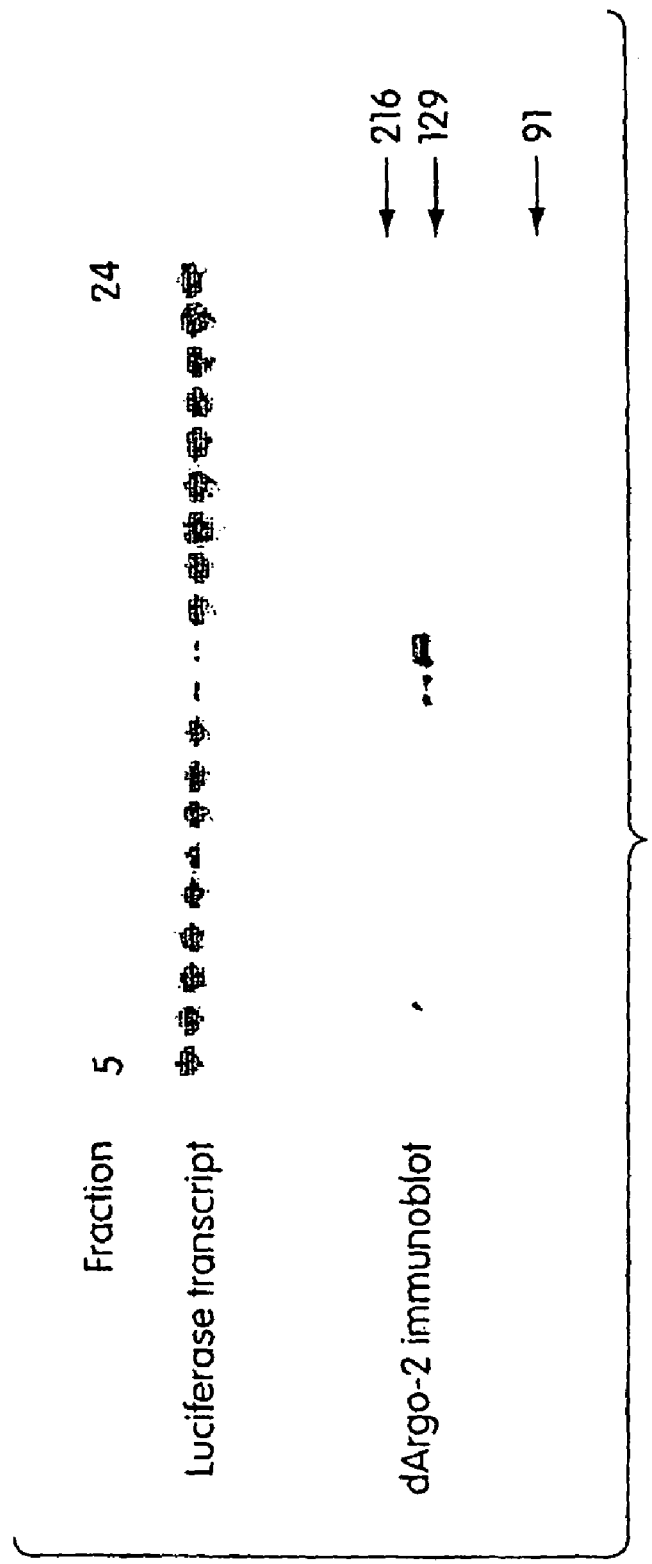
FIGS. 11-13: Fractionation of RISC over monoS, monoQ, Hydroxyapatite columns. *Drosophila* argonaute 2 protein also cofactionates.
Figure 12:
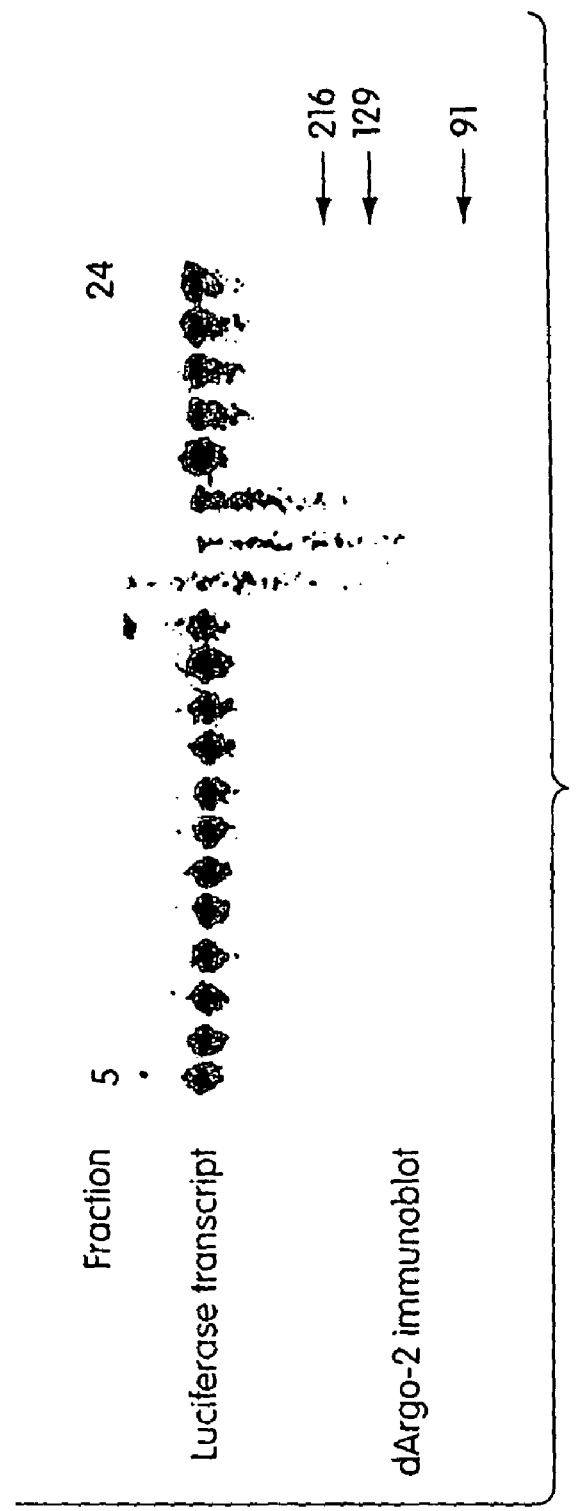
Figure 13:
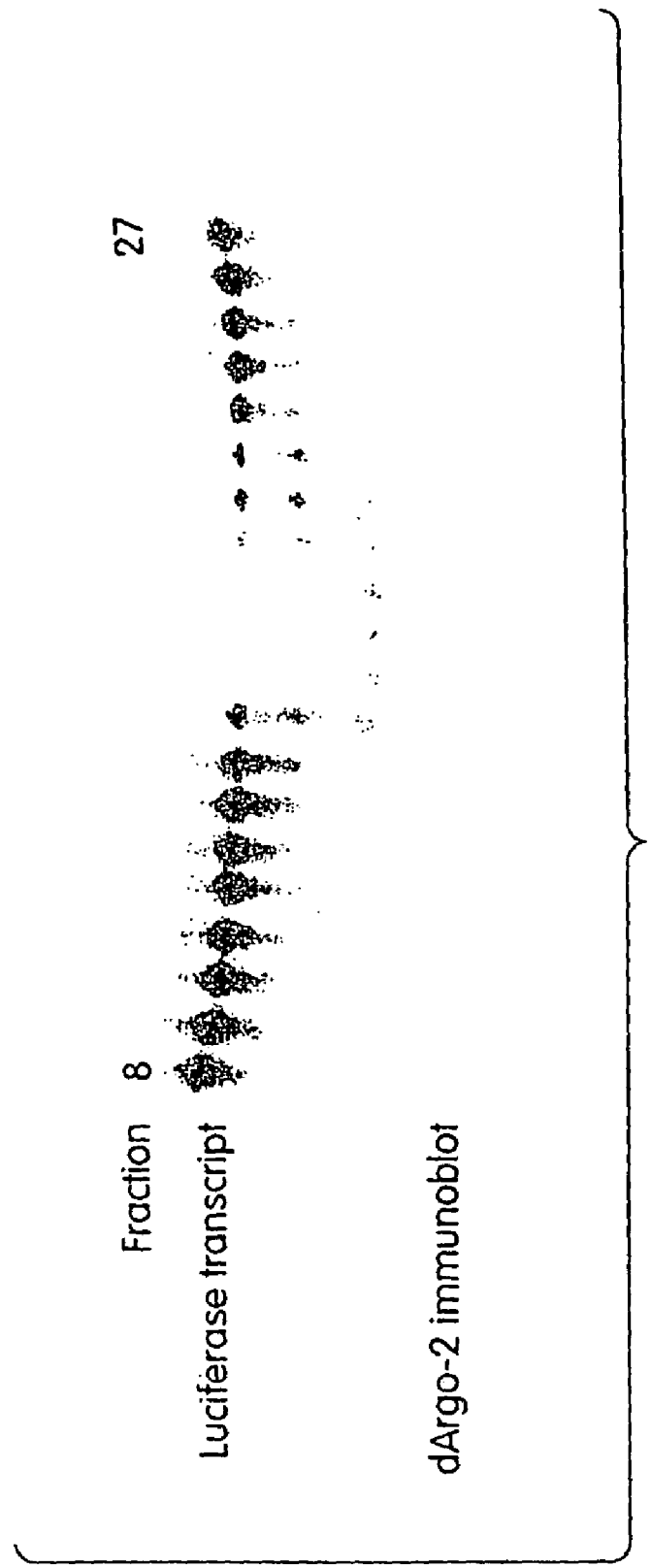
Figure 14:
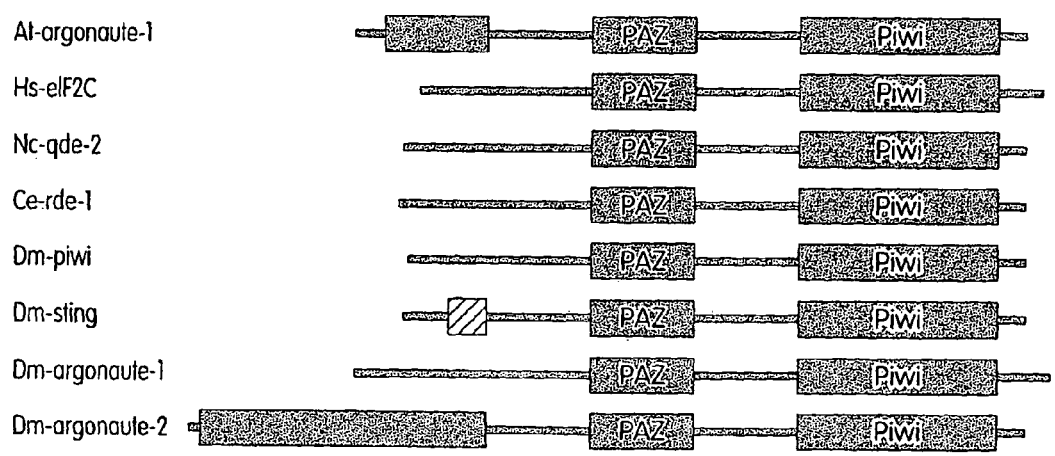
FIG. 14: Alignment of *Drosophila* argonaute 2 with other family members.
Figure 15:
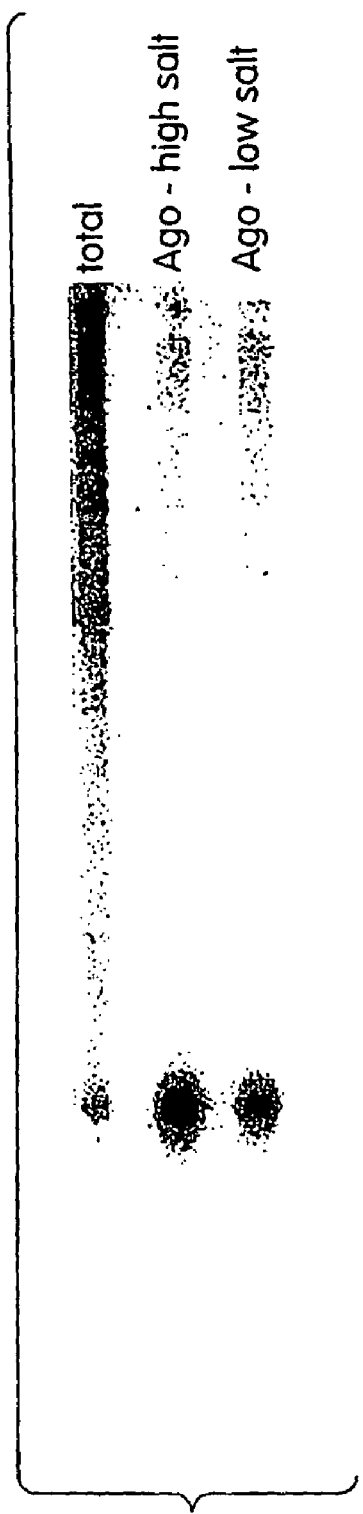
FIG. 15: Confirmation of *Drosophila* argonaute 2. S2 cells were transfected with labeled dsRNA and His tagged argonaute. Argonaute was isolated on nickel agarose and RNA component was identified on 15% acrylamide gel.
Figure 16:
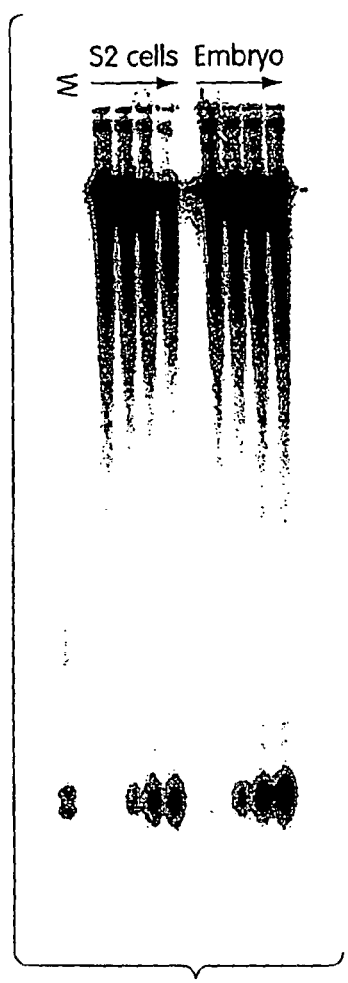
FIG. 16: S2 cell and embryo extracts were assayed for 22-mer generating activity.
Figure 17:
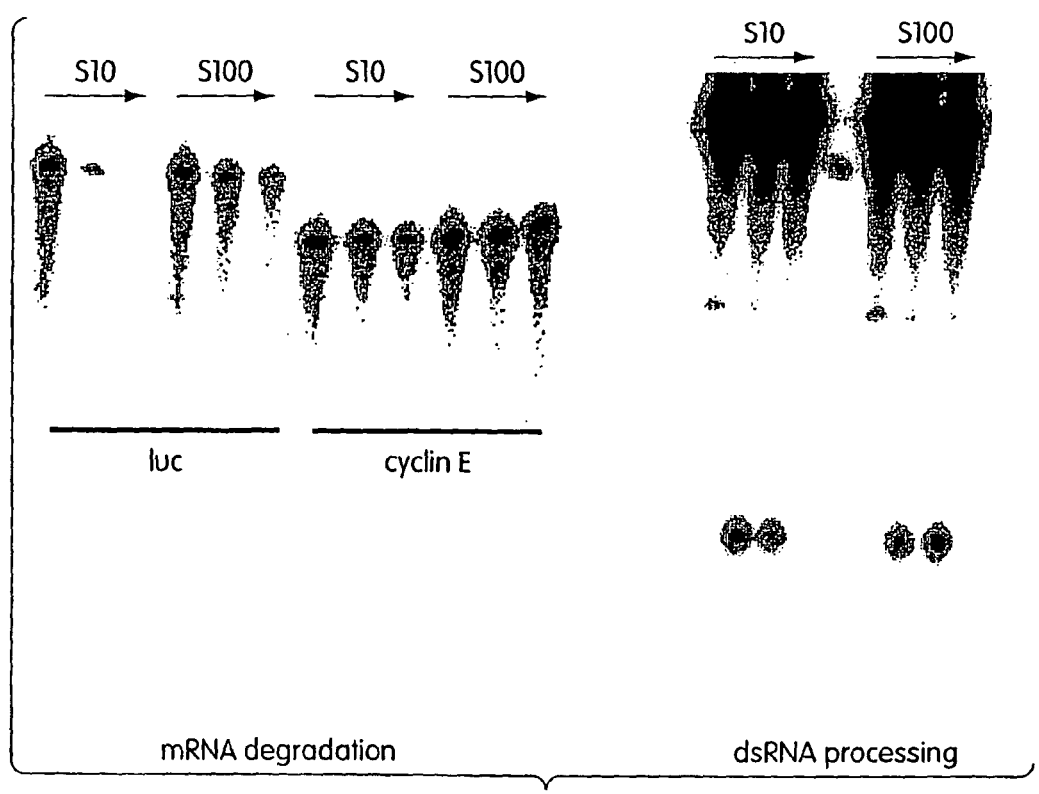
FIG. 17: RISC can be separated from 22-mer generating activity (dicer). Spinning extracts (S100) can clear RISC activity from supernatant (left panel) however, S100 spins still contain dicer activity (right panel).
Figure 18:
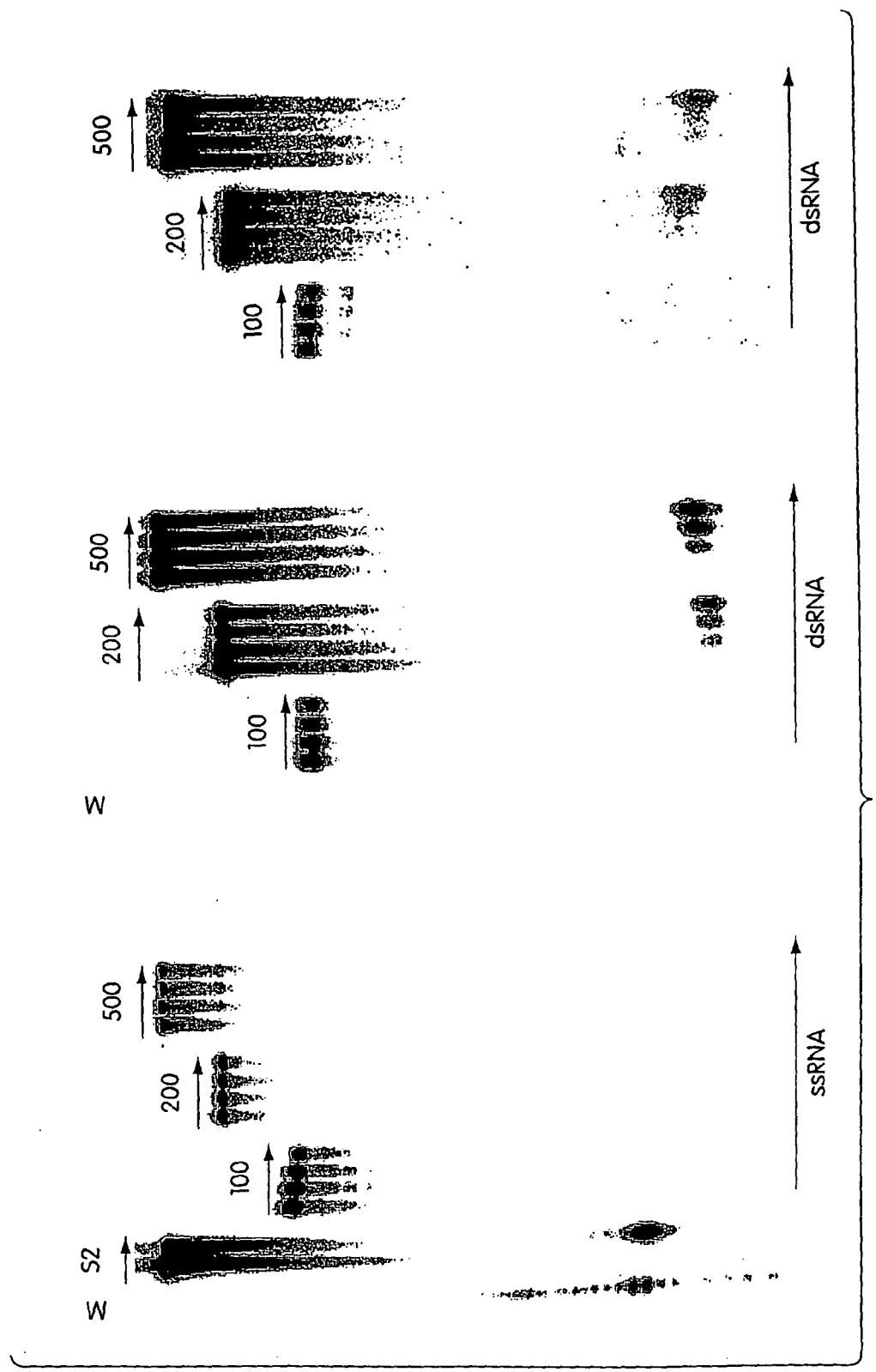
FIG. 18: Dicer is specific for dsRNA and prefers longer substrates.
Figure 19:
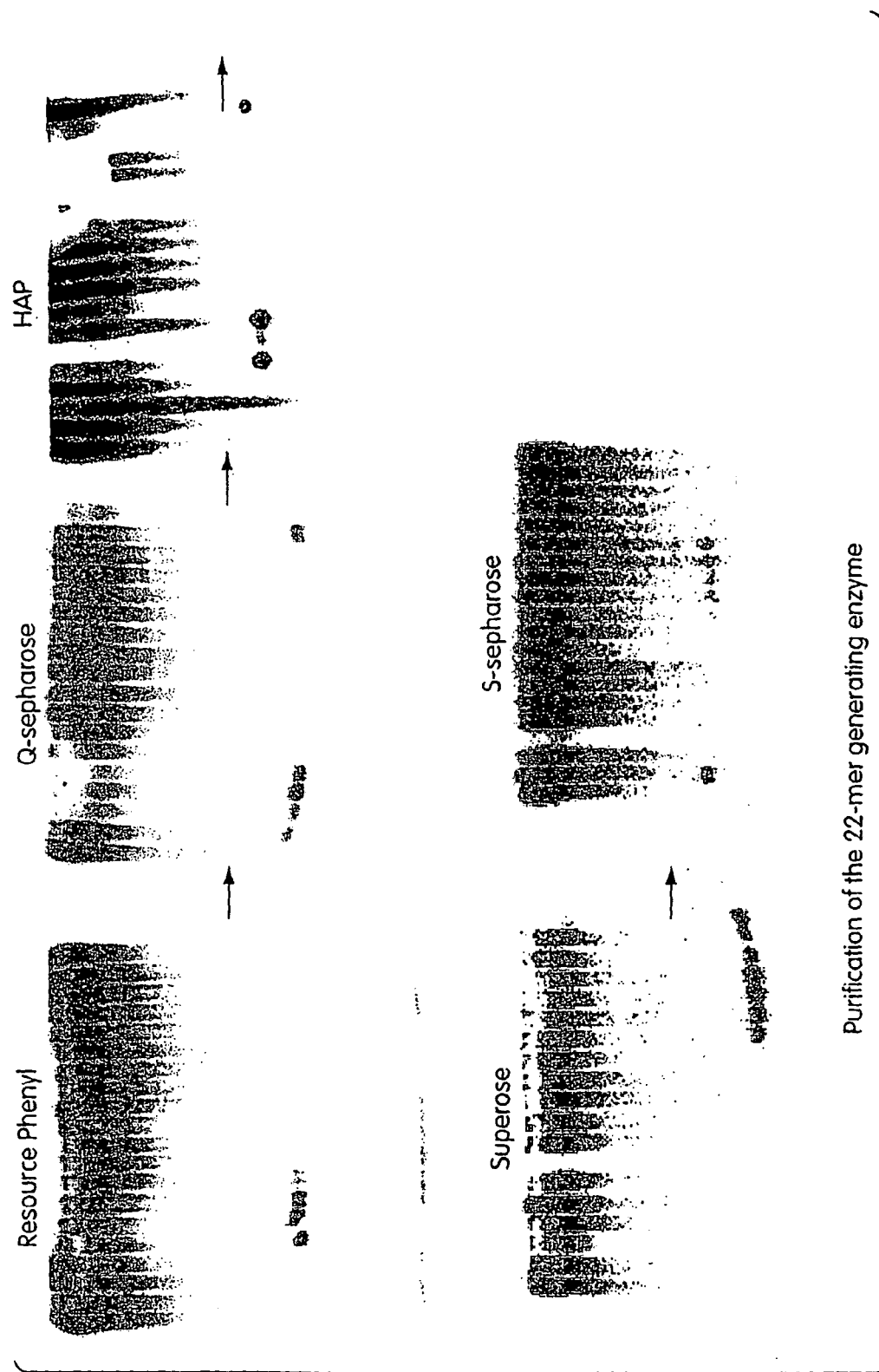
FIG. 19: Dicer was fractionated over several columns.
Figure 21:
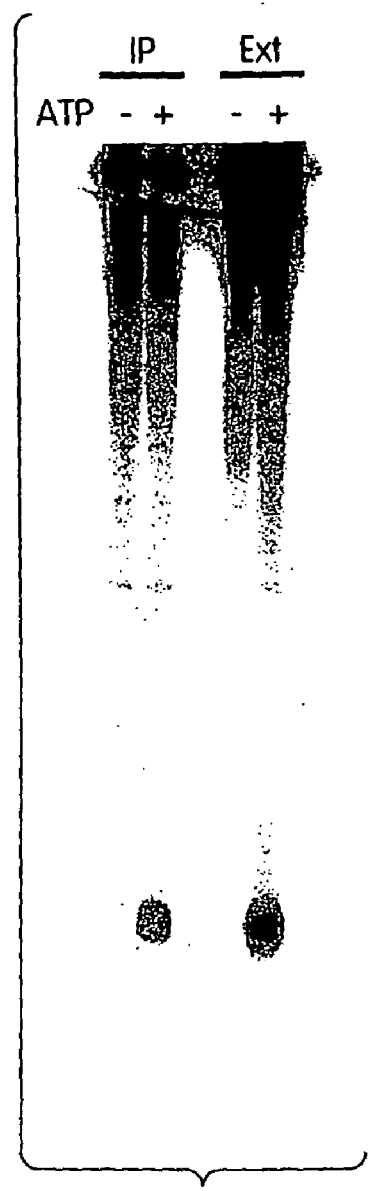
FIG. 21: Dicer requires ATP.
Figures 22A, 22B:
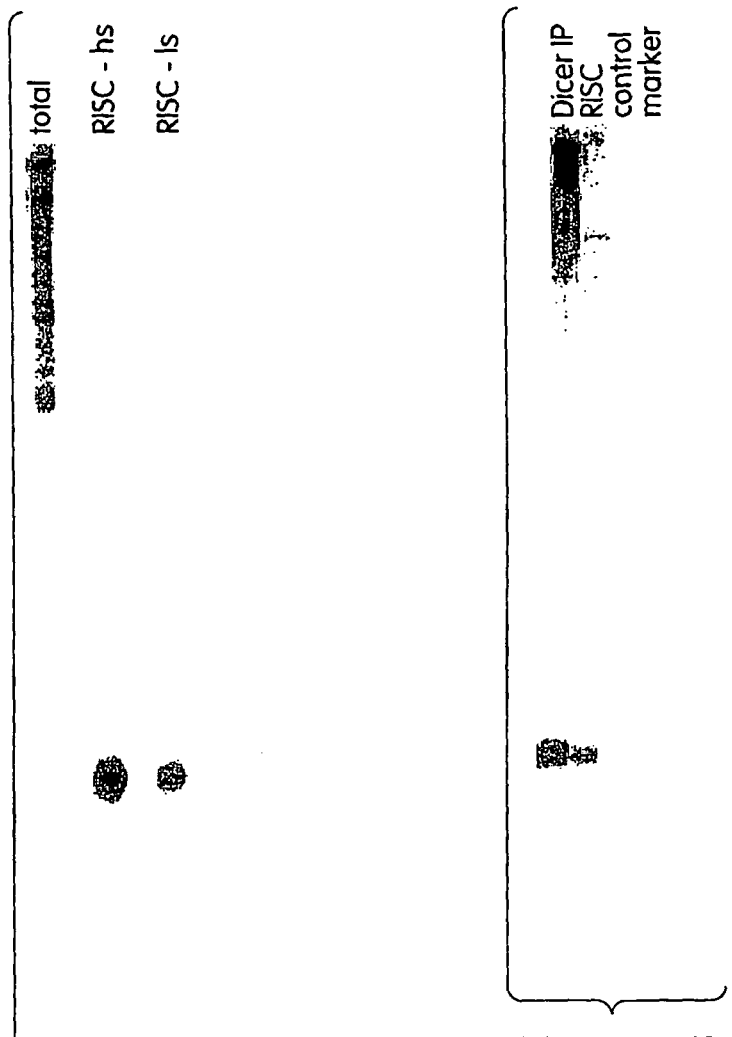
FIG. 22: Dicer produces RNAs that are the same size as RNAs present in RISC.
Figure 23:
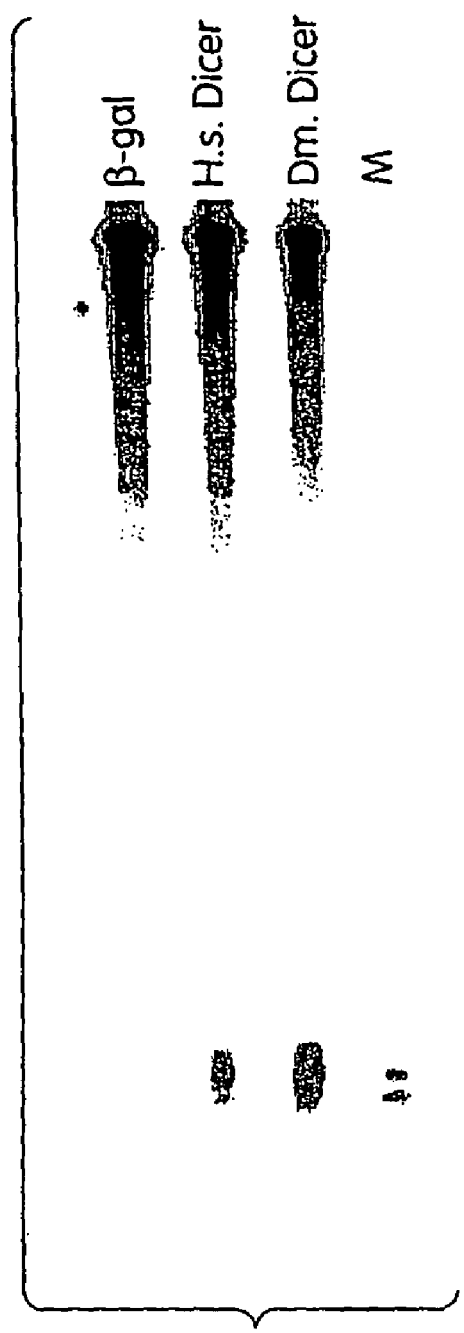
FIG. 23: Human dicer homolog when expressed and immunoprecipitated has 22-mer generating activity.
Figure 25:
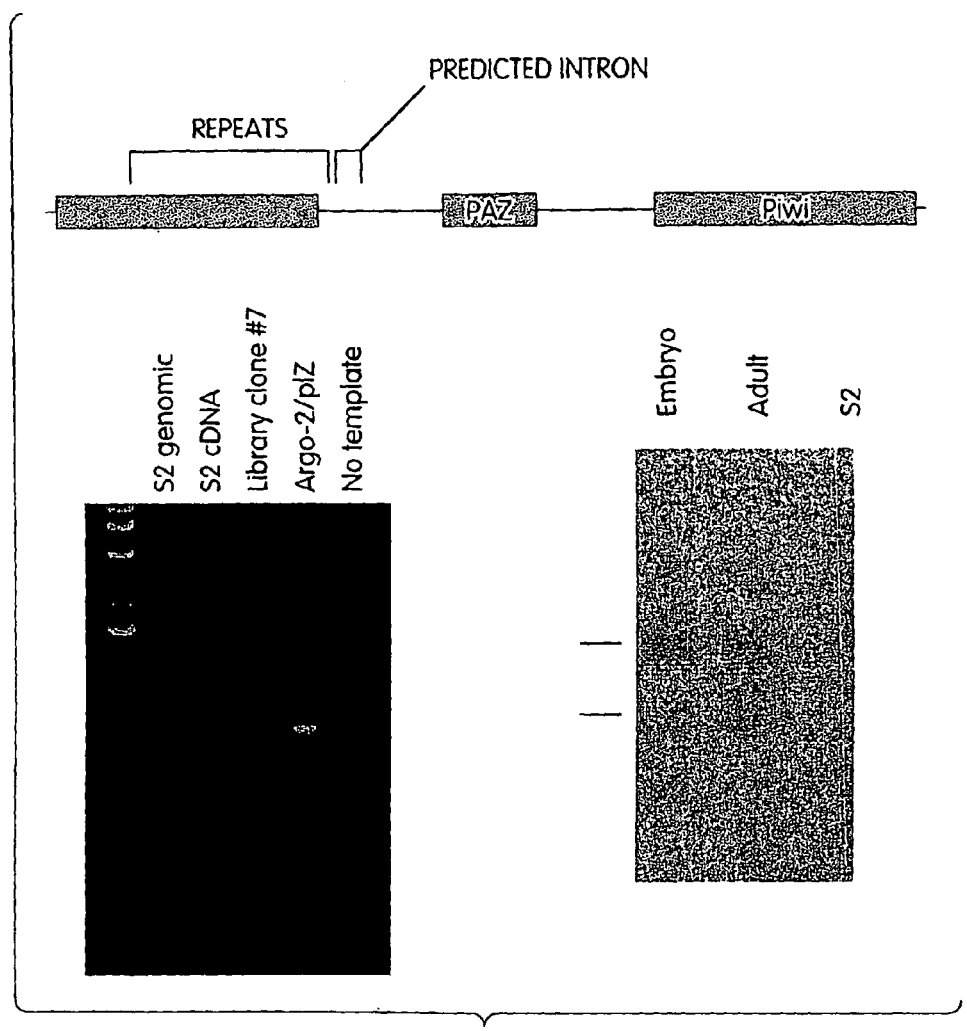
FIG. 25: Molecular characterization of *Drosophila* argonaute 2. The presence of an intron in coding sequence was determined by northern blotting using intron probe. This results in a different 5' reading frame then the published genome sequence. Number of polyglutamine repeats was determined by genomic PCR.
Figure 26:
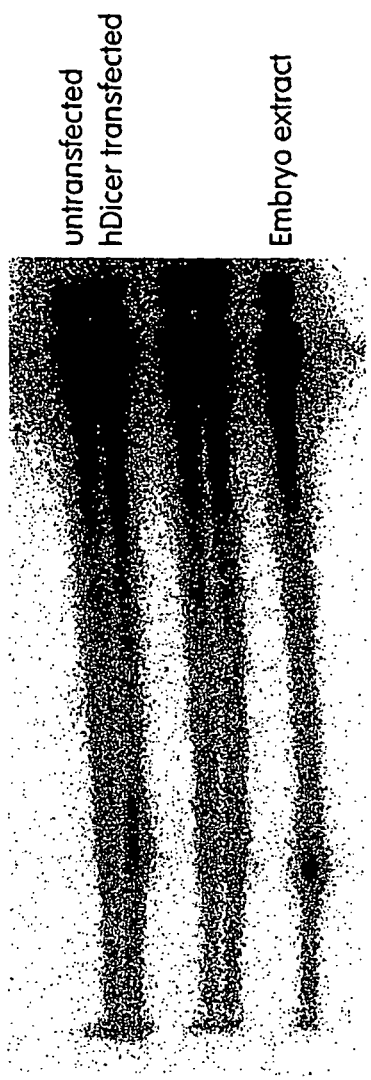
FIG. 26: Dicer activity can be created in human cells by expression of human dicer gene. Host cell was 293. Crude extracts had dicer activity, while activity was absent from untransfected cells. Activity is not dissimilar to that seen in *Drosophila* embryo extracts.

A notable feature of the Dicer family is its evolutionary conservation. Homologs are found in *C. elegans* (K12H4.8), *Arabidopsis* (e.g., CARPEL FACTORY (Jacobson et al., *Development* 126: 5231-5243, 1999), T25K16.4, AC012328_1), mammals (Helicase-MOI (Matsuda et al., *Biochim Biophys Acta* 1490: 163-169, 2000) and *S. pombe* (YC9A_SCHPO) (FIG. 8b, see Supplements 6, 7 for sequence comparisons). In fact, the human Dicer family member is capable of generating ~22 nt. RNAs from dsRNA substrates (Supplement 5) suggesting that these structurally similar proteins may all share similar biochemical functions. It has been demonstrated that exogenous dsRNAs can affect gene function in early mouse embryos (Wianny et al., *Nature Cell Biology* 2: 70-75, 2000), and our results suggest that this regulation may be accomplished by an evolutionarily conserved RNAi machinery.

In addition to RNaseIII and helicase motifs, searches of the PFAM database indicate that each Dicer family member also contains a ZAP domain (FIG. 8c) (Sonnhammer et al., *Proteins* 28: 405-420, 1997). This sequence was defined based solely upon its conservation in the Zwille/ARGONAUTE/Piwi family that has been implicated in RNAi by mutations in *C. elegans* (Rde-1) and *Neurospora* (Qde-2) (Tabara et al., *Cell* 99: 123-132, 1999; Catalanotto et al., *Nature* 404: 245, 2000). Although the function of this domain is unknown, it is intriguing that this region of homology is restricted to two gene families that participate in dsRNA-dependent silencing. Both the ARGONAUTE and Dicer families have also been implicated in common biological processes, namely the determination of stem-cell fates. A hypomorphic allele of carpel factory, a member of the Dicer family in *Arabidopsis*, is characterized by increased proliferation in floral meristems (Jacobsen et al., *Development* 126: 5231-5243, 1999). This phenotype and a number of other characteristic features are also shared by *Arabidopsis* ARGONAUTE (agol-1) mutants (Bohmert et al., *EMBO J.* 17: 170-180, 1998; C. Kidner and R. Martiennsen, pers. comm.). These genetic analyses begin to provide evidence that RNAi may be more than a defensive response to unusual RNAs but may also play important roles in the regulation of endogenous genes.

With the identification of Dicer as a catalyst of the initiation step of RNAi, we have begun to unravel the biochemical basis of this unusual mechanism of gene regulation. It will be of critical importance to determine whether the conserved family members from other organisms, particularly mammals, also play a role in dsRNA-mediated gene regulation.
Methods:

Plasmid constructs. A full-length cDNA encoding Drosha was obtained by PCR from an EST sequenced by the Berkeley *Drosophila* genome project. The Homeless clone was a gift from Gillespie and Berg (Univ. Washington). The T7 epitope-tag was added to the amino terminus of each by PCR, and the tagged cDNAs were cloned into pRIP, a retroviral vector designed specifically for expression in insect cells (E. Bernstein, unpublished). In this vector, expression is driven by the *Orgyia pseudotsugata* IE2 promoter (Invitrogen). Since no cDNA was available for CG4792/Dicer, a genomic clone was amplified from a bacmid (BACR23F10; obtained from the BACPAC Resource Center in the Dept. of Human Genetics at the Roswell Park Cancer Institute). Again, during amplification, a T7 epitope tag was added at the amino terminus of the coding sequence. The human Dicer gene was isolated from a cDNA library prepared from HaCaT cells (GJH, unpublished). A T7-tagged version of the complete coding sequence was cloned into pcDNA3 (Invitrogen) for expression in human cells (LinX-A).

Cell culture and extract preparation. S2 and embryo culture. S2 cells were cultured at 27° C. in 5% $CO_2$ in Schneider's insect media supplemented with 10% heat inactivated fetal bovine serum (Gemini) and 1% antibiotic-antimycotic solution (GIBCO BRL). Cells were harvested for extract preparation at $10 \times 10^6$ cells/ml. The cells were washed 1× in PBS and were resuspended in a hypotonic buffer (10 mM HEPES pH 7.0, 2 mM $MgCl_2$, 6 mM βME) and dounced. Cell lysates were spun 20,000×g for 20 minutes. Extracts were stored at −80° C. *Drosophila* embryos were reared in fly cages by standard methodologies and were collected every 12 hours. The embryos were dechorionated in 50% chlorox bleach and washed thoroughly with distilled water. Lysis buffer (10 mM Hepes, 10 mM KCl, 1.5 mM $MgCl_2$, 0.5 mM EGTA, 10 mM P-glycerophosphate, 1 mM DTT, 0.2 mM PMSF) was added to the embryos, and extracts were prepared by homogenization in a tissue grinder. Lysates were spun for two hours at 200,000×g and were frozen at −80° C. LinX-A cells, a highly-transfectable derivative of human 293 cells, (Lin Xie and GJH, unpublished) were maintained in DMEM/10% FCS.

Transfections and immunoprecipitations S2 cells were transfected using a calcium phosphate procedure essentially as previously described (Hammond et al., Nature 404: 293-296, 2000). Transfection rates were ~90% as monitored in controls using an in situ D-galactosidase assay. LinX-A cells were also transfected by calcium phosphate co-precipitation. For immunoprecipitations, cells (~$5 \times 10^6$ per IP) were transfected with various clones and lysed three days later in IP buffer (125 mM KOAc, 1 mM MgOAc, 1 mM $CaCl_2$, 5 mM EGTA, 20 mM Hepes pH 7.0, 1 mM DTT, 1% NP-40 plus Complete protease inhibitors, Roche). Lysates were spun for 10 minutes at 14,000×g and supernatants were added to T7 antibody-agarose beads (Novagen). Antibody binding proceeded for 4 hours at 4° C. Beads were centrifuged and washed in lysis buffer three times, and once in reaction buffer. The Dicer antiserum was raised in rabbits using a KLH-conjugated peptide corresponding to the C-terminal 8 amino acids of *Drosophila* Dicer-1 (CG4792).

Cleavage reactions. RNA preparation. Templates to be transcribed into dsRNA were generated by PCR with forward and reverse primers, each containing a T7 promoter sequence. RNAs were produced using Riboprobe (Promega) kits and were uniformly labeling during the transcription reaction with $^{32}$P-UTP. Single-stranded RNAs were purified from 1% agarose gels. dsRNA cleavage. Five microliters of embryo or S2 extracts were incubated for one hour at 30° C. with dsRNA in a reaction containing 20 mM Hepes pH 7.0, 2 mM MgOAc, 2 mM DTT, 1 mM ATP and 5% Superasin (Ambion). Immunoprecipitates were treated similarly except that a minimal volume of reaction buffer (including ATP and Superasin) and dsRNA were added to beads that had been washed in reaction buffer (see above). For ATP depletion, *Drosophila* embryo extracts were incubated for 20 minutes at 30° C. with 2 mM glucose and 0.375 U of hexokinase (Roche) prior to the addition of dsRNA.

Northern and Western analysis. Total RNA was prepared from *Drosophila* embryos (0-12 hour), from adult flies, and from S2 cells using Trizol (Lifetech). Messenger RNA was isolated by affinity selection using magnetic oligo-dT beads (Dynal). RNAs were electrophoresed on denaturing formaldehyde/agarose gels, blotted and probed with randomly primed DNAs corresponding to Dicer. For Western analysis, T7-tagged proteins were immunoprecipitated from whole cell lysates in IP buffer using anti-T7-antibody-agarose conjugates. Proteins were released from the beads by boiling in Laemmli buffer and were separated by electrophoresis on 8% SDS PAGE. Following transfer to nitrocellulose, proteins were visualized using an HRP-conjugated anti-T7 antibody (Novagen) and chemiluminescent detection (Supersignal, Pierce).

RNAi of Dicer. *Drosophila* S2 cells were transfected either with a dsRNA corresponding to mouse caspase 9 or with a mixture of two dsRNAs corresponding to *Drosophila* Dicer-1 and Dicer-2 (CG4792 and CG6493). Two days after the initial transfection, cells were again transfected with a mixture containing a GFP expression plasmid and either luciferase dsRNA or GFP dsRNA as previously described (Hammond et al., *Nature* 404: 293-296, 2000). Cells were assayed for Dicer activity or fluorescence three days after the second transfection. Quantification of fluorescent cells was done on a Coulter EPICS cell sorter after fixation. Control transfections indicated that Dicer activity was not affected by the introduction of caspase 9 dsRNA.

EXAMPLE 3

A Simplified Method for the Creation of Hairpin Constructs for RNA Interference

In numerous model organisms, double stranded RNAs have been shown to cause effective and specific suppression of gene function (Bosher and Labouesse, *Nature Cell Biology* 2: E31-E36, 2000). This response, termed RNA interference or post-transcriptional gene silencing, has evolved into a highly effective reverse genetic tool in *C. elegans*, *Drosophila*, plants and numerous other systems. In these cases, double-stranded RNAs can be introduced by injection, transfection or feeding; however, in all cases, the response is both transient and systemic. Recently, stable interference with gene expression has been achieved by expression of RNAs that form snap-back or hairpin structures (Fortier and Belote, *Genesis* 26: 240-244, 2000; Kennerdell and Carthew, *Nature Biotechnology* 18: 896-898, 2000; Lam and Thummel, *Current Biology* 10: 957-963, 2000; Shi et al., RNA 6: 1069-1076, 2000; Smith et al., *Nature* 407: 319-320, 2000; Tavernarakis et al., *Nature Genetics* 24: 180-183, 2000). This has the potential not only to allow stable silencing of gene expression but also inducible silencing as has been observed in trypanosomes and adult *Drosophila* (Fortier and Belote, *Genesis* 26: 240-244, 2000; Lam and Thummel, *Current Biology* 10: 957-963, 2000; Shi et al., *RNA* 6: 1069-1076, 2000). The utility of this approach is somewhat hampered by the difficulties that arise in the construction of bacterial plasmids containing the long inverted repeats that are necessary to provoke silencing. In a recent report, it was stated that more than 1,000 putative clones were screened to identify the desired construct (Tavemarakis et al., *Nature Genetics* 24: 180-183, 2000).

Figure 27:
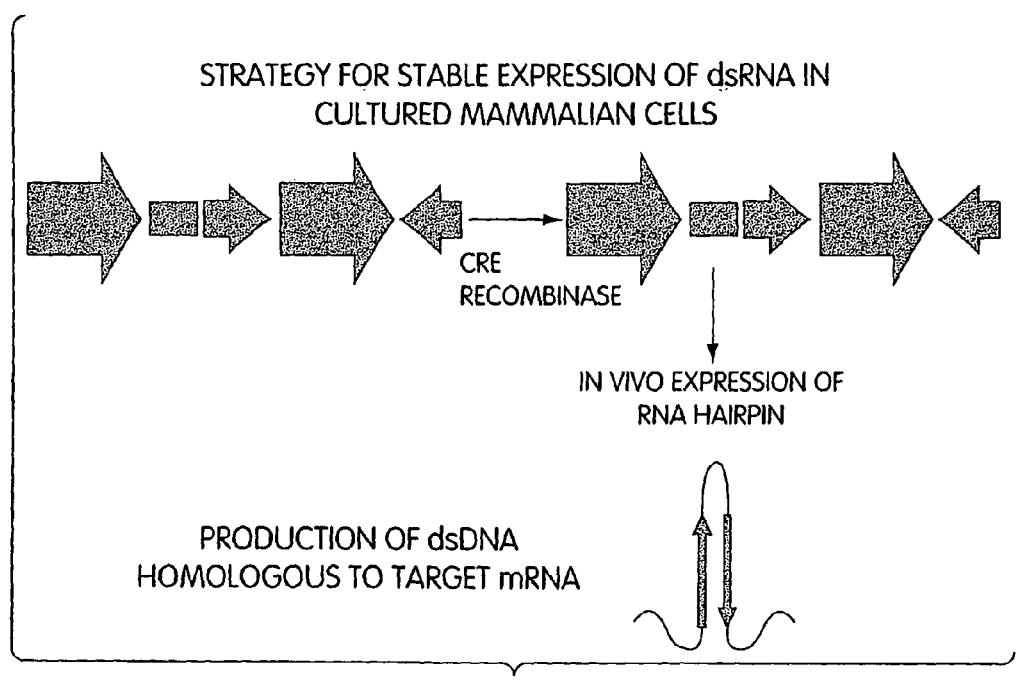
FIG. 27: A ~500 nt. fragment of the gene that is to be silenced (X) is inserted into the modified vector as a stable direct repeat using standard cloning procedures. Treatment with commercially available cre recombinase reverses sequences within the loxP sites (L) to create an inverted repeat. This can be stably maintained and amplified in an sbc mutant bacterial strain (DL759). Transcription in vitro from the promoter of choice (P) yields a hairpin RNA that causes silencing. A zeocin resistance marker is included to insure maintenance of the direct and inverted repeat structures; however this is non-essential in vitro and could be removed by pre-mRNA splicing if desired. (Smith et al. (2000) *Nature* 407: 319-20).

The presence of hairpin structures often induces plasmid rearrangement, in part due to the *E. coli* sbc proteins that recognize and cleave cruciform DNA structures (Connelly et al., *Genes Cell* 1: 285-291, 1996). We have developed a method for the construction of hairpins that does not require cloning of inverted repeats, per se. Instead, the fragment of the gene that is to be silenced is cloned as a direct repeat, and the inversion is accomplished by treatment with a site-specific recombinase, either in vitro (or potentially in vitro) (see FIG. 27). Following recombination, the inverted repeat structure is stable in a bacterial strain that lacks an intact SBC system (DL759). We have successfully used this strategy to construct numerous hairpin expression constructs that have been successfully used to provoke gene silencing in *Drosophila* cells.

In the following examples, we use this method to express long dsRNAs in a variety of mammalian cell types. We show that such long dsRNAs mediate RNAi in a variety of cell types. Additionally, since the vector described in FIG. 27 contains a selectable marker, dsRNAs produced in this manner can be stably expressed in cells. Accordingly, this method allows not only the examination of transient effects of RNA suppression in a cell, but also the effects of stable and prolonged RNA suppression.

Methods:

Plasmids expressing hairpin RNAs were constructed by cloning the first 500 bps of the GFP coding region into the FLIP cassette of pRIP-FLIP as a direct repeat. The FLIP cassette contains two directional cloning sites, the second of which is flanked by LoxP sites. The Zeocin gene, present between the cloning sites, maintains selection and stability. To create an inverted repeat for hairpin production, the direct repeat clones were exposed to Cre recombinase (Stratagene) in vitro and, afterwards, transformed into DL759 *E. coli*. These bacteria permit the replication of DNA containing cruciform structures, which tend to form inverted repeats.

EXAMPLE 4

Long dsRNAs Suppress Gene Expression in Mammalian Cells

Previous experiments have demonstrated that dsRNA, produced using a variety of methods including via the construction of hairpins, can suppress gene expression in *Drosophila* cells. We now demonstrate that dsRNA can also suppress gene expression in mammalian cells in culture. Additionally, the power of RNAi as a genetic tool would be greatly enhanced by the ability to engineer stable silencing of gene expression. We therefore undertook an effort to identify mammalian cells in which long dsRNAs could be used as RNAi triggers in the hope that these same cell lines would provide a platform upon which to develop stable silencing strategies. We demonstrate that RNA suppression can be mediated by stably expressing a long hairpin in a mammalian cell line. The ability to engineer stable silencing of gene expression in cultured mammalian cells, in addition to the ability to transiently silence gene expression, has many important applications.

A. RNAi in Pluripotent Murine P19 Cells.

We first sought to determine whether long dsRNA triggers could induce sequence-specific silencing in cultured murine cells, both to develop this approach as a tool for probing gene function and to allow mechanistic studies of dsRNA-induced silencing to be propagated to mammalian systems. We, therefore, attempted to extend previous studies in mouse embryos (Wianny et al., *Nat. Cell Biol.* 2: 70-75, 2000; Svoboda et al., *Development* 127: 4147-4156, 2000) by searching for RNAi-like mechanisms in pluripotent, embryonic cell types. We surveyed a number of cell lines of embryonic origin for the degree to which generalized suppression of gene expression occurred upon introduction of dsRNA. As an assay, we tested the effects of dsRNA on the expression of GFP as measured in situ by counting fluorescent cells. As expected, in both human embryonic kidney cells (293) and mouse embryo fibroblasts, GFP expression was virtually eliminated irrespective of the sequence of the cotransfected dsRNA. In some pluripotent teratocarcinoma and teratoma cell lines (e.g., N-Teral, F9), the PKR response was attenuated but still evident; however, in contrast, transfection of nonhomologous dsRNAs had no effect on the expression of reporter genes (e.g., GFP or luciferase) either in mouse embryonic stem cells or in p19 embryonal carcinoma cells (FIG. 28).

Transfection of P19 embryonal carcinoma cells with GFP in the presence of cognate dsRNA corresponding to the first ≈500 nts of the GFP coding sequence had a strikingly different effect. GFP expression was eliminated in the vast majority of cotransfected cells (FIG. 28), suggesting that these cultured murine cells might respond to dsRNA in a manner similar to that which we had previously demonstrated in cultured, *Drosophila* S2 cells (Hammond et al., *Nature* 404: 293-296, 2000).

To quantify the extent to which dsRNA could induce sequence-specific gene silencing, we used a dual luciferase reporter assay similar to that which had first been used to demonstrate RNAi in *Drosophila* embryo extracts (Tuscbl et al., *Genes Dev.* 13: 3191-3197, 1999). P19 EC cells were transfected with a mixture of two plasmids that individually direct the expression of firefly luciferase and *Renilla* luciferase. These were cotransfected with no dsRNA, with dsRNA that corresponds to the first ≈500 nts of the firefly luciferase, or with dsRNA corresponding to the first ~500 nts of GFP as a control. Cotransfection with GFP dsRNA gave luciferase activities that were similar to the no-dsRNA control, both in the firefly/*Renilla* activity ratio and in the absolute values of both activities. In contrast, in cells that received the firefly luciferase dsRNA, the ratio of firefly to *Renilla* luciferase activity was reduced by up to 30-fold (250 ng, FIG. 29B). For comparison, we carried out an identical set of experiments in *Drosophila* S2 cells. Although qualitatively similar results were obtained, the silencing response was more potent. At equivalent levels of dsRNA, S2 cells suppressed firefly luciferase activity to virtually background levels.

Figure 29A:
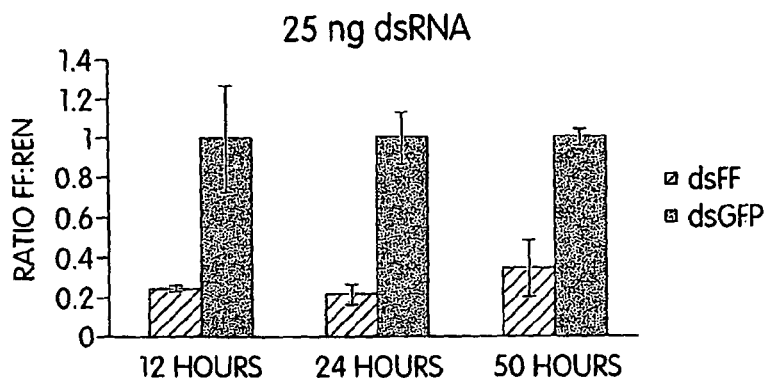
Figure 29B:
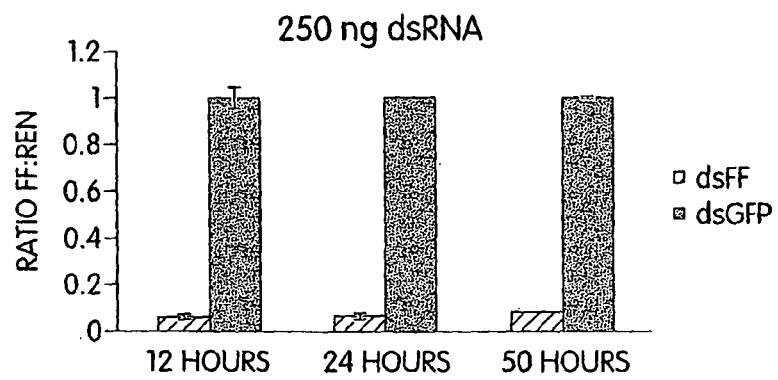
Figure 29C:
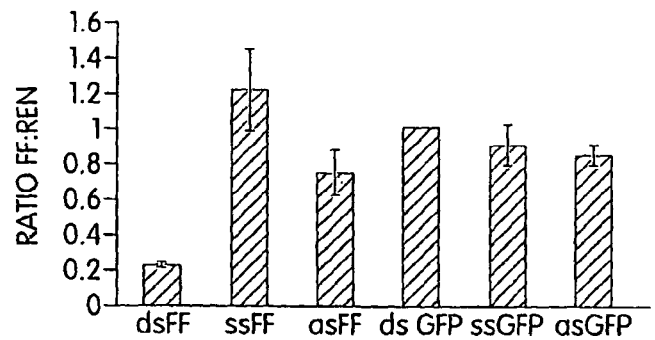
Figure 29D:
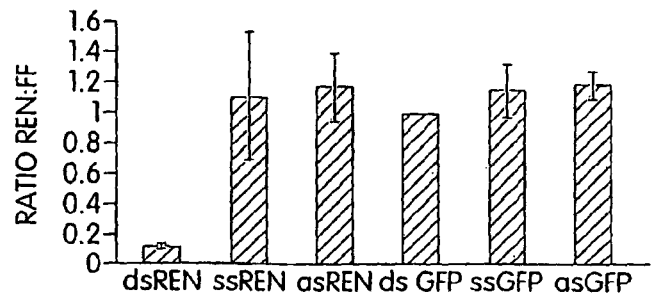

The complementary experiment, in which dsRNA was homologous to *Renilla* luciferase, was also performed. Again, in this case, suppression of the expression of the *Renilla* enzyme was ≈10-fold (FIG. 29D). Thus, the dsRNA response in P19 cells was flexible, and the silencing machinery was able to adapt to dsRNAs directed against any of the reporters that were tested.

We took two approaches to test whether this response was specific for dsRNA. Pretreatment of the trigger with purified RNase III, a dsRNA-specific ribonuclease, before transfection greatly reduced its ability to provoke silencing. Furthermore, transfection of cells with single-stranded antisense RNAs directed against either firefly or *Renilla* luciferase had little or no effect on expression of the reporters (FIGS. 29C and 29D). Considered together, these results provided a strong indication that double-stranded RNAs provoke a potent and specific silencing response in P19 embryonal carcinoma cells. Efficient silencing could be provoked with relatively low concentrations of dsRNA (25 ng/ml culture media; see FIG. 29A). The response was concentration-dependent, with maximal suppression of ≈20-fold being achieved at a dose of 1.5 μg/ml culture media. Silencing was established rapidly and was evident by 9 h post-transfection (the earliest time point examined). Furthermore, the response persisted without significant changes in the degree of suppression for up to 72 h following a single dose of dsRNA.

FIG. 30 further shows wild-type P19 cells which have been co-transfected with either RFP or GFP (right panel). Note the robust expression of RFP or GFR respectively approximately 42 hours post-transfection. We isolated P19 clones which stably express a 500 nt. GFP hairpin. Such clones were then transfected with either RFP or GFP, and expression of RFP or GFP was assessed by visual inspection of the cells. The left panel demonstrates that a 500 nt GFP hairpin specifically suppresses expression of GFP in P19 cells.

B. RNAi in Embryonic Stem Cells.

To assess whether the presence of a sequence-specific response to dsRNA was a peculiarity of P19 cells or whether it also extended to normal murine embryonic cells, we performed similar silencing assays in mouse embryonic stem cells. Cotransfection of embryonic stem cells with noncognate dsRNAs (e.g., GFP), again, had no dramatic effect on either the absolute values or the ratios of *Renilla* and firefly luciferase activity (FIG. 31). However, transfection with either firefly or *Renilla* luciferase dsRNA dramatically and specifically reduced the activity of the targeted enzyme (FIG. 31).

This result suggests that RNAi can operate in multiple murine cell types of embryonic origin, including normal embryonic stem cells. The ability to provoke silencing in a cell type that is normally used for the generation of genetic, mosaic animals suggests the possibility of eventually testing the biological effects of silencing both in culture and in reconstituted animal models. Our ability to successfully manipulate ES cell via RNAi allows the use of RNAi in the generation of transgenic and knock-out mice.

C. RNAi in Murine Somatic Cells.

RNAi effector pathways are likely to be present in mammalian somatic cells, based on the ability of siRNAs to induce transient silencing (Elbashir et al., *Nature* 411: 494-498, 2001). Furthermore, we have shown that RNAi initiator and effector pathways clearly exist in embryonic cells that can enforce silencing in response to long dsRNA triggers. We therefore sought to test whether the RNAi machinery might exist intact in some somatic cell lines.

Figure 32B:
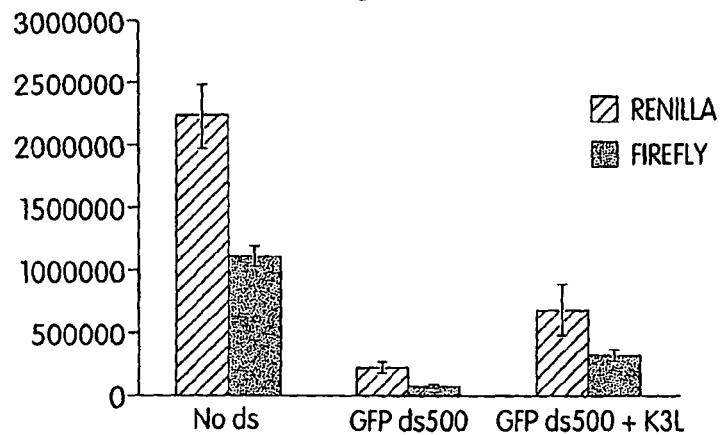

Transfection of HeLa cells with luciferase reporters in combination with long dsRNA triggers caused a nearly complete suppression of activity, irrespective of the RNA sequence. In a murine myoblast cell line, C2C12, we noted a mixture of two responses. dsRNAs homologous to firefly luciferase provoked a sequence-specific effect, producing a degree of suppression that was slightly more potent than was observed upon transfection with cognate ≈21-nt siRNA (Elbashir et al., *Nature* 411: 494-498, 2001) (see FIG. 32A). However, with long dsRNA triggers, the specific effect was superimposed upon a generalized suppression of reporter gene expression that was presumably because of PKR activation (FIG. 32B).

Numerous mammalian viruses have evolved the ability to block PKR as an aid to efficient infection. For example, adenoviruses express VA RNAs, which mimic dsRNA with respect to binding but not to activation of PKR (Clarke et al., *RNA* 1: 7-20, 1995). Vaccinia virus uses two strategies to evade PKR. The first is expression of E3L, which binds and masks dsRNAs (Kawagishi-Kobayashi et al., *Virology* 276: 424-434, 2000). The second is expression of K3L, which binds and inhibits PKR via its ability to mimic the natural substrate of this enzyme, eIF2α (Kawagishi-Kobayashi et al. 2000, supra).

Figure 32C:
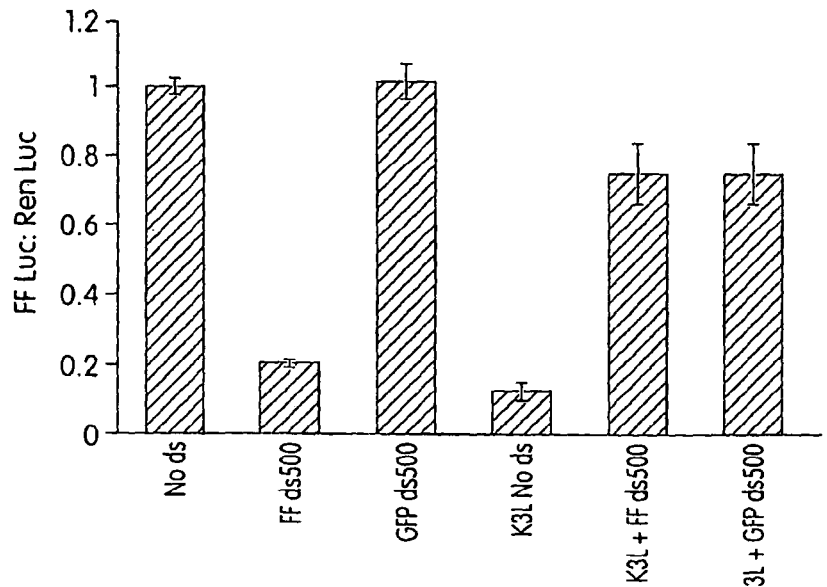

Transfection of C2C12 cells with a vector that directs K3L expression attenuates the generalized repression of reporter genes in response to dsRNA. However, this protein had no effect on the magnitude of specific inhibition by RNAi (FIG. 32C).

FIG. 33 further shows the results of a transient co-transfection assay performed in Hela cells, CHO cells, and P19 cells. The cell lines were each transfected with plasmids expressing *Photinus pyralis* (firefly) and *Renila reniformis* (sea pansy) luciferases. The cells lines were additionally transfected with 400 ng of 500 nt dsRNAs corresponding to either firefly luciferase (dsLUC) or dsGFP. The results demonstrate that dsRNA can specifically mediate suppression in a multiple mammalian cells types in culture.

These results raise the possibility that, at least in some cell lines and/or cell types, blocking nonspecific responses to dsRNA will enable the use of long dsRNAs for the study of gene function. This might be accomplished through the use of viral inhibitors, as described here, or through the use of cells isolated from animals that are genetically modified to lack undesirable responses.

D. Stable Suppression of Gene Expression Using RNAi.

To date, dsRNAs have been used to induce sequence-specific gene silencing in either cultured mammalian cells or in embryos only in a transient fashion. However, the most powerful applications of genetic manipulation are realized only with the creation of stable mutants. The ability to induce silencing by using long dsRNAs offers the opportunity to translate into mammalian cells work from model systems such as *Drosophila*, plants, and *C. elegans* wherein stable silencing has been achieved by enforced expression of hairpin RNAs (Kennerdell et al., *Nat. Biotechnol.* 18: 896-898, 2000; Smith et al., *Nature* 407: 319-320, 2000; Tavernarakis et al., *Nat. Genet.* 24:180-183, 2000).

P19 EC cells were transfected with a control vector or with an expression vector that directs expression of a ≈500-nt GFP hairpin RNA from an RNA polymerase II promoter (cytomegalovirus). Colonies arising from cells that had stably integrated either construct were selected and expanded into clonal cell lines. Each cell line was assayed for persistent RNAi by transient co-transfection with a mixture of two reporter genes, dsRED to mark transfected cells and GFP to test for stable silencing.

Figure 34A:
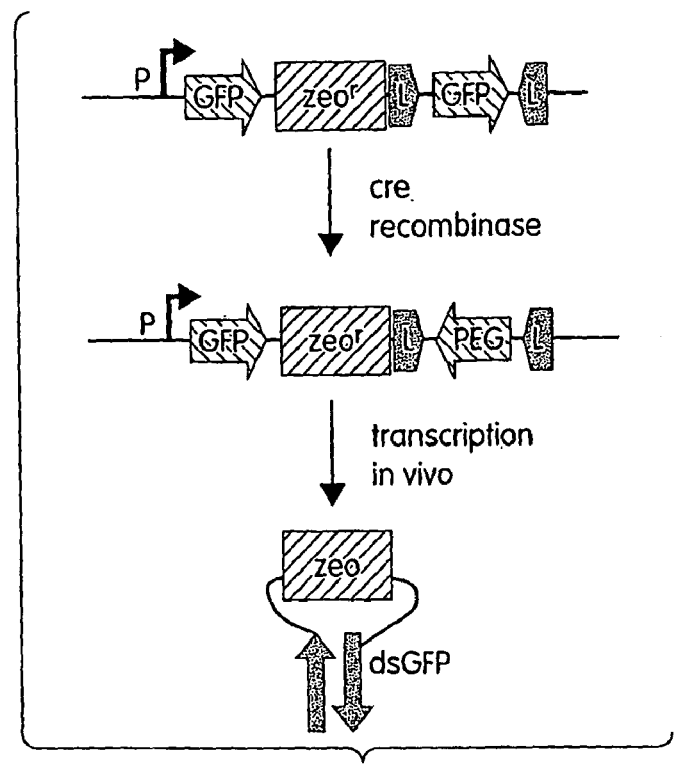
Figure 34B:
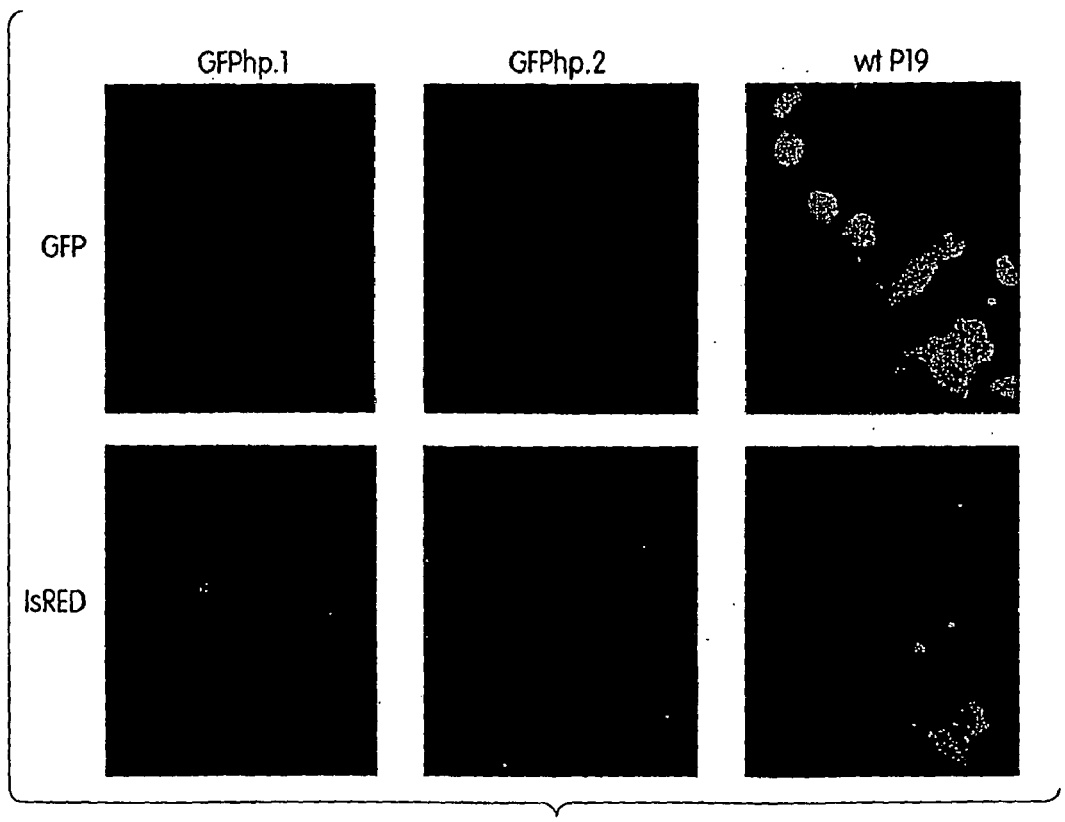

Transfection of clonal P19 EC cells that had stably integrated the control vector produced equal numbers of red and green cells, as would be expected in the absence of any specific silencing response (FIG. 34B), whereas cells that express the GFP hairpin RNA gave a very different result. These cells expressed the dsRED protein with an efficiency comparable to that observed in cells containing the control vector. However, the cells failed to express the cotransfected GFP reporter (FIG. 34B). These data provide a strong indication that continuous expression of a hairpin dsRNA can provoke stable, sequence-specific silencing of a target gene.

Figure 34C:
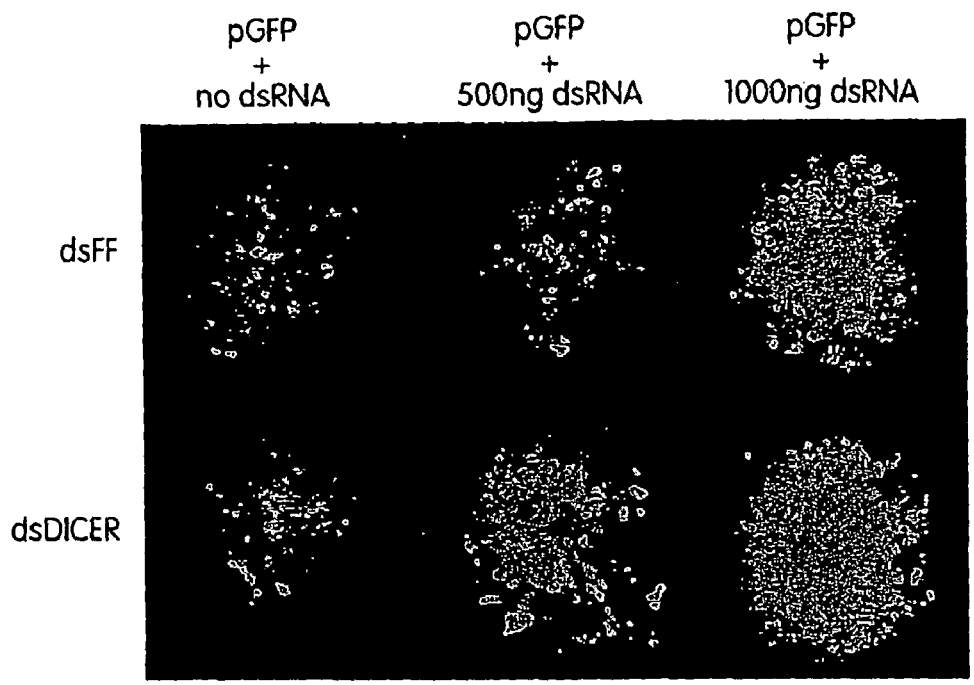

In *Drosophila* S2 cells and *C. elegans*, RNAi is initiated by the Dicer enzyme, which processes dsRNA into 22-nt siRNAs (Bernstein et al., *Nature* 409: 363-366, 2001; Grishok et al., *Cell* 106: 23-34, 2001; Hutvagner et al., *Science* 293: 834-838, 2001; Ketting et al., *Genes Dev.* 15: 2654-2659, 2001; Knight et al., *Science* 293: 2269-2271, 2001). In both, S2 cells and *C. elegans* experiments by using dsRNA to target Dicer suppress the RNAi response. Whether Dicer plays a central role in hairpin-induced gene silencing in P19 cells was tested by transfecting P19 cells stably transfected with GFP hairpin constructs with mouse Dicer dsRNA. Treatment with Dicer dsRNA, but not control dsRNA, resulted in depression of GFP (FIG. 34C).

E. dsRNA Induces Posttranscriptional Silencing.

Figure 34D:
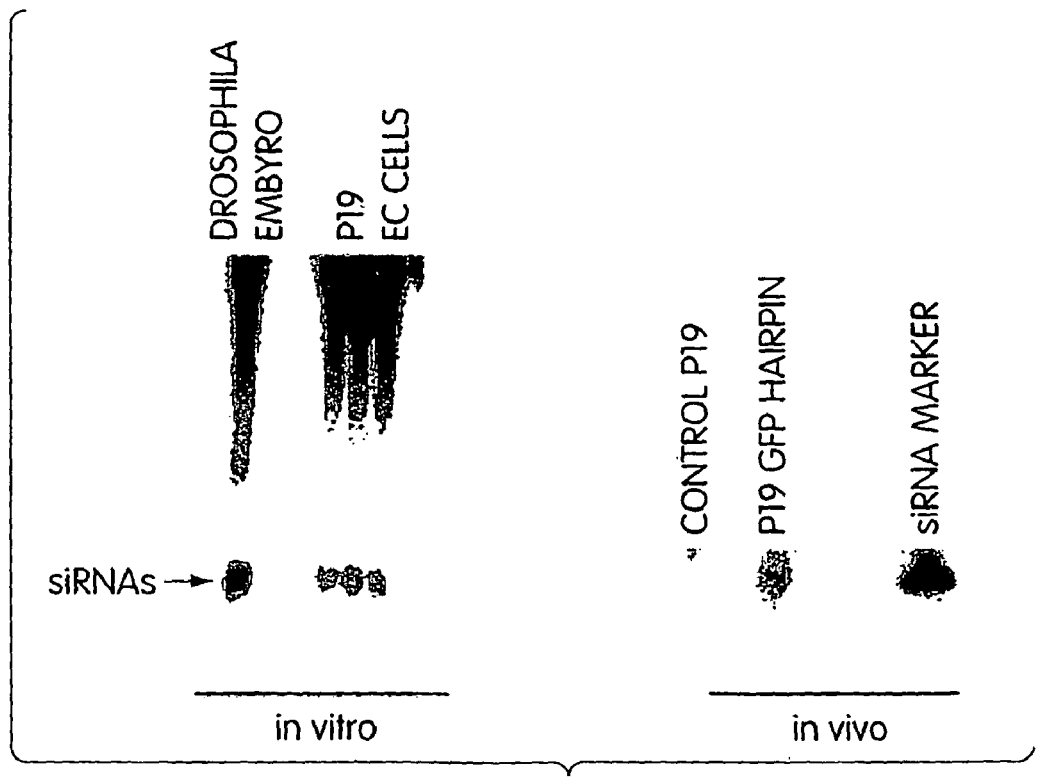

A key feature of RNAi is that it exerts its effect at the posttranscriptional level by destruction of targeted mRNAs (Hammond et al., *Nat. Rev. Genet.* 2: 110-119, 2001). To test whether dsRNAs induced silencing in mouse cells via post-transcriptional mechanisms, we used an assay identical to that, used initially to characterize RNAi responses in *Drosophila* embryo extracts (Tuschl et al., *Genes Dev.* 13: 3191-3197, 1999). We prepared lysates from P19 EC cells that were competent for in vitro translation of capped mRNAs corresponding to *Renilla* and firefly luciferase. Addition of non-specific dsRNAs to these extracts had no substantial effect on either the absolute amount of luciferase expression or on the ratio of firefly to *Renilla* luciferase (FIG. 35). In contrast, addition of dsRNA homologous to the firefly luciferase induced a dramatic and dose-dependent suppression of activity. Addition of RNA corresponding to only the antisense strand of the dsRNA had little effect, comparable to a non-specific dsRNA control, and pretreatment of the dsRNA silencing trigger with RNase III greatly reduced its potential to induce silencing in vitro. A second hallmark of RNAi is the production of small, ≈22-nt siRNAs, which determine the specificity of silencing. We found that such RNA species were generated from dsRNA in P19 cell extracts (FIG. 34D, in vitro), indicative of the presence of a mouse Dicer activity. These species were also produced in cells that stably express GFP hairpin RNAs (FIG. 34D, in vitro). Considered together, the posttranscriptional nature of dsRNA-induced silencing, the association of silencing with the production of ~22-nt siRNAs, and the dependence of this response on Dicer, a key player in the RNAi pathway, strongly suggests that dsRNA suppresses gene expression in murine cells via a conventional RNAi mechanism.

F. RNAi-Mediated Gene Silencing is Specific and Requires dsRNAs.

We carried out experiments to verify that the suppressive effects observed in the in vitro system were specific to double stranded RNA. Briefly, experiments were performed in accordance with the methods outlined above. Either dsRNA (ds), single-stranded RNA (ss), or antisense-RNA (as) corresponding to firefly (FF) or *Renilla* (Ren) luciferase was added to the translation reaction. Following reactions performed at 30° C. for 1 hour, dual luciferase assays were performed using an Analytical Scientific Instruments model 3010 Luminometer.

FIG. 36 summarizes the results of these experiments which demonstrate that the suppression of gene expression observed in this in vitro assay is specific for dsRNA. These results further support the conclusion that dsRNA suppresses gene expression in this mammalian in vitro system in a manner consistent with post-transcriptional silencing.

G. Mammalian Cells Soaked with dsRNAs Results in Gene Silencing.

Studies of post-transcriptional silencing in invertebrates have demonstrated that transfection or injection of the dsRNA is not necessary to achieve the suppressive affects. For example, dsRNA suppression in *C. elegans* can be observed by either soaking the worms in dsRNA, or by feeding the worms bacteria expressing the dsRNA of interest. We addressed whether dsRNA suppression in mammalian cells could be observed without transfection of the dsRNA. Such a result would present additional potential for easily using dsRNA suppression in mammalian cells, and would also allow the use of dsRNA to suppress gene expression in cell types which have been difficult to transfect (i.e., cell types with a low transfection efficiency, or cell types which have proven difficult to transfect at all).

P19 cells were grown in 6-well tissue culture plates to approximately 60% confluency in growth media (αMEM/ 10% FBS). Varying concentrations of firefly dsRNA were added to the cultures, and cells were cultured for 12 hours in growth media+dsRNA. Cells were then transfected with plasmids expressing firefly or sea pansy luciferase, as described in detail above. Dual luciferase assays were carried out 12 hours post-transfection using an Analytical Scientific Instruments model 3010 Luminometer.

FIG. 37 summarizes these results which demonstrate that dsRNA can suppress gene expression in mammalian cells without transfection. Culturing cells in the presence of dsRNA resulted in a dose dependent suppression of firefly luciferase gene expression.

Methods:

Cell Culture. P19 mouse embryonic carcinoma cells (American Type Culture Collection, CRL-1825) were cultured in α-MEM (GIBCO/BRL) supplemented with 10% heat-inactivated FBS and 1% antibiotic/antimycotic solution (GIBCO/BRL). Mouse embryo stem cells (J1, provided by S. Kim, Cold Spring Harbor Laboratory) were cultured in DMEM containing ESgro (Chemicon) according to the manufacturer's instructions. C2C12 murine myoblast cells (gift of N. Tonks, Cold Spring Harbor Laboratory) were cultured in DMEM (GIBCO/BRL) supplemented with 10% beat-inactivated FBS and 1% antibiotic/antimycotic solution (GIBCO/BRL).

RNA Preparation. For the production of dsRNA, transcription templates were generated by PCR; they contained T7 promoter sequences on each end of the template (see Hammond et al. 2000, Nature 404: 293-296). dsRNAs were prepared by using the RiboMax kit (Ambion, Austin, Tex.). Firefly and *Renilla* luciferase mRNA transcripts were synthesized by using the Riboprobe kit (Promega) and were gel purified before use.

Transfection and Gene Silencing Assays. Cells were transfected with indicated amounts of dsRNA and plasmid DNA by using FuGENE6 (Roche Biochemicals) according to the manufacturer's instructions. Cells were transfected at 50-70% confluence in 12-well plates containing either 1 or 2 ml of medium per well. Dual luciferase assays (Promega) were carried out by co-transfecting cells with plasmids contain firefly luciferase under the control of SV40 promoter (pGL3-Control, Promega) and *Renilla* luciferase under the control of the SV40 early enhancer/promoter region (pSV40, Promega). These plasmids were cotransfected by using a 1:1 or 10:1 ratio of pGL3-control (250 ng/well) to pRL-SV40. Both ratios yielded similar results. For some experiments, cells were transfected with vectors that direct expression of enhanced green fluorescent protein (EGFP)-US9 fusion protein (Kalejta et al., *Exp. Cell Res.* 248: 322-328, 1999) or red fluorescent protein (RFP) (pDsRed N1, CLONTECH). RNAi in S2 cells was performed as described (Hammond et al., *Nature* 404: 293-296, 2000).

Plasmids expressing hairpin RNAs (RNAs with a self-complimentary stem loop) were constructed by cloning the first 500 bp of the EGFP coding region (CLONTECH) into the FLIP cassette of pRIP-FLIP as a direct repeat. The FLIP cassette contains two directional cloning sites, the second of which sports flanking LoxP sites (see FIG. 35A). The Zeocin gene (Stratagene), present between the cloning sites, maintains selection and, thus, stability of the FLIP cassette. The FLIP cassette containing EGFP direct repeats was subcloned into pcDNA3 (Invitrogen). To create an inverted repeat for hairpin production, EGFP direct repeat clones were exposed to Cre recombinase (Stratagene) in vitro and, afterward, transformed into DL759 *Escherichia coli* (Connelly et al., *Genes Cells* 1: 285-291, 1996). These bacteria permit the replication of DNA containing cruciform structures, which tend to form from inverted repeats. DL759 transformants were screened for plasmids containing inverted repeats (≈50%).

Silencing of Dicer was accomplished by using a dsRNA comprising exon 25 of the mouse Dicer gene and corresponding to nucleotides 5284-5552 of the human Dicer cDNA.

In vitro Translation and in vitro Dicer Assays. Logarithmically growing cells were harvested in PBS containing 5 mM EGTA washed twice in PBS and once in hypotonic buffer (10 mM Hepes, pH 7.3/6 mM β-mercaptoethanol). Cells were suspended in 0.7 packed-cell volumes of hypotonic buffer containing Complete protease inhibitors (Roche Molecular Biochemicals) and 0.5 units/ml of RNasin (Promega). Cells were disrupted in a Dounce homogenizer with a type B pestle, and lysates were centrifuged at 30,000×g for 20 min. Supernatants were used in an in vitro translation assay containing capped m7G(5')pppG firefly and *Renilla* luciferase mRNA or in in vitro Dicer assays containing $^{32}$P-labeled dsRNA. For in vitro translation assays, 5 µl of extract were mixed with 100 ng of firefly and *Renilla* mRNA along with 1 µg of dsRNA (or buffer)/10 mM DTT/0.5 mM spermidine/200 mM Hepes, 3.3 mM MgOAc/800 mM KOAc/1 mM ATP/1 mM GTP/4 units of Rnasin/215 µg of creatine phosphate/1 µg of creatine phosphate kinase/1 mM amino acids (Promega). Reactions were carried out for 1 h at 30° C. and quenched by adding 1× passive lysis buffer (Promega). Extracts were then assayed for luciferase activity. In vitro assays for Dicer activity were performed as described (Bernstein et al., *Nature* 409: 363-366, 2001).

Construction of Stable Silencing Lines. Ten-centimeter plates of P19 cells were transfected with 5 µg of GFP hairpin expression plasmid and selected for stable integrants by using G-418 (300 ng/ml) for 14 days. Clones were selected and screened for silencing of GFP.

EXAMPLE 5

Compositions and Methods for Synthesizing siRNAs

Previous results have indicated that short synthetic RNAs (siRNAs) can efficiently induce RNA suppression. Since short RNAs do not activate the non-specific PKR response, they offer a means for efficiently silencing gene expression in a range of cell types. However, the current state of the art with respect to siRNAs has several limitations. Firstly, siRNAs are currently chemically synthesized at great cost (approx. $400/ siRNA). Such high costs make siRNAs impractical for either small laboratories or for use in large scale screening efforts. Accordingly, there is a need in the art for methods for generating siRNAs at reduced cost.

We provide compositions and methods for synthesizing siRNAs by T7 polymerase. This approach allows for the efficient synthesis of siRNAs at a cost consistent with standard RNA transcription reactions (approx. $16/siRNA). This greatly reduced cost makes the use of siRNA a reasonable approach for small laboratories, and also will facilitate their use in large-scale screening projects.

FIG. 38 shows the method for producing siRNAs using T7 polymerase. Briefly, T7 polymerase is used to transcribe both a sense and antisense transcript. The transcripts are then annealed to provide an siRNA. One of skill in the art will recognize that any one of the available RNA polymerases can be readily substituted for T7 to practice the invention (i.e., T3, Sp6, etc.).

This approach is amenable to the generation of a single siRNA species, as well as to the generation of a library of siRNAs. Such a library of siRNAs can be used in any number of high-throughput screens including cell based phenotypic screens and gene array based screens.

EXAMPLE 6

Generation of Short Hairpin dsRNA and Suppression of Gene Expression Using Such Short Hairpins Since the realization that small, endogenously encoded hairpin RNAs could regulate gene expression via elements of the RNAi machinery, we have sought to exploit this biological mechanism for the regulation of desired target genes. Here we show that short hairpin RNAs (shRNAs) can induce sequence-specific gene silencing in mammalian cells. As is normally done with siRNAs, silencing can be provoked by transfecting exogenously synthesized hairpins into cells.

However, silencing can also be triggered by endogenous expression of shRNAs. This observation opens the door to the production of continuous cells lines in which RNAi is used to stably suppress gene expression in mammalian cells. Furthermore, similar approaches should prove efficacious in the creation of transgenic animals and potentially in therapeutic strategies in which long-term suppression of gene function is essential to produce a desired effect.

Several groups (Grishok et al., Cell 106: 23-34, 2001; Ketting et al., Genes & Dev. 15: 2654-2659, 2001; Knight et al., Science 293: 2269-2271, 2001; Hutvagner et al., Science 293: 834-838, 2001) have shown that endogenous triggers of gene silencing, specifically small temporal RNAs (stRNAs) let-7 and lin-4, function at least in part through RNAi pathways. Specifically, these small RNAs are encoded by hairpin precursors that are processed by Dicer into mature, ~21-nt forms. Moreover, genetic studies in C. elegans have shown a requirement for Argonaute-family proteins in stRNA function. Specifically, alg-1 and alg-2, members of the EIF2c subfamily, are implicated both in stRNA processing and in their downstream effector functions (Grishok et al., 2001, supra). We have recently shown that a component of RISC, the effector nuclease of RNAi, is a member of the Argonaute family, prompting a model in which stRNAs may function through RISC-like complexes, which regulate mRNA translation rather than mRNA stability (Hammond et al., Science 293: 1146-1150, 2001).

A. Short Hairpin RNAs Triggeedr Gene Silencing in *Drosophila* Cells.

We wished to test the possibility that we might retarget these small, endogenously encoded hairpin RNAs to regulate genes of choice with the ultimate goal of subverting this regulatory system for manipulating gene expression stably in mammalian cell lines and in transgenic animals. Whether triggered by long dsRNAs or by siRNAs, RNAi is generally more potent in the suppression of gene expression in *Drosophila* S2 cells than in mammalian cells. We therefore chose this model system in which to test the efficacy of short hairpin RNAs (shRNAs) as inducers of gene silencing.

Neither stRNAs nor the broader group of miRNAs that has recently been discovered form perfect hairpin structures. Indeed, each of these RNAs is predicted to contain several bulged nucleotides within their rather short (~30-nt) stem structures. Because the position and character of these bulged nucleotides have been conserved throughout evolution and among at least a subset of miRNAs, we sought to design retargeted miRNA mimics to conserve these predicted structural features. Only the let-7 and lin-4 miRNAs have known mRNA targets (Wightman et al., Cell 75: 855-862, 1993; Slack et al., Mol. Cell. 5: 659-669, 2000). In both cases, pairing to binding sites within the regulated transcripts is imperfect, and in the case of lin-4, the presence of a bulged nucleotide is critical to suppression (Ha et al., Genes & Dev. 10: 3041-3050, 1996). We therefore also designed shRNAs that paired imperfectly with their target substrates. A subset of these shRNAs is depicted in FIG. 39A.

To permit rapid testing of large numbers of shRNA variants and quantitative comparison of the efficacy of suppression, we chose to use a dual-luciferase reporter system, as previously described for assays of RNAi in both *Drosophila* extracts (Tuschl et al., Genes & Dev. 13: 3191-3197, 1999) and mammalian cells (Caplen et al., Proc. Natl. Acad. Sci. 98: 9742-9747, 2001; Elbashir et al., Nature 411: 494-498, 2001). Cotransfection of firefly and *Renilla* luciferase reporter plasmids with either long dsRNAs or with siRNAs homologous to the firefly luciferase gene yielded an ~95% suppression of firefly luciferase without effect on *Renilla* luciferase (FIG. 39B; data not shown). Firefly luciferase could also be specifically silenced by co-transfection with homologous shRNAs. The most potent inhibitors were those composed of simple hairpin structures with complete homology to the substrate. Introduction of G-U basepairs either within the stem or within the substrate recognition sequence had little or no effect (FIGS. 39A and 39B; data not shown).

These results show that short hairpin RNAs can induce gene silencing in *Drosophila* S2 cells with potency similar to that of siRNAs (FIG. 39B). However, in our initial observation of RNA interference in *Drosophila* S2 cells, we noted a profound dependence of the efficiency of silencing on the length of the dsRNA trigger (Hammond et al., Nature 404: 293-296, 2000). Indeed, dsRNAs of fewer than ~200 nt triggered silencing very inefficiently. Silencing is initiated by an RNase III family nuclease, Dicer, that processes long dsRNAs into 22-nt siRNAs. In accord with their varying potency as initiators of silencing, long dsRNAs are processed much more readily than short RNAs by the Dicer enzyme (Bernstein et al., Nature 409: 363-366, 2001). We therefore tested whether shRNAs were substrates for the Dicer enzyme.

We had noted previously that let-7 (Ketting et al., Genes & Dev. 15: 2654-2659, 2001) and other miRNAs (E. Bernstein, unpublished data) are processed by Dicer with an unexpectedly high efficiency as compared with short, nonhairpin dsRNAs. Similarly, Dicer efficiently processed shRNAs that targeted firefly luciferase, irrespective of whether they were designed to mimic a natural Dicer substrate (let-7) or whether they were simple hairpin structures (FIG. 39C). These data suggest that recombinant shRNAs can be processed by Dicer into siRNAs and are consistent with the idea that these short hairpins trigger gene silencing via an RNAi pathway.

B. Short Hairpin RNAs Activated Gene Silencing in Mammalian Cells.

Mammalian cells contain several endogenous systems that were predicted to hamper the application of RNAi. Chief among these is a dsRNA-activated protein kinase, PKR, which effects a general suppression of translation via phosphorylation of EIF-2α (Williams, Biochem. Soc. Trans. 25: 509-513, 1997; Gil et al., Apoptosis 5: 107-114, 2000). Activation of these, and other dsRNA-responsive pathways, generally requires duplexes exceeding 30 bp in length, possibly to permit dimerization of the enzyme on its allosteric activator (e.g., Clarke et al., RNA 1: 7-20, 1995). Small RNAs that mimic Dicer products, siRNAs, presumably escape this limit and trigger specific silencing, in part because of their size. However, short duplex RNAs that lack signature features of siRNAs can efficiently induce silencing in *Drosophila* S2 cells but not in mammalian cells (A. A. Caudy, unpublished data). Endogenously encoded miRNAs may also escape PKR surveillance because of their size but perhaps also because of the discontinuity of their duplex structure. Given that shRNAs of <30 bp were effective inducers of RNAi in *Drosophila* S2 cells, we tested whether these RNAs could also induce sequence-specific silencing in mammalian cells.

Human embryonic kidney (HEK293T) cells were cotransfected with chemically synthesized shRNAs and with a mixture of firefly and *Renilla* luciferase reporter plasmids. As had been observed in S2 cells, shRNAs were effective inducers of gene silencing. Once again, hairpins designed to mimic let-7 were consistently less effective than were simple hairpin RNAs, and the introduction of mismatches between the antisense strand of the shRNA and the mRNA target abolished silencing (FIG. 40A; data not shown). Overall, shRNAs were somewhat less potent silencing triggers than were siRNAs. Whereas siRNAs homologous to firefly luciferase routinely yielded ~90%-95% suppression of gene expression, suppression levels achieved with shRNAs ranged from 80%-90% on average. As we also observe with siRNAs, the most important determinant of the potency of the silencing trigger is its sequence. We find that roughly 50% of both siRNAs and shRNAs are competent for suppressing gene expression. However, neither analysis of the predicted structures of the target mRNA nor analysis of alternative structures in siRNA duplexes or shRNA hairpins has proved of predictive value for choosing effective inhibitors of gene expression.

We have adopted as a standard, shRNA duplexes containing 29 bp. However, the size of the helix can be reduced to ~25 nt without significant loss of potency. Duplexes as short as 22 bp can still provoke detectable silencing, but do so less efficiently than do longer duplexes. In no case did we observe a reduction in the internal control reporter (*Renilla* luciferase) that would be consistent with an induction of nonspecific dsRNA responses.

The ability of shRNAs to induce gene silencing was not confined to 293T cells. Similar results were also obtained in a variety of other mammalian cell lines, including human cancer cells (HeLa), transformed monkey epithelial cells (COS-1), murine fibroblasts (NIH 3T3), and diploid human fibroblasts (IMR90; FIG. 40; data not shown).

C. Synthesis of Effective Inhibitors of Gene Expression Using T7 RNA Polymerse.

The use of siRNAs to provoke gene silencing is developing into a standard methodology for investigating gene function in mammalian cells. To date, siRNAs have been produced exclusively by chemical synthesis (e.g., Caplen et al., *Proc. Natl. Acad. Sci.* 98: 9742-9747, 2001; Elbashir et al., *Nature* 411: 494-498, 2001). However, the costs associated with this approach are significant, limiting its potential utility as a tool for investigating in parallel the functions of large numbers of genes. Short hairpin RNAs are presumably processed into active siRNAs in vitro by Dicer. Thus, these may be more tolerant of terminal structures, both with respect to nucleotide overhangs and with respect to phosphate termini. We therefore tested whether shRNAs could be prepared by in vitro transcription with T7 RNA polymerase.

Transcription templates that were predicted to generate siRNAs and shRNAs similar to those prepared by chemical RNA synthesis were prepared by DNA synthesis (FIG. 41A, C). These were tested for efficacy both in S2 cells (data not shown) and in human 293 cells (FIG. 41B,D). Overall, the performance of the T7-synthesized hairpin or siRNAs closely matched the performance of either produced by chemical synthesis, both with respect to the magnitude of inhibition and with respect to the relative efficiency of differing sequences. Because T7 polymerase prefers to initiate at twin guanosine residues, however, it was critical to consider initiation context when designing in vitro transcribed siRNAs (FIG. 41B). In contrast, shRNAs, which are processed by Dicer (see FIG. 39C), tolerate the addition of these bases at the 5' end of the transcript.

Studies in *Drosophila* embryo extracts indicate that siRNAs possess 5' phosphorylated termini, consistent with their production by an RNase III family nuclease. In vitro, this terminus is critical to the induction of RNAi by synthetic RNA oligonucleotides (Elbashir et al., *EMBO J.* 20: 6877-6888, 2001; Nykanen et al., *Cell* 107: 309-321, 2001). Chemically synthesized siRNAs are nonphosphorylated, and enzymatic addition of a 5' phosphate group in vitro prior to transfection does not increase the potency of the silencing effect (A. A. Caudy, unpublished data). This suggests either that the requirement for phosphorylated termini is less stringent in mammalian cells or that a kinase efficiently phosphorylates siRNAs in vitro. RNAs synthesized with T7 RNA polymerase, however, possess 5' triphosphate termini. We therefore explored the possibility of synthesizing siRNAs with T7 polymerase followed by treatment in vitro with pyrophosphatase to modify the termini to resemble those of siRNAs. Surprisingly, monophosphorylated siRNAs (data not shown) were as potent in inducing gene silencing as transcription products bearing triphosphate termini (FIG. 41B). This may suggest either that the requirement for monophosphorylated termini is less stringent in mammalian cells or that siRNAs are modified in vitro to achieve an appropriate terminal structure.

Considered together, our data suggest that both shRNAs and siRNA duplexes can be prepared by synthesis with T7 RNA polymerase in vitro. This significantly reduces the cost of RNAi in mammalian cells and paves the way for application of RNAi on a whole-genome scale.

D. Transcription of Small Hairpin RNAs In vitro by RNA Polymerase III.

Although siRNAs are an undeniably effective tool for probing gene function in mammalian cells, their suppressive effects are by definition of limited duration. Delivery of siRNAs can be accomplished by any of a number of transient transfection methodologies, and both the timing of peak suppression and the recovery of protein levels as silencing decays can vary with both the cell type and the target gene. Therefore, one limitation on siRNAs is the development of continuous cell lines in which the expression of a desired target is stably silenced.

Hairpin RNAs, consisting of long duplex structures, have been proved as effective triggers of stable gene silencing in plants, in *C. elegans*, and in *Drosophila* (Kennerdell et al., *Nat. Biotechnol.* 18: 896-898, 2000; Smith et al., *Nature* 407: 319-320, 2000; Tavernarakis et al., *Nat. Genet.* 24: 180-183, 2000). We have recently shown stable suppression of gene expression in cultured mammalian cells by continuous expression of a long hairpin RNA (Paddison et al., *Proc. Natl. Acad. Sci.* 99: 1443-1448, 2002). However, the scope of this approach was limited by the necessity of expressing such hairpins only in cells that lack a detectable PKR response. In principle, shRNAs could bypass such limitations and provide a tool for evoking stable suppression by RNA in mammalian somatic cells.

To test this possibility, we initially cloned sequences encoding a firefly luciferase shRNA into a CMV-based expression plasmid. This was predicted to generate a capped, polyadenylated RNA polymerase II transcript in which the hairpin was extended on both the 5' and 3' ends by vector sequences and poly(A). This construct was completely inert in silencing assays in 293T cells.

During our studies on chemically and T7-synthesized shRNAs, we noted that the presence of significant single-stranded extensions (either 5' or 3' of the duplex) reduced the efficacy of shRNAs. We therefore explored the use of alternative promoter strategies in an effort to produce more defined hairpin RNAs. In particular, RNA polymerase III promoters have well-defined initiation and termination sites and naturally produce a variety of small, stable RNA species. Although many Pol III promoters contain essential elements within the transcribed region, limiting their utility for our purposes; class III promoters use exclusively nontranscribed promoter sequences. Of these, the U6 snRNA promoter and the H1 RNA promoter have been well studied (Lobo et al., *Nucleic Acids Res.* 18: 2891-2899, 1990; Hannon et al., *J. Biol. Chem.* 266: 22796-22799, 1991; Chong et al., *J. Biol. Chem.* 276: 20727-20734, 2001).

Figure 42C:
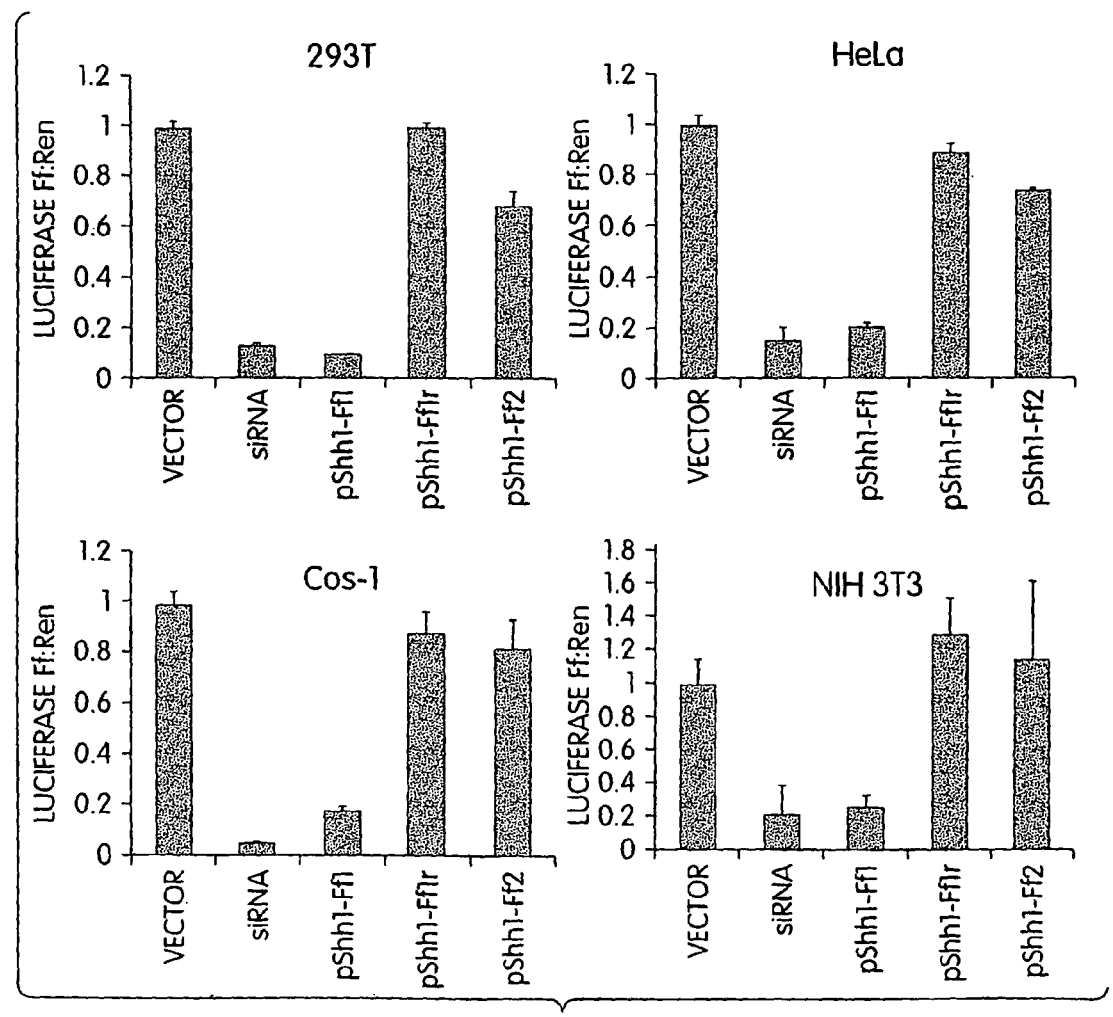

By placing a convenient cloning site immediately behind the U6 snRNA promoter, we have constructed pShh-1, an expression vector in which short hairpins are harnessed for gene silencing. Into this vector either of two shRNA sequences derived from firefly luciferase were cloned from synthetic oligonucleotides. These were cotransfected with firefly and *Renilla* luciferase expression plasmids into 293T cells. One of the two encoded shRNAs provoked effective silencing of firefly luciferase without altering the expression of the internal control (FIG. 42C). The second encoded shRNA also produced detectable, albeit weak, repression. In both cases, silencing was dependent on insertion of the shRNA in the correct orientation with respect to the promoter (FIG. 42C; data not shown). Although the shRNA itself is bilaterally symmetric, insertion in the incorrect orientation would affect Pol III termination and is predicted to produce a hairpin with both 5' and 3' single-stranded extensions. Similar results were also obtained in a number of other mammalian cell lines including HeLa, COS-1, NIH 3T3, and IMR90 (FIG. 42; data not shown). pShh1-Ff1 was, however, incapable of effecting suppression of the luciferase reporter in *Drosophila* cells, in which the human U6 promoter is inactive.

E. Dicer is Required for shRNA-Mediated Gene Silencing.

As a definitive test of whether the plasmid-encoded shRNAs brought about gene silencing via the mammalian RNAi pathway, we assessed the dependence of suppression on an essential component of the RNAi pathway. We transfected pShh1-Ff1 along with an siRNA homologous to human Dicer. FIG. 43 shows that treatment of cells with Dicer siRNAs is able to completely depress the silencing induced by pShh1-Ff1. Addition of an unrelated siRNA had no effect on the magnitude of suppression by pShh1-Ff1. Importantly, Dicer siRNAs had no effect on siRNA-induced silencing of firefly luciferase. These results are consistent with shRNAs operating via an RNAi pathway similar to those provoked by stRNAs and long dsRNAs. Furthermore, it suggests that siRNA-mediated silencing is less sensitive to depletion of the Dicer enzyme.

F. Stable shRNA-Mediated Gene Silencing of an Endogenous Gene.

The ultimate utility of encoded short hairpins will be in the creation of stable mutants that permit the study of the resulting phenotypes. We therefore tested whether we could create a cellular phenotype through stable suppression. Expression of activated alleles of the ras oncogene in primary mouse embryo fibroblasts (MEFs) induces a stable growth arrest that resembles, as a terminal phenotype, replicative senescence (Serrano et al., *Cell* 88: 593-602, 1997). Cells cease dividing and assume a typical large, flattened morphology. Senescence can be countered by mutations that inactivate the p53 tumor suppressor pathway (Serrano et al. 1997, supra). As a test of the ability of vector-encoded shRNAs to stably suppress an endogenous cellular gene, we generated a hairpin that was targeted to the mouse p53 gene. As shown in FIG. 44, MEFs transfected with pBabe-RasV12 fail to proliferate and show a senescent morphology when cotransfected with an empty control vector. As noted previously by Serrano et al., the terminally arrested state is achieved in 100% of drug-selected cells in culture by 8 d post-transfection. However, upon cotransfection of an activated ras expression construct with the pShh-p53, cells emerged from drug selection that not only fail to adopt a senescent morphology but also maintain the ability to proliferate for a minimum of several weeks in culture (FIG. 44). These data strongly suggest that shRNA expression constructs can be used for the creation of continuous mammalian cell lines in which selected target genes are stably suppressed.

G. Simultaneous Introduction of Multiple Hairpin RNAs Does Not Produce Synergy.

In an attempt to further understand the mechanisms by which short hairpins suppress gene expression, we examined the effects of transfecting cells with a mixture of two different short hairpins corresponding to firefly luciferase. FIG. 45 summarizes the results of experiments which suggest that there is no synergistic affects on suppression of firefly luciferase gene expression obtained when cells are exposed to a mixture of such short hairpins.

Methods:

Cell culture. HEK 293T, HeLa, COS-1, MEF, and IMR90 cells were cultured in DMEM (GIBCO BRL) supplemented with 10% heat-inactivated fetal bovine serum (FBS) and 1% antibiotic/antimycotic solution (GIBCO BRL). NIH 3T3 cells were cultured in DMEM supplemented with 10% heat-inactivated calf serum and 1% antibiotic/antimycotic solution.

RNA preparation. Both shRNAs and siRNAs were produced in vitro using chemically synthesized DNA oligonucleotide templates (Sigma) and the T7 Megashortscript kit (Ambion). Transcription templates were designed such that they contained T7 promoter sequences at the 5' end. shRNA transcripts subjected to in vitro Dicer processing were synthesized using a Riboprobe kit (Promega). Chemically synthesized RNAs were obtained from Dharmacon, Inc.

Transfection and gene silencing assays. Cells were transfected with indicated amounts of siRNA, shRNA, and plasmid DNA using standard calcium phosphate procedures at 50%-70% confluence in 6-well plates. Dual luciferase assays (Promega) were carried out by cotransfecting cells with plasmids containing firefly luciferase under the control of the is SV40 promoter (pGL3-Control, Promega) and *Renilla* luciferase under the control of the SV40 early enhancer/promoter region (pSV40, Promega). Plasmids were cotransfected using a 1:1 ratio of pGL3-Control (250 ng/well) to pRL-SV40. RNAi in S2 cells was performed as previously described (Hammond et al., *Nature* 404: 293-296, 2000). For stable silencing, primary MEFs (a gift from S. Lowe, Cold Spring Harbor Laboratory, NY) were cotransfected using Fugene 6 with pBabe-Ha-rasV12 and pShh-p53 (no resistance marker), according to the manufacturer's recommendations. Selection was for the presence of the activated Ha-rasV12 plasmid, which carries a puromycin-resistance marker. The pShh-p53 plasmid was present in excess, as is standard in a cotransfection experiment. We have now generated a version of the U6 promoter vector (pSHAG-1) that is compatible with the GATEWAY system (Invitrogen), and this can be used to transport the shRNA expression cassette into a variety of recipient vectors that carry cis-linked selectable markers. Furthermore, we have validated delivery of shRNAs using retroviral vectors. Updated plasmid information can be obtained at:

http://www.cshl.org/public/science/hannon.html.

Plasmids expressing hairpin RNAs. The U6 promoter region from −265 to +1 was amplified by PCR, adding 5' KpnI and 3' EcoRV sites for cloning into pBSSK+. A linker/terminator oligonucleotide set bearing the U6 terminator sequence and linker ends of 5' EcoRV and 3' NotI was cloned into the promoter construct, resulting in a U6 cassette with an EcoRV site for insertion of new sequences. This vector has been named pShh1. Blunt-ended, double-stranded DNA oligonucleotides encoding shRNAs with between 19 and 29 bases of homology to the targeted gene were ligated into the EcoRV site to produce expression constructs. The oligonucleotide sequence used to construct Ff1 was: TCCAATTCAGCGG-GAGCCACCTGATGAAGCTTGATCGGGTG- GCTCTCGCTGAGTTGGAATCCATTTTTTT (SEQ ID NO: 38). This sequence is preceded by the sequence GGAT, which is supplied by the vector, and contains a tract of more than five Ts as a Pol III terminator.

In vitro Dicer assays. In vitro assays for Dicer activity were performed as described (Bernstein et al., Nature 409: 363-366, 2001).

EXAMPLE 7

Encoded Short Hairpins Function In vitro

An object of the present invention is to improve methods for generating siRNAs and short hairpins for use in specifically suppressing gene expression. Example 6 demonstrates that siRNAs and short hairpins are highly effective in specifically suppressing gene expression. Accordingly, it would be advantageous to combine the efficient suppression of gene expression attainable using short hairpins and siRNAs with a method to encode such RNA on a plasmid and express it either transiently or stably.

FIG. 46 demonstrates that short hairpins encoded on a plasmid are effective in suppressing gene expression. DNA oligonucleotides encoding 29 nucleotide hairpins corresponding to firefly luciferase were inserted into a vector containing the U6 promoter. Three independent constructs were examined for their ability to specifically suppress firefly luciferase gene expression in 293T cells. siOligo1-2, siOligo1-6, and siOligo1-19 (construct in the correct orientation) each suppressed gene expression as effectively as siRNA. In contrast, siOligo1-10 (construct in the incorrect orientation) did not suppress gene expression. Additionally, an independent construct targeted to a different portion of the firefly luciferase gene did not effectively suppress gene expression in either orientation (SiOligo2-23, SiOligo2-36).

The results summarized in FIG. 46 demonstrate that transient expression of siRNAs and short hairpins encoded on a plasmid can efficiently suppress gene expression. One of skill can choose from amongst a range of vectors to either transiently or stably express an siRNA or short hairpin. Non-limiting examples of vectors and strategies to stably express short dsRNAs are presented in FIGS. 47-49.

EXAMPLE 8 dsRNA Suppression in the Absence of a PKR Response

One potential impediment to the use of RNAi to suppress gene expression in some cell types, is the non-specific PKR response that can be triggered by long dsRNAs. Numerous mammalian viruses have evolved the ability to block PKR in order to aid in the infection of potential host cells. For example, adenoviruses express RNAs which mimic dsRNA but do not activate the PKR response. Vaccinia virus uses two strategies to evade PKR: the expression of E3L which binds and masks dsRNA; the expression of K3L to mimic the natural PKR substrate eIF2α.

Our understanding of the mechanisms by which viruses avoid the PKR response allows us to design approaches to circumvent the PKR response in cell types in which in might be advantageous to suppression gene expression with long dsRNAs. Possible approaches include treating cells with an agent that inhibits protein kinase RNA-activated (PKR) apoptosis, such as by treatment with agents which inhibit expression of PKR, cause its destruction, and/or inhibit the kinase activity of PKR. Accordingly, RNAi suppression of gene expression in such cell types could involve first inhibiting the PKR response, and then delivering a dsRNA identical or similar to a target gene.

A. In a murine myoblast cell line, C2C12, we noted that the cells responded to long dsRNAs with a mixture of specific and non-specific (presumably PKR) responses. In order to attenuate the non-specific PKR response while maintaining the robust and specific suppression due to the long dsRNA, C2C12 cells were transfected with a vector that directs K3L expression. This additional step successfully attenuated the PKR response, however expression of K3L protein had no effect on the magnitude of specific inhibition.

B. However, since the efficacy of such a two step approach had not been previously demonstrated, it was formerly possible that dsRNA suppression would not be possible in cells with a PKR response. FIG. 50 summarizes results which demonstrate that such a two step approach is possible, and that robust and specific dsRNA mediated suppression is possible in cells which had formerly possessed a robust PKR response.

Briefly, dual luciferase assay were carried out as described in detail above. The experiments were carried out using PKR$^{-/-}$ MEFs harvested from E13.5 PKR$^{-/-}$ mouse embryos. MEFs typically have a robust PKR response, and thus treatment with long dsRNAs typically results in non-specific suppression of gene expression and apoptosis. However, in PKR$^{-/-}$ cells examined 12, 42, and 82 hours after transfection, expression of ds*Renilla* luciferase RNA specifically suppresses expression *Renilla reniformis* (sea pansy) luciferase. This suppression is stable over time.

These results demonstrate that the non-specific PKR response can be blocked without affecting specific suppression of gene expression mediated by dsRNA. This allows the use of long dsRNAs to suppress gene expression in a diverse range of cell types, including those that would be previously intractable due to the confounding influences of the non-specific PKR response to long dsRNA.

EXAMPLE 9

Suppression of Gene Expression using dsRNA which Corresponds to Non-Coding Sequence Current models for the mechanisms which drive RNAi have suggested that the dsRNA construct must contain coding sequence corresponding to the gene of interest. Although evidence has demonstrated that such coding sequence need not be a perfect match to the endogenous coding sequence (i.e., it may be similar), it has been widely held that the dsRNA construct must correspond to coding sequence. We present evidence that contradicts the teachings of the prior art, and demonstrate that dsRNA corresponding to non-coding regions of a gene can suppress gene function in vitro. These results are significant not only because they demonstrate that dsRNA identical or similar to non-coding sequences (i.e., promoter sequences, enhancer sequences, or intronic sequences) can mediate suppression, but also because we demonstrate the in vitro suppression of gene expression using dsRNA technology in a mouse model.

We generated doubled stranded RNA corresponding to four segments of the mouse tyrosinase gene promoter. Three of these segments correspond to the proximal promoter and one corresponds to an enhancer (FIG. 51). The tyrosinase gene encodes the rate limiting enzyme involved in the melanin biosynthetic pathway (Bilodeau et al., *Pigment Cell Research* 14: 328-336, 2001). Accordingly, suppression of the tyrosinase gene is expected to inhibit pigmentation.

Double stranded RNA corresponding to each of the above promoter segments was injected into the pronuclei of fertilized eggs. Pups were born after 19 days. In total 42/136 (31%) of the embryos were carried to term. This number is within the expected range for transgenesis (30-40%). Two pups out of 42 (5%) appear totally unpigmented at birth, consistent with suppression of tyrosinase function.

Methods:

dsRNA from non-coding promoter region of tyrosinase gene. Four segments of the mouse tyrosinase gene promoter were amplified by PCR using primers which incorporated T7 RNA polymerase promoters into the PCR products (shown in bold—FIG. 51). Sequences of the mouse tyrosinase gene 5' flanking regions were obtained from GenBank (accession number D00439 and X51743). The sequence of the tyrosinase enhancer, located approximately 12 kb upstream of the transcriptional start site, was also obtained from GenBank (accession number X76647).

The sequences of the primers used were as follows: note the sequence of the T7 RNA polymerase promoter is shown in bold:

(a) Tyrosinase enhancer (~12 kb upstream):

```
(a) Tyrosinase enhancer (~12 kb upstream):
                                        (SEQ ID NO: 39)
5' TAATACGACTCACTATAGGGCAAGGTCATAGTTCCTGCCAGCTG 3'

(SEQ ID NO: 40)
5' TAATACGACTCACTATAGGGCAGATATTTTCTTACCACCCACCC 3'

(b) -1404 to -1007:
                                        (SEQ ID NO: 41)
5' TAATACGACTCACTATAGGGTTAAGTTTAACAGGAGAAGCTGGA 3'

(SEQ ID NO: 42)
5' TAATACGACTCACTATAGGGAAATCATTGCTTTCCTGATAATGC 3'

(c) -1003 to -506:
                                        (SEQ ID NO: 43)
5' TAATACGACTCACTATAGGGTAGATTTCCGCAGCCCCAGTGTTC 3'

(SEQ ID NO: 44)
5' TAATACGACTCACTATAGGGGTTGCCTCTCATTTTTCCTTGATT 3'

(d) -505 to -85:
                                        (SEQ ID NO: 45)
5' TAATACGACTCACTATAGGGTATTTTAGACTGATTACTTTTATA
A 3'

(SEQ ID NO: 46)
5' TAATACGACTCACTATAGGGTCACATGTTTTGGCTAAGACCTAT 3'
```

PCR products were gel purified from 1% TAE agarose gels using QiaExII Gel Extraction Kit (Qiagen). Double stranded RNA was produced from these templates using T7-Megashortscript Kit (Ambion). Enzymes and unincorporated nucleotides were removed using Qiaquick MinElute PCR Purification Kit. RNA was phenol/chloroform extracted twice, and ethanol precipitated. Pellets were resuspended in injection buffer ((10 mM Tris (pH 7.5), 0.15 nM EDTA (pH 8.0)) at a concentration of 20 ng/ul and run on a 1% TAE agarose gel to confirm integrity.

Generation of mice: An equal mixture of double stranded RNA from each of the above primer sets was injected into the pronuclei of fertilized eggs from C57BL6J mice. A total of 136 injections was performed, and 34 embryos were implanted into each of 4 pseudopregnant CD-1 females. Pups were born after 19 days. In total, 42/136 (31%) of the embryos were carried to term. 2/42 pups (5%) appear totally unpigmented at birth.

It is not clear whether the RNAi mediated by dsRNA identical or similar to non-coding sequence works via the same mechanism as PTGS observed in the presence of dsRNA identical or similar to coding sequence. However, whether these results ultimately reveal similar or differing mechanisms does not diminish the tremendous utility of the compositions and methods of the present invention to suppress expression of one or more genes in vitro or in vitro.

The present invention demonstrates that dsRNA ranging in length from 20-500 nt can readily suppress expression of target genes both in vitro and in vitro. Furthermore, the present invention demonstrates that the dsRNAs can be generated using a variety of methods including the formation of hairpins, and that these dsRNAs can be expressed either stably or transiently. Finally, the present invention demonstrates that dsRNA identical or similar to non-coding sequences can suppress target gene expression.

EXAMPLE 10

RNA interference in Adult Mice

RNA interference is an evolutionarily conserved surveillance mechanism that responds to double-stranded RNA by sequence-specific silencing of homologous genes. Here we show that transgene expression can be suppressed in adult mice by synthetic small interfering RNAs and by small-hairpin RNAs transcribed in vitro from DNA templates. We also show the therapeutic potential of this technique by demonstrating effective targeting of a sequence from hepatitis C virus by RNA interference in vitro.

Small interfering RNAs (siRNAs) mimic intermediates in the RNA-interference (RNAi) pathway and can silence genes in somatic cells without activating non-specific suppression by double-stranded RNA-dependent protein kinase (Elbashir et al., Nature 411: 494-498, 2001). To investigate whether siRNAs also inhibit gene expression in vitro, we used a modification of hydrodynamic transfection methods (Zhang et al., Hum. Gene Therapy 10: 1735-1737, 1999; Liu et al., Gene Therapy 6: 1258-1266, 1999; Chang et al., J. Virol. 75: 3469-3473, 2001) to deliver naked siRNAs to the livers of adult mice. Either an siRNA derived from firefly luciferase or an unrelated siRNA was co-injected with a luciferase-expression plasmid (for construct description and sequences, see FIG. 52). We monitored luciferase expression in living animals using quantitative whole-body imaging (Contag, et al., Photochem. Photobiol. 66: 523-531, 1997) (see FIG. 53a, 54a), and found that it was dependent on reporter-plasmid dose.

In each experiment, serum measurements of a co-injected human α-1 antitrypsin (hAAT) plasmid (Yant et al., Nature Genet. 25: 3541, 2000) served to normalize transfection efficiency and to monitor non-specific translational inhibition. Average serum concentrations of hAAT after 74 h were similar in all groups.

Figure 53A:
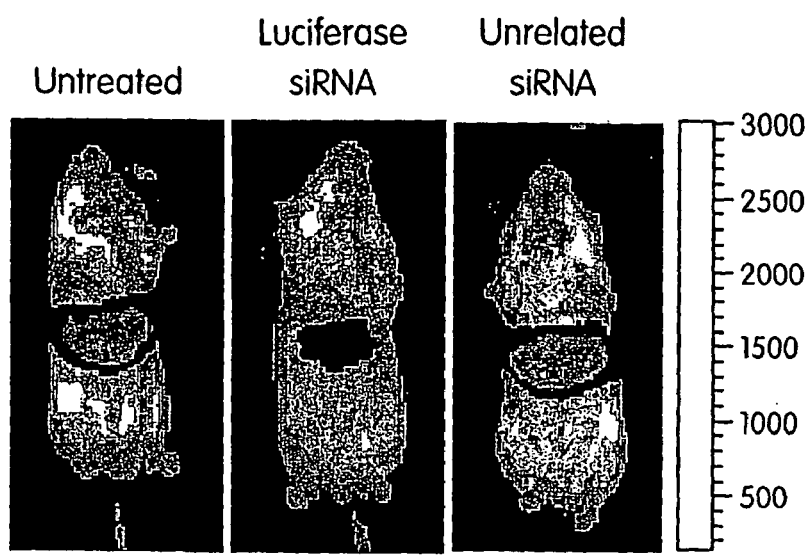
Figure 53B:
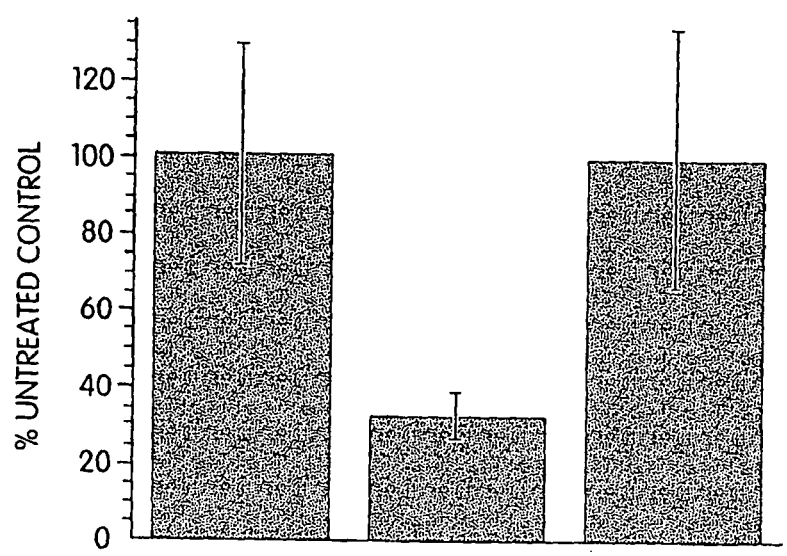

Our results indicate that there was specific, siRNA-mediated inhibition of luciferase expression in adult mice (P<0.0115) and that unrelated siRNAs had no effect (P<0.864; FIG. 53a, 53b). In 11 independent experiments, luciferase siRNAs reduced luciferase expression (as judged by emitted light) by an average of 81% (±2.2%). These findings indicate that RNAi can downregulate gene expression in adult mice.

As RNAi degrades respiratory syncitial virus RNAs in culture (Bitko et al. 2001, BMC Microbiol. 1: 34), we investigated whether RNAi could be directed against a human pathogenic RNA expressed in a mouse, namely that of hepatitis C virus (HCV). Infection by HCV (an RNA virus that infects 1 in 40 people worldwide) is the most common reason for liver transplantation in the United States and Europe. We fused the NS5B region (non-structural protein 5B, viral-polymerase-encoding region) of this virus with luciferase RNA and monitored RNAi by co-transfection in vitro. An siRNA targeting the NS5B region reduced luciferase expression from the chimaeric HCV NS5B protein-luciferase fusion by 75% (±6.8%; 6 animals per group). This result suggests that it may be feasible to use RNAi as a therapy against other important human pathogens.

Although our results show that siRNAs are functional in mice, delivery remains a major obstacle. Unlike siRNAs, functional small-hairpin RNAs (shRNAs) can be expressed in vitro from DNA templates using RNA polymerase III promoters (Paddison et al., *Genes Dev.* 16: 948-958, 2002; Tuschl, *Nature Biotechnol.* 20: 446-448, 2002); they are as effective as siRNAs in inducing gene suppression. Expression of a cognate shRNA (pShh1-Ff1) inhibited luciferase expression by up to 98% (+0.6%), with an average suppression of 92.8% (+3.39%) in three independent experiments (see FIG. 54*a*, 54*b*). An empty shRNA-expression vector had no effect; reversing the orientation of the shRNA (pShh1-Ff1 rev) insert prevents gene silencing because it alters the termination by RNA polymerase III and generates an improperly structured shRNA. These findings indicate that plasmid-encoded shRNAs can induce a potent and specific RNAi response in adult mice.

RNAi may find application in functional genomics or in identifying targets for designer drugs. It is a more promising system than gene-knockout mice because groups of genes can be simultaneously rendered ineffective without the need for time-consuming crosses. Gene therapy currently depends on the ectopic expression of exogenous proteins; however, RNAi may eventually complement this gain-of-function approach by silencing disease-related genes with DNA constructs that direct the expression of shRNAs. Our method of RNAi delivery could also be tailored to take advantage of developing viral and non-viral gene-transfer vectors in a clinical context.

EXAMPLE 11

Germ-line transmission of RNAi in mice

MicroRNA molecules (miRNAs) are small, noncoding RNA molecules that have been found in a diverse array of eukaryotes, including mammals. miRNA precursors share a characteristic secondary structure, forming short 'hairpin' RNAs. Genetic and biochemical studies have indicated that miRNAs are processed to their mature forms by Dicer, an RNAse III family nuclease, and function through RNA-mediated interference (RNAi) and related pathways to regulate the expression of target genes (Hannon, *Nature* 418: 244-251, 2002; Pasquinelli et al., *Ann. Rev. Cell. Dev. Biol.* 18: 495-513, 2002). Recently, we and others have remodeled miRNAs to permit experimental manipulation of gene expression in mammalian cells and have dubbed these synthetic silencing triggers 'short hairpin RNAs' (shRNAs) (Paddison et al., *Cancer Cell* 2: 17-23, 2002). Silencing by shRNAs requires the RNAi machinery and correlates with the production of small interfering RNAs (siRNAs), which are a signature of RNAi.

Expression of shRNAs can elicit either transient or stable silencing, depending upon whether the expression cassette is integrated into the genome of the recipient cultured cell (Paddison et al., *Cancer Cell* 2: 17-23, 2002). shRNA expression vectors also induce gene silencing in adult mice following transient delivery (Lewis et al., *Nat. Genet.* 32: 107-108, 2002; McCaffrey et al., *Nature* 418: 38-39, 2002). However, for shRNAs to be a viable genetic tool in mice, stable manipulation of gene expression is essential. Hemann and colleagues have demonstrated long-term suppression of gene expression in vitro following retroviral delivery of shRNA-expression cassettes to hematopoietic stem cells (Hemann et al., *Nat. Genet.* in the press, 2003). Here we sought to test whether shRNA-expression cassettes that were passed through the mouse germ-line could enforce heritable gene silencing.

We began by taking standard transgenesis approaches (Gordon et al., *Methods Enzymol.* 225: 747-771, 1993) using shRNAs directed against a variety of targets with expected phenotypes, including the genes encoding tyrosinase (albino), myosin VIIIa (shaker), Bmp-5 (crinkled ears), Hox a-10 (limb defects), homogentisate 1,2,-dioxygenase (urine turns black upon exposure to air), Hairless (hair loss) and melanocortin 1 receptor (yellow). Three constructs per gene were linearized and injected into pronuclei to produce transgenic founder animals. Although we noted the presence of the transgene in some animals, virtually none showed a distinct or reproducible phenotype that was expected for a hypomorphic allele of the targeted gene.

Therefore, we decided to take another approach: verifying the presence of the shRNA and its activity toward a target gene in cultured embryonic stem (ES) cells and then asking whether those cells retained suppression in a chimeric animal in vitro. We also planned to test whether such cells could pass a functional RNAi-inducing construct through the mouse germ-line. For these studies, we chose to examine a novel gene, Neil1, which is proposed to have a role in DNA repair. Oxidative damage accounts for 10,000 DNA lesions per cell per day in humans and is thought to contribute to carcinogenesis, aging and tissue damage following ischemia (Ames et al., *Proc. Natl. Acad. Sci. USA* 90: 7915-7922, 1993; Jackson et al., *Mutat. Res.* 477: 7-21, 2001). Oxidative DNA damage includes abasic sites, strand breaks and at least 20 oxidized bases, many of which are cytotoxic or pro-mutagenic (Dizdaroglu et al., *Free Radic. Biol. Med.* 32: 1102-1115, 2002). DNA N-glycosylases initiate the base excision repair pathway by recognizing specific bases in DNA and cleaving the sugar base bond to release the damaged base (David et al., *Chem. Rev.* 98: 1221-1262, 1998).

The Neil genes are a newly discovered family of mammalian DNA N-glycosylases related to the Fpg/Nei family of proteins from *Escherichia coli* (Hazra et al., *Proc. Natl. Acad. Sci. USA* 99: 3523-3528, 2002; Bandaru et al., *DNA Repair* 1: 517-529, 2002). Neil1 recognizes and removes a wide spectrum of oxidized pyrimidines and ring-opened purines from DNA, including thymine glycol (Tg), 2,6-diamino-4-hydroxy-5-formamidopyrimidine (FapyG) and 4,6-diamino-5-formidopyrimidine (FapyA). Tg, FapyG and FapyA are among the most prevalent oxidized bases produced by ionizing radiation (Dizdaroglu et al. *Free Radic. Biol. Med.* 32: 1102-1115, 2002) and can block replicative DNA polymerases, which can, in turn, cause cell death (Asagoshi et al. *J. Biol. Chem.* 277: 14589-14597, 2002; Clark et al., Biochemistry 28: 775-779, 1989).

The Nth1 and Ogg1 glycosylases each remove subsets of oxidized DNA bases that overlap with substrates of Neil1 (Nishimura, *Free Radic. Biol. Med.* 32: 813-821, 2002; Asagoshi et al., *Biochemistry* 39: 11389-11398, 2000; Dizdaroglu et al., *Biochemistry* 38: 243-246, 1999). However, mice with null mutations in either Nth1 (Ocampo et al., *Mol. Cell. Biol.* 22: 6111-6121, 2002; Takao et al., *EMBO J.* 21: 3486-3493, 2002) or Ogg1 (Klungland et al., *Proc. Natl. Acad. Sci. USA* 96: 13300-13305, 1999; Minowa et al., *Proc. Natl. Acad.*

*Sci. USA* 97: 4156-4161, 2000) are viable, raising the possibility that Neil1 activity tempers the loss of Nth1 or Ogg1. Recently, a residual Tg-DNA glycosylase activity in Nth1$^{-/-}$ mice has been identified as Neil1 (Takao et al., *J. Biol. Chem.* 277: 4220542213, 2002).

We constructed a single shRNA expression vector targeting a sequence near the 5' end of the Neil1 coding region. This vector was introduced into mouse embryonic stem cells by electroporation, and individual stable integrants were tested for expression of the Neil1 protein (see the weblink: http://www.cshl.edu/public/SCIENCE/hannon.btml for detailed procedures). The majority of cell lines showed an ~80% reduction in Neil1 protein, which correlated with a similar change in levels of Neil1 mRNA. These cells showed an approximately two-fold increase in their sensitivity to ionizing radiation, consistent with a role for Neil1 in DNA repair. Two independent ES cell lines were injected into BL/6 blastocysts, and several high-percentage chimeras were obtained. These chimeras were out-crossed, and germ-line transmission of the shRNA-expression construct was noted in numerous $F_1$ progeny (13/27 for one line and 12/26 for the other).

Figure 56B:
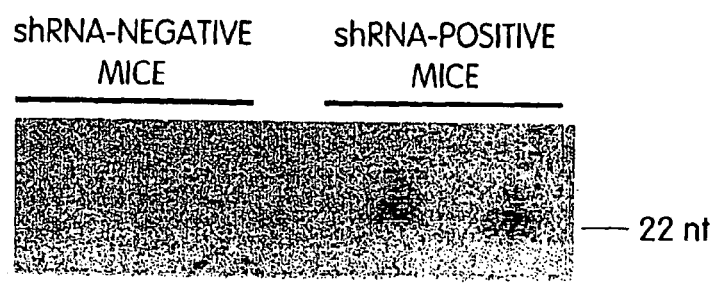

To determine whether the silencing of Neil1 that had been observed in ES cells was transmitted faithfully, we examined Neil1 mRNA and protein levels. Both were reduced by approximately the same extent that had been observed in the engineered ES cells (FIGS. 55, 56). Consistent with this having occurred through the RNAi pathway, we detected the presence of siRNAs corresponding to the shRNA sequence in $F_1$ animals that carry the shRNA expression vector but not in those that lack the vector (FIG. 56b).

The aforementioned data demonstrate that shRNAs can be used to create germ-line transgenic mice in which RNAi has silenced a target gene. These observations open the door to using of RNAi as a complement to standard knock-out methodologies and provide a means to rapidly assess the consequences of suppressing a gene of interest in a living animal. Coupled with activator-dependent U6 promoters, the use of shRNAs will ultimately provide methods for tissue-specific, inducible and reversible suppression of gene expression in mice.

EXAMPLE 12

Dicer Cleaves a Single siRNA From the End of Each shRNA

We performed the following experiments in order to understand how Dicer processes shRNAs, and in order to permit comparison of the efficiency of different silencing triggers.

We began by producing ~70 chemically synthesized shRNAs, targeting various endogenous genes and reporters. We initially focused on a detailed analysis of one set of four shRNAs that target firefly luciferase (FIG. 57a). The individual species differed in two distinct ways. First, the stems of the shRNAs were either 19 or 29 nucleotides in length. Second, each shRNA either contained or lacked a 2 nucleotide 3' overhang, identical to that produced by processing of pri-miRNAs by Drosha. Each species was end-labeled by enzymatic phosphorylation and incubated with recombinant human Dicer. The 29 nt. shRNA bearing the 3' overhang was converted almost quantitatively into a 22 nt product by Dicer (FIG. 57b). In contrast, the 29 nt shRNA that lacked the overhang generated very little 22 nt labeled product, although there was a substantial depletion of the starting material. Neither 19 nt shRNA was cleaved to a significant extent by the Dicer enzyme. This result was not due to the lack of dsRNA in the 19 nt shRNAs as all shRNA substrates were efficiently cleaved by bacterial RNAseIII (FIG. 57c). Parallel analysis of identical shRNA substrates that were produced by in vitro transcription with T7 polymerase and uniformly labeled clarified the results obtained with end-labeled substrates (not shown). Specifically, 19 nt shRNAs were not cleaved. However, both the overhung and the blunt 29 nucleotide shRNAs gave rise to 22 nt products, albeit at reduced levels in the latter case. These results suggest that Dicer requires a minimum stem length for productive cleavage. Furthermore, they are consistent with a hypothesis that the presence of a correct 3' overhang enhances the efficiency and specificity of cleavage, directing Dicer to cut ~22 nucleotides from the end of the substrate.

A number of previous studies have suggested that Dicer might function as an end-recognizing endonuclease, without positing a role for the 3' overhang. Processive Dicer cleavage was first implied by in vitro analysis of RISC cleavage (Zamore et al., *Cell* 101: 25-33, 2000). In *Drosophila* embryo extracts programmed for RISC assembly using a long dsRNA, phased cleavage sites occurred at approximately 22 nucleotide intervals along an mRNA substrate. Similarly, analysis of *C. elegans* Dicer in whole cell extracts (Ketting et al., *Genes Dev* 15: 2654-9, 2001) or purified human Dicer in vitro (Zhang et al., *EMBO J.* 21: 5875-85, 2002) showed accumulation of discretely sized cleavage intermediates. Blocking of the ends of dsRNAs using either fold-back structures or chimeric RNA-DNA hybrids attenuated, but did not abolish, the ability of human Dicer to generate siRNAs (Zhang et al., *EMBO J.* 21: 5875-85, 2002). Finally, Lund and colleagues suggested that Dicer cleaved ~22 nt from the blunt end of an extended pre-miRNA, designed in part to mimic a pri-miRNA (see Lund et al., *Science* 303: 95-8, 2004).

Our results suggest that while the overhang is not obligate for Dicer processing of its substrates (see Zhang et al., *EMBO J* 21: 5875-85, 2002, and FIG. 57b), this structure does aid in determining the specificity of cleavage. Furthermore, time courses of processing of blunt and overhung 29 nt shRNAs do show a more rapid processing of the overhung substrate if reactions are performed in the linear range for the enzyme (not shown).

To map more precisely the position of Dicer cleavage in the shRNA, we used primer extension analysis. The shRNAs described in FIG. 57a were reacted with recombinant human Dicer as shown in FIG. 57b. Total RNA was recovered from the processing reactions and used in primer extension assays. Consistent with direct analysis of the RNA, shRNAs with 19 nt stems failed to yield discrete extension products. The extension products that would be predicted from the unreacted substrate are not seen due to secondary structure of the uncleaved precursor (FIG. 58a). Both of the 29 nt shRNAs give rise to extension products with the overhung precursor giving a relatively discrete product of 20 nucleotides, as predicted for a cleavage precisely 22 nt from the 3' end of the substrate (FIG. 58b). The blunt-ended precursor gave a distribution of products, as was predicted from the analysis of uniformly and end-labeled RNAs.

In *Drosophila*, *Dicer2* acts in a complex with a double-stranded RNA binding protein, R2D2 (Liu et al., *Science* 301: 1921-5, 2003). Similarly, biochemical evidence from *C. elegans* suggests that its Dicer binds RDE-1, RDE-4 and DRH-1 (Tabara et al., *Cell* 109: 861-71, 2002). These results suggest that the human enzyme might also function as part of a larger complex, which could show altered cleavage specificities. Therefore, we also mapped the cleavage of our shRNAs in vitro. Precursors were transfected into cells, and the processed form of each was isolated by virtue of its co-immunoprecipitation with human Argonaute proteins, Ago1 and Ago2. Primer extension suggested identical cleavage specificities upon exposure of shRNAs to Dicer in vitro and in living cells (FIG. 58c).

EXAMPLE 13 shRNAs are Generally More Effective Than siRNAs

Since each shRNA gave rise to a single, predictable 22 nt sequence in RISC, we compared the efficacy of shRNAs and siRNAs. Toward this goal, we selected 43 sequences targeting a total of 6 genes (3-9 sequences per gene). For each sequence, we synthesized a 21 nt siRNA (19 base stem) and 19 and 29 nt shRNAs that were predicted to give Dicer products that were either identical to the siRNAs or that differed by the addition of one 3' nucleotide (FIG. 59a). Each RNA species was transfected into HeLa cells at a relatively high concentration (100 nM). The level of suppression was determined by semi-quantitative RT-PCR and the performance of each shRNA compared to the performance of the corresponding siRNA (FIG. 59b). Comparison of 19 nt shRNAs with siRNAs revealed that there was little difference in endpoint inhibition with these species (left panel). A comparison of siRNAs with 29 nt shRNAs gave a different result. Clustering of the comparison data points above the diagonal indicated consistently better endpoint inhibition with the 29 nt shRNAs (right panel).

The generally better endpoint inhibition observed with 29 nt shRNAs led us to investigate in more detail the performance of these silencing triggers as compared to siRNAs. Seventeen complete sets comprising an siRNA, a 19 nt shRNA and a 29 nt shRNA were examined for suppression in titration experiments. In all cases, the 19 nt shRNAs performed as well as or worse than the corresponding siRNAs. In contrast, 29 nt shRNAs exceeded the performance of siRNAs in the majority of cases. Four representative examples, targeting MAPK-14 are shown in FIG. 59c. Several 29 nt shR-NAs (e.g., see MAPK14-1) showed both significantly greater endpoint inhibition and efficacy at lower concentrations than the corresponding siRNA. In other cases (e.g., see MAPK14-2 and MAPK-14-4), the maximal level of suppression for the 29 nt. shRNA was approximately two-fold greater than the maximal level of suppression for the corresponding siRNA. Finally, in a minority of cases, exemplified by MAPK14-3, the performance of the three types of silencing triggers was similar. Importantly, in only one case out of 17 did we note that the 29 nt shRNA with a 2 nt. 3' overhang performed less effectively than the corresponding siRNA (data not shown).

EXAMPLE 14 siRNAs and shRNAs Give Similar Profiles of Off-Target Effects at Saturation

Sequence specificity is a critical parameter in RNAi experiments. Microarray analysis has revealed down-regulation of many non-targeted transcripts following transfection of siR-NAs into HeLa cells (Jackson et al., *Nat Biotechnol* 21: 635-7, 2003). Notably, these gene expression signatures differed between different siRNAs targeting the same gene. Many of the "off target" transcripts contained sites of partial identity to the individual siRNA, possibly explaining the source of the effects. To examine potential off-target effects of synthetic shRNAs, we compared shRNA signatures with those of siR-NAs derived from the same target sequence. Using microarray gene expression profiling, we obtained a genome-wide view of transcript suppression in response to siRNA and shRNA transfection. FIG. 60 (*a* and *b*) shows heat maps of signatures produced in HeLa cells 24 hours after transfection of 19 nt and 29 nt shRNAs compared with those generated by corresponding siRNAs. 19 nt shRNAs produced signatures that resembled, but were not identical to, those of corresponding siRNAs. In contrast, the signatures of the 29 nt shRNAs (FIG. 60a) were nearly identical to those of the siRNAs.

These results indicate that off target effects may be inherent to the use of synthetic RNAs for eliciting RNAi and cannot be ameliorated by intracellular processing of an upstream precursor in the RNAi pathway. Furthermore, the agreement between the signatures of 29 nt shRNAs and siRNAs is consistent with precise intracellular processing of the shRNA to generate a single siRNA rather than a random sampling of the hairpin stem by Dicer. The basis of the divergence between the signature of the 19 nt shRNA and the corresponding siRNA is presently unclear.

Considered together, our results indicate that chemically synthesized, 29 nt shRNAs are often substantially more effective triggers of RNAi than are siRNAs. While not wishing to be bound by any particular theory, a possible mechanistic explanation for this finding may lie in the fact that 29 nt shRNAs are substrates for Dicer processing both in vitro and in vivo. We originally suggested that siRNAs might be passed from Dicer to RISC in a solid state reaction on the basis of an interaction between Dicer and Argonaute2 in *Drosophila* S2 cell extracts (Hammond et al., *Science* 293: 1146-50, 2001). More recently, results from several laboratories have strongly suggested a model for assembly of the RNAi effector complex in which a multi-protein assembly containing Dicer and accessory proteins interacts with an Argonaute protein and actively loads one strand of the siRNA or miRNA into RISC (Lee et al., *Cell* 117: 69-81, 2004; Pham et al., *Cell* 117: 83-94, 2004; Tomari et al., *Cell* 116: 831-41, 2004). Our result is consistent with a model where Dicer substrates, derived from nuclear processing of pri-miRNAs or cytoplasmic delivery of pre-miRNA mimetics, are loaded into RISC more effectively than siRNAs. Our data support such a model, since it is not the hairpin structure of the synthetic RNA that determines its increased efficacy but the fact that the shRNA is a Dicer substrate that correlates with enhanced potency. Again, not wishing to be bound by any particular theory, it is possible that even siRNAs enter RISC via a Dicer-mediated assembly pathway. Our data may also reflect an increased affinity of Dicer for longer duplexes substrates. Alternatively, hairpin RNAs, such as miRNA precursors, might interact with specific cellular proteins that facilitate delivery of these substrates to Dicer, whereas siRNAs might not benefit from such chaperones.

Overall, our results provide an improved method for triggering RNAi in mammalian cells that uses higher potency RNAi triggers. Mapping the single 22 nt sequence that appears in RISC from each of these shRNAs now permits the combination of this more effective triggering method with rules for effective siRNA design.

Methods

RNA Sequence Design

Each set of RNAs began with the choice of a single 19-mer sequence. These 19mers were used directly to create siRNAs. To create shRNAs with 19-mer stems, we appended a 4-base loop (either CCAA or UUGG) to the end of the 19-mer sense strand target sequence followed by the 9-mer complementary sequence and a UU overhang. To create 29-mer stems, we increased the length of the 19-mer target sequence by adding 1 base upstream and 9 bases downstream from the target region and used the same loop sequence and UU overhang. All synthetic RNA molecules used in this study were purchased from Dharmacon.

Dicer Processing

RNA hairpins corresponding to luciferase were end-labeled with [γ-$^{32}$P] ATP and T4 Polynucleotide kinase. 0.1 pmoles of RNA were then processed with 2 units of Dicer (Stratagene) at 37° C. for 2 hours. Reaction products were trizol extracted, isopropanol precipitated, run on an 18% polyacrylamide, 8M urea denaturing gel. For RNaseIII digestion, 0.1 pmoles were digested with 1 unit of *E. coli* RNase III (NEB) for 30 minutes at 37° C. and analyzed as described above. For primer extension analysis, hairpins were processed with Dicer at 37° C. for 2 hours, followed by heat inactivation of the enzyme. DNA primers were 5' labeled with PNK and annealed to 0.05 pmole of RNA as follows: 95° C. for one minute, 10 minutes at 50° C. and then 1 min on ice. Extensions were carried out at 42° C. for 1 hour using MoMLV reverse transcriptase. Products were analyzed by electrophoresis on a 8M Urea/20% polyacrylamide gel. For analysis of in vitro processing, LinxA cells were transfected in 10 cm plates using Mirus TKO (10 μg hairpin RNA) or Mirus LT4 reagent for DNA transfection (12 μg of tagged Ago1/Ago 2 DNA; J. Liu, unpublished). Cells were lysed and immunoprecipitated after 48 hours using with myc Antibody (9E14) Antibody. Immuno-precipitations were washed 3× in lysis buffer and treated with DNase for 15 minutes. Immunoprecipitates were then primer extended as described above.

siRNA and shRNA Transfections and mRNA Quantitation

HeLa cells were transfected in 96-well plates by use of Oligofectamine (Invitrogen) with the final nanomolar concentrations of each synthetic RNA indicated in the graphs. RNA quantitation was performed by Real-time PCR, using appropriate Applied Biosystems TaqMan™ primer probe sets. The primer probe set used for MAPK14 was Hs00176247_m_1. RNA values were normalized to RNA for HGUS (probe 4310888E).

Microarray Gene Expression Profiling

HeLa cells were transfected in 6-well plates by use of Oligofectamine. RNA from transfected cells was hybridized competitively with RNA from mock-transfected cells (treated with transfection reagent in the absence of synthetic RNA). Total RNA was purified by Qiagen RNeasy kit, and processed as described previously (Hughes et al., *Nat Biotechnol* 19: 342-7, 2001) for hybridization to microarrays containing oligonucleotides corresponding to approximately 21,000 human genes. Ratio hybridizations were performed with fluorescent label reversal to eliminate dye bias. Microarrays were purchased from Agilent Technologies. Error models have been described previously (Hughes et al., *Nat Biotechnol* 19: 342-7, 2001). Data were analyzed using Rosetta Resolver™ software.

SUPPLEMENTARY TABLE 1

Sequences of the siRNAs used in this study

| Gene | Accession number | Target sequence ID | Target sequence |
|---|---|---|---|
| IGF1R | NM_000875 | IGF1R-1 | GGAUGCACCAUCUUCAAGG (SEQ ID NO: 47) |
| IGF1R | NM_000875 | IGF1R-2 | GACAAAAUCCCCAUCAGGA (SEQ ID NO: 48) |
| IGF1R | NM_000875 | IGF1R-3 | ACCGCAAAGUCUUUGAGAA (SEQ ID NO: 49) |
| IGF1R | NM_000875 | IGF1R-4 | GUCCUGACAUGCUGUUUGA (SEQ ID NO: 50) |
| IGF1R | NM_000875 | IGF1R-5 | GACCACCAUCAACAAUGAG (SEQ ID NO: 51) |
| IGF1R | NM_000875 | IGF1R-6 | CAAAUUAUGUGUUUCCGAA (SEQ ID NO: 52) |
| IGF1R | NM_000875 | IGF1R-7 | CGCAUGUGCUGGCAGUAUA (SEQ ID NO: 53) |
| IGF1R | NM_000875 | IGF1R-8 | CCGAAGAUUUCACAGUCAA (SEQ ID NO: 54) |
| IGF1R | NM_000875 | IGF1R-9 | ACCAUUGAUUCUGUUACUU (SEQ ID NO: 55) |
| KIF11 | NM_004523 | KIF11-1 | CUGACAAGAGCUCAAGGAA (SEQ ID NO: 56) |
| KIF11 | NM_004523 | KIF11-2 | CGUUCUGGAGCUGUUGAUA (SEQ ID NO: 57) |
| KIF11 | NM_004523 | KIFI1-3 | GAGCCCAGAUCAACCUUUA (SEQ ID NO: 58) |
| KIF11 | NM_004523 | KIF11-4 | GGCAUUAACACACUGGAGA (SEQ ID NO: 59) |
| KIF11 | NM_004523 | KIF11-5 | GAUGGCAGCUCAAAGCAAA (SEQ ID NO: 60) |
| KIF11 | NM_004523 | KIFI1-6 | CAGCAGAAAUCUAAGGAUA (SEQ ID NO: 61) |
| KIF14 | NM_014875 | KIF14-1 | CAGGGAUGCUGUUUGGAUA (SEQ ID NO: 62) |
| KIF14 | NM_014875 | KIF14-2 | ACUGACAACAAAGUGCAGC (SEQ ID NO: 63) |
| KIF14 | NM_014875 | KIF14-3 | AAACUGGGAGGCUACUUAC (SEQ ID NO: 64) |
| KIF14 | NM_014875 | KIF14-4 | CACUGAAUGUGGGAGGUGA (SEQ ID NO: 65) |
| KIF14 | NM_014875 | KIF14-5 | GUCUGGGUGGAAAUUCAAA (SEQ ID NO: 66) |
| KIF14 | NM_014875 | KIF14-6 | CAUCUUUGCUGAAUCGAAA (SEQ ID NO: 67) |

SUPPLEMENTARY TABLE 1-continued

Sequences of the siRNAs used in this study

| Gene | Accession number | Target sequence ID | Target sequence |
|---|---|---|---|
| KIF14 | NM_014875 | KIF14-7 | GGGAUUGACGGCAGUAAGA (SEQ ID NO: 68) |
| KIF14 | NM_014875 | KIF14-8 | CAGGUAAAGUCAGAGACAU (SEQ ID NO: 69) |
| KIF14 | NM_014875 | KIF14-9 | CUCACAUUGUCCACCAGGA (SEQ ID NO: 70) |
| KNSL1 | NM_004523 | KNSL1-1 | GACCUGUGCCUUUUAGAGA (SEQ ID NO: 71) |
| KNSL1 | NM_004523 | KNSL1-2 | AAAGGACAACUGCAGCUAC (SEQ ID NO: 72) |
| KNSL1 | NM_004523 | KNSL1-3 | GACUUCAUUGACAGUGGCC (SEQ ID NO: 73) |
| MAPK14 | NM_139012 | MAPK14-1 | AAUAUCCUCAGGGGUGGAG (SEQ ID NO: 74) |
| MAPK14 | NM_139012 | MAPK14-2 | GUGCCUCUUGUUGCAGAGA (SEQ ID NO: 75) |
| MAPK14 | NM_139012 | MAPK14-3 | GAAGCUCUCCAGACCAUUU (SEQ ID NO: 76) |
| MAPK14 | NM_001315 | MAPK14-4 | CUCCUGAGAUCAUGCUGAA (SEQ ID NO: 77) |
| MAPK14 | NM_001315 | MAPK14-5 | GCUGUUGACUGGAAGAACA (SEQ ID NO: 78) |
| MAPK14 | NM_001315 | MAPK14-6 | GGAAUUCAAUGAUGUGUAU (SEQ ID NO: 79) |
| MAPK14 | NM_001315 | MAPK14-7 | CCAUUUCAGUCCAUCAUUC (SEQ ID NO: 80) |
| PLK | NM_005030 | PLK-1 | CCCUGUGUGGGACUCCUAA (SEQ ID NO: 81) |
| PLK | NM_005030 | PLK-2 | CCGAGUUAUUCAUCGAGAC (SEQ ID NO: 82) |
| PLK | NM_005030 | PLK-3 | GUUCUUUACUUCUGGCUAU (SEQ ID NO: 83) |
| PLK | NM_005030 | PLK-4 | CGCCUCAUCCUCUACAAUG (SEQ ID NO: 84) |
| PLK | NM_005030 | PLK-5 | AAGAGACCUACCUCCGGAU (SEQ ID NO: 85) |
| PLK | NM_005030 | PLK-6 | GGUGUUCGCGGGCAAGAUU (SEQ ID NO: 86) |
| PLK | NM_005030 | PLK-7 | CUCCUUAAAUAUUCCGCA (SEQ ID NO: 87) |
| PLK | NM_005030 | PLK-8 | AAGAAGAACCAGUGGUUCG (SEQ ID NO: 88) |
| PLK | NM_005030 | PLK-9 | CUGAGCCUGAGGCCCGAUA (SEQ ID NO: 89) |

Literature Cited

1. A. Fire et al., Nature 391, 806-11. (Feb. 19, 1998).
2. M. T. Ruiz, O. Voinnet, D. C. Baulcombe, Plant Cell 10, 93746. (June, 1998).
3. B. R. Williams, Biochem Soc Trans 25, 509-13. (May, 1997).
4. G. J. Hannon, Nature 418, 244-51. (Jul. 11, 2002).
5. A. J. Hamilton, D. C. Baulcombe, Science 286, 950-2 (1999).
6. P. D. Zamore, T. Tuschl, P. A. Sharp, D. P. Bartel, Cell 101, 25-33 (2000).
7. S. M. Hammond, E. Bernstein, D. Beach, G. J. Hannon, Nature 404, 293-6 (2000).
8. E. Bernstein, A. A. Caudy, S. M. Hammond, G. J. Hannon, Nature 409, 363-6. (Jan. 18, 2001).
9. S. M. Hammond, S. Boettcher, A. A. Caudy, R. Kobayashi, G. J. Hannon, Science 293, 1146-50. (Aug. 10, 2001).
10. T. Tuschl, P. D. Zamore, R. Lehmann, D. P. Bartel, P. A. Sharp, Genes Dev 13, 3191-7 (1999).
11. N. J. Caplen, S. Parrish, F. Imani, A. Fire, R. A. Morgan, Proc Natl Acad Sci USA 98, 9742-7. (Aug. 14, 2001).
12. S. M. Elbashir et al., Nature 411, 494-8. (May 24, 2001).
13. S. M. Elbashir, J. Martinez, A. Patkaniowska, W. Lendeckel, T. Tuschl, Embo J 20, 6877-88. (Dec. 3, 2001).
14. D. P. Bartel, Cell 116, 281-97 (Jan. 23, 2004).
15. Y. Lee et al., Nature 425, 415-9 (Sep. 25, 2003).
16. G. Hutvagner et al., Science 293, 834-8. (Aug. 3, 2001).
17. R. F. Ketting et al., Genes Dev 15, 2654-9. (Oct. 15, 2001).
18. A. Grishok et al., Cell 106, 23-34. (Jul. 13, 2001).
19. S. W. Knight, B. L. Bass, Science 293, 2269-71. (Sep. 21, 2001).
20. T. R. Brummelkamp, R. Bemards, R. Agami, Science 21, 21 (2002).
21. P. J. Paddison, A. A. Caudy, E. Bernstein, G. J. Hannon, D. S. Conklin, Genes Dev 16, 948-58. (Apr. 15, 2002).
22. Y. Zeng, E. J. Wagner, B. R. Cullen, Mol Cell 9, 1327-33. (June, 2002).
23. G. Sui et al., Proc Natl Acad Sci USA 99, 5515-20. (Apr. 16, 2002).
24. N. S. Lee et al., Nat Biotechnol 20, 500-5. (May, 2002).
25. C. P. Paul, P. D. Good, I. Winer, D. R. Engelke, Nat Biotechnol 20, 505-8. (May, 2002).
26. R. C. Lee, V. Ambros, Science 294, 862-4. (Oct. 26, 2001).
27. N. C. Lau, L. P. Lim, E. G. Weinstein, D. P. Bartel, Science 294, 858-62. (Oct. 26, 2001).
28. M. Lagos-Quintana, R. Rauhut, W. Lendeckel, T. Tuschl, Science 294, 853-8. (Oct. 26, 2001).
29. D. S. Schwarz et al., Cell 115, 199-208 (Oct. 17, 2003).

30. J. M. Silva, R. Sachidanandam, G. J. Hannon, Nat Genet. 35, 303-5 (December, 2003).
31. A. Khvorova, A. Reynolds, S. D. Jayasena, Cell 115, 209-16 (Oct. 17, 2003).
32. Y. S. Lee et al., Cell 117, 69-81 (Apr. 2, 2004).
33. J. W. Pham, J. L. Pellino, Y. S. Lee, R. W. Carthew, E. J. Sontheimer, Cell 117, 83-94 (Apr. 2, 2004).
34. Y. Tomari et al., Cell 116, 831-41 (Mar. 19, 2004).
35. H. Zhang, F. A. Kolb, V. Brondani, E. Billy, W. Filipowicz, Embo J 21, 5875-85. (Nov. 1, 2002).
36. E. Lund, S. Guttinger, A. Calado, J. E. Dahlberg, U. Kutay, Science 303, 95-8 (Jan. 2, 2004).
37. J. B. Ma, K. Ye, D. J. Patel, Nature 429, 318-22 (May 20, 2004).
38. A. Lingel, B. Simon, E. Izaurralde, M. Sattler, Nat Struct Mol Biol 11, 576-7 (June, 2004).
39. A. Lingel, B. Simon, E. Izaurralde, M. Sattler, Nature 426, 465-9 (Nov. 27, 2003).
40. J. J. Song et al., Nat Struct Biol 10, 1026-32 (December, 2003).
41. K. S. Yan et al., Nature 426, 468-74 (Nov. 27, 2003).
42. Q. Liu et al., Science 301, 1921-5 (Sep. 26, 2003).
43. H. Tabara, E. Yigit, H. Siomi, C. C. Mello, Cell 109, 861-71. (Jun. 28, 2002).
44. A. L. Jackson et al., Nat Biotechnol 21, 635-7 (June, 2003).
45. N. Doi et al., Curr Biol 13, 41-6. (Jan. 8, 2003).
46. T. R. Hughes et al., Nat Biotechnol 19, 342-7 (April, 2001).

V. Equivalents

Those skilled in the art will recognize, or be able to ascertain using no more than routine experimentation, many equivalents to the specific embodiments of the invention described herein. Such equivalents are intended to be encompassed by the following claims. All of the above-cited references and publications are hereby incorporated by reference.

We claim:

1. A method for attenuating expression of a target gene in a mammalian cell, the method comprising
   introducing into mammalian cells a library of RNA expression constructs, each expression construct comprising:
   (i) an RNA polymerase promoter, and
   (ii) a sequence encoding a short hairpin RNA molecule comprising a double-stranded region wherein the double-stranded region consists of at least 20 nucleotides but not more than 29 nucleotides,
   wherein the short hairpin RNA molecule is a substrate for Dicer-dependent cleavage and does not trigger a protein kinase RNA-activated (PKR) response in the mammalian cell,
   wherein the double-stranded region of the short hairpin RNA molecule comprises a sequence that is complementary to a portion of the target gene, and
   wherein the short hairpin RNA molecule is stably expressed in the mammalian cell in an amount sufficient to attenuate expression of the target gene in a sequence specific manner, and is expressed in the cell without use of a PK inhibitor, whereby expression of the target gene is inhibited.

2. The method of claim 1, wherein the expression construct further comprises LTR sequences located 5' and 3' of the sequence encoding the short hairpin RNA molecule.

3. The method of claim 1, wherein the short hairpin RNA molecule comprises a double-stranded region consisting of at least 21 nucleotides.

4. The method of claim 1, wherein the short hairpin RNA molecule comprises a double-stranded region consisting of at least 22 nucleotides.

5. The method of claim 1, wherein the short hairpin RNA molecule comprises a double-stranded region consisting of at least 25 nucleotides.

6. The method of claim 1, wherein the short hairpin RNA molecule comprises a double-stranded region consisting of 29 nucleotides.

7. The method of claim 1, wherein the short hairpin RNA molecule has a total length of 70 nucleotides.

8. The method of claim 1, wherein the RNA polymerase promoter comprises a pol II promoter or a pol III promoter.

9. The method of claim 8, wherein the pol III promoter comprises a U6, an H1, or an SRP promoter.

10. The method of claim 8, wherein the pol II promoter comprises a U1 or a CMV promoter.

* * * * *

SEQUENCE LISTING

```
<160> NUMBER OF SEQ ID NOS: 93

<210> SEQ ID NO 1
<211> LENGTH: 5775
<212> TYPE: DNA
<213> ORGANISM: Homo sapiens
<220> FEATURE:
<221> NAME/KEY: CDS
<222> LOCATION: (1)...(5775)

<400> SEQUENCE: 1 atg aaa agc cct gct ttg caa ccc ctc agc atg gca ggc ctg cag ctc      48
Met Lys Ser Pro Ala Leu Gln Pro Leu Ser Met Ala Gly Leu Gln Leu
1               5                   10                  15 atg acc cct gct tcc tca cca atg ggt cct ttc ttt gga ctg cca tgg      96
Met Thr Pro Ala Ser Ser Pro Met Gly Pro Phe Phe Gly Leu Pro Trp
            20                  25                  30 caa caa gaa gca att cat gat aac att tat acg cca aga aaa tat cag     144
Gln Gln Glu Ala Ile His Asp Asn Ile Tyr Thr Pro Arg Lys Tyr Gln
        35                  40                  45 gtt gaa ctg ctt gaa gca gct ctg gat cat aat acc atc gtc tgt tta     192
Val Glu Leu Leu Glu Ala Ala Leu Asp His Asn Thr Ile Val Cys Leu
    50                  55                  60 aac act ggc tca ggg aag aca ttt att gct agt act cta cta aag         240
Asn Thr Gly Ser Gly Lys Thr Phe Ile Ala Ser Thr Leu Leu Lys
65                  70                  75                  80 agc tgt ctc tat cta gat cta ggg gag act tca gct aga aat gga aaa     288
Ser Cys Leu Tyr Leu Asp Leu Gly Glu Thr Ser Ala Arg Asn Gly Lys
                85                  90                  95 agg acg gtg ttc ttg gtc aac tct gca aac cag gtt gct caa caa gtg     336
Arg Thr Val Phe Leu Val Asn Ser Ala Asn Gln Val Ala Gln Gln Val
            100                 105                 110 tca gct gtc aga act cat tca gat ctc aag gtt ggg gaa tac tca aac     384
Ser Ala Val Arg Thr His Ser Asp Leu Lys Val Gly Glu Tyr Ser Asn
        115                 120                 125 cta gaa gta aat gca tct tgg aca aaa gag aga tgg aac caa gag ttt     432
Leu Glu Val Asn Ala Ser Trp Thr Lys Glu Arg Trp Asn Gln Glu Phe
    130                 135                 140 act aag cac cag gtt ctc att atg act tgc tat gtc gcc ttg aat gtt     480
Thr Lys His Gln Val Leu Ile Met Thr Cys Tyr Val Ala Leu Asn Val
145                 150                 155                 160 ttg aaa aat ggt tac tta tca ctg tca gac att aac ctt ttg gtg ttt     528
Leu Lys Asn Gly Tyr Leu Ser Leu Ser Asp Ile Asn Leu Leu Val Phe
```

```
                   165                 170                 175
gat gag tgt cat ctt gca atc cta gac cac ccc tat cga gaa ttt atg        576
Asp Glu Cys His Leu Ala Ile Leu Asp His Pro Tyr Arg Glu Phe Met
                180                 185                 190 aag ctc tgt gaa att tgt cca tca tgt cct cgc att ttg gga cta act        624
Lys Leu Cys Glu Ile Cys Pro Ser Cys Pro Arg Ile Leu Gly Leu Thr
            195                 200                 205 gct tcc att tta aat ggg aaa tgg gat cca gag gat ttg gaa gaa aag        672
Ala Ser Ile Leu Asn Gly Lys Trp Asp Pro Glu Asp Leu Glu Glu Lys
        210                 215                 220 ttt cag aaa cta gag aaa att ctt aag agt aat gct gaa act gca act        720
Phe Gln Lys Leu Glu Lys Ile Leu Lys Ser Asn Ala Glu Thr Ala Thr
225                 230                 235                 240 gac ctg gtg gtc tta gac agg tat act tct cag cca tgt gag att gtg        768
Asp Leu Val Val Leu Asp Arg Tyr Thr Ser Gln Pro Cys Glu Ile Val
                245                 250                 255 gtg gat tgt gga cca ttt act gac aga agt ggg ctt tat gaa aga ctg        816
Val Asp Cys Gly Pro Phe Thr Asp Arg Ser Gly Leu Tyr Glu Arg Leu
            260                 265                 270 ctg atg gaa tta gaa gaa gca ctt aat ttt atc aat gat tgt aat ata        864
Leu Met Glu Leu Glu Glu Ala Leu Asn Phe Ile Asn Asp Cys Asn Ile
        275                 280                 285 tct gta cat tca aaa gaa aga gat tct act tta att tcg aaa cag ata        912
Ser Val His Ser Lys Glu Arg Asp Ser Thr Leu Ile Ser Lys Gln Ile
290                 295                 300 cta tca gac tgt cgt gcc gta ttg gta gtt ctg gga ccc tgg tgt gca        960
Leu Ser Asp Cys Arg Ala Val Leu Val Val Leu Gly Pro Trp Cys Ala
305                 310                 315                 320 gat aaa gta gct gga atg atg gta aga gaa cta cag aaa tac atc aaa        1008
Asp Lys Val Ala Gly Met Met Val Arg Glu Leu Gln Lys Tyr Ile Lys
                325                 330                 335 cat gag caa gag gag ctg cac agg aaa ttt tta ttg ttt aca gac act        1056
His Glu Gln Glu Glu Leu His Arg Lys Phe Leu Leu Phe Thr Asp Thr
            340                 345                 350 ttc cta agg aaa ata cat gca cta tgt gaa gag cac ttc tca cct gcc        1104
Phe Leu Arg Lys Ile His Ala Leu Cys Glu Glu His Phe Ser Pro Ala
        355                 360                 365 tca ctt gac ctg aaa ttt gta act cct aaa gta atc aaa ctg ctc gaa        1152
Ser Leu Asp Leu Lys Phe Val Thr Pro Lys Val Ile Lys Leu Leu Glu
370                 375                 380 atc tta cgc aaa tat aaa cca tat gag cga cac agt ttt gaa agc gtt        1200
Ile Leu Arg Lys Tyr Lys Pro Tyr Glu Arg His Ser Phe Glu Ser Val
385                 390                 395                 400 gag tgg tat aat aat aga aat cag gat aat tat gtg tca tgg agt gat        1248
Glu Trp Tyr Asn Asn Arg Asn Gln Asp Asn Tyr Val Ser Trp Ser Asp
                405                 410                 415 tct gag gat gat gat gag gat gaa gaa att gaa gaa aaa gag aag cca        1296
Ser Glu Asp Asp Asp Glu Asp Glu Glu Ile Glu Glu Lys Glu Lys Pro
            420                 425                 430 gag aca aat ttt cct tct cct ttt acc aac att ttg tgc gga att att        1344
Glu Thr Asn Phe Pro Ser Pro Phe Thr Asn Ile Leu Cys Gly Ile Ile
        435                 440                 445 ttt gtg gaa aga aga tac aca gca gtt gtc tta aac aga ttg ata aag        1392
Phe Val Glu Arg Arg Tyr Thr Ala Val Val Leu Asn Arg Leu Ile Lys
450                 455                 460 gaa gct ggc aaa caa gat cca gag ctg gct tat atc agt agc aat ttc        1440
Glu Ala Gly Lys Gln Asp Pro Glu Leu Ala Tyr Ile Ser Ser Asn Phe
465                 470                 475                 480 ata act gga cat ggc att ggg aag aat cag cct cgc aac aac acg atg        1488
Ile Thr Gly His Gly Ile Gly Lys Asn Gln Pro Arg Asn Asn Thr Met
```

-continued

|     |     |     |     |     |     |     |     |     |     |     |     |     |     |     |     |     |
|---|---|---|---|---|---|---|---|---|---|---|---|---|---|---|---|---|
|     |     |     | 485 |     |     |     |     | 490 |     |     |     |     | 495 |     |     |     |

```
gaa gca gaa ttc aga aaa cag gaa gag gta ctt agg aaa ttt cga gca     1536
Glu Ala Glu Phe Arg Lys Gln Glu Glu Val Leu Arg Lys Phe Arg Ala
            500                 505                 510 cat gag acc aac ctg ctt att gca aca agt att gta gaa gag ggt gtt     1584
His Glu Thr Asn Leu Leu Ile Ala Thr Ser Ile Val Glu Glu Gly Val
            515                 520                 525 gat ata cca aaa tgc aac ttg gtg gtt cgt ttt gat ttg ccc aca gaa     1632
Asp Ile Pro Lys Cys Asn Leu Val Val Arg Phe Asp Leu Pro Thr Glu
    530                 535                 540 tat cga tcc tat gtt caa tct aaa gga aga gca agg gca ccc atc tct     1680
Tyr Arg Ser Tyr Val Gln Ser Lys Gly Arg Ala Arg Ala Pro Ile Ser
545                 550                 555                 560 aat tat ata atg tta gcg gat aca gac aaa ata aaa agt ttt gaa gaa     1728
Asn Tyr Ile Met Leu Ala Asp Thr Asp Lys Ile Lys Ser Phe Glu Glu
                565                 570                 575 gac ctt aaa acc tac aaa gct att gaa aag atc ttg aga aac aag tgt     1776
Asp Leu Lys Thr Tyr Lys Ala Ile Glu Lys Ile Leu Arg Asn Lys Cys
            580                 585                 590 tcc aag tcg gtt gat act ggt gag act gac att gat cct gtc atg gat     1824
Ser Lys Ser Val Asp Thr Gly Glu Thr Asp Ile Asp Pro Val Met Asp
            595                 600                 605 gat gat cac gtt ttc cca cca tat gtg ttg agg cct gac gat ggt ggt     1872
Asp Asp His Val Phe Pro Pro Tyr Val Leu Arg Pro Asp Asp Gly Gly
    610                 615                 620 cca cga gtc aca atc aac acg gcc att gga cac atc aat aga tac tgt     1920
Pro Arg Val Thr Ile Asn Thr Ala Ile Gly His Ile Asn Arg Tyr Cys
625                 630                 635                 640 gct aga tta cca agt gat ccg ttt act cat cta gct cct aaa tgc aga     1968
Ala Arg Leu Pro Ser Asp Pro Phe Thr His Leu Ala Pro Lys Cys Arg
                645                 650                 655 acc cga gag ttg cct gat ggt aca ttt tat tca act ctt tat ctg cca     2016
Thr Arg Glu Leu Pro Asp Gly Thr Phe Tyr Ser Thr Leu Tyr Leu Pro
            660                 665                 670 att aac tca cct ctt cga gcc tcc att gtt ggt cca cca atg agc tgt     2064
Ile Asn Ser Pro Leu Arg Ala Ser Ile Val Gly Pro Pro Met Ser Cys
            675                 680                 685 gta cga ttg gct gaa aga gtt gtc gct ctc att tgc tgt gag aaa ctg     2112
Val Arg Leu Ala Glu Arg Val Val Ala Leu Ile Cys Cys Glu Lys Leu
    690                 695                 700 cac aaa att ggc gaa ctg gat gac cat ttg atg cca gtt ggg aaa gag     2160
His Lys Ile Gly Glu Leu Asp Asp His Leu Met Pro Val Gly Lys Glu
705                 710                 715                 720 act gtt aaa tat gaa gag gag ctt gat ttg cat gat gaa gaa gag acc     2208
Thr Val Lys Tyr Glu Glu Glu Leu Asp Leu His Asp Glu Glu Glu Thr
                725                 730                 735 agt gtt cca gga aga cca ggt tcc acg aaa cga agg cag tgc tac cca     2256
Ser Val Pro Gly Arg Pro Gly Ser Thr Lys Arg Arg Gln Cys Tyr Pro
            740                 745                 750 aaa gca att cca gag tgt ttg agg gat agt tat ccc aga cct gat cag     2304
Lys Ala Ile Pro Glu Cys Leu Arg Asp Ser Tyr Pro Arg Pro Asp Gln
            755                 760                 765 ccc tgt tac ctg tat gtg ata gga atg gtt tta act aca cct tta cct     2352
Pro Cys Tyr Leu Tyr Val Ile Gly Met Val Leu Thr Thr Pro Leu Pro
    770                 775                 780 gat gaa ctc aac ttt aga agg cgg aag ctc tat cct cct gaa gat acc     2400
Asp Glu Leu Asn Phe Arg Arg Arg Lys Leu Tyr Pro Pro Glu Asp Thr
785                 790                 795                 800 aca aga tgc ttt gga ata ctg acg gcc aaa ccc ata cct cag att cca     2448
Thr Arg Cys Phe Gly Ile Leu Thr Ala Lys Pro Ile Pro Gln Ile Pro
```

|  |  |  |  |  |  |  |  |  |  |  |  |  |  |  |  |
|---|---|---|---|---|---|---|---|---|---|---|---|---|---|---|---|
|  |  | 805 |  |  |  | 810 |  |  |  | 815 |  |  |  |  |  |
| cac | ttt | cct | gtg | tac | aca | cgc | tct | gga | gag | gtt | acc | ata | tcc | att | gag | 2496 |
| His | Phe | Pro | Val | Tyr | Thr | Arg | Ser | Gly | Glu | Val | Thr | Ile | Ser | Ile | Glu |
|  |  | 820 |  |  |  | 825 |  |  |  | 830 |  |  |  |  |  |
| ttg | aag | aag | tct | ggt | ttc | atg | ttg | tct | cta | caa | atg | ctt | gag | ttg | att | 2544 |
| Leu | Lys | Lys | Ser | Gly | Phe | Met | Leu | Ser | Leu | Gln | Met | Leu | Glu | Leu | Ile |
|  | 835 |  |  |  |  | 840 |  |  |  | 845 |  |  |  |  |  |
| aca | aga | ctt | cac | cag | tat | ata | ttc | tca | cat | att | ctt | cgg | ctt | gaa | aaa | 2592 |
| Thr | Arg | Leu | His | Gln | Tyr | Ile | Phe | Ser | His | Ile | Leu | Arg | Leu | Glu | Lys |
| 850 |  |  |  |  | 855 |  |  |  | 860 |  |  |  |  |  |  |
| cct | gca | cta | gaa | ttt | aaa | cct | aca | gac | gct | gat | tca | gca | tac | tgt | gtt | 2640 |
| Pro | Ala | Leu | Glu | Phe | Lys | Pro | Thr | Asp | Ala | Asp | Ser | Ala | Tyr | Cys | Val |
| 865 |  |  |  | 870 |  |  |  | 875 |  |  |  |  | 880 |  |  |
| cta | cct | ctt | aat | gtt | gtt | aat | gac | tcc | agc | act | ttg | gat | att | gac | ttt | 2688 |
| Leu | Pro | Leu | Asn | Val | Val | Asn | Asp | Ser | Ser | Thr | Leu | Asp | Ile | Asp | Phe |
|  |  |  |  | 885 |  |  |  | 890 |  |  |  | 895 |  |  |  |
| aaa | ttc | atg | gaa | gat | att | gag | aag | tct | gaa | gct | cgc | ata | ggc | att | ccc | 2736 |
| Lys | Phe | Met | Glu | Asp | Ile | Glu | Lys | Ser | Glu | Ala | Arg | Ile | Gly | Ile | Pro |
|  |  |  | 900 |  |  |  | 905 |  |  |  | 910 |  |  |  |  |
| agt | aca | aag | tat | aca | aaa | gaa | aca | ccc | ttt | gtt | ttt | aaa | tta | gaa | gat | 2784 |
| Ser | Thr | Lys | Tyr | Thr | Lys | Glu | Thr | Pro | Phe | Val | Phe | Lys | Leu | Glu | Asp |
|  | 915 |  |  |  |  | 920 |  |  |  | 925 |  |  |  |  |  |
| tac | caa | gat | gcc | gtt | atc | att | cca | aga | tat | cgc | aat | ttt | gat | cag | cct | 2832 |
| Tyr | Gln | Asp | Ala | Val | Ile | Ile | Pro | Arg | Tyr | Arg | Asn | Phe | Asp | Gln | Pro |
| 930 |  |  |  |  | 935 |  |  |  | 940 |  |  |  |  |  |  |
| cat | cga | ttt | tat | gta | gct | gat | gtg | tac | act | gat | ctt | acc | cca | ctc | agt | 2880 |
| His | Arg | Phe | Tyr | Val | Ala | Asp | Val | Tyr | Thr | Asp | Leu | Thr | Pro | Leu | Ser |
| 945 |  |  |  | 950 |  |  |  | 955 |  |  |  |  | 960 |  |  |
| aaa | ttt | cct | tcc | cct | gag | tat | gaa | act | ttt | gca | gaa | tat | tat | aaa | aca | 2928 |
| Lys | Phe | Pro | Ser | Pro | Glu | Tyr | Glu | Thr | Phe | Ala | Glu | Tyr | Tyr | Lys | Thr |
|  |  |  | 965 |  |  |  | 970 |  |  |  | 975 |  |  |  |  |
| aag | tac | aac | ctt | gac | cta | acc | aat | ctc | aac | cag | cca | ctg | ctg | gat | gtg | 2976 |
| Lys | Tyr | Asn | Leu | Asp | Leu | Thr | Asn | Leu | Asn | Gln | Pro | Leu | Leu | Asp | Val |
|  |  | 980 |  |  |  | 985 |  |  |  | 990 |  |  |  |  |  |
| gac | cac | aca | tct | tca | aga | ctt | aat | ctt | ttg | aca | cct | cga | cat | ttg | aat | 3024 |
| Asp | His | Thr | Ser | Ser | Arg | Leu | Asn | Leu | Leu | Thr | Pro | Arg | His | Leu | Asn |
|  | 995 |  |  |  |  | 1000 |  |  |  | 1005 |  |  |  |  |  |
| cag | aag | ggg | aaa | gcg | ctt | cct | tta | agc | agt | gct | gag | aag | agg | aaa | gcc | 3072 |
| Gln | Lys | Gly | Lys | Ala | Leu | Pro | Leu | Ser | Ser | Ala | Glu | Lys | Arg | Lys | Ala |
|  | 1010 |  |  |  |  | 1015 |  |  |  | 1020 |  |  |  |  |  |
| aaa | tgg | gaa | agt | ctg | cag | aat | aaa | cag | ata | ctg | gtt | cca | gaa | ctc | tgt | 3120 |
| Lys | Trp | Glu | Ser | Leu | Gln | Asn | Lys | Gln | Ile | Leu | Val | Pro | Glu | Leu | Cys |
| 1025 |  |  |  | 1030 |  |  |  | 1035 |  |  |  |  | 1040 |  |  |
| gct | ata | cat | cca | att | cca | gca | tca | ctg | tgg | aga | aaa | gct | gtt | tgt | ctc | 3168 |
| Ala | Ile | His | Pro | Ile | Pro | Ala | Ser | Leu | Trp | Arg | Lys | Ala | Val | Cys | Leu |
|  |  |  |  | 1045 |  |  |  | 1050 |  |  |  | 1055 |  |  |  |
| ccc | agc | ata | ctt | tat | cgc | ctt | cac | tgc | ctt | ttg | act | gca | gag | gag | cta | 3216 |
| Pro | Ser | Ile | Leu | Tyr | Arg | Leu | His | Cys | Leu | Leu | Thr | Ala | Glu | Glu | Leu |
|  |  |  | 1060 |  |  |  | 1065 |  |  |  | 1070 |  |  |  |  |
| aga | gcc | cag | act | gcc | agc | gat | gct | ggc | gtg | gga | gtc | aga | tca | ctt | cct | 3264 |
| Arg | Ala | Gln | Thr | Ala | Ser | Asp | Ala | Gly | Val | Gly | Val | Arg | Ser | Leu | Pro |
|  | 1075 |  |  |  |  | 1080 |  |  |  | 1085 |  |  |  |  |  |
| gcg | gat | ttt | aga | tac | cct | aac | tta | gac | ttc | ggg | tgg | aaa | aaa | tct | att | 3312 |
| Ala | Asp | Phe | Arg | Tyr | Pro | Asn | Leu | Asp | Phe | Gly | Trp | Lys | Lys | Ser | Ile |
|  | 1090 |  |  |  |  | 1095 |  |  |  | 1100 |  |  |  |  |  |
| gac | agc | aaa | tct | ttc | atc | tca | att | tct | aac | tcc | tct | tca | gct | gaa | aat | 3360 |
| Asp | Ser | Lys | Ser | Phe | Ile | Ser | Ile | Ser | Asn | Ser | Ser | Ser | Ala | Glu | Asn |
| 1105 |  |  |  | 1110 |  |  |  | 1115 |  |  |  |  | 1120 |  |  |
| gat | aat | tac | tgt | aag | cac | agc | aca | att | gtc | cct | gaa | aat | gct | gca | cat | 3408 |
| Asp | Asn | Tyr | Cys | Lys | His | Ser | Thr | Ile | Val | Pro | Glu | Asn | Ala | Ala | His |

-continued

```
                 1125                1130                1135
caa ggt gct aat aga acc tcc tct cta gaa aat cat gac caa atg tct       3456
Gln Gly Ala Asn Arg Thr Ser Ser Leu Glu Asn His Asp Gln Met Ser
         1140                1145                1150 gtg aac tgc aga acg ttg ctc agc gag tcc cct ggt aag ctc cac gtt       3504
Val Asn Cys Arg Thr Leu Leu Ser Glu Ser Pro Gly Lys Leu His Val
     1155                1160                1165 gaa gtt tca gca gat ctt aca gca att aat ggt ctt tct tac aat caa       3552
Glu Val Ser Ala Asp Leu Thr Ala Ile Asn Gly Leu Ser Tyr Asn Gln
 1170                1175                1180 aat ctc gcc aat ggc agt tat gat tta gct aac aga gac ttt tgc caa       3600
Asn Leu Ala Asn Gly Ser Tyr Asp Leu Ala Asn Arg Asp Phe Cys Gln
1185                1190                1195                1200 gga aat cag cta aat tac tac aag cag gaa ata ccc gtg caa cca act       3648
Gly Asn Gln Leu Asn Tyr Tyr Lys Gln Glu Ile Pro Val Gln Pro Thr
                 1205                1210                1215 acc tca tat tcc att cag aat tta tac agt tac gag aac cag ccc cag       3696
Thr Ser Tyr Ser Ile Gln Asn Leu Tyr Ser Tyr Glu Asn Gln Pro Gln
         1220                1225                1230 ccc agc gat gaa tgt act ctc ctg agt aat aaa tac ctt gat gga aat       3744
Pro Ser Asp Glu Cys Thr Leu Leu Ser Asn Lys Tyr Leu Asp Gly Asn
     1235                1240                1245 gct aac aaa tct acc tca gat gga agt cct gtg atg gcc gta atg cct       3792
Ala Asn Lys Ser Thr Ser Asp Gly Ser Pro Val Met Ala Val Met Pro
 1250                1255                1260 ggt acg aca gac act att caa gtg ctc aag ggc agg atg gat tct gag       3840
Gly Thr Thr Asp Thr Ile Gln Val Leu Lys Gly Arg Met Asp Ser Glu
1265                1270                1275                1280 cag agc cct tct att ggg tac tcc tca agg act ctt ggc ccc aat cct       3888
Gln Ser Pro Ser Ile Gly Tyr Ser Ser Arg Thr Leu Gly Pro Asn Pro
                 1285                1290                1295 gga ctt att ctt cag gct ttg act ctg tca aac gct agt gat gga ttt       3936
Gly Leu Ile Leu Gln Ala Leu Thr Leu Ser Asn Ala Ser Asp Gly Phe
         1300                1305                1310 aac ctg gag cgg ctt gaa atg ctt ggc gac tcc ttt tta aag cat gcc       3984
Asn Leu Glu Arg Leu Glu Met Leu Gly Asp Ser Phe Leu Lys His Ala
     1315                1320                1325 atc acc aca tat cta ttt tgc act tac cct gat gcg cat gag ggc cgc       4032
Ile Thr Thr Tyr Leu Phe Cys Thr Tyr Pro Asp Ala His Glu Gly Arg
 1330                1335                1340 ctt tca tat atg aga agc aaa aag gtc agc aac tgt aat ctg tat cgc       4080
Leu Ser Tyr Met Arg Ser Lys Lys Val Ser Asn Cys Asn Leu Tyr Arg
1345                1350                1355                1360 ctt gga aaa aag aag gga cta ccc agc cgc atg gtg gtg tca ata ttt       4128
Leu Gly Lys Lys Lys Gly Leu Pro Ser Arg Met Val Val Ser Ile Phe
                 1365                1370                1375 gat ccc cct gtg aat tgg ctt cct cct ggt tat gta gta aat caa gac       4176
Asp Pro Pro Val Asn Trp Leu Pro Pro Gly Tyr Val Val Asn Gln Asp
         1380                1385                1390 aaa agc aac aca gat aaa tgg gaa aaa gat gaa atg aca aaa gac tgc       4224
Lys Ser Asn Thr Asp Lys Trp Glu Lys Asp Glu Met Thr Lys Asp Cys
     1395                1400                1405 atg ctg gcg aat ggc aaa ctg gat gag gat tac gag gag gag gat gag       4272
Met Leu Ala Asn Gly Lys Leu Asp Glu Asp Tyr Glu Glu Glu Asp Glu
 1410                1415                1420 gag gag gag agc ctg atg tgg agg gct ccg aag gaa gag gct gac tat       4320
Glu Glu Glu Ser Leu Met Trp Arg Ala Pro Lys Glu Glu Ala Asp Tyr
1425                1430                1435                1440 gaa gat gat ttc ctg gag tat gat cag gaa cat atc aga ttt ata gat       4368
Glu Asp Asp Phe Leu Glu Tyr Asp Gln Glu His Ile Arg Phe Ile Asp
```

```
                    1445                1450                1455 aat atg tta atg ggg tca gga gct ttt gta aag aaa atc tct ctt tct    4416
Asn Met Leu Met Gly Ser Gly Ala Phe Val Lys Lys Ile Ser Leu Ser
        1460                1465                1470 cct ttt tca acc act gat tct gca tat gaa tgg aaa atg ccc aaa aaa    4464
Pro Phe Ser Thr Thr Asp Ser Ala Tyr Glu Trp Lys Met Pro Lys Lys
    1475                1480                1485 tcc tcc tta ggt agt atg cca ttt tca tca gat ttt gag gat ttt gac    4512
Ser Ser Leu Gly Ser Met Pro Phe Ser Ser Asp Phe Glu Asp Phe Asp
        1490                1495                1500 tac agc tct tgg gat gca atg tgc tat ctg gat cct agc aaa gct gtt    4560
Tyr Ser Ser Trp Asp Ala Met Cys Tyr Leu Asp Pro Ser Lys Ala Val
1505                1510                1515                1520 gaa gaa gat gac ttt gtg gtg ggg ttc tgg aat cca tca gaa gaa aac    4608
Glu Glu Asp Asp Phe Val Val Gly Phe Trp Asn Pro Ser Glu Glu Asn
            1525                1530                1535 tgt ggt gtt gac acg gga aag cag tcc att tct tac gac ttg cac act    4656
Cys Gly Val Asp Thr Gly Lys Gln Ser Ile Ser Tyr Asp Leu His Thr
        1540                1545                1550 gag cag tgt att gct gac aaa agc ata gcg gac tgt gtg gaa gcc ctg    4704
Glu Gln Cys Ile Ala Asp Lys Ser Ile Ala Asp Cys Val Glu Ala Leu
    1555                1560                1565 ctg ggc tgc tat tta acc agc tgt ggg gag agg gct gct cag ctt ttc    4752
Leu Gly Cys Tyr Leu Thr Ser Cys Gly Glu Arg Ala Ala Gln Leu Phe
1570                1575                1580 ctc tgt tca ctg ggg ctg aag gtg ctc ccg gta att aaa agg act gat    4800
Leu Cys Ser Leu Gly Leu Lys Val Leu Pro Val Ile Lys Arg Thr Asp
1585                1590                1595                1600 cgg gaa aag gcc ctg tgc cct act cgg gag aat ttc aac agc caa caa    4848
Arg Glu Lys Ala Leu Cys Pro Thr Arg Glu Asn Phe Asn Ser Gln Gln
            1605                1610                1615 aag aac ctt tca gtg agc tgt gct gct gct tct gtg gcc agt tca cgc    4896
Lys Asn Leu Ser Val Ser Cys Ala Ala Ala Ser Val Ala Ser Ser Arg
        1620                1625                1630 tct tct gta ttg aaa gac tcg gaa tat ggt tgt ttg aag att cca cca    4944
Ser Ser Val Leu Lys Asp Ser Glu Tyr Gly Cys Leu Lys Ile Pro Pro
    1635                1640                1645 aga tgt atg ttt gat cat cca gat gca gat aaa aca ctg aat cac ctt    4992
Arg Cys Met Phe Asp His Pro Asp Ala Asp Lys Thr Leu Asn His Leu
1650                1655                1660 ata tcg ggg ttt gaa aat ttt gaa aag aaa atc aac tac aga ttc aag    5040
Ile Ser Gly Phe Glu Asn Phe Glu Lys Lys Ile Asn Tyr Arg Phe Lys
1665                1670                1675                1680 aat aag gct tac ctt ctc cag gct ttt aca cat gcc tcc tac cac tac    5088
Asn Lys Ala Tyr Leu Leu Gln Ala Phe Thr His Ala Ser Tyr His Tyr
            1685                1690                1695 aat act atc act gat tgt tac cag cgc tta gaa ttc ctg gga gat gcg    5136
Asn Thr Ile Thr Asp Cys Tyr Gln Arg Leu Glu Phe Leu Gly Asp Ala
        1700                1705                1710 att ttg gac tac ctc ata acc aag cac ctt tat gaa gac ccg cgg cag    5184
Ile Leu Asp Tyr Leu Ile Thr Lys His Leu Tyr Glu Asp Pro Arg Gln
    1715                1720                1725 cac tcc ccg ggg gtc ctg aca gac ctg cgg tct gcc ctg gtc aac aac    5232
His Ser Pro Gly Val Leu Thr Asp Leu Arg Ser Ala Leu Val Asn Asn
1730                1735                1740 acc atc ttt gca tcg ctg gct gta aag tac gac tac cac aag tac ttc    5280
Thr Ile Phe Ala Ser Leu Ala Val Lys Tyr Asp Tyr His Lys Tyr Phe
1745                1750                1755                1760 aaa gct gtc tct cct gag ctc ttc cat gtc att gat gac ttt gtg cag    5328
Lys Ala Val Ser Pro Glu Leu Phe His Val Ile Asp Asp Phe Val Gln
```

```
                        1765                1770                1775
ttt cag ctt gag aag aat gaa atg caa gga atg gat tct gag ctt agg          5376
Phe Gln Leu Glu Lys Asn Glu Met Gln Gly Met Asp Ser Glu Leu Arg
            1780                1785                1790 aga tct gag gag gat gaa gag aaa gaa gag gat att gaa gtt cca aag          5424
Arg Ser Glu Glu Asp Glu Glu Lys Glu Glu Asp Ile Glu Val Pro Lys
        1795                1800                1805 gcc atg ggg gat att ttt gag tcg ctt gct ggt gcc att tac atg gat          5472
Ala Met Gly Asp Ile Phe Glu Ser Leu Ala Gly Ala Ile Tyr Met Asp
    1810                1815                1820 agt ggg atg tca ctg gag aca gtc tgg cag gtg tac tat ccc atg atg          5520
Ser Gly Met Ser Leu Glu Thr Val Trp Gln Val Tyr Tyr Pro Met Met
1825                1830                1835                1840 cgg cca cta ata gaa aag ttt tct gca aat gta ccc cgt tcc cct gtg          5568
Arg Pro Leu Ile Glu Lys Phe Ser Ala Asn Val Pro Arg Ser Pro Val
                1845                1850                1855 cga gaa ttg ctt gaa atg gaa cca gaa act gcc aaa ttt agc ccg gct          5616
Arg Glu Leu Leu Glu Met Glu Pro Glu Thr Ala Lys Phe Ser Pro Ala
            1860                1865                1870 gag aga act tac gac ggg aag gtc aga gtc act gtg gaa gta gta gga          5664
Glu Arg Thr Tyr Asp Gly Lys Val Arg Val Thr Val Glu Val Val Gly
        1875                1880                1885 aag ggg aaa ttt aaa ggt gtt ggt cga agt tac agg att gcc aaa tct          5712
Lys Gly Lys Phe Lys Gly Val Gly Arg Ser Tyr Arg Ile Ala Lys Ser
    1890                1895                1900 gca gca gca aga aga gcc ctc cga agc ctc aaa gct aat caa cct cag          5760
Ala Ala Ala Arg Arg Ala Leu Arg Ser Leu Lys Ala Asn Gln Pro Gln
1905                1910                1915                1920 gtt ccc aat agc tga                                                      5775
Val Pro Asn Ser *

<210> SEQ ID NO 2
<211> LENGTH: 1924
<212> TYPE: PRT
<213> ORGANISM: Homo sapiens

<400> SEQUENCE: 2

Met Lys Ser Pro Ala Leu Gln Pro Leu Ser Met Ala Gly Leu Gln Leu
1               5                   10                  15

Met Thr Pro Ala Ser Ser Pro Met Gly Pro Phe Phe Gly Leu Pro Trp
            20                  25                  30

Gln Gln Glu Ala Ile His Asp Asn Ile Tyr Thr Pro Arg Lys Tyr Gln
        35                  40                  45

Val Glu Leu Leu Glu Ala Ala Leu Asp His Asn Thr Ile Val Cys Leu
    50                  55                  60

Asn Thr Gly Ser Gly Lys Thr Phe Ile Ala Ser Thr Thr Leu Leu Lys
65                  70                  75                  80

Ser Cys Leu Tyr Leu Asp Leu Gly Glu Thr Ser Ala Arg Asn Gly Lys
                85                  90                  95

Arg Thr Val Phe Leu Val Asn Ser Ala Asn Gln Val Ala Gln Gln Val
            100                 105                 110

Ser Ala Val Arg Thr His Ser Asp Leu Lys Val Gly Glu Tyr Ser Asn
        115                 120                 125

Leu Glu Val Asn Ala Ser Trp Thr Lys Glu Arg Trp Asn Gln Glu Phe
    130                 135                 140

Thr Lys His Gln Val Leu Ile Met Thr Cys Tyr Val Ala Leu Asn Val
145                 150                 155                 160

Leu Lys Asn Gly Tyr Leu Ser Leu Ser Asp Ile Asn Leu Leu Val Phe
```

-continued

```
                165                 170                 175
Asp Glu Cys His Leu Ala Ile Leu Asp His Pro Tyr Arg Glu Phe Met
            180                 185                 190
Lys Leu Cys Glu Ile Cys Pro Ser Cys Pro Arg Ile Leu Gly Leu Thr
            195                 200                 205
Ala Ser Ile Leu Asn Gly Lys Trp Asp Pro Glu Asp Leu Glu Glu Lys
            210                 215                 220
Phe Gln Lys Leu Glu Lys Ile Leu Lys Ser Asn Ala Glu Thr Ala Thr
225                 230                 235                 240
Asp Leu Val Val Leu Asp Arg Tyr Thr Ser Gln Pro Cys Glu Ile Val
                245                 250                 255
Val Asp Cys Gly Pro Phe Thr Asp Arg Ser Gly Leu Tyr Glu Arg Leu
            260                 265                 270
Leu Met Glu Leu Glu Glu Ala Leu Asn Phe Ile Asn Asp Cys Asn Ile
            275                 280                 285
Ser Val His Ser Lys Glu Arg Asp Ser Thr Leu Ile Ser Lys Gln Ile
            290                 295                 300
Leu Ser Asp Cys Arg Ala Val Leu Val Val Leu Gly Pro Trp Cys Ala
305                 310                 315                 320
Asp Lys Val Ala Gly Met Met Val Arg Glu Leu Gln Lys Tyr Ile Lys
                325                 330                 335
His Glu Gln Glu Leu His Arg Lys Phe Leu Leu Phe Thr Asp Thr
            340                 345                 350
Phe Leu Arg Lys Ile His Ala Leu Cys Glu Glu His Phe Ser Pro Ala
            355                 360                 365
Ser Leu Asp Leu Lys Phe Val Thr Pro Lys Val Ile Lys Leu Leu Glu
            370                 375                 380
Ile Leu Arg Lys Tyr Lys Pro Tyr Glu Arg His Ser Phe Glu Ser Val
385                 390                 395                 400
Glu Trp Tyr Asn Asn Arg Asn Gln Asp Asn Tyr Val Ser Trp Ser Asp
                405                 410                 415
Ser Glu Asp Asp Asp Glu Asp Glu Glu Ile Glu Glu Lys Glu Lys Pro
            420                 425                 430
Glu Thr Asn Phe Pro Ser Pro Phe Thr Asn Ile Leu Cys Gly Ile Ile
            435                 440                 445
Phe Val Glu Arg Arg Tyr Thr Ala Val Val Leu Asn Arg Leu Ile Lys
            450                 455                 460
Glu Ala Gly Lys Gln Asp Pro Glu Leu Ala Tyr Ile Ser Ser Asn Phe
465                 470                 475                 480
Ile Thr Gly His Gly Ile Gly Lys Asn Gln Pro Arg Asn Asn Thr Met
                485                 490                 495
Glu Ala Glu Phe Arg Lys Gln Glu Glu Val Leu Arg Lys Phe Arg Ala
            500                 505                 510
His Glu Thr Asn Leu Leu Ile Ala Thr Ser Ile Val Glu Glu Gly Val
            515                 520                 525
Asp Ile Pro Lys Cys Asn Leu Val Val Arg Phe Asp Leu Pro Thr Glu
            530                 535                 540
Tyr Arg Ser Tyr Val Gln Ser Lys Gly Arg Ala Arg Ala Pro Ile Ser
545                 550                 555                 560
Asn Tyr Ile Met Leu Ala Asp Thr Asp Lys Ile Lys Ser Phe Glu Glu
                565                 570                 575
Asp Leu Lys Thr Tyr Lys Ala Ile Glu Lys Ile Leu Arg Asn Lys Cys
            580                 585                 590
```

-continued

```
Ser Lys Ser Val Asp Thr Gly Glu Thr Asp Ile Asp Pro Val Met Asp
        595                 600                 605

Asp Asp His Val Phe Pro Pro Tyr Val Leu Arg Pro Asp Asp Gly Gly
610                 615                 620

Pro Arg Val Thr Ile Asn Thr Ala Ile Gly His Ile Asn Arg Tyr Cys
625                 630                 635                 640

Ala Arg Leu Pro Ser Asp Pro Phe Thr His Leu Ala Pro Lys Cys Arg
                645                 650                 655

Thr Arg Glu Leu Pro Asp Gly Thr Phe Tyr Ser Thr Leu Tyr Leu Pro
            660                 665                 670

Ile Asn Ser Pro Leu Arg Ala Ser Ile Val Gly Pro Pro Met Ser Cys
        675                 680                 685

Val Arg Leu Ala Glu Arg Val Val Ala Leu Ile Cys Cys Glu Lys Leu
    690                 695                 700

His Lys Ile Gly Glu Leu Asp Asp His Leu Met Pro Val Gly Lys Glu
705                 710                 715                 720

Thr Val Lys Tyr Glu Glu Leu Asp Leu His Asp Glu Glu Glu Thr
                725                 730                 735

Ser Val Pro Gly Arg Pro Gly Ser Thr Lys Arg Arg Gln Cys Tyr Pro
            740                 745                 750

Lys Ala Ile Pro Glu Cys Leu Arg Asp Ser Tyr Pro Arg Pro Asp Gln
        755                 760                 765

Pro Cys Tyr Leu Tyr Val Ile Gly Met Val Leu Thr Thr Pro Leu Pro
    770                 775                 780

Asp Glu Leu Asn Phe Arg Arg Lys Leu Tyr Pro Pro Glu Asp Thr
785                 790                 795                 800

Thr Arg Cys Phe Gly Ile Leu Thr Ala Lys Pro Ile Pro Gln Ile Pro
                805                 810                 815

His Phe Pro Val Tyr Thr Arg Ser Gly Glu Val Thr Ile Ser Ile Glu
            820                 825                 830

Leu Lys Lys Ser Gly Phe Met Leu Ser Leu Gln Met Leu Glu Leu Ile
        835                 840                 845

Thr Arg Leu His Gln Tyr Ile Phe Ser His Ile Leu Arg Leu Glu Lys
    850                 855                 860

Pro Ala Leu Glu Phe Lys Pro Thr Asp Ala Asp Ser Ala Tyr Cys Val
865                 870                 875                 880

Leu Pro Leu Asn Val Val Asn Asp Ser Ser Thr Leu Asp Ile Asp Phe
                885                 890                 895

Lys Phe Met Glu Asp Ile Glu Lys Ser Glu Ala Arg Ile Gly Ile Pro
            900                 905                 910

Ser Thr Lys Tyr Thr Lys Glu Thr Pro Phe Val Phe Lys Leu Glu Asp
        915                 920                 925

Tyr Gln Asp Ala Val Ile Ile Pro Arg Tyr Arg Asn Phe Asp Gln Pro
    930                 935                 940

His Arg Phe Tyr Val Ala Asp Val Tyr Thr Asp Leu Thr Pro Leu Ser
945                 950                 955                 960

Lys Phe Pro Ser Pro Glu Tyr Glu Thr Phe Ala Glu Tyr Tyr Lys Thr
                965                 970                 975

Lys Tyr Asn Leu Asp Leu Thr Asn Leu Asn Gln Pro Leu Leu Asp Val
            980                 985                 990

Asp His Thr Ser Ser Arg Leu Asn Leu Leu Thr Pro Arg His Leu Asn
        995                 1000                1005

Gln Lys Gly Lys Ala Leu Pro Leu Ser Ser Ala Glu Lys Arg Lys Ala
        1010                1015                1020
```

-continued

```
Lys Trp Glu Ser Leu Gln Asn Lys Gln Ile Leu Val Pro Glu Leu Cys
1025                1030                1035                1040

Ala Ile His Pro Ile Pro Ala Ser Leu Trp Arg Lys Ala Val Cys Leu
            1045                1050                1055

Pro Ser Ile Leu Tyr Arg Leu His Cys Leu Leu Thr Ala Glu Glu Leu
        1060                1065                1070

Arg Ala Gln Thr Ala Ser Asp Ala Gly Val Gly Val Arg Ser Leu Pro
    1075                1080                1085

Ala Asp Phe Arg Tyr Pro Asn Leu Asp Phe Gly Trp Lys Lys Ser Ile
1090                1095                1100

Asp Ser Lys Ser Phe Ile Ser Ile Ser Asn Ser Ser Ser Ala Glu Asn
1105                1110                1115                1120

Asp Asn Tyr Cys Lys His Ser Thr Ile Val Pro Glu Asn Ala Ala His
            1125                1130                1135

Gln Gly Ala Asn Arg Thr Ser Ser Leu Glu Asn His Asp Gln Met Ser
        1140                1145                1150

Val Asn Cys Arg Thr Leu Leu Ser Glu Ser Pro Gly Lys Leu His Val
    1155                1160                1165

Glu Val Ser Ala Asp Leu Thr Ala Ile Asn Gly Leu Ser Tyr Asn Gln
1170                1175                1180

Asn Leu Ala Asn Gly Ser Tyr Asp Leu Ala Asn Arg Asp Phe Cys Gln
1185                1190                1195                1200

Gly Asn Gln Leu Asn Tyr Tyr Lys Gln Glu Ile Pro Val Gln Pro Thr
            1205                1210                1215

Thr Ser Tyr Ser Ile Gln Asn Leu Tyr Ser Tyr Glu Asn Gln Pro Gln
        1220                1225                1230

Pro Ser Asp Glu Cys Thr Leu Leu Ser Asn Lys Tyr Leu Asp Gly Asn
    1235                1240                1245

Ala Asn Lys Ser Thr Ser Asp Gly Ser Pro Val Met Ala Val Met Pro
1250                1255                1260

Gly Thr Thr Asp Thr Ile Gln Val Leu Lys Gly Arg Met Asp Ser Glu
1265                1270                1275                1280

Gln Ser Pro Ser Ile Gly Tyr Ser Ser Arg Thr Leu Gly Pro Asn Pro
            1285                1290                1295

Gly Leu Ile Leu Gln Ala Leu Thr Leu Ser Asn Ala Ser Asp Gly Phe
        1300                1305                1310

Asn Leu Glu Arg Leu Glu Met Leu Gly Asp Ser Phe Leu Lys His Ala
    1315                1320                1325

Ile Thr Thr Tyr Leu Phe Cys Thr Tyr Pro Asp Ala His Glu Gly Arg
1330                1335                1340

Leu Ser Tyr Met Arg Ser Lys Lys Val Ser Asn Cys Asn Leu Tyr Arg
1345                1350                1355                1360

Leu Gly Lys Lys Lys Gly Leu Pro Ser Arg Met Val Val Ser Ile Phe
            1365                1370                1375

Asp Pro Pro Val Asn Trp Leu Pro Pro Gly Tyr Val Val Asn Gln Asp
        1380                1385                1390

Lys Ser Asn Thr Asp Lys Trp Glu Lys Asp Glu Met Thr Lys Asp Cys
    1395                1400                1405

Met Leu Ala Asn Gly Lys Leu Asp Glu Asp Tyr Glu Glu Glu Asp Glu
1410                1415                1420

Glu Glu Glu Ser Leu Met Trp Arg Ala Pro Lys Glu Glu Ala Asp Tyr
1425                1430                1435                1440

Glu Asp Asp Phe Leu Glu Tyr Asp Gln Glu His Ile Arg Phe Ile Asp
```

```
                 1445                1450                1455
Asn Met Leu Met Gly Ser Gly Ala Phe Val Lys Lys Ile Ser Leu Ser
            1460                1465                1470

Pro Phe Ser Thr Thr Asp Ser Ala Tyr Glu Trp Lys Met Pro Lys Lys
        1475                1480                1485

Ser Ser Leu Gly Ser Met Pro Phe Ser Ser Asp Phe Glu Asp Phe Asp
    1490                1495                1500

Tyr Ser Ser Trp Asp Ala Met Cys Tyr Leu Asp Pro Ser Lys Ala Val
1505                1510                1515                1520

Glu Glu Asp Asp Phe Val Val Gly Phe Trp Asn Pro Ser Glu Glu Asn
                1525                1530                1535

Cys Gly Val Asp Thr Gly Lys Gln Ser Ile Ser Tyr Asp Leu His Thr
            1540                1545                1550

Glu Gln Cys Ile Ala Asp Lys Ser Ile Ala Asp Cys Val Glu Ala Leu
        1555                1560                1565

Leu Gly Cys Tyr Leu Thr Ser Cys Gly Glu Arg Ala Ala Gln Leu Phe
    1570                1575                1580

Leu Cys Ser Leu Gly Leu Lys Val Leu Pro Val Ile Lys Arg Thr Asp
1585                1590                1595                1600

Arg Glu Lys Ala Leu Cys Pro Thr Arg Glu Asn Phe Asn Ser Gln Gln
                1605                1610                1615

Lys Asn Leu Ser Val Ser Cys Ala Ala Ser Val Ala Ser Ser Arg
            1620                1625                1630

Ser Ser Val Leu Lys Asp Ser Glu Tyr Gly Cys Leu Lys Ile Pro Pro
        1635                1640                1645

Arg Cys Met Phe Asp His Pro Asp Ala Asp Lys Thr Leu Asn His Leu
    1650                1655                1660

Ile Ser Gly Phe Glu Asn Phe Glu Lys Lys Ile Asn Tyr Arg Phe Lys
1665                1670                1675                1680

Asn Lys Ala Tyr Leu Leu Gln Ala Phe Thr His Ala Ser Tyr His Tyr
                1685                1690                1695

Asn Thr Ile Thr Asp Cys Tyr Gln Arg Leu Glu Phe Leu Gly Asp Ala
            1700                1705                1710

Ile Leu Asp Tyr Leu Ile Thr Lys His Leu Tyr Glu Asp Pro Arg Gln
        1715                1720                1725

His Ser Pro Gly Val Leu Thr Asp Leu Arg Ser Ala Leu Val Asn Asn
    1730                1735                1740

Thr Ile Phe Ala Ser Leu Ala Val Lys Tyr Asp Tyr His Lys Tyr Phe
1745                1750                1755                1760

Lys Ala Val Ser Pro Glu Leu Phe His Val Ile Asp Asp Phe Val Gln
                1765                1770                1775

Phe Gln Leu Glu Lys Asn Glu Met Gln Gly Met Asp Ser Glu Leu Arg
            1780                1785                1790

Arg Ser Glu Glu Asp Glu Glu Lys Glu Glu Asp Ile Glu Val Pro Lys
        1795                1800                1805

Ala Met Gly Asp Ile Phe Glu Ser Leu Ala Gly Ala Ile Tyr Met Asp
    1810                1815                1820

Ser Gly Met Ser Leu Glu Thr Val Trp Gln Val Tyr Tyr Pro Met Met
1825                1830                1835                1840

Arg Pro Leu Ile Glu Lys Phe Ser Ala Asn Val Pro Arg Ser Pro Val
                1845                1850                1855

Arg Glu Leu Leu Glu Met Glu Pro Glu Thr Ala Lys Phe Ser Pro Ala
            1860                1865                1870
```

```
Glu Arg Thr Tyr Asp Gly Lys Val Arg Val Thr Val Glu Val Val Gly
        1875                1880                1885

Lys Gly Lys Phe Lys Gly Val Gly Arg Ser Tyr Arg Ile Ala Lys Ser
    1890                1895                1900

Ala Ala Ala Arg Arg Ala Leu Arg Ser Leu Lys Ala Asn Gln Pro Gln
1905                1910                1915                1920

Val Pro Asn Ser

<210> SEQ ID NO 3
<211> LENGTH: 6750
<212> TYPE: DNA
<213> ORGANISM: Drosophila melanogaster
<220> FEATURE:
<221> NAME/KEY: CDS
<222> LOCATION: (1)...(6750)

<400> SEQUENCE: 3 atg gcg ttc cac tgg tgc gac aac aat ctg cac acc acc gtg ttc acg      48
Met Ala Phe His Trp Cys Asp Asn Asn Leu His Thr Thr Val Phe Thr
1               5                  10                  15 ccg cgc gac ttt cag gtg gag cta ctg gcc acc gcc tac gag cgg aac      96
Pro Arg Asp Phe Gln Val Glu Leu Leu Ala Thr Ala Tyr Glu Arg Asn
            20                  25                  30 acg att att tgc ctg ggc cat cga agt tcc aag gag ttt ata gcc ctc     144
Thr Ile Ile Cys Leu Gly His Arg Ser Ser Lys Glu Phe Ile Ala Leu
        35                  40                  45 aag ctg ctc cag gag ctg tcg cgt cga gca cgc cga cat ggt cgt gtc     192
Lys Leu Leu Gln Glu Leu Ser Arg Arg Ala Arg Arg His Gly Arg Val
    50                  55                  60 agt gtc tat ctc agt tgc gag gtt ggc acc agc acg gaa cca tgc tcc     240
Ser Val Tyr Leu Ser Cys Glu Val Gly Thr Ser Thr Glu Pro Cys Ser
65                  70                  75                  80 atc tac acg atg ctc acc cac ttg act gac ctg cgg gtg tgg cag gag     288
Ile Tyr Thr Met Leu Thr His Leu Thr Asp Leu Arg Val Trp Gln Glu
                85                  90                  95 cag ccg gat atg caa att ccc ttt gat cat tgc tgg acg gac tat cac     336
Gln Pro Asp Met Gln Ile Pro Phe Asp His Cys Trp Thr Asp Tyr His
            100                 105                 110 gtt tcc atc cta cgg cca gag gga ttt ctt tat ctg ctc gaa act cgc     384
Val Ser Ile Leu Arg Pro Glu Gly Phe Leu Tyr Leu Leu Glu Thr Arg
        115                 120                 125 gag ctg ctg ctg agc agc gtc gaa ctg atc gtg ctg gaa gat tgt cat     432
Glu Leu Leu Leu Ser Ser Val Glu Leu Ile Val Leu Glu Asp Cys His
    130                 135                 140 gac agc gcc gtt tat cag agg ata agg cct ctg ttc gag aat cac att     480
Asp Ser Ala Val Tyr Gln Arg Ile Arg Pro Leu Phe Glu Asn His Ile
145                 150                 155                 160 atg cca gcg cca ccg gcg gac agg cca cgg att ctc gga ctc gct gga     528
Met Pro Ala Pro Pro Ala Asp Arg Pro Arg Ile Leu Gly Leu Ala Gly
                165                 170                 175 ccg ctg cac agc gcc gga tgt gag ctg cag caa ctg agc gcc atg ctg     576
Pro Leu His Ser Ala Gly Cys Glu Leu Gln Gln Leu Ser Ala Met Leu
            180                 185                 190 gcc acc ctg gag cag agt gtg ctt tgc cag atc gag acg gcc agt gat     624
Ala Thr Leu Glu Gln Ser Val Leu Cys Gln Ile Glu Thr Ala Ser Asp
        195                 200                 205 att gtc acc gtg ttg cgt tac tgt tcc cga ccg cac gaa tac atc gta     672
Ile Val Thr Val Leu Arg Tyr Cys Ser Arg Pro His Glu Tyr Ile Val
    210                 215                 220 cag tgc gcc ccc ttc gag atg gac gaa ctg tcc ctg gtg ctt gcc gat     720
Gln Cys Ala Pro Phe Glu Met Asp Glu Leu Ser Leu Val Leu Ala Asp
```

```
                225                 230                 235                 240
gtg ctc aac aca cac aag tcc ttt tta ttg gac cac cgc tac gat ccc       768
Val Leu Asn Thr His Lys Ser Phe Leu Leu Asp His Arg Tyr Asp Pro
                    245                 250                 255 tac gaa atc tac ggc aca gac cag ttt atg gac gaa ctg aaa gac ata       816
Tyr Glu Ile Tyr Gly Thr Asp Gln Phe Met Asp Glu Leu Lys Asp Ile
                    260                 265                 270 ccc gat ccc aag gtg gac ccc ctg aac gtc atc aac tca cta ctg gtc       864
Pro Asp Pro Lys Val Asp Pro Leu Asn Val Ile Asn Ser Leu Leu Val
                    275                 280                 285 gtg ctg cac gag atg ggt cct tgg tgc acg cag cgg gct gca cat cac       912
Val Leu His Glu Met Gly Pro Trp Cys Thr Gln Arg Ala Ala His His
                    290                 295                 300 ttt tac caa tgc aat gag aag tta aag gtg aag acg ccg cac gaa cgt       960
Phe Tyr Gln Cys Asn Glu Lys Leu Lys Val Lys Thr Pro His Glu Arg
305                 310                 315                 320 cac tac ttg ctg tac tgc cta gtg agc acg gcc ctt atc caa ctg tac      1008
His Tyr Leu Leu Tyr Cys Leu Val Ser Thr Ala Leu Ile Gln Leu Tyr
                    325                 330                 335 tcc ctc tgc gaa cac gca ttc cat cga cat tta gga agt ggc agc gat      1056
Ser Leu Cys Glu His Ala Phe His Arg His Leu Gly Ser Gly Ser Asp
                    340                 345                 350 tca cgc cag acc atc gaa cgc tat tcc agc ccc aag gtg cga cgt ctg      1104
Ser Arg Gln Thr Ile Glu Arg Tyr Ser Ser Pro Lys Val Arg Arg Leu
                    355                 360                 365 ttg cag aca ctg agg tgc ttc aag ccg gaa gag gtg cac acc caa gcg      1152
Leu Gln Thr Leu Arg Cys Phe Lys Pro Glu Glu Val His Thr Gln Ala
                    370                 375                 380 gac gga ctg cgc aga atg cgg cat cag gtg gat cag gcg gac ttc aat      1200
Asp Gly Leu Arg Arg Met Arg His Gln Val Asp Gln Ala Asp Phe Asn
385                 390                 395                 400 cgg tta tct cat acg ctg gaa agc aag tgc cga atg gtg gat caa atg      1248
Arg Leu Ser His Thr Leu Glu Ser Lys Cys Arg Met Val Asp Gln Met
                    405                 410                 415 gac caa ccg ccg acg gag aca cga gcc ctg gtg gcc act ctt gag cag      1296
Asp Gln Pro Pro Thr Glu Thr Arg Ala Leu Val Ala Thr Leu Glu Gln
                    420                 425                 430 att ctg cac acg aca gag gac agg cag acg aac aga agc gcc gct cgg      1344
Ile Leu His Thr Thr Glu Asp Arg Gln Thr Asn Arg Ser Ala Ala Arg
                    435                 440                 445 gtg act cct act cct act ccc gct cat gcg aag ccg aaa cct agc tct      1392
Val Thr Pro Thr Pro Thr Pro Ala His Ala Lys Pro Lys Pro Ser Ser
                    450                 455                 460 ggt gcc aac act gca caa cca cga act cgt aga cgt gtg tac acc agg      1440
Gly Ala Asn Thr Ala Gln Pro Arg Thr Arg Arg Arg Val Tyr Thr Arg
465                 470                 475                 480 cgc cac cac cgg gat cac aat gat ggc agc gac acg ctc tgc gca ctg      1488
Arg His His Arg Asp His Asn Asp Gly Ser Asp Thr Leu Cys Ala Leu
                    485                 490                 495 att tac tgc aac cag aac cac acg gct cgc gtg ctc ttt gag ctt cta      1536
Ile Tyr Cys Asn Gln Asn His Thr Ala Arg Val Leu Phe Glu Leu Leu
                    500                 505                 510 gcg gag att agc aga cgt gat ccc gat ctc aag ttc cta cgc tgc cag      1584
Ala Glu Ile Ser Arg Arg Asp Pro Asp Leu Lys Phe Leu Arg Cys Gln
                    515                 520                 525 tac acc acg gac cgg gtg gca gat ccc acc acg gag ccc aaa gag gct      1632
Tyr Thr Thr Asp Arg Val Ala Asp Pro Thr Thr Glu Pro Lys Glu Ala
                    530                 535                 540 gag ttg gag cac cgg cgg cag gaa gag gtg cta aag cgc ttc cgc atg      1680
Glu Leu Glu His Arg Arg Gln Glu Glu Val Leu Lys Arg Phe Arg Met
```

```
          545            550            555            560
cat gac tgc aat gtc ctg atc ggt act tcg gtg ctg gaa gag ggc atc        1728
His Asp Cys Asn Val Leu Ile Gly Thr Ser Val Leu Glu Glu Gly Ile
                565                570                575 gat gtg ccc aag tgc aat ttg gtt gtg cgc tgg gat ccg cca acc aca        1776
Asp Val Pro Lys Cys Asn Leu Val Val Arg Trp Asp Pro Pro Thr Thr
                580                585                590 tat cgc agt tac gtt cag tgc aaa ggt cga gcc cgt gct gct cca gcc        1824
Tyr Arg Ser Tyr Val Gln Cys Lys Gly Arg Ala Arg Ala Ala Pro Ala
                595                600                605 tat cat gtc att ctc gtc gct ccg agt tat aaa agc cca act gtg ggg        1872
Tyr His Val Ile Leu Val Ala Pro Ser Tyr Lys Ser Pro Thr Val Gly
                610                615                620 tca gtg cag ctg acc gat cgg agt cat cgg tat att tgc gcg act ggt        1920
Ser Val Gln Leu Thr Asp Arg Ser His Arg Tyr Ile Cys Ala Thr Gly
625                630                635                640 gat act aca gag gcg gac agc gac tct gat gat tca gcg atg cca aac        1968
Asp Thr Thr Glu Ala Asp Ser Asp Ser Asp Asp Ser Ala Met Pro Asn
                        645                650                655 tcg tcc ggc tcg gat ccc tat act ttt ggc acg gca cgc gga acc gtg        2016
Ser Ser Gly Ser Asp Pro Tyr Thr Phe Gly Thr Ala Arg Gly Thr Val
                660                665                670 aag atc ctc aac ccc gaa gtg ttc agt aaa caa cca ccg aca gcg tgc        2064
Lys Ile Leu Asn Pro Glu Val Phe Ser Lys Gln Pro Pro Thr Ala Cys
                675                680                685 gac att aag ctg cag gag atc cag gac gaa ttg cca gcc gca gcg cag        2112
Asp Ile Lys Leu Gln Glu Ile Gln Asp Glu Leu Pro Ala Ala Ala Gln
                690                695                700 ctg gat acg agc aac tcc agc gac gaa gcc gtc agc atg agt aac acg        2160
Leu Asp Thr Ser Asn Ser Ser Asp Glu Ala Val Ser Met Ser Asn Thr
705                710                715                720 tct cca agc gag agc agt aca gaa caa aaa tcc aga cgc ttc cag tgc        2208
Ser Pro Ser Glu Ser Ser Thr Glu Gln Lys Ser Arg Arg Phe Gln Cys
                        725                730                735 gag ctg agc tct tta acg gag cca gaa gac aca agt gat act aca gcc        2256
Glu Leu Ser Ser Leu Thr Glu Pro Glu Asp Thr Ser Asp Thr Thr Ala
                740                745                750 gaa atc gat act gct cat agt tta gcc agc acc acg aag gac ttg gtg        2304
Glu Ile Asp Thr Ala His Ser Leu Ala Ser Thr Thr Lys Asp Leu Val
                755                760                765 cat caa atg gca cag tat cgc gaa atc gag cag atg ctg cta tcc aag        2352
His Gln Met Ala Gln Tyr Arg Glu Ile Glu Gln Met Leu Leu Ser Lys
                770                775                780 tgc gcc aac aca gag ccg ccg gag cag gag cag agt gag gcg gaa cgt        2400
Cys Ala Asn Thr Glu Pro Pro Glu Gln Glu Gln Ser Glu Ala Glu Arg
785                790                795                800 ttt agt gcc tgc ctg gcc gca tac cga ccc aag ccg cac ctg cta aca        2448
Phe Ser Ala Cys Leu Ala Ala Tyr Arg Pro Lys Pro His Leu Leu Thr
                        805                810                815 ggc gcc tcc gtg gat ctg ggt tct gct ata gct ttg gtc aac aag tac        2496
Gly Ala Ser Val Asp Leu Gly Ser Ala Ile Ala Leu Val Asn Lys Tyr
                820                825                830 tgc gcc cga ctg cca agc gac acg ttc acc aag ttg acg gcg ttg tgg        2544
Cys Ala Arg Leu Pro Ser Asp Thr Phe Thr Lys Leu Thr Ala Leu Trp
                835                840                845 cgc tgc acc cga aac gaa agg gct gga gtg acc ctg ttt cag tac aca        2592
Arg Cys Thr Arg Asn Glu Arg Ala Gly Val Thr Leu Phe Gln Tyr Thr
850                855                860 ctc cgt ctg ccc atc aac tcg cca ttg aag cat gac att gtg ggt ctt        2640
Leu Arg Leu Pro Ile Asn Ser Pro Leu Lys His Asp Ile Val Gly Leu
```

```
                  865                 870                 875                 880 ccg atg cca act caa aca ttg gcc cgc cga ctg gct gcc ttg cag gct       2688
Pro Met Pro Thr Gln Thr Leu Ala Arg Arg Leu Ala Ala Leu Gln Ala
                885                 890                 895 tgc gtg gaa ctg cac agg atc ggt gag tta gac gat cag ttg cag cct       2736
Cys Val Glu Leu His Arg Ile Gly Glu Leu Asp Asp Gln Leu Gln Pro
                900                 905                 910 atc ggc aag gag gga ttt cgt gcc ctg gag ccg gac tgg gag tgc ttt       2784
Ile Gly Lys Glu Gly Phe Arg Ala Leu Glu Pro Asp Trp Glu Cys Phe
            915                 920                 925 gaa ctg gag cca gag gac gaa cag att gtg cag cta agc gat gaa cca       2832
Glu Leu Glu Pro Glu Asp Glu Gln Ile Val Gln Leu Ser Asp Glu Pro
        930                 935                 940 cgt ccg gga aca acg aag cgt cgt cag tac tat tac aaa cgc att gca       2880
Arg Pro Gly Thr Thr Lys Arg Arg Gln Tyr Tyr Tyr Lys Arg Ile Ala
945                 950                 955                 960 tcc gaa ttt tgc gat tgc cgt ccc gtt gcc gga gcg cca tgc tat ttg       2928
Ser Glu Phe Cys Asp Cys Arg Pro Val Ala Gly Ala Pro Cys Tyr Leu
                965                 970                 975 tac ttt atc caa ctg acg ctc caa tgt ccg att ccc gaa gag caa aac       2976
Tyr Phe Ile Gln Leu Thr Leu Gln Cys Pro Ile Pro Glu Glu Gln Asn
            980                 985                 990 acg cgg gga cgc aag att tat ccg ccc gaa gat gcg cag cag gga ttc       3024
Thr Arg Gly Arg Lys Ile Tyr Pro Pro Glu Asp Ala Gln Gln Gly Phe
        995                 1000                1005 ggc att cta acc acc aaa cgg ata ccc aag ctg agt gct ttc tcg ata       3072
Gly Ile Leu Thr Thr Lys Arg Ile Pro Lys Leu Ser Ala Phe Ser Ile
    1010                1015                1020 ttc acg cgt tcc ggt gag gtg aag gtt tcc ctg gag tta gct aag gaa       3120
Phe Thr Arg Ser Gly Glu Val Lys Val Ser Leu Glu Leu Ala Lys Glu
1025                1030                1035                1040 cgc gtg att cta act agc gaa caa ata gtc tgc atc aac gga ttt tta       3168
Arg Val Ile Leu Thr Ser Glu Gln Ile Val Cys Ile Asn Gly Phe Leu
                1045                1050                1055 aac tac acg ttc acc aat gta ctg cgt ttg caa aag ttt ctg atg ctc       3216
Asn Tyr Thr Phe Thr Asn Val Leu Arg Leu Gln Lys Phe Leu Met Leu
            1060                1065                1070 ttc gat ccg gac tcc acg gaa aat tgt gta ttc att gtg ccc acc gtg       3264
Phe Asp Pro Asp Ser Thr Glu Asn Cys Val Phe Ile Val Pro Thr Val
        1075                1080                1085 aag gca cca gct ggc ggc aag cac atc gac tgg cag ttt ctg gag ctg       3312
Lys Ala Pro Ala Gly Gly Lys His Ile Asp Trp Gln Phe Leu Glu Leu
    1090                1095                1100 atc caa gcg aat gga aat aca atg cca cgg gca gtg ccc gat gag gag       3360
Ile Gln Ala Asn Gly Asn Thr Met Pro Arg Ala Val Pro Asp Glu Glu
1105                1110                1115                1120 cgc cag gcg cag ccg ttt gat ccg caa cgc ttc cag gat gcc gtc gtt       3408
Arg Gln Ala Gln Pro Phe Asp Pro Gln Arg Phe Gln Asp Ala Val Val
                1125                1130                1135 atg ccg tgg tat cgc aac cag gat caa ccg cag tat ttc tat gtg gcg       3456
Met Pro Trp Tyr Arg Asn Gln Asp Gln Pro Gln Tyr Phe Tyr Val Ala
            1140                1145                1150 gag ata tgt cca cat cta tcc cca ctc agc tgc ttc cct ggt gac aac       3504
Glu Ile Cys Pro His Leu Ser Pro Leu Ser Cys Phe Pro Gly Asp Asn
        1155                1160                1165 tac cgc acg ttc aag cac tac tac ctc gtc aag tat ggt ctg acc ata       3552
Tyr Arg Thr Phe Lys His Tyr Tyr Leu Val Lys Tyr Gly Leu Thr Ile
    1170                1175                1180 cag aat acc tcg cag ccg cta ttg gac gtg gat cac acc agt gcg cgg       3600
Gln Asn Thr Ser Gln Pro Leu Leu Asp Val Asp His Thr Ser Ala Arg
```

```
                    1185              1190              1195              1200
tta aac ttc ctc acg cca cga tac gtt aat cgc aag ggc gtt gct ctg       3648
Leu Asn Phe Leu Thr Pro Arg Tyr Val Asn Arg Lys Gly Val Ala Leu
                    1205              1210              1215 ccc act agt tcg gag gag aca aag cgg gca aag cgc gag aat ctc gaa       3696
Pro Thr Ser Ser Glu Glu Thr Lys Arg Ala Lys Arg Glu Asn Leu Glu
                    1220              1225              1230 cag aag cag atc ctt gtg cca gag ctc tgc act gtg cat cca ttc ccc       3744
Gln Lys Gln Ile Leu Val Pro Glu Leu Cys Thr Val His Pro Phe Pro
                    1235              1240              1245 gcc tcc ttg tgg cga act gcc gtg tgc ctg ccc tgc atc ctg tac cgc       3792
Ala Ser Leu Trp Arg Thr Ala Val Cys Leu Pro Cys Ile Leu Tyr Arg
                    1250              1255              1260 ata aat ggt ctt cta ttg gcc gac gat att cgg aaa cag gtt tct gcg       3840
Ile Asn Gly Leu Leu Leu Ala Asp Asp Ile Arg Lys Gln Val Ser Ala
1265                1270              1275              1280 gat ctg ggg ctg gga agg caa cag atc gaa gat gag gat ttc gag tgg       3888
Asp Leu Gly Leu Gly Arg Gln Gln Ile Glu Asp Glu Asp Phe Glu Trp
                    1285              1290              1295 ccc atg ctg gac ttt ggg tgg agt cta tcg gag gtg ctc aag aaa tcg       3936
Pro Met Leu Asp Phe Gly Trp Ser Leu Ser Glu Val Leu Lys Lys Ser
                    1300              1305              1310 cgg gag tcc aaa caa aag gag tcc ctt aag gat gat act att aat ggc       3984
Arg Glu Ser Lys Gln Lys Glu Ser Leu Lys Asp Asp Thr Ile Asn Gly
                    1315              1320              1325 aaa gac tta gct gat gtt gaa aag aaa ccg act agc gag gag acc caa       4032
Lys Asp Leu Ala Asp Val Glu Lys Lys Pro Thr Ser Glu Glu Thr Gln
                    1330              1335              1340 cta gat aag gat tca aaa gac gat aag gtt gag aaa agt gct att gaa       4080
Leu Asp Lys Asp Ser Lys Asp Asp Lys Val Glu Lys Ser Ala Ile Glu
1345                1350              1355              1360 cta atc att gag gga gag gag aag ctg caa gag gct gat gac ttc att       4128
Leu Ile Ile Glu Gly Glu Glu Lys Leu Gln Glu Ala Asp Asp Phe Ile
                    1365              1370              1375 gag ata ggc act tgg tca aac gat atg gcc gac gat ata gct agt ttt       4176
Glu Ile Gly Thr Trp Ser Asn Asp Met Ala Asp Asp Ile Ala Ser Phe
                    1380              1385              1390 aac caa gaa gac gac gac gag gat gac gcc ttc cat ctc cca gtt tta       4224
Asn Gln Glu Asp Asp Asp Glu Asp Asp Ala Phe His Leu Pro Val Leu
                    1395              1400              1405 ccg gca aac gtt aag ttc tgt gat cag caa acg cgc tac ggt tcg ccc       4272
Pro Ala Asn Val Lys Phe Cys Asp Gln Gln Thr Arg Tyr Gly Ser Pro
                    1410              1415              1420 aca ttt tgg gat gtg agc aat ggc gaa agc ggc ttc aag ggt cca aag       4320
Thr Phe Trp Asp Val Ser Asn Gly Glu Ser Gly Phe Lys Gly Pro Lys
1425                1430              1435              1440 agc agt cag aat aag cag ggt ggc aag ggc aaa gca aag ggt ccg gca       4368
Ser Ser Gln Asn Lys Gln Gly Gly Lys Gly Lys Ala Lys Gly Pro Ala
                    1445              1450              1455 aag ccc aca ttt aac tat tat gac tcg gac aat tcg ctg ggt tcc agc       4416
Lys Pro Thr Phe Asn Tyr Tyr Asp Ser Asp Asn Ser Leu Gly Ser Ser
                    1460              1465              1470 tac gat gac gac gat aac gca ggt ccg ctc aat tac atg cat cac aac       4464
Tyr Asp Asp Asp Asp Asn Ala Gly Pro Leu Asn Tyr Met His His Asn
                    1475              1480              1485 tac agt tcg gat gac gac gat gtg gca gat gat atc gat gcg gga cgc       4512
Tyr Ser Ser Asp Asp Asp Asp Val Ala Asp Asp Ile Asp Ala Gly Arg
                    1490              1495              1500 att gcg ttc acc tcc aag aat gaa gcg gag act att gaa acc gca cag       4560
Ile Ala Phe Thr Ser Lys Asn Glu Ala Glu Thr Ile Glu Thr Ala Gln
```

| | |
|---|---|
| gaa gtg gaa aag cgc cag aag cag ctg tcc atc atc cag gcg acc aat<br>Glu Val Glu Lys Arg Gln Lys Gln Leu Ser Ile Ile Gln Ala Thr Asn<br>                  1525                      1530                  1535 | 4608 |
| gct aac gag cgg cag tat cag cag aca aag aac ctg ctc att gga ttc<br>Ala Asn Glu Arg Gln Tyr Gln Gln Thr Lys Asn Leu Leu Ile Gly Phe<br>    1540                    1545                  1550 | 4656 |
| aat ttt aag cat gag gac cag aag gaa cct gcc act ata aga tat gaa<br>Asn Phe Lys His Glu Asp Gln Lys Glu Pro Ala Thr Ile Arg Tyr Glu<br>        1555                  1560              1565 | 4704 |
| gaa tcc ata gct aag ctc aaa acg gaa ata gaa tcc ggc ggc atg ttg<br>Glu Ser Ile Ala Lys Leu Lys Thr Glu Ile Glu Ser Gly Gly Met Leu<br>1570                1575                  1580 | 4752 |
| gtg ccg cac gac cag cag ttg gtt cta aaa aga agt gat gcc gct gag<br>Val Pro His Asp Gln Gln Leu Val Leu Lys Arg Ser Asp Ala Ala Glu<br>1585                1590                1595              1600 | 4800 |
| gct cag gtt gca aag gta tcg atg atg gag cta ttg aag cag ctg ctg<br>Ala Gln Val Ala Lys Val Ser Met Met Glu Leu Leu Lys Gln Leu Leu<br>                  1605                  1610              1615 | 4848 |
| ccg tat gta aat gaa gat gtg ctg gcc aaa aag ctg ggt gat agg cgc<br>Pro Tyr Val Asn Glu Asp Val Leu Ala Lys Lys Leu Gly Asp Arg Arg<br>    1620                    1625                  1630 | 4896 |
| gag ctt ctg ctg tcg gat ttg gta gag cta aat gca gat tgg gta gcg<br>Glu Leu Leu Leu Ser Asp Leu Val Glu Leu Asn Ala Asp Trp Val Ala<br>        1635                  1640              1645 | 4944 |
| cga cat gag cag gag acc tac aat gta atg gga tgc gga gat agt ttt<br>Arg His Glu Gln Glu Thr Tyr Asn Val Met Gly Cys Gly Asp Ser Phe<br>            1650                  1655              1660 | 4992 |
| gac aac tat aac gat cat cat cgg ctg aac ttg gat gaa aag caa ctg<br>Asp Asn Tyr Asn Asp His His Arg Leu Asn Leu Asp Glu Lys Gln Leu<br>1665                1670                1675              1680 | 5040 |
| aaa ctg caa tac gaa cga att gaa att gag cca cct act tcc acg aag<br>Lys Leu Gln Tyr Glu Arg Ile Glu Ile Glu Pro Pro Thr Ser Thr Lys<br>                1685                  1690              1695 | 5088 |
| gcc ata acc tca gcc ata tta cca gct ggc ttc agt ttc gat cga caa<br>Ala Ile Thr Ser Ala Ile Leu Pro Ala Gly Phe Ser Phe Asp Arg Gln<br>            1700                  1705              1710 | 5136 |
| ccg gat cta gtg ggc cat cca gga ccc agt ccc agc atc att ttg caa<br>Pro Asp Leu Val Gly His Pro Gly Pro Ser Pro Ser Ile Ile Leu Gln<br>        1715                  1720              1725 | 5184 |
| gcc ctc aca atg tcc aat gct aac gat ggc atc aat ctg gag cga ctg<br>Ala Leu Thr Met Ser Asn Ala Asn Asp Gly Ile Asn Leu Glu Arg Leu<br>    1730                    1735                  1740 | 5232 |
| gag aca att gga gat tcc ttt cta aag tat gcc att acc acc tac ttg<br>Glu Thr Ile Gly Asp Ser Phe Leu Lys Tyr Ala Ile Thr Thr Tyr Leu<br>1745                1750                  1755              1760 | 5280 |
| tac atc acc tac gag aat gtg cac gag gga aaa cta agt cac ctg cgc<br>Tyr Ile Thr Tyr Glu Asn Val His Glu Gly Lys Leu Ser His Leu Arg<br>                1765                  1770              1775 | 5328 |
| tcc aag cag gtt gcc aat ctc aat ctc tat cgt ctg ggc aga cgt aag<br>Ser Lys Gln Val Ala Asn Leu Asn Leu Tyr Arg Leu Gly Arg Arg Lys<br>            1780                  1785              1790 | 5376 |
| aga ctg ggt gaa tat atg ata gcc act aaa ttc gag ccg cac gac aat<br>Arg Leu Gly Glu Tyr Met Ile Ala Thr Lys Phe Glu Pro His Asp Asn<br>                1795                  1800              1805 | 5424 |
| tgg ctg cca ccc tgc tac tac gtg cca aag gag cta gag aag gcg ctc<br>Trp Leu Pro Pro Cys Tyr Tyr Val Pro Lys Glu Leu Glu Lys Ala Leu<br>    1810                    1815                  1820 | 5472 |
| atc gag gcg aag atc ccc act cac cat tgg aag ctg gcc gat ctg cta<br>Ile Glu Ala Lys Ile Pro Thr His His Trp Lys Leu Ala Asp Leu Leu | 5520 |

-continued

```
         1825           1830           1835           1840 gac att aag aac cta agc agt gtg caa atc tgc gag atg gtt cgc gaa    5568
Asp Ile Lys Asn Leu Ser Ser Val Gln Ile Cys Glu Met Val Arg Glu
             1845           1850           1855 aaa gcc gat gcc ctg ggc ttg gag cag aat ggg ggt gcc caa aat gga    5616
Lys Ala Asp Ala Leu Gly Leu Glu Gln Asn Gly Gly Ala Gln Asn Gly
         1860           1865           1870 caa ctt gac gac tcc aat gat agc tgc aat gat ttt agc tgt ttt att    5664
Gln Leu Asp Asp Ser Asn Asp Ser Cys Asn Asp Phe Ser Cys Phe Ile
             1875           1880           1885 ccc tac aac ctt gtt tcg caa cac agc att ccg gat aag tct att gcc    5712
Pro Tyr Asn Leu Val Ser Gln His Ser Ile Pro Asp Lys Ser Ile Ala
         1890           1895           1900 gat tgc gtc gaa gcc ctc att gga gcc tat ctc att gag tgc gga ccc    5760
Asp Cys Val Glu Ala Leu Ile Gly Ala Tyr Leu Ile Glu Cys Gly Pro
1905           1910           1915           1920 cga ggg gct tta ctc ttt atg gcc tgg ctg ggc gtg aga gtc ctc cct    5808
Arg Gly Ala Leu Leu Phe Met Ala Trp Leu Gly Val Arg Val Leu Pro
             1925           1930           1935 atc aca agg cag ttg gac ggg ggt aac cag gag caa cga ata ccc ggt    5856
Ile Thr Arg Gln Leu Asp Gly Gly Asn Gln Glu Gln Arg Ile Pro Gly
         1940           1945           1950 agc aca aaa ccg aat gcc gaa aat gtg gtc acc gtt tac ggt gca tgg    5904
Ser Thr Lys Pro Asn Ala Glu Asn Val Val Thr Val Tyr Gly Ala Trp
             1955           1960           1965 ccc acg ccg cgt agt cca ctg ctg cac ttt gct cca aat gct acg gag    5952
Pro Thr Pro Arg Ser Pro Leu Leu His Phe Ala Pro Asn Ala Thr Glu
         1970           1975           1980 gag ctg gac cag tta cta agc ggc ttt gag gag ttt gag gag agt ttg    6000
Glu Leu Asp Gln Leu Leu Ser Gly Phe Glu Glu Phe Glu Glu Ser Leu
1985           1990           1995           2000 gga tac aag ttc cgg gat cgg tcg tac ctg ttg caa gcc atg aca cat    6048
Gly Tyr Lys Phe Arg Asp Arg Ser Tyr Leu Leu Gln Ala Met Thr His
             2005           2010           2015 gcc agt tac acg ccc aat cga ttg acg gat tgc tat cag cgt ctg gag    6096
Ala Ser Tyr Thr Pro Asn Arg Leu Thr Asp Cys Tyr Gln Arg Leu Glu
         2020           2025           2030 ttc ctg ggc gat gct gtt cta gat tac ctc att acg cgg cat tta tac    6144
Phe Leu Gly Asp Ala Val Leu Asp Tyr Leu Ile Thr Arg His Leu Tyr
             2035           2040           2045 gaa gat ccc cgc cag cat tct cca ggc gca tta acg gat ttg cgg tca    6192
Glu Asp Pro Arg Gln His Ser Pro Gly Ala Leu Thr Asp Leu Arg Ser
         2050           2055           2060 gca ctg gtg aat aat aca ata ttc gcc tcc ctg gct gtt cgc cat ggc    6240
Ala Leu Val Asn Asn Thr Ile Phe Ala Ser Leu Ala Val Arg His Gly
2065           2070           2075           2080 ttc cac aag ttc ttc cgg cac ctc tcg ccg ggc ctt aac gat gtg att    6288
Phe His Lys Phe Phe Arg His Leu Ser Pro Gly Leu Asn Asp Val Ile
             2085           2090           2095 gac cgt ttt gtg cgg atc cag cag gag aat gga cac tgc atc agt gag    6336
Asp Arg Phe Val Arg Ile Gln Gln Glu Asn Gly His Cys Ile Ser Glu
         2100           2105           2110 gag tac tac tta ttg tcc gag gag gag tgc gat gac gcc gag gac gtt    6384
Glu Tyr Tyr Leu Leu Ser Glu Glu Glu Cys Asp Asp Ala Glu Asp Val
             2115           2120           2125 gag gtg ccc aag gca ttg ggc gac gtt ttc gag tcg atc gca ggt gcc    6432
Glu Val Pro Lys Ala Leu Gly Asp Val Phe Glu Ser Ile Ala Gly Ala
         2130           2135           2140 att ttt ctc gac tca aac atg tcg ctg gac gtg gtt tgg cac gta tat    6480
Ile Phe Leu Asp Ser Asn Met Ser Leu Asp Val Val Trp His Val Tyr
```

```
                2145                2150                2155                2160
agc aac atg atg agc ccg gag atc gag cag ttc agc aac tca gtg cca       6528
Ser Asn Met Met Ser Pro Glu Ile Glu Gln Phe Ser Asn Ser Val Pro
                2165                2170                2175
aaa tcg ccc att cgg gag ctc ctc gag ctg gag ccg gaa acc gcc aag       6576
Lys Ser Pro Ile Arg Glu Leu Leu Glu Leu Glu Pro Glu Thr Ala Lys
                2180                2185                2190
ttc ggc aag ccc gag aag ctg gcg gat ggg cga cgg gtg cgc gtt acc       6624
Phe Gly Lys Pro Glu Lys Leu Ala Asp Gly Arg Arg Val Arg Val Thr
                2195                2200                2205
gtg gat gtc ttc tgc aaa gga acc ttc cgt ggc atc gga cgc aac tat       6672
Val Asp Val Phe Cys Lys Gly Thr Phe Arg Gly Ile Gly Arg Asn Tyr
                2210                2215                2220
cgc att gcc aag tgc acg gcg gcc aaa tgc gca ttg cgc caa ctc aaa       6720
Arg Ile Ala Lys Cys Thr Ala Ala Lys Cys Ala Leu Arg Gln Leu Lys
2225                2230                2235                2240
aag cag ggc ttg ata gcc aaa aaa gac taa                                6750
Lys Gln Gly Leu Ile Ala Lys Lys Asp *
                2245

<210> SEQ ID NO 4
<211> LENGTH: 2249
<212> TYPE: PRT
<213> ORGANISM: Drosophila melanogaster

<400> SEQUENCE: 4

Met Ala Phe His Trp Cys Asp Asn Asn Leu His Thr Thr Val Phe Thr
1               5                   10                  15

Pro Arg Asp Phe Gln Val Glu Leu Leu Ala Thr Ala Tyr Glu Arg Asn
                20                  25                  30

Thr Ile Ile Cys Leu Gly His Arg Ser Lys Glu Phe Ile Ala Leu
            35                  40                  45

Lys Leu Leu Gln Glu Leu Ser Arg Arg Ala Arg Arg His Gly Arg Val
50                  55                  60

Ser Val Tyr Leu Ser Cys Glu Val Gly Thr Ser Thr Glu Pro Cys Ser
65                  70                  75                  80

Ile Tyr Thr Met Leu Thr His Leu Thr Asp Leu Arg Val Trp Gln Glu
                85                  90                  95

Gln Pro Asp Met Gln Ile Pro Phe Asp His Cys Trp Thr Asp Tyr His
                100                 105                 110

Val Ser Ile Leu Arg Pro Glu Gly Phe Leu Tyr Leu Glu Thr Arg
            115                 120                 125

Glu Leu Leu Ser Ser Val Glu Leu Ile Val Leu Glu Asp Cys His
        130                 135                 140

Asp Ser Ala Val Tyr Gln Arg Ile Arg Pro Leu Phe Glu Asn His Ile
145                 150                 155                 160

Met Pro Ala Pro Pro Ala Asp Arg Pro Arg Ile Leu Gly Leu Ala Gly
                165                 170                 175

Pro Leu His Ser Ala Gly Cys Glu Leu Gln Gln Leu Ser Ala Met Leu
            180                 185                 190

Ala Thr Leu Glu Gln Ser Val Leu Cys Gln Ile Glu Thr Ala Ser Asp
        195                 200                 205

Ile Val Thr Val Leu Arg Tyr Cys Ser Arg Pro His Glu Tyr Ile Val
    210                 215                 220

Gln Cys Ala Pro Phe Glu Met Asp Glu Leu Ser Leu Val Leu Ala Asp
225                 230                 235                 240

Val Leu Asn Thr His Lys Ser Phe Leu Leu Asp His Arg Tyr Asp Pro
```

```
            245                 250                 255
Tyr Glu Ile Tyr Gly Thr Asp Gln Phe Met Asp Glu Leu Lys Asp Ile
            260                 265                 270

Pro Asp Pro Lys Val Asp Pro Leu Asn Val Ile Asn Ser Leu Leu Val
            275                 280                 285

Val Leu His Glu Met Gly Pro Trp Cys Thr Gln Arg Ala Ala His His
            290                 295                 300

Phe Tyr Gln Cys Asn Glu Lys Leu Lys Val Lys Thr Pro His Glu Arg
305                 310                 315                 320

His Tyr Leu Leu Tyr Cys Leu Val Ser Thr Ala Leu Ile Gln Leu Tyr
                    325                 330                 335

Ser Leu Cys Glu His Ala Phe His Arg His Leu Gly Ser Gly Ser Asp
                340                 345                 350

Ser Arg Gln Thr Ile Glu Arg Tyr Ser Ser Pro Lys Val Arg Arg Leu
            355                 360                 365

Leu Gln Thr Leu Arg Cys Phe Lys Pro Glu Glu Val His Thr Gln Ala
        370                 375                 380

Asp Gly Leu Arg Arg Met Arg His Gln Val Asp Gln Ala Asp Phe Asn
385                 390                 395                 400

Arg Leu Ser His Thr Leu Glu Ser Lys Cys Arg Met Val Asp Gln Met
                    405                 410                 415

Asp Gln Pro Pro Thr Glu Thr Arg Ala Leu Val Ala Thr Leu Glu Gln
                420                 425                 430

Ile Leu His Thr Thr Glu Asp Arg Gln Thr Asn Arg Ser Ala Ala Arg
            435                 440                 445

Val Thr Pro Thr Pro Thr Pro Ala His Ala Lys Pro Lys Pro Ser Ser
        450                 455                 460

Gly Ala Asn Thr Ala Gln Pro Arg Thr Arg Arg Val Tyr Thr Arg
465                 470                 475                 480

Arg His His Arg Asp His Asn Asp Gly Ser Asp Thr Leu Cys Ala Leu
                    485                 490                 495

Ile Tyr Cys Asn Gln Asn His Thr Ala Arg Val Leu Phe Glu Leu Leu
                500                 505                 510

Ala Glu Ile Ser Arg Arg Asp Pro Asp Leu Lys Phe Leu Arg Cys Gln
            515                 520                 525

Tyr Thr Thr Asp Arg Val Ala Asp Pro Thr Thr Glu Pro Lys Glu Ala
        530                 535                 540

Glu Leu Glu His Arg Arg Gln Glu Glu Val Leu Lys Arg Phe Arg Met
545                 550                 555                 560

His Asp Cys Asn Val Leu Ile Gly Thr Ser Val Leu Glu Glu Gly Ile
                    565                 570                 575

Asp Val Pro Lys Cys Asn Leu Val Val Arg Trp Asp Pro Pro Thr Thr
                580                 585                 590

Tyr Arg Ser Tyr Val Gln Cys Lys Gly Arg Ala Arg Ala Ala Pro Ala
            595                 600                 605

Tyr His Val Ile Leu Val Ala Pro Ser Tyr Lys Ser Pro Thr Val Gly
        610                 615                 620

Ser Val Gln Leu Thr Asp Arg Ser His Arg Tyr Ile Cys Ala Thr Gly
625                 630                 635                 640

Asp Thr Thr Glu Ala Asp Ser Asp Ser Asp Ser Ala Met Pro Asn
                    645                 650                 655

Ser Ser Gly Ser Asp Pro Tyr Thr Phe Gly Thr Ala Arg Gly Thr Val
                660                 665                 670
```

```
Lys Ile Leu Asn Pro Glu Val Phe Ser Lys Gln Pro Pro Thr Ala Cys
        675                 680                 685

Asp Ile Lys Leu Gln Glu Ile Gln Asp Glu Leu Pro Ala Ala Ala Gln
    690                 695                 700

Leu Asp Thr Ser Asn Ser Ser Asp Glu Ala Val Ser Met Ser Asn Thr
705                 710                 715                 720

Ser Pro Ser Glu Ser Ser Thr Glu Gln Lys Ser Arg Arg Phe Gln Cys
                725                 730                 735

Glu Leu Ser Ser Leu Thr Glu Pro Glu Asp Thr Ser Asp Thr Thr Ala
            740                 745                 750

Glu Ile Asp Thr Ala His Ser Leu Ala Ser Thr Thr Lys Asp Leu Val
        755                 760                 765

His Gln Met Ala Gln Tyr Arg Glu Ile Glu Gln Met Leu Leu Ser Lys
    770                 775                 780

Cys Ala Asn Thr Glu Pro Pro Glu Gln Glu Gln Ser Glu Ala Glu Arg
785                 790                 795                 800

Phe Ser Ala Cys Leu Ala Ala Tyr Arg Pro Lys Pro His Leu Leu Thr
                805                 810                 815

Gly Ala Ser Val Asp Leu Gly Ser Ala Ile Ala Leu Val Asn Lys Tyr
            820                 825                 830

Cys Ala Arg Leu Pro Ser Asp Thr Phe Thr Lys Leu Thr Ala Leu Trp
        835                 840                 845

Arg Cys Thr Arg Asn Glu Arg Ala Gly Val Thr Leu Phe Gln Tyr Thr
    850                 855                 860

Leu Arg Leu Pro Ile Asn Ser Pro Leu Lys His Asp Ile Val Gly Leu
865                 870                 875                 880

Pro Met Pro Thr Gln Thr Leu Ala Arg Arg Leu Ala Ala Leu Gln Ala
                885                 890                 895

Cys Val Glu Leu His Arg Ile Gly Glu Leu Asp Asp Gln Leu Gln Pro
            900                 905                 910

Ile Gly Lys Glu Gly Phe Arg Ala Leu Glu Pro Asp Trp Glu Cys Phe
        915                 920                 925

Glu Leu Glu Pro Glu Asp Glu Gln Ile Val Gln Leu Ser Asp Glu Pro
    930                 935                 940

Arg Pro Gly Thr Thr Lys Arg Arg Gln Tyr Tyr Tyr Lys Arg Ile Ala
945                 950                 955                 960

Ser Glu Phe Cys Asp Cys Arg Pro Val Ala Gly Ala Pro Cys Tyr Leu
                965                 970                 975

Tyr Phe Ile Gln Leu Thr Leu Gln Cys Pro Ile Pro Glu Glu Gln Asn
            980                 985                 990

Thr Arg Gly Arg Lys Ile Tyr Pro Pro Glu Asp Ala Gln Gln Gly Phe
        995                 1000                1005

Gly Ile Leu Thr Thr Lys Arg Ile Pro Lys Leu Ser Ala Phe Ser Ile
    1010                1015                1020

Phe Thr Arg Ser Gly Glu Val Lys Val Ser Leu Glu Leu Ala Lys Glu
1025                1030                1035                1040

Arg Val Ile Leu Thr Ser Glu Gln Ile Val Cys Ile Asn Gly Phe Leu
                1045                1050                1055

Asn Tyr Thr Phe Thr Asn Val Leu Arg Leu Gln Lys Phe Leu Met Leu
            1060                1065                1070

Phe Asp Pro Asp Ser Thr Glu Asn Cys Val Phe Ile Val Pro Thr Val
        1075                1080                1085

Lys Ala Pro Ala Gly Gly Lys His Ile Asp Trp Gln Phe Leu Glu Leu
    1090                1095                1100
```

Ile Gln Ala Asn Gly Asn Thr Met Pro Arg Ala Val Pro Asp Glu Glu
1105                1110                1115                1120

Arg Gln Ala Gln Pro Phe Asp Pro Gln Arg Phe Gln Asp Ala Val Val
                1125                1130                1135

Met Pro Trp Tyr Arg Asn Gln Asp Gln Pro Gln Tyr Phe Tyr Val Ala
                1140                1145                1150

Glu Ile Cys Pro His Leu Ser Pro Leu Ser Cys Phe Pro Gly Asp Asn
                1155                1160                1165

Tyr Arg Thr Phe Lys His Tyr Tyr Leu Val Lys Tyr Gly Leu Thr Ile
                1170                1175                1180

Gln Asn Thr Ser Gln Pro Leu Leu Asp Val Asp His Thr Ser Ala Arg
1185                1190                1195                1200

Leu Asn Phe Leu Thr Pro Arg Tyr Val Asn Arg Lys Gly Val Ala Leu
                1205                1210                1215

Pro Thr Ser Ser Glu Glu Thr Lys Arg Ala Lys Arg Glu Asn Leu Glu
                1220                1225                1230

Gln Lys Gln Ile Leu Val Pro Glu Leu Cys Thr Val His Pro Phe Pro
                1235                1240                1245

Ala Ser Leu Trp Arg Thr Ala Val Cys Leu Pro Cys Ile Leu Tyr Arg
                1250                1255                1260

Ile Asn Gly Leu Leu Leu Ala Asp Asp Ile Arg Lys Gln Val Ser Ala
1265                1270                1275                1280

Asp Leu Gly Leu Gly Arg Gln Gln Ile Glu Asp Glu Asp Phe Glu Trp
                1285                1290                1295

Pro Met Leu Asp Phe Gly Trp Ser Leu Ser Glu Val Leu Lys Lys Ser
                1300                1305                1310

Arg Glu Ser Lys Gln Lys Glu Ser Leu Lys Asp Thr Ile Asn Gly
                1315                1320                1325

Lys Asp Leu Ala Asp Val Glu Lys Lys Pro Thr Ser Glu Glu Thr Gln
                1330                1335                1340

Leu Asp Lys Asp Ser Lys Asp Asp Lys Val Glu Lys Ser Ala Ile Glu
1345                1350                1355                1360

Leu Ile Ile Glu Gly Glu Glu Lys Leu Gln Glu Ala Asp Asp Phe Ile
                1365                1370                1375

Glu Ile Gly Thr Trp Ser Asn Asp Met Ala Asp Asp Ile Ala Ser Phe
                1380                1385                1390

Asn Gln Glu Asp Asp Asp Glu Asp Asp Ala Phe His Leu Pro Val Leu
                1395                1400                1405

Pro Ala Asn Val Lys Phe Cys Asp Gln Gln Thr Arg Tyr Gly Ser Pro
                1410                1415                1420

Thr Phe Trp Asp Val Ser Asn Gly Glu Ser Gly Phe Lys Gly Pro Lys
1425                1430                1435                1440

Ser Ser Gln Asn Lys Gln Gly Gly Lys Gly Lys Ala Lys Gly Pro Ala
                1445                1450                1455

Lys Pro Thr Phe Asn Tyr Tyr Asp Ser Asp Asn Ser Leu Gly Ser Ser
                1460                1465                1470

Tyr Asp Asp Asp Asp Asn Ala Gly Pro Leu Asn Tyr Met His His Asn
                1475                1480                1485

Tyr Ser Ser Asp Asp Asp Val Ala Asp Asp Ile Asp Ala Gly Arg
                1490                1495                1500

Ile Ala Phe Thr Ser Lys Asn Glu Ala Glu Thr Ile Glu Thr Ala Gln
1505                1510                1515                1520

Glu Val Glu Lys Arg Gln Lys Gln Leu Ser Ile Ile Gln Ala Thr Asn

-continued

Ala Asn Glu Arg Gln Tyr Gln Gln Thr Lys Asn Leu Leu Ile Gly Phe
1525                1530                1535
                1540                1545                1550

Asn Phe Lys His Glu Asp Gln Lys Glu Pro Ala Thr Ile Arg Tyr Glu
        1555                1560                1565

Glu Ser Ile Ala Lys Leu Lys Thr Glu Ile Glu Ser Gly Gly Met Leu
    1570                1575                1580

Val Pro His Asp Gln Gln Leu Val Leu Lys Arg Ser Asp Ala Ala Glu
1585                1590                1595                1600

Ala Gln Val Ala Lys Val Ser Met Met Glu Leu Leu Lys Gln Leu Leu
            1605                1610                1615

Pro Tyr Val Asn Glu Asp Val Leu Ala Lys Lys Leu Gly Asp Arg Arg
        1620                1625                1630

Glu Leu Leu Leu Ser Asp Leu Val Glu Leu Asn Ala Asp Trp Val Ala
    1635                1640                1645

Arg His Glu Gln Glu Thr Tyr Asn Val Met Gly Cys Gly Asp Ser Phe
1650                1655                1660

Asp Asn Tyr Asn Asp His His Arg Leu Asn Leu Asp Glu Lys Gln Leu
1665                1670                1675                1680

Lys Leu Gln Tyr Glu Arg Ile Glu Ile Glu Pro Pro Thr Ser Thr Lys
            1685                1690                1695

Ala Ile Thr Ser Ala Ile Leu Pro Ala Gly Phe Ser Phe Asp Arg Gln
        1700                1705                1710

Pro Asp Leu Val Gly His Pro Gly Pro Ser Pro Ser Ile Ile Leu Gln
        1715                1720                1725

Ala Leu Thr Met Ser Asn Ala Asn Asp Gly Ile Asn Leu Glu Arg Leu
    1730                1735                1740

Glu Thr Ile Gly Asp Ser Phe Leu Lys Tyr Ala Ile Thr Thr Tyr Leu
1745                1750                1755                1760

Tyr Ile Thr Tyr Glu Asn Val His Glu Gly Lys Leu Ser His Leu Arg
            1765                1770                1775

Ser Lys Gln Val Ala Asn Leu Asn Leu Tyr Arg Leu Gly Arg Arg Lys
            1780                1785                1790

Arg Leu Gly Glu Tyr Met Ile Ala Thr Lys Phe Glu Pro His Asp Asn
    1795                1800                1805

Trp Leu Pro Pro Cys Tyr Tyr Val Pro Lys Glu Leu Glu Lys Ala Leu
        1810                1815                1820

Ile Glu Ala Lys Ile Pro Thr His His Trp Lys Leu Ala Asp Leu Leu
1825                1830                1835                1840

Asp Ile Lys Asn Leu Ser Ser Val Gln Ile Cys Glu Met Val Arg Glu
            1845                1850                1855

Lys Ala Asp Ala Leu Gly Leu Glu Gln Asn Gly Gly Ala Gln Asn Gly
        1860                1865                1870

Gln Leu Asp Asp Ser Asn Asp Ser Cys Asn Asp Phe Ser Cys Phe Ile
        1875                1880                1885

Pro Tyr Asn Leu Val Ser Gln His Ser Ile Pro Asp Lys Ser Ile Ala
    1890                1895                1900

Asp Cys Val Glu Ala Leu Ile Gly Ala Tyr Leu Ile Glu Cys Gly Pro
1905                1910                1915                1920

Arg Gly Ala Leu Leu Phe Met Ala Trp Leu Gly Val Arg Val Leu Pro
            1925                1930                1935

Ile Thr Arg Gln Leu Asp Gly Gly Asn Gln Glu Gln Arg Ile Pro Gly
        1940                1945                1950

-continued

```
Ser Thr Lys Pro Asn Ala Glu Asn Val Thr Val Tyr Gly Ala Trp
        1955                1960                1965

Pro Thr Pro Arg Ser Pro Leu Leu His Phe Ala Pro Asn Ala Thr Glu
    1970                1975                1980

Glu Leu Asp Gln Leu Leu Ser Gly Phe Glu Glu Phe Glu Glu Ser Leu
1985                1990                1995                2000

Gly Tyr Lys Phe Arg Asp Arg Ser Tyr Leu Leu Gln Ala Met Thr His
            2005                2010                2015

Ala Ser Tyr Thr Pro Asn Arg Leu Thr Asp Cys Tyr Gln Arg Leu Glu
                2020                2025                2030

Phe Leu Gly Asp Ala Val Leu Asp Tyr Leu Ile Thr Arg His Leu Tyr
            2035                2040                2045

Glu Asp Pro Arg Gln His Ser Pro Gly Ala Leu Thr Asp Leu Arg Ser
                2050                2055                2060

Ala Leu Val Asn Asn Thr Ile Phe Ala Ser Leu Ala Val Arg His Gly
2065                2070                2075                2080

Phe His Lys Phe Phe Arg His Leu Ser Pro Gly Leu Asn Asp Val Ile
            2085                2090                2095

Asp Arg Phe Val Arg Ile Gln Gln Glu Asn Gly His Cys Ile Ser Glu
                2100                2105                2110

Glu Tyr Tyr Leu Leu Ser Glu Glu Cys Asp Asp Ala Glu Asp Val
            2115                2120                2125

Glu Val Pro Lys Ala Leu Gly Asp Val Phe Glu Ser Ile Ala Gly Ala
                2130                2135                2140

Ile Phe Leu Asp Ser Asn Met Ser Leu Asp Val Val Trp His Val Tyr
2145                2150                2155                2160

Ser Asn Met Met Ser Pro Glu Ile Glu Gln Phe Ser Asn Ser Val Pro
            2165                2170                2175

Lys Ser Pro Ile Arg Glu Leu Leu Glu Leu Glu Pro Glu Thr Ala Lys
                2180                2185                2190

Phe Gly Lys Pro Glu Lys Leu Ala Asp Gly Arg Arg Val Arg Val Thr
            2195                2200                2205

Val Asp Val Phe Cys Lys Gly Thr Phe Arg Gly Ile Gly Arg Asn Tyr
                2210                2215                2220

Arg Ile Ala Lys Cys Thr Ala Ala Lys Cys Ala Leu Arg Gln Leu Lys
2225                2230                2235                2240

Lys Gln Gly Leu Ile Ala Lys Lys Asp
            2245

<210> SEQ ID NO 5
<211> LENGTH: 1145
<212> TYPE: PRT
<213> ORGANISM: Drosophila melanogaster

<400> SEQUENCE: 5

Met Gly Lys Lys Asp Lys Asn Lys Lys Gly Gly Gln Asp Ser Ala Ala
1               5                   10                  15

Ala Pro Gln Pro Gln Gln Gln Lys Gln Gln Gln Arg Gln Gln
            20                  25                  30

Gln Pro Gln Gln Leu Gln Gln Pro Gln Gln Leu Gln Gln Pro Gln Gln
        35                  40                  45

Leu Gln Gln Pro Gln Gln Gln Gln Gln Pro His Gln Gln Gln
    50                  55                  60

Gln Gln Ser Ser Arg Gln Gln Pro Ser Thr Ser Ser Gly Gly Ser Arg
65                  70                  75                  80
```

-continued

```
Ala Ser Gly Phe Gln Gln Gly Gln Gln Lys Ser Gln Asp Ala
            85                  90                  95

Glu Gly Trp Thr Ala Gln Lys Lys Gln Gly Lys Gln Gln Val Gln Gly
            100                 105                 110

Trp Thr Lys Gln Gly Gln Gln Gly His Gln Gln Gly Arg Gln Gly
            115                 120                 125

Gln Asp Gly Gly Tyr Gln Gln Arg Pro Pro Gly Gln Gln Gly Gly
    130                 135                 140

His Gln Gln Gly Arg Gln Gly Gln Glu Gly Gly Tyr Gln Gln Arg Pro
145                 150                 155                 160

Pro Gly Gln Gln Gln Gly Gly His Gln Gln Gly Arg Gln Gly Gln Glu
                165                 170                 175

Gly Gly Tyr Gln Gln Arg Pro Ser Gly Gln Gln Gly Gly His Gln
            180                 185                 190

Gln Gly Arg Gln Gly Gln Glu Gly Gly Tyr Gln Gln Arg Pro Pro Gly
        195                 200                 205

Gln Gln Gln Gly Gly His Gln Gln Gly Arg Gln Gly Gln Glu Gly Gly
        210                 215                 220

Tyr Gln Gln Arg Pro Ser Gly Gln Gln Gln Gly Gly His Gln Gln Gly
225                 230                 235                 240

Arg Gln Gly Gln Glu Gly Gly Tyr Gln Gln Arg Pro Ser Gly Gln Gln
                245                 250                 255

Gln Gly Gly His Gln Gln Gly Arg Gln Gly Gln Glu Gly Gly Tyr Gln
            260                 265                 270

Gln Arg Pro Ser Gly Gln Gln Gly Gly His Gln Gln Gly Arg Gln
            275                 280                 285

Gly Gln Glu Gly Gly Tyr Gln Gln Arg Pro Pro Gly Gln Gln Pro Asn
    290                 295                 300

Gln Thr Gln Ser Gln Gly Gln Tyr Gln Ser Arg Gly Pro Pro Gln Gln
305                 310                 315                 320

Gln Gln Ala Ala Pro Leu Pro Leu Pro Pro Gln Pro Ala Gly Ser Ile
                325                 330                 335

Lys Arg Gly Thr Ile Gly Lys Pro Gly Gln Val Gly Ile Asn Tyr Leu
            340                 345                 350

Asp Leu Asp Leu Ser Lys Met Pro Ser Val Ala Tyr His Tyr Asp Val
            355                 360                 365

Lys Ile Met Pro Glu Arg Pro Lys Lys Phe Tyr Arg Gln Ala Phe Glu
    370                 375                 380

Gln Phe Arg Val Asp Gln Leu Gly Gly Ala Val Leu Ala Tyr Asp Gly
385                 390                 395                 400

Lys Ala Ser Cys Tyr Ser Val Asp Lys Leu Pro Leu Asn Ser Gln Asn
                405                 410                 415

Pro Glu Val Thr Val Thr Asp Arg Asn Gly Arg Thr Leu Arg Tyr Thr
            420                 425                 430

Ile Glu Ile Lys Glu Thr Gly Asp Ser Thr Ile Asp Leu Lys Ser Leu
    435                 440                 445

Thr Thr Tyr Met Asn Asp Arg Ile Phe Asp Lys Pro Met Arg Ala Met
450                 455                 460

Gln Cys Val Glu Val Leu Ala Ser Pro Cys His Asn Lys Ala Ile
465                 470                 475                 480

Arg Val Gly Arg Ser Phe Phe Lys Met Ser Asp Pro Asn Asn Arg His
                485                 490                 495

Glu Leu Asp Asp Gly Tyr Glu Ala Leu Val Gly Leu Tyr Gln Ala Phe
            500                 505                 510
```

```
Met Leu Gly Asp Arg Pro Phe Leu Asn Val Asp Ile Ser His Lys Ser
            515                 520                 525
Phe Pro Ile Ser Met Pro Met Ile Glu Tyr Leu Glu Arg Phe Ser Leu
        530                 535                 540
Lys Ala Lys Ile Asn Asn Thr Thr Asn Leu Asp Tyr Ser Arg Arg Phe
545                 550                 555                 560
Leu Glu Pro Phe Leu Arg Gly Ile Asn Val Val Tyr Thr Pro Pro Gln
                565                 570                 575
Ser Phe Gln Ser Ala Pro Arg Val Tyr Arg Val Asn Gly Leu Ser Arg
            580                 585                 590
Ala Pro Ala Ser Ser Glu Thr Phe Glu His Asp Gly Lys Lys Val Thr
        595                 600                 605
Ile Ala Ser Tyr Phe His Ser Arg Asn Tyr Pro Leu Lys Phe Pro Gln
    610                 615                 620
Leu His Cys Leu Asn Val Gly Ser Ser Ile Lys Ser Ile Leu Leu Pro
625                 630                 635                 640
Ile Glu Leu Cys Ser Ile Glu Glu Gly Gln Ala Leu Asn Arg Lys Asp
                645                 650                 655
Gly Ala Thr Gln Val Ala Asn Met Ile Lys Tyr Ala Ala Thr Ser Thr
            660                 665                 670
Asn Val Arg Lys Arg Lys Ile Met Asn Leu Leu Gln Tyr Phe Gln His
        675                 680                 685
Asn Leu Asp Pro Thr Ile Ser Arg Phe Gly Ile Arg Ile Ala Asn Asp
    690                 695                 700
Phe Ile Val Val Ser Thr Arg Val Leu Ser Pro Pro Gln Val Glu Tyr
705                 710                 715                 720
His Ser Lys Arg Phe Thr Met Val Lys Asn Gly Ser Trp Arg Met Asp
                725                 730                 735
Gly Met Lys Phe Leu Glu Pro Lys Pro Lys Ala His Lys Cys Ala Val
            740                 745                 750
Leu Tyr Cys Asp Pro Arg Ser Gly Arg Lys Met Asn Tyr Thr Gln Leu
        755                 760                 765
Asn Asp Phe Gly Asn Leu Ile Ile Ser Gln Gly Lys Ala Val Asn Ile
    770                 775                 780
Ser Leu Asp Ser Asp Val Thr Tyr Arg Pro Phe Thr Asp Asp Glu Arg
785                 790                 795                 800
Ser Leu Asp Thr Ile Phe Ala Asp Leu Lys Arg Ser Gln His Asp Leu
                805                 810                 815
Ala Ile Val Ile Ile Pro Gln Phe Arg Ile Ser Tyr Asp Thr Ile Lys
            820                 825                 830
Gln Lys Ala Glu Leu Gln His Gly Ile Leu Thr Gln Cys Ile Lys Gln
        835                 840                 845
Phe Thr Val Glu Arg Lys Cys Asn Asn Gln Thr Ile Gly Asn Ile Leu
    850                 855                 860
Leu Lys Ile Asn Ser Lys Leu Asn Gly Ile Asn His Lys Ile Lys Asp
865                 870                 875                 880
Asp Pro Arg Leu Pro Met Met Lys Asn Thr Met Tyr Ile Gly Ala Asp
                885                 890                 895
Val Thr His Pro Ser Pro Asp Gln Arg Glu Ile Pro Ser Val Val Gly
            900                 905                 910
Val Ala Ala Ser His Asp Pro Tyr Gly Ala Ser Tyr Asn Met Gln Tyr
        915                 920                 925
Arg Leu Gln Arg Gly Ala Leu Glu Glu Ile Glu Asp Met Phe Ser Ile
```

```
                930             935             940
Thr Leu Glu His Leu Arg Val Tyr Lys Glu Tyr Arg Asn Ala Tyr Pro
945             950             955             960

Asp His Ile Ile Tyr Tyr Arg Asp Gly Val Ser Asp Gly Gln Phe Pro
            965             970             975

Lys Ile Lys Asn Glu Glu Leu Arg Cys Ile Lys Gln Ala Cys Asp Lys
            980             985             990

Val Gly Cys Lys Pro Lys Ile Cys Cys Val Ile Val Lys Arg His
            995            1000            1005

His Thr Arg Phe Phe Pro Ser Gly Asp Val Thr Thr Ser Asn Lys Phe
           1010            1015            1020

Asn Asn Val Asp Pro Gly Thr Val Val Asp Arg Thr Ile Val His Pro
1025            1030            1035            1040

Asn Glu Met Gln Phe Phe Met Val Ser Gly Gln Ala Ile Gln Gly Thr
                1045            1050            1055

Ala Lys Pro Thr Arg Tyr Asn Val Ile Glu Asn Thr Gly Asn Leu Asp
            1060            1065            1070

Ile Asp Leu Leu Gln Gln Leu Thr Tyr Asn Leu Cys His Met Phe Pro
            1075            1080            1085

Arg Cys Asn Arg Ser Val Ser Tyr Pro Ala Pro Ala Tyr Leu Ala His
            1090            1095            1100

Leu Val Ala Ala Arg Gly Arg Val Tyr Leu Thr Gly Thr Asn Arg Phe
1105            1110            1115            1120

Leu Asp Leu Lys Lys Glu Tyr Ala Lys Arg Thr Ile Val Pro Glu Phe
            1125            1130            1135

Met Lys Lys Asn Pro Met Tyr Phe Val
            1140            1145

<210> SEQ ID NO 6
<211> LENGTH: 21
<212> TYPE: RNA
<213> ORGANISM: Photinus pyralis

<400> SEQUENCE: 6
ucgaaguacu cagcguaagu g                                              21

<210> SEQ ID NO 7
<211> LENGTH: 21
<212> TYPE: RNA
<213> ORGANISM: Photinus pyralis

<400> SEQUENCE: 7
cuuacgcuga guacuucgaa a                                              21

<210> SEQ ID NO 8
<211> LENGTH: 62
<212> TYPE: RNA
<213> ORGANISM: Photinus pyralis

<400> SEQUENCE: 8
caucgacuga aucccuggu aauccguugu uaacaacgga uuaccaggga uuucagucga    60
ug                                                                   62

<210> SEQ ID NO 9
<211> LENGTH: 81
<212> TYPE: RNA
<213> ORGANISM: Photinus pyralis

<400> SEQUENCE: 9
```

```
caucgacuga aucccuggu aauccguuug gggcucugcc cugcuauggg auaaauggau    60
uaucagggau uuuagucgau g                                            81
```

<210> SEQ ID NO 10
<211> LENGTH: 82
<212> TYPE: RNA
<213> ORGANISM: Photinus pyralis

<400> SEQUENCE: 10

```
caucgacuga aucccgccg uaauccguuu ggggcucugc ccugcuaugg gauaaaugga    60
uuaucaggga uuuuagucga ug                                           82
```

<210> SEQ ID NO 11
<211> LENGTH: 64
<212> TYPE: RNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 34, 35,
      36, 37, 38, 39, 40, 41, 42, 43, 44, 45, 46, 47, 48, 49,
      50, 51, 52, 53, 54, 55, 56, 57, 58, 59, 60, 61, 62
<223> OTHER INFORMATION: n = A,T,C or G
<220> FEATURE:
<223> OTHER INFORMATION: generic structure for 29 nt. shRNA with 3'
      overhang

<400> SEQUENCE: 11

```
nnnnnnnnnn nnnnnnnnnn nnnnnnnnnc caannnnnnn nnnnnnnnnn nnnnnnnnnn    60 nnuu                                                               64
```

<210> SEQ ID NO 12
<211> LENGTH: 62
<212> TYPE: RNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 34, 35,
      36, 37, 38, 39, 40, 41, 42, 43, 44, 45, 46, 47, 48, 49,
      50, 51, 52, 53, 54, 55, 56, 57, 58, 59, 60, 61, 62
<223> OTHER INFORMATION: n = A,T,C or G
<220> FEATURE:
<223> OTHER INFORMATION: generic structure for 29 nt. shRNA without 3'
      overhang

<400> SEQUENCE: 12

```
nnnnnnnnnn nnnnnnnnnn nnnnnnnnnc caannnnnnn nnnnnnnnnn nnnnnnnnnn    60 nn                                                                 62
```

<210> SEQ ID NO 13
<211> LENGTH: 23
<212> TYPE: RNA
<213> ORGANISM: Photinus pyralis

<400> SEQUENCE: 13

```
ggucgaagua cucagcguaa gaa                                          23
```

<210> SEQ ID NO 14
<211> LENGTH: 23
<212> TYPE: RNA
<213> ORGANISM: Photinus pyralis

<400> SEQUENCE: 14

```
ggcuuacgcu gaguacuucg aaa                                          23
```

<210> SEQ ID NO 15
<211> LENGTH: 21
<212> TYPE: RNA
<213> ORGANISM: Photinus pyralis

<400> SEQUENCE: 15
gguuguggau cuggauaccg g                                              21

<210> SEQ ID NO 16
<211> LENGTH: 21
<212> TYPE: RNA
<213> ORGANISM: Photinus pyralis

<400> SEQUENCE: 16
gguauccaga uccacaaccu u                                              21

<210> SEQ ID NO 17
<211> LENGTH: 21
<212> TYPE: RNA
<213> ORGANISM: Photinus pyralis

<400> SEQUENCE: 17
ggugccaacc cuauucuccu u                                              21

<210> SEQ ID NO 18
<211> LENGTH: 21
<212> TYPE: RNA
<213> ORGANISM: Photinus pyralis

<400> SEQUENCE: 18
ggagaauagg guuggcacca g                                              21

<210> SEQ ID NO 19
<211> LENGTH: 22
<212> TYPE: RNA
<213> ORGANISM: Photinus pyralis

<400> SEQUENCE: 19
ggcuaugaag agaguacgcc cu                                             22

<210> SEQ ID NO 20
<211> LENGTH: 22
<212> TYPE: RNA
<213> ORGANISM: Photinus pyralis

<400> SEQUENCE: 20
ggcguacucu cuucauagcc uu                                             22

<210> SEQ ID NO 21
<211> LENGTH: 64
<212> TYPE: RNA
<213> ORGANISM: Photinus pyralis

<400> SEQUENCE: 21
ggucgaagua cucagcguaa gugaugucca cuuaagugggu guuguuugu guuggguguu    60 uugg                                                                 64

<210> SEQ ID NO 22
<211> LENGTH: 60
<212> TYPE: RNA
<213> ORGANISM: Photinus pyralis

<400> SEQUENCE: 22

```
ggucgaagua cucagcguaa gugaugwuccu uaagggaguu guuuguguug gguguuuugg    60
```

<210> SEQ ID NO 23
<211> LENGTH: 56
<212> TYPE: RNA
<213> ORGANISM: Photinus pyralis

<400> SEQUENCE: 23

```
ggucgaagua cucagcguaa gugauguuua aguguugwuu uguuugggug uuuugg         56
```

<210> SEQ ID NO 24
<211> LENGTH: 50
<212> TYPE: RNA
<213> ORGANISM: Photinus pyralis

<400> SEQUENCE: 24

```
ggucgaagua cucagcguaa gugauuaauu guuuguguug gguguuuugg                50
```

<210> SEQ ID NO 25
<211> LENGTH: 70
<212> TYPE: RNA
<213> ORGANISM: Photinus pyralis

<400> SEQUENCE: 25

```
ggcucgaguc gaaguacuca gcguaaguga ugwuccacuua agugggwuguu guuuguguug   60
gguguuuugg                                                            70
```

<210> SEQ ID NO 26
<211> LENGTH: 70
<212> TYPE: RNA
<213> ORGANISM: Photinus pyralis

<400> SEQUENCE: 26

```
ggucgaagua cucagcguaa gugaugucca cuuaaguggg uguuguuugu guugggwuguu    60
uuggcucgag                                                            70
```

<210> SEQ ID NO 27
<211> LENGTH: 69
<212> TYPE: RNA
<213> ORGANISM: Photinus pyralis

<400> SEQUENCE: 27

```
ggauuccaau ucagcgggag ccaccugaug aagcuugauc ggguggcucu cgcugaguug     60
gaauccauu                                                             69
```

<210> SEQ ID NO 28
<211> LENGTH: 64
<212> TYPE: RNA
<213> ORGANISM: Artificial Sequence
<220> FEATURE:
<223> OTHER INFORMATION: shRNA targeting mouse p53

<400> SEQUENCE: 28

```
ggucuaagug gagcccuucg aguguuagaa gcuugugaca cucggagggc uucacuuggg     60
ccuu                                                                  64
```

<210> SEQ ID NO 29
<211> LENGTH: 21
<212> TYPE: RNA
<213> ORGANISM: Photinus pyralis

<400> SEQUENCE: 29

```
cuuacgcuga guacuucgau u                                              21

<210> SEQ ID NO 30
<211> LENGTH: 21
<212> TYPE: RNA
<213> ORGANISM: Photinus pyralis

<400> SEQUENCE: 30
ucgaaguacu cagcguaagu u                                              21

<210> SEQ ID NO 31
<211> LENGTH: 21
<212> TYPE: RNA
<213> ORGANISM: Photinus pyralis

<400> SEQUENCE: 31
agcuucauaa ggcgcaugcu u                                              21

<210> SEQ ID NO 32
<211> LENGTH: 21
<212> TYPE: RNA
<213> ORGANISM: Photinus pyralis

<400> SEQUENCE: 32
gcaugcgccu uaugaagcuu u                                              21

<210> SEQ ID NO 33
<211> LENGTH: 23
<212> TYPE: RNA
<213> ORGANISM: Artificial Sequence
<220> FEATURE:
<223> OTHER INFORMATION: siRNA targeting HCV NS5B

<400> SEQUENCE: 33
cugugagauc uacggagccu guu                                            23

<210> SEQ ID NO 34
<211> LENGTH: 23
<212> TYPE: RNA
<213> ORGANISM: Artificial Sequence
<220> FEATURE:
<223> OTHER INFORMATION: siRNA targeting HCV NS5B

<400> SEQUENCE: 34
caggcuccgu agaucucaca guu                                            23

<210> SEQ ID NO 35
<211> LENGTH: 69
<212> TYPE: RNA
<213> ORGANISM: Photinus pyralis

<400> SEQUENCE: 35
ggauuccaau ucagcgggag ccaccugaug aagcuugauc ggguggcucu cgcugaguug    60
gaauccauu                                                            69

<210> SEQ ID NO 36
<211> LENGTH: 29
<212> TYPE: RNA
<213> ORGANISM: Photinus pyralis

<400> SEQUENCE: 36
aguugcgccc gcgaaugaua uuuauaaug                                      29
```

```
<210> SEQ ID NO 37
<211> LENGTH: 19
<212> TYPE: DNA
<213> ORGANISM: Homo sapiens

<400> SEQUENCE: 37
tcaaccagcc actgctgga                                                  19

<210> SEQ ID NO 38
<211> LENGTH: 71
<212> TYPE: DNA
<213> ORGANISM: Photinus pyralis

<400> SEQUENCE: 38
tccaattcag cgggagccac ctgatgaagc ttgatcgggt ggctctcgct gagttggaat      60 ccatttttt t                                                           71

<210> SEQ ID NO 39
<211> LENGTH: 44
<212> TYPE: DNA
<213> ORGANISM: Artificial Sequence
<220> FEATURE:
<223> OTHER INFORMATION: Tyrosinase enhancer PCR primer

<400> SEQUENCE: 39
taatacgact cactataggg caaggtcata gttcctgcca gctg                      44

<210> SEQ ID NO 40
<211> LENGTH: 44
<212> TYPE: DNA
<213> ORGANISM: Artificial Sequence
<220> FEATURE:
<223> OTHER INFORMATION: Tyrosinase enhancer PCR primer

<400> SEQUENCE: 40
taatacgact cactataggg cagatatttt cttaccaccc accc                      44

<210> SEQ ID NO 41
<211> LENGTH: 44
<212> TYPE: DNA
<213> ORGANISM: Artificial Sequence
<220> FEATURE:
<223> OTHER INFORMATION: Tyrosinase enhancer PCR primer

<400> SEQUENCE: 41
taatacgact cactataggg ttaagtttaa caggagaagc tgga                      44

<210> SEQ ID NO 42
<211> LENGTH: 44
<212> TYPE: DNA
<213> ORGANISM: Artificial Sequence
<220> FEATURE:
<223> OTHER INFORMATION: Tyrosinase enhancer PCR primer

<400> SEQUENCE: 42
taatacgact cactataggg aaatcattgc tttcctgata atgc                      44

<210> SEQ ID NO 43
<211> LENGTH: 44
<212> TYPE: DNA
<213> ORGANISM: Artificial Sequence
<220> FEATURE:
<223> OTHER INFORMATION: Tyrosinase enhancer PCR primer

<400> SEQUENCE: 43
taatacgact cactataggg tagatttccg cagccccagt gttc                      44
```

```
<210> SEQ ID NO 44
<211> LENGTH: 44
<212> TYPE: DNA
<213> ORGANISM: Artificial Sequence
<220> FEATURE:
<223> OTHER INFORMATION: Tyrosinase enhancer PCR primer

<400> SEQUENCE: 44
taatacgact cactataggg gttgcctctc attttccctt gatt              44

<210> SEQ ID NO 45
<211> LENGTH: 45
<212> TYPE: DNA
<213> ORGANISM: Artificial Sequence
<220> FEATURE:
<223> OTHER INFORMATION: Tyrosinase enhancer PCR primer

<400> SEQUENCE: 45
taatacgact cactataggg tattttagac tgattacttt tataa             45

<210> SEQ ID NO 46
<211> LENGTH: 44
<212> TYPE: DNA
<213> ORGANISM: Artificial Sequence
<220> FEATURE:
<223> OTHER INFORMATION: Tyrosinase enhancer PCR primer

<400> SEQUENCE: 46
taatacgact cactataggg tcacatgttt tggctaagac ctat              44

<210> SEQ ID NO 47
<211> LENGTH: 19
<212> TYPE: RNA
<213> ORGANISM: Homo sapiens

<400> SEQUENCE: 47
ggaugcacca ucuucaagg                                          19

<210> SEQ ID NO 48
<211> LENGTH: 19
<212> TYPE: RNA
<213> ORGANISM: Homo sapiens

<400> SEQUENCE: 48
gacaaaaucc ccaucagga                                          19

<210> SEQ ID NO 49
<211> LENGTH: 19
<212> TYPE: RNA
<213> ORGANISM: Homo sapiens

<400> SEQUENCE: 49
accgcaaagu cuuugagaa                                          19

<210> SEQ ID NO 50
<211> LENGTH: 19
<212> TYPE: RNA
<213> ORGANISM: Homo sapiens

<400> SEQUENCE: 50
guccugacau gcuguuuga                                          19

<210> SEQ ID NO 51
<211> LENGTH: 19
```

```
<212> TYPE: RNA
<213> ORGANISM: Homo sapiens

<400> SEQUENCE: 51
gaccaccauc aacaaugag                                               19

<210> SEQ ID NO 52
<211> LENGTH: 19
<212> TYPE: RNA
<213> ORGANISM: Homo sapiens

<400> SEQUENCE: 52
caaauuaugu guuccgaa                                                19

<210> SEQ ID NO 53
<211> LENGTH: 19
<212> TYPE: RNA
<213> ORGANISM: Homo sapiens

<400> SEQUENCE: 53
cgcaugugcu ggcaguaua                                               19

<210> SEQ ID NO 54
<211> LENGTH: 19
<212> TYPE: RNA
<213> ORGANISM: Homo sapiens

<400> SEQUENCE: 54
ccgaagauuu cacagucaa                                               19

<210> SEQ ID NO 55
<211> LENGTH: 19
<212> TYPE: RNA
<213> ORGANISM: Homo sapiens

<400> SEQUENCE: 55
accauugauu cuguuacuu                                               19

<210> SEQ ID NO 56
<211> LENGTH: 19
<212> TYPE: RNA
<213> ORGANISM: Homo sapiens

<400> SEQUENCE: 56
cugacaagag cucaaggaa                                               19

<210> SEQ ID NO 57
<211> LENGTH: 19
<212> TYPE: RNA
<213> ORGANISM: Homo sapiens

<400> SEQUENCE: 57
cguucuggag cuguugaua                                               19

<210> SEQ ID NO 58
<211> LENGTH: 19
<212> TYPE: RNA
<213> ORGANISM: Homo sapiens

<400> SEQUENCE: 58
gagcccagau caaccuuua                                               19

<210> SEQ ID NO 59
<211> LENGTH: 19
```

```
<212> TYPE: RNA
<213> ORGANISM: Homo sapiens

<400> SEQUENCE: 59
ggcauuaaca cacuggaga                                              19

<210> SEQ ID NO 60
<211> LENGTH: 19
<212> TYPE: RNA
<213> ORGANISM: Homo sapiens

<400> SEQUENCE: 60
gauggcagcu caaagcaaa                                              19

<210> SEQ ID NO 61
<211> LENGTH: 19
<212> TYPE: RNA
<213> ORGANISM: Homo sapiens

<400> SEQUENCE: 61
cagcagaaau cuaaggaua                                              19

<210> SEQ ID NO 62
<211> LENGTH: 19
<212> TYPE: RNA
<213> ORGANISM: Homo sapiens

<400> SEQUENCE: 62
cagggaugcu guuuggaua                                              19

<210> SEQ ID NO 63
<211> LENGTH: 19
<212> TYPE: RNA
<213> ORGANISM: Homo sapiens

<400> SEQUENCE: 63
acugacaaca aagugcagc                                              19

<210> SEQ ID NO 64
<211> LENGTH: 19
<212> TYPE: RNA
<213> ORGANISM: Homo sapiens

<400> SEQUENCE: 64
aaacugggag gcuacuuac                                              19

<210> SEQ ID NO 65
<211> LENGTH: 19
<212> TYPE: RNA
<213> ORGANISM: Homo sapiens

<400> SEQUENCE: 65
cacugaaugu gggagguga                                              19

<210> SEQ ID NO 66
<211> LENGTH: 19
<212> TYPE: RNA
<213> ORGANISM: Homo sapiens

<400> SEQUENCE: 66
gucugggugg aaauucaaa                                              19

<210> SEQ ID NO 67
<211> LENGTH: 19
```

<212> TYPE: RNA
<213> ORGANISM: Homo sapiens

<400> SEQUENCE: 67
caucuuugcu gaaucgaaa                                                    19

<210> SEQ ID NO 68
<211> LENGTH: 19
<212> TYPE: RNA
<213> ORGANISM: Homo sapiens

<400> SEQUENCE: 68
gggauugacg gcaguaaga                                                    19

<210> SEQ ID NO 69
<211> LENGTH: 19
<212> TYPE: RNA
<213> ORGANISM: Homo sapiens

<400> SEQUENCE: 69
cagguaaagu cagagacau                                                    19

<210> SEQ ID NO 70
<211> LENGTH: 19
<212> TYPE: RNA
<213> ORGANISM: Homo sapiens

<400> SEQUENCE: 70
cucacauugu ccaccagga                                                    19

<210> SEQ ID NO 71
<211> LENGTH: 19
<212> TYPE: RNA
<213> ORGANISM: Homo sapiens

<400> SEQUENCE: 71
gaccugugcc uuuuagaga                                                    19

<210> SEQ ID NO 72
<211> LENGTH: 19
<212> TYPE: RNA
<213> ORGANISM: Homo sapiens

<400> SEQUENCE: 72
aaaggacaac ugcagcuac                                                    19

<210> SEQ ID NO 73
<211> LENGTH: 19
<212> TYPE: RNA
<213> ORGANISM: Homo sapiens

<400> SEQUENCE: 73
gacuucauug acaguggcc                                                    19

<210> SEQ ID NO 74
<211> LENGTH: 19
<212> TYPE: RNA
<213> ORGANISM: Homo sapiens

<400> SEQUENCE: 74
aauauccuca gggguggag                                                    19

<210> SEQ ID NO 75
<211> LENGTH: 19

```
<212> TYPE: RNA
<213> ORGANISM: Homo sapiens

<400> SEQUENCE: 75
gugccucuug uugcagaga                                          19

<210> SEQ ID NO 76
<211> LENGTH: 19
<212> TYPE: RNA
<213> ORGANISM: Homo sapiens

<400> SEQUENCE: 76
gaagcucucc agaccauuu                                          19

<210> SEQ ID NO 77
<211> LENGTH: 19
<212> TYPE: RNA
<213> ORGANISM: Homo sapiens

<400> SEQUENCE: 77
cuccugagau caugcugaa                                          19

<210> SEQ ID NO 78
<211> LENGTH: 19
<212> TYPE: RNA
<213> ORGANISM: Homo sapiens

<400> SEQUENCE: 78
gcuguugacu ggaagaaca                                          19

<210> SEQ ID NO 79
<211> LENGTH: 19
<212> TYPE: RNA
<213> ORGANISM: Homo sapiens

<400> SEQUENCE: 79
ggaauucaau gauguguau                                          19

<210> SEQ ID NO 80
<211> LENGTH: 19
<212> TYPE: RNA
<213> ORGANISM: Homo sapiens

<400> SEQUENCE: 80
ccauuucagu ccaucauuc                                          19

<210> SEQ ID NO 81
<211> LENGTH: 19
<212> TYPE: RNA
<213> ORGANISM: Homo sapiens

<400> SEQUENCE: 81
cccugugugg gacuccuaa                                          19

<210> SEQ ID NO 82
<211> LENGTH: 19
<212> TYPE: RNA
<213> ORGANISM: Homo sapiens

<400> SEQUENCE: 82
ccgaguuauu caucgagac                                          19

<210> SEQ ID NO 83
<211> LENGTH: 19
```

```
<212> TYPE: RNA
<213> ORGANISM: Homo sapiens

<400> SEQUENCE: 83
guucuuuacu ucuggcuau                                                19

<210> SEQ ID NO 84
<211> LENGTH: 19
<212> TYPE: RNA
<213> ORGANISM: Homo sapiens

<400> SEQUENCE: 84
cgccucaucc ucuacaaug                                                19

<210> SEQ ID NO 85
<211> LENGTH: 19
<212> TYPE: RNA
<213> ORGANISM: Homo sapiens

<400> SEQUENCE: 85
aagagaccua ccuccggau                                                19

<210> SEQ ID NO 86
<211> LENGTH: 19
<212> TYPE: RNA
<213> ORGANISM: Homo sapiens

<400> SEQUENCE: 86
gguguucgcg ggcaagauu                                                19

<210> SEQ ID NO 87
<211> LENGTH: 19
<212> TYPE: RNA
<213> ORGANISM: Homo sapiens

<400> SEQUENCE: 87
cuccuuaaau auuccgca                                                 19

<210> SEQ ID NO 88
<211> LENGTH: 19
<212> TYPE: RNA
<213> ORGANISM: Homo sapiens

<400> SEQUENCE: 88
aagaagaacc agugguucg                                                19

<210> SEQ ID NO 89
<211> LENGTH: 19
<212> TYPE: RNA
<213> ORGANISM: Homo sapiens

<400> SEQUENCE: 89
cugagccuga ggcccgaua                                                19

<210> SEQ ID NO 90
<211> LENGTH: 44
<212> TYPE: RNA
<213> ORGANISM: Artificial Sequence
<220> FEATURE:
<223> OTHER INFORMATION: generic structure for 19 nt. shRNA with 3'
      overhang
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 24, 25, 26, 27, 28, 29, 30, 31, 32, 33, 34, 35,
      36, 37, 38, 39, 40, 41, 42
```

```
<223> OTHER INFORMATION: n = A,T,C or G

<400> SEQUENCE: 90
nnnnnnnnnn nnnnnnnnnc caannnnnnn nnnnnnnnnn nnuu            44

<210> SEQ ID NO 91
<211> LENGTH: 42
<212> TYPE: RNA
<213> ORGANISM: Artificial Sequence
<220> FEATURE:
<223> OTHER INFORMATION: generic structure for 19 nt. shRNA without 3'
      overhang
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 24, 25, 26, 27, 28, 29, 30, 31, 32, 33, 34, 35,
      36, 37, 38, 39, 40, 41, 42
<223> OTHER INFORMATION: n = A,T,C or G

<400> SEQUENCE: 91
nnnnnnnnnn nnnnnnnnnc caannnnnnn nnnnnnnnnn nn              42

<210> SEQ ID NO 92
<211> LENGTH: 44
<212> TYPE: RNA
<213> ORGANISM: Artificial Sequence
<220> FEATURE:
<223> OTHER INFORMATION: generic structure for synthetic 19 nt. shRNA
      with 3' overhang
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 24, 25, 26, 27, 28, 29, 30, 31, 32, 33, 34, 35,
      36, 37, 38, 39, 40, 41, 42
<223> OTHER INFORMATION: n = A,T,C or G

<400> SEQUENCE: 92
nnnnnnnnnn nnnnnnnnnu uggnnnnnnn nnnnnnnnnn nnuu            44

<210> SEQ ID NO 93
<211> LENGTH: 64
<212> TYPE: RNA
<213> ORGANISM: Artificial Sequence
<220> FEATURE:
<223> OTHER INFORMATION: generic structure for synthetic 29 nt. shRNA
      with 3' overhang
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 34, 35,
      36, 37, 38, 39, 40, 41, 42, 43, 44, 45, 46, 47, 48, 49,
      50, 51, 52, 53, 54, 55, 56, 57, 58, 59, 60, 61, 62
<223> OTHER INFORMATION: n = A,T,C or G

<400> SEQUENCE: 93
nnnnnnnnnn nnnnnnnnnn nnnnnnnnnu uggnnnnnnn nnnnnnnnnn nnnnnnnnnn   60 nnuu                                                                64
```